(12) United States Patent
Boddy et al.

(10) Patent No.: US 7,396,669 B2
(45) Date of Patent: Jul. 8, 2008

(54) MAMMALIAN ENDONUCLEASES AND METHODS OF USE

(75) Inventors: Michael N. Boddy, San Diego, CA (US); Veronique Blais, San Diego, CA (US); Xiao-Bo Chen, Tucson, AZ (US); Clare H. McGowan, Del Mar, CA (US); Pierre-Henri L. Gaillard, La Jolla, CA (US); Paul R. Russell, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 320 days.

(21) Appl. No.: 10/880,881

(22) Filed: Jun. 30, 2004

(65) Prior Publication Data

US 2006/0003434 A1    Jan. 5, 2006

(51) Int. Cl.
*C12N 9/16*     (2006.01)
*C07K 14/00*    (2006.01)
*C12Q 1/44*     (2006.01)
*C12P 21/06*    (2006.01)
*C12N 15/00*    (2006.01)
*C12N 5/10*     (2006.01)
*C12N 1/21*     (2006.01)
*C07H 21/04*    (2006.01)

(52) U.S. Cl. ............ 435/196; 435/19; 435/320.1; 435/69.1; 435/325; 435/252.3; 530/350; 536/23.2; 536/23.5; 536/23.1

(58) Field of Classification Search .......... 435/196, 435/19, 320.1, 69.1, 325, 252.3; 530/350; 536/23.2, 23.5, 23.1
See application file for complete search history.

(56) References Cited

U.S. PATENT DOCUMENTS 6,440,732 B1 *  8/2002  Russell et al. .............. 435/325

OTHER PUBLICATIONS

Ogrunc, M., et al. (3003) J. Biol. Chem. 278(24), 21715-21720.*
Ceccia, A., et al. (2003) J. Biol. Chem. 278(27), 25172-25178.*
Sequence search, U.S. Appl. No. 10/880,881 and U.S. Patent 6,440,732.*
Branden et al.,Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*

* cited by examiner

*Primary Examiner*—Delia M. Ramirez
(74) *Attorney, Agent, or Firm*—Olson & Cepuritis, Ltd.

(57) ABSTRACT

Isolated mammalian Mus81-Eme endonuclease complexes comprise an Mus81 protein portion and an Eme protein portion. A method of identifying a chemical compound that modulates mammalian cellular response to DNA damage comprises contacting a chemical compound to be tested with a biochemical mixture containing an isolated mammalian Mus81-Eme1 endonuclease complex, a source of magnesium ion, and a suitable DNA substrate; measuring the activity level of mammalian Mus81-Eme endonuclease complex in the mixture; comparing the measured activity level to the activity level of a substantially similar mixture of isolated Mus81-Eme1 endonuclease, magnesium ion, and DNA substrate in the absence of the chemical compound to be tested; and selecting a chemical compound that increases or decreases the endonuclease activity. Isolated mammalian Eme1 and Eme2 proteins derived from humans and murine species and isolated nucleic acids encoding the proteins are also described.

2 Claims, 52 Drawing Sheets

Hmus81(1)    SEQ ID NO:1

```
gatatctgca gaattcgccc tt atg gcg gcc ccg gtc cgc ctg ggc cgg aag    52
cgc ccg ctg cct gcc tgt ccc aac ccg ctc ttc gtt cgc tgg ctg acc    100
gag tgg cgg gac gag gcg acc cgc agc agg cac cgc acg cgc ttc gta    148
ttt cag aag gcg ctg cgt tcc ctc cga cgg tac cca ctg ccg ctg cgc    196
agc ggg aag gaa gct aag atc cta cag cac ttc gga gac ggg ctc tgc    244
cgg atg ctg gac gag cgg ctg cag cgg cac cga aca tcg ggc ggt gac    292
cat gcc ccg gac tca cca tct gga gag aac agt cca gcc ccg cag ggg    340
cga ctt gcg gaa gtc cag gac tct tcc atg cca gtt cct gcc cag ccc    388
aaa gcg gga ggc tct ggc agc tac tgg cca gct cgg cac tca gga gcc    436
cga gtg ata ctg ctg gtg ctc tac cgg gag cac ctg aat cct aat ggt    484
cac cac ttc tta acc aag gag gag ctg ctg cag agg tgt gct cag aag    532
tcc ccc agg gta gcc cct ggg agt gcc cca ccc tgg cca gcc ctc cgc    580
tcc ctc ctt cac agg aac ctg gtc ctc agg aca cac cag cca gcc agg    628
tac tca ttg acc cca gag ggc ctg gag ctg gcc cag aag ttg gcc gag    676
tca gaa ggc ctg agc ttg ctg aat gtg ggc atc ggg ccc aag gag ccc    724
cct ggg gag gag aca gca gtg cca gga gca gct tca gca gag ctt gcc    772
agt gaa gca ggg gtc cag cag cag cca ctg gag ctg agg cct gga gag    820
tac agg gtg ctg ttg tgt gtg gac att ggc gag acc cgg ggc ggc ggg    868
cac agg ccg gag ctg ctc cga gag cta cag cgg ctg cac gtg acc cac    916
acg gtg cgc aag ctg cac gtt gga gat ttt gtg tgg gtg gct cag gag    964
acc aat cct aga gac cca gca aac cct ggg gag ttg gta ctg gat cac    1012
att gtg gag cgc aag cga ctg gat gac ctt tgc agc agc atc atc gac    1060
ggc cgc ttc cgg gag cag aag ttc cga ctg aag cgc tgt ggt ctg gag    1108
cgc cgg gta tac ctg gtg gaa gag cat ggt tcc gtc cac aac ctc agc    1156
ctt cct gag agc aca ctg ctg cag gct gtc acc aac act cag gtc att    1204
gat ggc ttt ttt gtg aag cgc aca gca gac att aag gag tca gcc gcc    1252
tac ctg gcc ctc ttg act cgg ggc ctg cag aga ctc tac cag ggc cac    1300
acc cta cgc agc cgc ccc tgg gga acc cct ggg aac cct gaa tca ggg    1348
gcc atg acc tct cca aac cct ctc tgc tca ctc ctc acc ttc agt gac    1396
ttc aac gca gga gcc atc aag aat aag gcc cag tcg gtg cga gaa gtg    1444
ttt gcc cgg cag ctg atg cag gtg cgc gga gtg agt ggg gag aag gca    1492
gca gcc ctg gtg gat cga tac agc acc cct gcc agc ctc ctg gcc gcc    1540
tat gat gcc tgt gcc acc ccc aag gaa caa gag aca ctg ctg agc acc    1588
att aag tgt ggg cgt cta cag agg aat ctg ggg cct gct ctg agc agg    1636
acc tta tcc cag ctc tac tgc agc tac ggc ccc ttg acc tgagtcaagg    1685
gcgaattc                                                            1693
```

FIG. 1A

Hmus81(1)    SEQ ID NO:2

| | | | | | | | | | | | | | | |
|---|---|---|---|---|---|---|---|---|---|---|---|---|---|---|
|Met|Ala|Ala|Pro|Val|Arg|Leu|Gly|Arg|Lys|Arg|Pro|Leu|Pro|Ala|Cys|
|1| | |5| | | | |10| | | | |15| |
|Pro|Asn|Pro|Leu|Phe|Val|Arg|Trp|Leu|Thr|Glu|Trp|Arg|Asp|Glu|Ala|
| | | |20| | | |25| | | | |30| | |
|Thr|Arg|Ser|Arg|His|Arg|Thr|Arg|Phe|Val|Phe|Gln|Lys|Ala|Leu|Arg|
| | |35| | | |40| | | | |45| | | |
|Ser|Leu|Arg|Arg|Tyr|Pro|Leu|Pro|Leu|Arg|Ser|Gly|Lys|Glu|Ala|Lys|
|50| | | | |55| | | | |60| | | | |
|Ile|Leu|Gln|His|Phe|Gly|Asp|Gly|Leu|Cys|Arg|Met|Leu|Asp|Glu|Arg|
|65| | | | |70| | | | |75| | | | |80|
|Leu|Gln|Arg|His|Arg|Thr|Ser|Gly|Gly|Asp|His|Ala|Pro|Asp|Ser|Pro|
| | | | |85| | | | |90| | | | |95| |
|Ser|Gly|Glu|Asn|Ser|Pro|Ala|Pro|Gln|Gly|Arg|Leu|Ala|Glu|Val|Gln|
| | | |100| | | | |105| | | | |110| | |
|Asp|Ser|Ser|Met|Pro|Val|Pro|Ala|Gln|Pro|Lys|Ala|Gly|Gly|Ser|Gly|
| | |115| | | | |120| | | | |125| | | |
|Ser|Tyr|Trp|Pro|Ala|Arg|His|Ser|Gly|Ala|Arg|Val|Ile|Leu|Leu|Val|
| |130| | | | |135| | | | |140| | | | |
|Leu|Tyr|Arg|Glu|His|Leu|Asn|Pro|Asn|Gly|His|His|Phe|Leu|Thr|Lys|
|145| | | | |150| | | | |155| | | | |160|
|Glu|Glu|Leu|Leu|Gln|Arg|Cys|Ala|Gln|Lys|Ser|Pro|Arg|Val|Ala|Pro|
| | | | |165| | | | |170| | | | |175| |
|Gly|Ser|Ala|Pro|Pro|Trp|Pro|Ala|Leu|Arg|Ser|Leu|Leu|His|Arg|Asn|
| | | |180| | | | |185| | | | |190| | |
|Leu|Val|Leu|Arg|Thr|His|Gln|Pro|Ala|Arg|Tyr|Ser|Leu|Thr|Pro|Glu|
| | |195| | | | |200| | | | |205| | | |
|Gly|Leu|Glu|Leu|Ala|Gln|Lys|Leu|Ala|Glu|Ser|Glu|Gly|Leu|Ser|Leu|
| |210| | | | |215| | | | |220| | | | |
|Leu|Asn|Val|Gly|Ile|Gly|Pro|Lys|Glu|Pro|Pro|Gly|Glu|Glu|Thr|Ala|
|225| | | | |230| | | | |235| | | | |240|
|Val|Pro|Gly|Ala|Ala|Ser|Ala|Glu|Leu|Ala|Ser|Glu|Ala|Gly|Val|Gln|
| | | | |245| | | | |250| | | | |255| |
|Gln|Gln|Pro|Leu|Glu|Leu|Arg|Pro|Gly|Glu|Tyr|Arg|Val|Leu|Leu|Cys|
| | | |260| | | | |265| | | | |270| | |
|Val|Asp|Ile|Gly|Glu|Thr|Arg|Gly|Gly|Gly|His|Arg|Pro|Glu|Leu|Leu|
| | |275| | | | |280| | | | |285| | | |
|Arg|Glu|Leu|Gln|Arg|Leu|His|Val|Thr|His|Thr|Val|Arg|Lys|Leu|His|
| |290| | | | |295| | | | |300| | | | |
|Val|Gly|Asp|Phe|Val|Trp|Val|Ala|Gln|Glu|Thr|Asn|Pro|Arg|Asp|Pro|
|305| | | | |310| | | | |315| | | | |320|
|Ala|Asn|Pro|Gly|Glu|Leu|Val|Leu|Asp|His|Ile|Val|Glu|Arg|Lys|Arg|
| | | | |325| | | | |330| | | | |335| |
|Leu|Asp|Asp|Leu|Cys|Ser|Ser|Ile|Ile|Asp|Gly|Arg|Phe|Arg|Glu|Gln|
| | | |340| | | | |345| | | | |350| | |
|Lys|Phe|Arg|Leu|Lys|Arg|Cys|Gly|Leu|Glu|Arg|Arg|Val|Tyr|Leu|Val|
| | |355| | | | |360| | | | |365| | | |
|Glu|Glu|His|Gly|Ser|Val|His|Asn|Leu|Ser|Leu|Pro|Glu|Ser|Thr|Leu|
| |370| | | | |375| | | | |380| | | | |
|Leu|Gln|Ala|Val|Thr|Asn|Thr|Gln|Val|Ile|Asp|Gly|Phe|Phe|Val|Lys|
|385| | | | |390| | | | |395| | | | |400|
|Arg|Thr|Ala|Asp|Ile|Lys|Glu|Ser|Ala|Ala|Tyr|Leu|Ala|Leu|Leu|Thr|
| | | | |405| | | | |410| | | | |415| |
|Arg|Gly|Leu|Gln|Arg|Leu|Tyr|Gln|Gly|His|Thr|Leu|Arg|Ser|Arg|Pro|
| | | |420| | | | |425| | | | |430| | |

FIG. 1A Cont.

```
Trp Gly Thr Pro Gly Asn Pro Glu Ser Gly Ala Met Thr Ser Pro Asn
        435             440             445
Pro Leu Cys Ser Leu Leu Thr Phe Ser Asp Phe Asn Ala Gly Ala Ile
        450             455             460
Lys Asn Lys Ala Gln Ser Val Arg Glu Val Phe Ala Arg Gln Leu Met
465             470             475             480
Gln Val Arg Gly Val Ser Gly Glu Lys Ala Ala Ala Leu Val Asp Arg
                485             490             495
Tyr Ser Thr Pro Ala Ser Leu Leu Ala Ala Tyr Asp Ala Cys Ala Thr
            500             505             510
Pro Lys Glu Gln Glu Thr Leu Leu Ser Thr Ile Lys Cys Gly Arg Leu
        515             520             525
Gln Arg Asn Leu Gly Pro Ala Leu Ser Arg Thr Leu Ser Gln Leu Tyr
        530             535             540
Cys Ser Tyr Gly Pro Leu Thr
545             550
```

FIG. 1A Cont.

Hmus81(2)      SEQ ID NO:3

```
gcggccgcag gctctcttct cgttagtgcc ccctgtgttt ggggccccgt gatctcaacg  60
gtcctgccct cggtctccct cttccccgc ccgccctgg gccaggtgtt cgaatcccga  120
ctccagaact ggcggcgtcc cagtccgcg ggcgtggagc gccggaggac ccgccctcgg  180
gctcatggcg gccccggtcc gcctgggccg gaagcgcccg ctgcctgcct gtcccaaccc  240
gctcttcgtt cgctggctga ccgagtggcg ggacgaggcg acccgcagca ggcaccgcac  300
gcgcttcgta tttcagaagg cgctgcgttc cctccgacgg tacccactgc cgctgcgcag  360
cgggaaggaa gctaagatcc tacagcactt cggagacggg ctctgccgga tgctggacga  420
gcggctgcag cggcaccgaa catcgggcgg tgaccatgcc ccggactcac catctggaga  480
gaacagtcca gccccgcagg ggcgacttgc ggaagtccag gactcttcca tgccagttcc  540
tgcccagccc aaagcgggag gctctgcag ctactggcca gctcggcact caggagcccg  600
agtgatactg ctggtgctct accgggagca cctgaatcct aatggtcacc acttcttaac  660
caaggaggag ctgctgcaga ggtgtgctca gaagtccccc agggtagccc ctgggagtgc  720
cccaccctgg ccagccctcc gctccctcct tcacaggaac ctggtcctca ggacacacca  780
gccagccagg tactcattga ccccagaggg cctggagctg cccagaagt tggccgagtc  840
agaaggcctg agcttgctga atgtgggcat cgggcccaag gagcccctg gggaggagac  900
agcagtgcca ggagcagctt cagcagagct tgccagtgaa gcaggggtcc agcagcagcc  960
actggagctg aggcctggag agtacaggggt gctgttgtgt gtggacattg gcgagaccgc 1020
ggggggcggg cacaggccgg agctgctccg agagctacag cggctgcacg tgacccacac 1080
ggtgcgcaag ctgcacgttg agattttgt gtgggtggct caggagacca atcctagaga 1140
cccagcaaac cctggggagt tggtactgga tcacattgtg gagcgcaagc gactggatga 1200
cctttgcagc agcatcatcg acggccgctt ccgggagcag aagttccgac tgaagcgctg 1260
tggtctggag cgccgggtat acctggtgga agagcatggt tccgtccaca acctcagctt 1320
tcttgagagc acacttgtgc aggctgtcac caacactcag gtcattgatg gcttttttgt 1380
gaagcgcaca gcagacatta aggagtcagc cgcctacctg gccctcttga ctcggggcct 1440
gcagagactc taccaggtga gcagaggccc ctttcccagt gtcgggacag agcccacaag 1500
gaattcacct tgcctgggcc ctgtgcatcc ccaaaagaag caaggtgggt gagatcccca 1560
tttctcaggc tggcccccca aggctgagga ctgggcaggg gctggctgga gttgttcctt 1620
cgagctccag cctggcctca gtcccttctt ccctcagggc cacacctac gcagccgccc 1680
ctggggaacc cctgggaacc ctgaatcagg gccatgacc tctccaaacc ctctctgctc 1740
actcctcacc ttcagtgact tcaacgcagg agccatcaag aataaggccc agtcggtgcg 1800
agaagtgttt gcccggcagc tgatgcaggt gcgcggagtg agtggggaga aggcagcagc 1860
cctggtggat cgatacagca ccctgccag cctcctggcc gcctatgatg cctgtgccac 1920
ccccaaggaa caagagacac tgctgagcac cattaagtgt gggcgtctac agaggaatct 1980
ggggcctgct ctgagcagga ccttatccca gctctactgc agctacggcc ccttgacctg 2040
agcttatgcc gtgaaacagc ccccagcccc cgtctgtccc caacccagg ctagccagcc 2100
ttttaacaac atctttggg gtacaattag aatctaagtg tttgcagcca tatgtgtcat 2160
gtagaagatg cctagccctg ggaccttgt gaaatacgca ggaaccaggg ataccatctg 2220
gtccagtggt ttttaaacaa agctgcttag cacctggaat tccctggtca gggagatgga 2280
gtcagtgggg cattgcagct tggaatctat tttatgtcac cagttggtcc tcatcaaata 2340
aaatttcctt aggagtgcag agggctcatt gggaaataa aataataaa aataaataaa 2400
acttcctaaa agaaaagatt gaaaccaaa aaaaaaaaa aaaaaacct cgtgccgaat 2460
tc                                                               2462
```

FIG. 1B

Hmus81(2)    SEQ ID NO:4

```
Met Ala Ala Pro Val Arg Leu Gly Arg Lys Arg Pro Leu Pro Ala Cys
 1           5                   10                  15
Pro Asn Pro Leu Phe Val Arg Trp Leu Thr Glu Trp Arg Asp Glu Ala
            20                  25                  30
Thr Arg Ser Arg His Arg Thr Arg Phe Val Phe Gln Lys Ala Leu Arg
            35                  40                  45
Ser Leu Arg Arg Tyr Pro Leu Pro Leu Arg Ser Gly Lys Glu Ala Lys
    50                  55                  60
Ile Leu Gln His Phe Gly Asp Gly Leu Cys Arg Met Leu Asp Glu Arg
65                  70                  75                  80
Leu Gln Arg His Arg Thr Ser Gly Gly Asp His Ala Pro Asp Ser Pro
            85                  90                  95
Ser Gly Glu Asn Ser Pro Ala Pro Gln Gly Arg Leu Ala Glu Val Gln
            100                 105                 110
Asp Ser Ser Met Pro Val Pro Ala Gln Pro Lys Ala Gly Gly Ser Gly
            115                 120                 125
Ser Tyr Trp Pro Ala Arg His Ser Gly Ala Arg Val Ile Leu Leu Val
    130                 135                 140
Leu Tyr Arg Glu His Leu Asn Pro Asn Gly His His Phe Leu Thr Lys
145                 150                 155                 160
Glu Glu Leu Leu Gln Arg Cys Ala Gln Lys Ser Pro Arg Val Ala Pro
            165                 170                 175
Gly Ser Ala Pro Pro Trp Pro Ala Leu Arg Ser Leu Leu His Arg Asn
            180                 185                 190
Leu Val Leu Arg Thr His Gln Pro Ala Arg Tyr Ser Leu Thr Pro Glu
            195                 200                 205
Gly Leu Glu Leu Ala Gln Lys Leu Ala Glu Ser Glu Gly Leu Ser Leu
    210                 215                 220
Leu Asn Val Gly Ile Gly Pro Lys Glu Pro Pro Gly Glu Glu Thr Ala
225                 230                 235                 240
Val Pro Gly Ala Ala Ser Ala Glu Leu Ala Ser Glu Ala Gly Val Gln
            245                 250                 255
Gln Gln Pro Leu Glu Leu Arg Pro Gly Glu Tyr Arg Val Leu Leu Cys
            260                 265                 270
Val Asp Ile Gly Glu Thr Arg Gly Gly Gly His Arg Pro Glu Leu Leu
    275                 280                 285
Arg Glu Leu Gln Arg Leu His Val Thr His Thr Val Arg Lys Leu His
    290                 295                 300
Val Gly Asp Phe Val Trp Val Ala Gln Glu Thr Asn Pro Arg Asp Pro
305                 310                 315                 320
Ala Asn Pro Gly Glu Leu Val Leu Asp His Ile Val Glu Arg Lys Arg
            325                 330                 335
Leu Asp Asp Leu Cys Ser Ser Ile Ile Asp Gly Arg Phe Arg Glu Gln
            340                 345                 350
Lys Phe Arg Leu Lys Arg Cys Gly Leu Glu Arg Arg Val Tyr Leu Val
    355                 360                 365
Glu Glu His Gly Ser Val His Asn Leu Ser Phe Leu Glu Ser Thr Leu
    370                 375                 380
Val Gln Ala Val Thr Asn Thr Gln Val Ile Asp Gly Phe Phe Val Lys
385                 390                 395                 400
Arg Thr Ala Asp Ile Lys Glu Ser Ala Ala Tyr Leu Ala Leu Leu Thr
            405                 410                 415
Arg Gly Leu Gln Arg Leu Tyr Gln Val Ser Arg Gly Pro Phe Pro Ser
            420                 425                 430
Val Gly Thr Glu Pro Thr Arg Asn Ser Pro Cys Leu Gly Pro Val His
            435                 440                 445
Pro Gln Lys Lys Gln Gly Gly
    450                 455
```

FIG. 1B Cont.

Hmus81(3)    SEQ ID NO:5

```
gatatctgca gaattcgccc ttgacatggc ggccccggtc cgcctgggcc ggaagcgccc   60
gctgcctgcc tgtcccaacc cgctcttcgt tcgctggctg accgagtggc gggacgaggc  120
gacccgcagc aggcgccgca cgcgcttcgt atttcagaag gcgctgcgtt ccctccgacg  180
gtacccactg ccgctgcgca gcgggaagga agctaagatc ctacagcact cggagacgg   240
gctctgccgg atgctggacg agcggctgca gcggcaccga acatcgggcg gtgaccatgc  300
cccggactca ccatctggag agaacagtcc agccccgcag gggcgacttg cggaagtcca  360
ggactcttcc atgccagttc ctgcccagcc caaagcggga ggctctggca gctactggcc  420
agctcggcac tcaggagccc gagtgatact gctggtgctc taccgggagc acctgaatcc  480
taatggtcac cacttcttaa ccaaggagga gctgctgcag aggtgtgctc agaagtcccc  540
cagggtagcc cctgggagtg ctcgaccctg ccagccctc cgctccctcc ttcacaggaa  600
cctggtcctc aggacacacc agccagccag gtactcattg accccagagg gcctggagct  660
ggcccagaag ttggccgagt cagaaggcct gagcttgctg aatgtgggca tcgggcccaa  720
ggagccccct ggggaggaga cagcagtgcc aggagcagct tcagcagagc ttgccagtga  780
agcagggtc cagcagcagc cactggagct gaggcctgga gagtacaggg tgctgttgtg   840
tgtggacatt ggcgagaccc gggggggcgg gcacaggccg gagctgctcc gagagctaca  900
gcggctgcac gtgacccaca cggtgcgcaa gctgcacgtt ggagattttg tgtgggtggc  960
ccaggagacc aatcctagag acccagcaaa ccctggggag ttggtactgg atcacattgt 1020
ggagcgcaag cgactggatg acctttgcag cagcatcatc gacggccgct ccgggagca  1080
gaagttccgg ctgaagcgct gtggtctgga gcgcgggta tacctggtgg aagagcatgg  1140
ttccgtccac aacctcagcc ttcctgagag cacactgctg caggctgtca ccaacactca 1200
ggtcattgat ggcttttttg tgaagcgcac agcagacatt aaggagtcag ccgcctacct 1260
ggccctcttg acgcggggcc tgcagagact ctaccagtga cttcaacgca ggagccatca 1320
agaataaggc ccagtcggtc cgagaagtgt ttgcccggca gctgatgcag gtgcgcggag 1380
tgagtgggga gaaggcagca gccctggtgg atcgatacag caccctgcc agcctcctgg  1440
ccgcctatga tgcctgtgcc accccaagg aacaagagac actgctgagc accattaagt  1500
gtgggcgtct acagaggaat ctggggcctg ctctgagcag gaccttatcc cagctctact 1560
gcagctacgg ccccttgacc tgagtcaagg gcgaattc                         1598
```

FIG. 1C

Hmus81(3)     SEQ ID NO:6

```
Met Ala Ala Pro Val Arg Leu Gly Arg Lys Arg Pro Leu Pro Ala Cys
 1           5               10              15
Pro Asn Pro Leu Phe Val Arg Trp Leu Thr Glu Trp Arg Asp Glu Ala
            20              25              30
Thr Arg Ser Arg Arg Arg Thr Arg Phe Val Phe Gln Lys Ala Leu Arg
            35              40              45
Ser Leu Arg Arg Tyr Pro Leu Pro Leu Arg Ser Gly Lys Glu Ala Lys
    50              55              60
Ile Leu Gln His Phe Gly Asp Gly Leu Cys Arg Met Leu Asp Glu Arg
65              70              75              80
Leu Gln Arg His Arg Thr Ser Gly Gly Asp His Ala Pro Asp Ser Pro
            85              90              95
Ser Gly Glu Asn Ser Pro Ala Pro Gln Gly Arg Leu Ala Glu Val Gln
            100             105             110
Asp Ser Ser Met Pro Val Pro Ala Gln Pro Lys Ala Gly Gly Ser Gly
            115             120             125
Ser Tyr Trp Pro Ala Arg His Ser Gly Ala Arg Val Ile Leu Leu Val
    130             135             140
Leu Tyr Arg Glu His Leu Asn Pro Asn Gly His His Phe Leu Thr Lys
145             150             155             160
Glu Glu Leu Leu Gln Arg Cys Ala Gln Lys Ser Pro Arg Val Ala Pro
            165             170             175
Gly Ser Ala Arg Pro Trp Pro Ala Leu Arg Ser Leu Leu His Arg Asn
            180             185             190
Leu Val Leu Arg Thr His Gln Pro Ala Arg Tyr Ser Leu Thr Pro Glu
            195             200             205
Gly Leu Glu Leu Ala Gln Lys Leu Ala Glu Ser Glu Gly Leu Ser Leu
    210             215             220
Leu Asn Val Gly Ile Gly Pro Lys Glu Pro Pro Gly Glu Glu Thr Ala
225             230             235             240
Val Pro Gly Ala Ala Ser Ala Glu Leu Ala Ser Glu Ala Gly Val Gln
            245             250             255
Gln Gln Pro Leu Glu Leu Arg Pro Gly Glu Tyr Arg Val Leu Leu Cys
            260             265             270
Val Asp Ile Gly Glu Thr Arg Gly Gly Gly His Arg Pro Glu Leu Leu
            275             280             285
Arg Glu Leu Gln Arg Leu His Val Thr His Thr Val Arg Lys Leu His
    290             295             300
Val Gly Asp Phe Val Trp Val Ala Gln Glu Thr Asn Pro Arg Asp Pro
305             310             315             320
Ala Asn Pro Gly Glu Leu Val Leu Asp His Ile Val Glu Arg Lys Arg
            325             330             335
Leu Asp Asp Leu Cys Ser Ser Ile Ile Asp Gly Arg Phe Arg Glu Gln
            340             345             350
Lys Phe Arg Leu Lys Arg Cys Gly Leu Glu Arg Arg Val Tyr Leu Val
        355             360             365
Glu Glu His Gly Ser Val His Asn Leu Ser Leu Pro Glu Ser Thr Leu
    370             375             380
Leu Gln Ala Val Thr Asn Thr Gln Val Ile Asp Gly Phe Phe Val Lys
385             390             395             400
Arg Thr Ala Asp Ile Lys Glu Ser Ala Ala Tyr Leu Ala Leu Leu Thr
            405             410             415
Arg Gly Leu Gln Arg Leu Tyr Gln
            420
```

FIG. 1C Cont.

Hmus81(3)     SEQ ID NO:7

```
gatatctgca gaattcgccc ttgacatggc ggccccggtc cgcctgggcc ggaagcgccc 60
gctgcctgcc tgtcccaacc cgctcttcgt tcgctggctg accgagtggc gggacgaggc 120
gacccgcagc aggcgccgca cgcgcttcgt atttcagaag gcgctgcgtt ccctccgacg 180
gtacccactg ccgctgcgca gcgggaagga agctaagatc ctacagcact tcggagacgg 240
gctctgccgg atgctggacg agcggctgca gcggcaccga acatcgggcg gtgaccatgc 300
cccggactca ccatctggag agaacagtcc agccccgcag gggcgacttg cggaagtcca 360
ggactcttcc atgccagttc ctgcccagcc caaagcggga ggctctggca gctactggcc 420
agctcggcac tcaggagccc gagtgatact gctggtgctc taccgggagc acctgaatcc 480
taatggtcac cacttcttaa ccaaggagga gctgctgcag aggtgtgctc agaagtcccc 540
cagggtagcc cctgggagtg ctcgaccctg ccagccctc cgctccctcc ttcacaggaa 600
cctggtcctc aggacacacc agccagccag gtactcattg accccagagg gcctggagct 660
ggcccagaag ttggccgagt cagaaggcct gagcttgctg aatgtgggca tcgggcccaa 720
ggagccccct ggggaggaga cagcagtgcc aggagcagct tcagcagagc ttgccagtga 780
agcagggtc cagcagcagc cactggagct gaggcctgga gagtacaggg tgctgttgtg 840
tgtggacatt ggcgagaccc ggggggggcgg gcacaggccg gagctgctcc gagagctaca 900
gcggctgcac gtgacccaca cggtgcgcaa gctgcacgtt ggagattttg tgtgggtggc 960
ccaggagacc aatcctagag acccagcagc aaaccctggg gagttggtac tggatcacat 1020
tgtggagcgc aagcgactgg atgacctttg cagcagcatc atcgacggcc gcttccggga 1080
gcagaagttc cggctgaagc gctgtggtct ggagcgccgg gtatacctgg tggaagagca 1140
tggttccgtc cacaacctca gccttcctga gagcacactg ctgcaggctg tcaccaacac 1200
tcaggtcatt gatggctttt ttgtgaagcg cacagcagac attaaggagt cagccgccta 1260
cctggccctc ttgacgcggg gcctgcagag actctaccag ggccacaccc tacgcagccg 1320
cccctgggga accctggga accctgaatc aggggccatg acctctccaa accctctctg 1380
ctcactcctc accttcagtg acttcaacgc aggagccatc aagaataagg cccagtcggt 1440
gcgagaagtg tttgcccggc agctgatgca ggtgcgcgga gtgagtgggg agaaggcagc 1500
agccctggtg gatcgataca gcacccctgc cagcctcctg ccgcctatg atgcctgtgc 1560
cacccccaag gaacaagaga cactgctgag caccattaag tgtgggcgtc tacagaggaa 1620
tctggggcct gctctgagca ggaccttatc ccagctctac tgcagctacg gcccttgac 1680
ctgagtcaag ggcgaattc                                            1699
```

FIG. 1D

Hmus81(3)    SEQ ID NO:8

```
Met Ala Ala Pro Val Arg Leu Gly Arg Lys Arg Pro Leu Pro Ala Cys
1               5                   10                  15
Pro Asn Pro Leu Phe Val Arg Trp Leu Thr Glu Trp Arg Asp Glu Ala
            20                  25                  30
Thr Arg Ser Arg Arg Arg Thr Arg Phe Val Phe Gln Lys Ala Leu Arg
        35                  40                  45
Ser Leu Arg Arg Tyr Pro Leu Pro Leu Arg Ser Gly Lys Glu Ala Lys
    50                  55                  60
Ile Leu Gln His Phe Gly Asp Gly Leu Cys Arg Met Leu Asp Glu Arg
65                  70                  75                  80
Leu Gln Arg His Arg Thr Ser Gly Gly Asp His Ala Pro Asp Ser Pro
            85                  90                  95
Ser Gly Glu Asn Ser Pro Ala Pro Gln Gly Arg Leu Ala Glu Val Gln
            100                 105                 110
Asp Ser Ser Met Pro Val Pro Ala Gln Pro Lys Ala Gly Gly Ser Gly
            115                 120                 125
Ser Tyr Trp Pro Ala Arg His Ser Gly Ala Arg Val Ile Leu Leu Val
    130                 135                 140
Leu Tyr Arg Glu His Leu Asn Pro Asn Gly His His Phe Leu Thr Lys
145                 150                 155                 160
Glu Glu Leu Leu Gln Arg Cys Ala Gln Lys Ser Pro Arg Val Ala Pro
                165                 170                 175
Gly Ser Ala Arg Pro Trp Pro Ala Leu Arg Ser Leu Leu His Arg Asn
            180                 185                 190
Leu Val Leu Arg Thr His Gln Pro Ala Arg Tyr Ser Leu Thr Pro Glu
        195                 200                 205
Gly Leu Glu Leu Ala Gln Lys Leu Ala Glu Ser Glu Gly Leu Ser Leu
    210                 215                 220
Leu Asn Val Gly Ile Gly Pro Lys Glu Pro Pro Gly Glu Glu Thr Ala
225                 230                 235                 240
Val Pro Gly Ala Ala Ser Ala Glu Leu Ala Ser Glu Ala Gly Val Gln
            245                 250                 255
Gln Gln Pro Leu Glu Leu Arg Pro Gly Glu Tyr Arg Val Leu Leu Cys
            260                 265                 270
Val Asp Ile Gly Glu Thr Arg Gly Gly His Arg Pro Glu Leu Leu
            275                 280                 285
Arg Glu Leu Gln Arg Leu His Val Thr His Thr Val Arg Lys Leu His
    290                 295                 300
Val Gly Asp Phe Val Trp Val Ala Gln Glu Thr Asn Pro Arg Asp Pro
305                 310                 315                 320
Ala Ala Asn Pro Gly Glu Leu Val Leu Asp His Ile Val Glu Arg Lys
            325                 330                 335
Arg Leu Asp Asp Leu Cys Ser Ser Ile Ile Asp Gly Arg Phe Arg Glu
            340                 345                 350
Gln Lys Phe Arg Leu Lys Arg Cys Gly Leu Glu Arg Arg Val Tyr Leu
        355                 360                 365
Val Glu Glu His Gly Ser Val His Asn Leu Ser Leu Pro Glu Ser Thr
    370                 375                 380
Leu Leu Gln Ala Val Thr Asn Thr Gln Val Ile Asp Gly Phe Phe Val
385                 390                 395                 400
Lys Arg Thr Ala Asp Ile Lys Glu Ser Ala Ala Tyr Leu Ala Leu Leu
            405                 410                 415
Thr Arg Gly Leu Gln Arg Leu Tyr Gln Gly His Thr Leu Arg Ser Arg
            420                 425                 430
Pro Trp Gly Thr Pro Gly Asn Pro Glu Ser Gly Ala Met Thr Ser Pro
        435                 440                 445
Asn Pro Leu Cys Ser Leu Leu Thr Phe Ser Asp Phe Asn Ala Gly Ala
    450                 455                 460
Ile Lys Asn Lys Ala Gln Ser Val Arg Glu Val Phe Ala Arg Gln Leu
465                 470                 475                 480
Met Gln Val Arg Gly Val Ser Gly Glu Lys Ala Ala Ala Leu Val Asp
            485                 490                 495
```

FIG. 1D Cont.

```
Arg Tyr Ser Thr Pro Ala Ser Leu Leu Ala Ala Tyr Asp Ala Cys Ala
            500             505             510
Thr Pro Lys Glu Gln Glu Thr Leu Leu Ser Thr Ile Lys Cys Gly Arg
            515             520             525
Leu Gln Arg Asn Leu Gly Pro Ala Leu Ser Arg Thr Leu Ser Gln Leu
    530             535             540
Tyr Cys Ser Tyr Gly Pro Leu Thr
545             550
```

Formatted Alignments

| | | | |
|---|---|---|---|
| Heme1C | 1 | MALKKSSPSLDSGDSDSEELPTFAFLKKEPSSTKRRQPEREEKIVVVDISDCEASCPPAPELFSPPVPDIAETVTQTQPVRLLSSESE | 88 |
| Heme1B | 1 | MALKKSSPSLDSGDSDSEELPTFAFLKKEPSSTKRRQPEREEKIVVVDISDCEASCPPAPELFSPPVPDIAETVTQTQPVRLLSSESE | 88 |
| Heme1A | 1 | MALKKSSPSLDSGDSDSEELPTFAFLKKEPSSTKRRQPEREEKIVVVDISDCEASCPPAPELFSPPVPDIAETVTQTQPVRLLSSESE | 88 |
| Heme1C | 89 | DEEEFIPLAQRLTCKFLTHKQLSPEDSSPVKSVLDHQNNEGASCDWKKQPFPKIPEVPLHDTPERSAADNKDLILDPCCQLPAYLST | 176 |
| Heme1B | 89 | DEEEFIPLAQRLTCKFLTHKQLSPEDSSPVKSVLDHQNNEGASCDWKKQPFPKIPEVPLHDTPERSAADNKDLILDPCCQLPAYLST | 176 |
| Heme1A | 89 | DEEEFIPLAQRLTCKFLTHKQLSPEDSSPVKSVLDHQNNEGASCDWKK-PFPKIPEVPLHDTPERSAADNKDLILDPCCQLPAYLST | 175 |
| Heme1C | 177 | CPGQSSLAVTKTNSDILPPQKKTKPSQKVQGRGSHGCRQQRQAROKESTLRRQERKNAALVTRMKAQRPEECLKHIIVVLDPVLLQM | 264 |
| Heme1B | 177 | CPGQSSLAVTKTNSDILPPQKKTKPSQKVQGRGSHGCRQQRQAROKESTLRRQERKNAALVTRMKAQRPEECLKHIIVVLDPVLLQM | 264 |
| Heme1A | 176 | CPGQSSLAVTKTNSDILPPQKKTKPSQKVQGRGSHGCRQQRQAROKESTLRRQERKNAALVTRMKAQRPEECLKHIIVVLDPVLLQM | 263 |
| Heme1C | 265 | EGGGQLLGALQTMECRCVIEAQAVPCSVTWRRRAGPSE--------------GSLDSTMKGKETLQGFVTDIT | 323 |
| Heme1B | 265 | EGGGQLLGALQTMECRCVIEAQAVPCSVTWRRRAGPSEDREDWVEEPTVLVLLRAEAFVSMIDNGKQGSLDSTMKGKETLQGFVTDIT | 352 |
| Heme1A | 264 | EGGGQLLGALQTMECRCVIEAQAVPCSVTWRRRAGPSEDREDWVEEPTVLVLLRAEAFVSMIDNGKQGSLDSTMKGKETLQGFVTDIT | 351 |
| Heme1C | 324 | AKTAGKALSLVIVDQEKCFS----------------------AQNPPRRGKQGANKQTKKQQQRQPEASIGSMVSRVDAEEALVDLQLHTEAQAQIV | 398 |
| Heme1B | 353 | AKTAGKALSLVIVDQEKCFSLELLFPDFLPCTSAQNPPRRGKQGANKQTKKQQQRQPEASIGSMVSRVDAEEALVDLQLHTEAQAQIV | 427 |
| Heme1A | 352 | AKTAGKALSLVIVDQEKCFSLELLFPDFLPCTSAQNPPRRGKQGANKQTKKQQQRQPEASIGSMVSRVDAEEALVDLQLHTEAQAQIV | 439 |
| Heme1C | 399 | QSWKELADFTCAFTKAVAEAPFKKLRDETTFSFCLESDWAGGVKVDLAGRGLALVWRRQIQQLNRVSLEMASAVVNAYPSPQLLVQAY | 486 |
| Heme1B | 428 | QSWKELADFTCAFTKAVAEAPFKKLRDETTFSFCLESDWAGGVKVDLAGRGLALVWRRQIQQLNRVSLEMASAVVNAYPSPQLLVQAY | 515 |
| Heme1A | 440 | QSWKELADFTCAFTKAVAEAPFKKLRDETTFSFCLESDWAGGVKVDLAGRGLALVWRRQIQQLNRVSLEMASAVVNAYPSPQLLVQAY | 527 |
| Heme1C | 487 | QQCFSDKERQNLLADIQVRRGEGVTSTSRRIGPELSRCIYLQMTTLQPHLSLDSAD | 542 |
| Heme1B | 516 | QQCFSDKERQNLLADIQVRRGEGVTSTSRRIGPELSRRIYLQMTTLQPHLSLDSAD | 571 |
| Heme1A | 528 | QQCFSDKERQNLLADIQVRRGEGVTSTSRRIGPELSRRIYLQMTTLQPHLSLDSAD | 583 |

FIG. 6A

Heme1A DNA    SEQ ID NO: 9

```
acttccgggc cctgcgtggc agttgaaaga gtggcgggag aagttgcagg gaattatttg   60
atagcacata ctg atg gct cta aag aag tca tca ccc tca ctg gat tct     109
ggt gat agt gac tct gag gag ttg cca aca ttt gcc ttt ctg aag aag    157
gaa cca tct tca aca aag agg aga cag cct gaa agg gaa gag aag att    205
gta gtg gtt gac atc tca gat tgt gaa gcc tcc tgt cct cca gca cca    253
gag tta ttt tca cca cct gtc cca gac ata gct gaa act gtc aca caa    301
aca cag cca gtc agg ttg cta agc agt gaa agt gaa gat gaa gaa gaa    349
ttt att cct ctg gct caa agg ctt aca tgt aag ttt ctg acc cac aag    397
caa ctg agc cct gag gac tct agc tcc cca gtt aaa agt gtt ttg gat    445
cat caa aat aat gaa ggt gca tca tgt gac tgg aaa aag ccc ttt cca    493
aag atc cct gaa gtt ccc ctc cat gat acc cca gag agg agt gca gca    541
gat aac aag gac ctg atc tta gat cca tgc tgt cag ctt cca gcc tac    589
ctg tct acc tgc cct ggc cag agc agc agc ttg gca gta acc aaa aca    637
aat tct gac atc ctt cca ccc cag aag aaa acc aag ccg agt cag aag    685
gtc cag gga aga ggc tca cac gga tgc cgg cag cag aga caa gca agg    733
cag aag gaa agc acc ctg aga aga cag gaa aga aag aat gca gca ctg    781
gtt acc agg atg aaa gcc cag agg cca gag gaa tgc tta aaa cac atc    829
att gta gtg ctg gat cca gtg ctc tta cag atg gaa ggt ggg ggc cag    877
ctc cta gga gca ctg cag acc atg gag tgc cgc tgt gtg att gag gcg    925
cag gct gtg cct tgc agt gtc act tgg agg aga agg gct ggg ccg tct    973
gag gac aga gag gac tgg gtg gag gag cca aca gta ctg gtg ttg ctc   1021
cgg gca gag gca ttt gtg tcc atg atc gac aat gga aag cag gga agc   1069
ctg gac agc act atg aaa ggg aag gaa acg ctt cag ggc ttt gta act   1117
gac atc aca gca aag aca gca ggg aaa gct ctg tca ctg gtg att gtg   1165
gat cag gag aaa tgc ttc agc ctg gag ctg ctg ttc ttt gat ttc ctc   1213
ccc tgc acc agt gct cag aat cct cca aga aga ggg aaa cag gga gca   1261
aat aaa cag acc aag aag cag cag cag aga caa cca gag gcc agc ata   1309
ggg tcc atg gta tcc agg gta gac gct gaa gag gca ttg gtg gat ctg   1357
cag cta cac aca gaa gcc cag gct caa att gtg cag agc tgg aaa gag   1405
ctg gcc gac ttc aca tgc gca ttc aca aag gct gtg gct gag gcg ccc   1453
ttc aag aag ctc cga gat gaa act acc ttc tcc ttc tgt ctg gag agt   1501
gac tgg gct gga ggg gtg aag gtg gac ctt gct ggc agg gga ctc gca   1549
cta gtc tgg agg aga cag att cag cag ctg aac cga gtc agc ctg gaa   1597
atg gcc agt gca gtt gtg aat gcc tat ccc tcc cca cag ctc ctg gta   1645
cag gct tat cag cag tgt ttt tcg gat aaa gaa cgc cag aat ttg ctc   1693
gca gac ata cag gtg cgc cgt ggg gaa ggt gtg aca tcc act tct cgc   1741
cgc att gga cca gaa cta tcc agg cgt atc tac ctt cag atg acc act   1789
tta cag cca cat ctc tct tta gat agt gct gac tga ttctagccct        1835
cagggatgag gatgaaaagc tggaaacttc cacttcccca acctcagagc ctgactgtaa 1895
tgaagagact ggcagcacct cctggaacac aagcctaggt gaggcccagt ctttcttggg 1955
tcttattatt tgtgaaggtc tctctgcctg tcggctgggg cagagactga aatactgcca 2015
cctacctttg gcatttaatg ttcctctcct ggcaaaaatt cactgccaca gacaaaccac 2075
ccccactcct acccagccag ccctcaaaac acaaaggaac aaagacagtc cactcagaca 2135
cttatttaat aactgtagaa atccaaaaga attagcatca aatcttgaag tcgtgagtga 2195
agctgcgggt tggcttgact gggctcagcc actgagctgc ctcaaccggc caaggaacgg 2255
gattatgatg actatgcgga cttctatatt gtcttcatct cattgtgtgt attatgtatt 2315
tagtttcaat aaagcatttg taccaatg                                    2343
```

FIG. 6B

Heme1B DNA    SEQ ID NO: 11

```
acttccgggc cctgcgtggc agttgaaaga gtggcgggag aagttgcagg gaattatttg   60
atagcacata ctg atg gct cta aag aag tca tca ccc tca ctg gat tct    109
ggt gat agt gac tct gag gag ttg cca aca ttt gcc ttt ctg aag aag    157
gaa cca tct tca aca aag agg aga cag cct gaa agg gaa gag aag att    205
gta gtg gtt gac atc tca gat tgt gaa gcc tcc tgt cct cca gca cca    253
gag tta ttt tca cca cct gtc cca gac ata gct gaa act gtc aca caa    301
aca cag cca gtc agg ttg cta agc agt gaa agt gaa gat gaa gaa gaa    349
ttt att cct ctg gct caa agg ctt aca tgt aag ttt ctg acc cac aag    397
caa ctg agc cct gag gac tct agc tcc cca gtt aaa agt gtt ttg gat    445
cat caa aat aat gaa ggt gca tca tgt gac tgg aaa aag cag ccc ttt    493
cca aag atc cct gaa gtt ccc ctc cat gat acc cca gag agg agt gca    541
gca gat aac aag gac ctg atc tta gat cca tgc tgt cag ctt cca gcc    589
tac ctg tct acc tgc cct ggc cag agc agc agc ttg gca gta acc aaa    637
aca aat tct gac atc ctt cca ccc cag aag aaa acc aag ccg agt cag    685
aag gtc cag gga aga ggc tca cac gga tgc cgg cag cag aga caa gca    733
agg cag aag gaa agc acc ctg aga aga cag gaa aga aag aat gca gca    781
ctg gtt acc agg atg aaa gcc cag agg cca gag gaa tgc tta aaa cac    829
atc att gta gtg ctg gat cca gtg ctc tta cag atg gaa ggt ggg ggc    877
cag ctc cta gga gca ctg cag acc atg gag tgc cgc tgt gtg att gag    925
gcg cag gct gtg cct tgc agt gtc act tgg agg aga agg gct ggg ccg    973
tct gag gac aga gag gac tgg gtg gag gag cca aca gta ctg gtg ttg   1021
ctc cgg gca gag gca ttt gtg tcc atg atc gac aat gga aag cag gga   1069
agc ctg gac agc act atg aaa ggg aag gaa acg ctt cag ggc ttt gta   1117
act gac atc aca gca aag aca gca ggg aaa gct ctg tca ctg gtg att   1165
gtg gat cag gag aaa tgc ttc agt gct cag aat cct cca aga aga ggg   1213
aaa cag gga gca aat aaa cag acc aag aag cag cag cag aga caa cca   1261
gag gcc agc ata ggg tcc atg gta tcc agg gta gac gct gaa gag gca   1309
ttg gtg gat ctg cag cta cac aca gaa gcc cag gct caa att gtg cag   1357
agc tgg aaa gag ctg gcc gac ttc aca tgc gca ttc aca aag gct gtg   1405
gct gag gcg ccc ttc aag aag ctc cga gat gaa act acc ttc tcc ttc   1453
tgt ctg gag agt gac tgg gct gga ggg gtg aag gtg gac ctt gct ggc   1501
agg gga ctc gca cta gtc tgg agg aga cag att cag cag ctg aac cga   1549
gtc agc ctg gaa atg gcc agt gca gtt gtg aat gcc tat ccc tcc cca   1597
cag ctc ctg gta cag gct tat cag cag tgt ttt tcg gat aaa gaa cgc   1645
cag aat ttg ctc gca gac ata cag gtg cgc cgt ggg gaa ggt gtg aca   1693
tcc act tct cgc cgc att gga cca gaa cta tcc agg cgt atc tac ctt   1741
cag atg acc act tta cag cca cat ctc tct tta gat agt gct gac      1786
tgattctagc cctcaggggat gaggatgaaa agctggaaac ttccacttcc ccaacctcag  1846
agcctgactg taatgaagag actggcagca cctcctggaa cacaagccta ggtgaggccc  1906
agtctttctt gggtcttatt atttgtgaag gtctctctgc ctgtcggctg gggcagagac  1966
tgaaatactg ccacctacct ttggcattta atgttcctct cctggcaaaa attcactgcc  2026
acagacaaac caccccccact cctacccagc cagccctcaa aacacaaagg aacaaagaca  2086
gtccactcag acacttattt aataactgta gaaatccaaa agaattagca tcaaatcttg  2146
aagtcgtgag tgaagctgcg ggttggcttg actgggctca gccactgagc tgcctcaacc  2206
ggccaaggaa cgggattatg atgactatgc ggacttctat attgtcttca tctcattgtg  2266
tgtattatgt atttagtttc aataaagcat ttgtaccaat g                     2307
```

FIG. 6C

HemelC DNA    SEQ ID NO: 13

```
cttccgggcc ctgcgtggca gttgaaagag tggcgggaga agttgcaggg aattatttga   60
tagcacatac tg atg gct cta aag aag tca tca ccc tca ctg gat tct ggt  111
gat agt gac tct gag gag ttg cca aca ttt gcc ttt ctg aag aag gaa    159
cca tct tca aca aag agg aga cag cct gaa agg gaa gag aag att gta    207
gtg gtt gac atc tca gat tgt gaa gcc tcc tgt cct cca gca cca gag    255
tta ttt tca cca cct gtc cca gac ata gct gaa act gtc aca caa aca    303
cag cca gtc agg ttg cta agc agt gaa agt gaa gat gaa gaa gaa ttt    351
att cct ctg gct caa agg ctt aca tgt aag ttt ctg acc cac aag caa    399
ctg agc cct gag gac tct agc tcc cca gtt aaa agt gtt tgt gat cat    447
caa aat aat gaa ggt gca tca tgt gac tgg aaa aag cag ccc ttt cca    495
aag atc cct gaa gtt ccc ctc cat gat acc cca gag agg agt gca gca    543
gat aac aag gac ctg atc tta gat cca tgc tgt cag ctt cca gcc tac    591
ctg tct acc tgc cct ggc cag agc agc agc ttg gca gta acc aaa aca    639
aat tct gac atc ctt cca ccc cag aag aaa acc aag ccg agt cag aag    687
gtc cag gga aga ggc tca cac gga tgc cgg cag cag aga caa gca agg    735
cag aag gaa agc acc ctg aga aga cag gaa aga aag aat gca gca ctg    783
gtt acc agg atg aaa gcc cag agg cca gag gaa tgc tta aaa cac atc    831
att gta gtg ctg gat cca gtg ctc tta cag atg gaa ggt ggg ggc cag    879
ctc cta gga gca ctg cag acc atg gag tgc gcc tgt gtg att gag gcg    927
cag gct gtg cct tgc agt gtc act tgg agg aga agg gct ggg ccg tct    975
gag gga agc ctg gac agc act atg aaa ggg aag gaa acg ctt cag ggc   1023
ttt gta act gac atc aca gca aag aca gca ggg aaa gct ctg tca ctg   1071
gtg att gtg gat cag gag aaa tgc ttc agt gct cag aat cct cca aga   1119
aga ggg aaa cag gga gca aat aaa cag acc aag aag cag cag cag aga   1167
caa cca gag gcc agc ata ggg tcc atg gta tcc agg gta gac gct gaa   1215
gag gca ttg gtg gat ctg cag cta cac aca gaa gcc cag gct caa att   1263
gtg cag agc tgg aaa gag ctg gcc gac ttc aca tgc gca ttc aca aag   1311
gct gtg gct gag gcg ccc ttc aag aag ctc cga gat gaa act acc ttc   1359
tcc ttc tgt ctg gag agt gac tgg gct gga ggg gtg aag gtg gac ctt   1407
gct ggc agg gga ctc gca cta gtc tgg agg aga cag att cag cag ctg   1455
aac cga gtc agc ctg gaa atg gcc agt gca gtt gtg aat gcc tat ccc   1503
tcc cca cag ctc ctg gta cag gct tat cag cag tgt ttt tcg gat aaa   1551
gaa cgc cag aat ttg ctc gca gac ata cag gtg cgc cgt ggg gaa ggt   1599
gtg aca tcc act tct cgc cgc att gga cca gaa cta tcc agg tgt atc   1647
tac ctt cag atg acc act tta cag cca cat ctc tct tta gat agt gct   1695
gac tgattctagc cctcagggat gaggatgaaa agctggaaac ttccacttcc        1748
ccaacctcag agcctgactg taatgaagag actggcagca cctcctggaa cacaagccta 1808
ggtgaggccc agtctttctt gggtcttatt atttgtgaag gtctctctgc ctgtcggctg 1868
gggcagagac tgaaatactg ccacctacct ttggcattta atgttcctct cctggcaaaa 1928
attcactgcc acagacaaac cacccccact cctacccagc cagccctcaa aacacaaagg 1988
aacaaagaca gtccactcag acacttattt aataactgta gaaatccaaa agaattagca 2048
tcaaatcttg aagtcgtgag tgaagctgcg ggttggcttg actgggctca gccactgagc 2108
tgcctcaacc ggccaaggaa cgggattatg atgactatgc ggacttctat attgtcttca 2168
tctcattgtg tgtattatgt atttagtttc aataaagcat tgtaccaat g           2219
```

Heme2A DNA    SEQ ID NO: 15

```
atggcgcggg ttggacccgg gagggcgggg gtctcttgcc agggccgggg ccggggacgg   60
ggcgggagcg gtcagcggcg acctccaacc tgggagatct cagactccga cgctgaggac  120
tccgccggct cggaggccgc cgcgagagcc cgggacccag cgggtgagcg cagggcggct  180
gccgaggcgt tgcggctgct gcggccggag caggtgctga agcgcctcgc ggtgtgcgtg  240
gacacagcca tcctggaaga cgccggtgcc gacgtcctga tggaggccct ggaggccctg  300
ggctgcgagt gccgcatcga gccccagcgc ccggcccgca gcctgcggtg gacccgagcg  360
agtcccgacc cctgccccg cagcctgcct cctgaagtgt gggctgcagg tgaacaggaa  420
ttgctgctgc tgctggagcc cgaggagttt ctgcagggcg tgccacact gacccagatc  480
tctggcccaa cccactgggt gccctgatc tccccgaga ccaccgcccg gccccacctg  540
gctgtcatcg ggctggatgc ctacctgtgg taccgctcac tctcatgccc acagcagggc  600
tggctgggac gggggttcag gggaggtggg ctctggcaga ggccaagctc ggcagggca  660
ggccccatgg ggagcgggga ggaatggtca cctctgctca ggtctcgcca gcacgtttcc  720
cggggggacac agcagccaga gagcccgaag gtggccggtg ccgaggtggc cgtcagctgg  780
ccggaggtgg aagaggtgag ggcctgtctg agctgggccc tggtactcct gcagctctgg  840
gcaaacctgg acgtgctact ggtggcctct tggcaggagc tgagtcggca cgtgtgcgcc  900
gttaccaagg ctctcgccca gtatcccctc aagtgcgtga tgccaaggct gaaggggggc  960
aggatcacct caaggcagta ccgggaatcc caggccttct ccttctgcac agcagggcgc 1020
tgggcagccg gcgagccagt ggcaagagac ggcgcagggc tgcaggcggc ctggcggagg 1080
cagatcaggc agttcagtcg ggtcagccca gccgtggctg atgcagttgt cacagccttc 1140
ccctccccc gccttctgca gcaggcgctg gaggcctgca gcacggagcg ggagcgcatg 1200
ggcctcctgg ccgaccttcc tgtgccgccc agtgaaggcg ggcgtccccg cagggtgggg 1260
cctgacctct cccgccgcat ctgcctcttc ctgaccacag ccaaccctga tctcctgctg 1320
gacctgggct cctga                                                  1335
```

FIG. 7B

Heme2B DNA    SEQ ID NO: 17

```
atg gcg cgg gtt gga ccc ggg agg gcg ggg gtc tct tgc cag ggc cgg      48
ggc cgg gga cgg ggc ggg agc ggt cag cgg cga cct cca acc tgg gag      96
atc tca gac tcc gac gct gag gac tcc gcc ggc tcg gag gcc gcc gcg     144
aga gcc cgg gac cca gcg ggt gag cgc agg gcg gct gcc gag gcg ttg     192
cgg ctg ctg cgg ccg gag cag gtg ctg aag cgc ctc gcg gta ggg cgc     240
tcg cga ggg tgg aag gaa gca gtg acc gcg ctc ctc tcc ccc ggt ccc     288
agc cat cct gga aga cgc cgg tgc cga cgt cct gat gga ggc cct gga     336
ggc cct ggg ctg cga gtg ccg cat cga gcc cca gcg ccc ggc ccg cag     384
cct gcg gtg gac ccg agc gag tcc cga ccc ctg ccc ccg cag cgt gag     432
tgg tcg cgg gtt ccc gag ggc cag ccg cga gtt ggc tgt ttt gct tcc     480
atg att tca gcc ctg gag ctg tcc ctg agg cag ctg ccc tgg gcc gtg     528
cgc gtc tcg cgg atg ggt aaa gca agg atg gag aac ggg aag tgg agg     576
tgc cca agc cgt tct gct ggt ata gag ccg agc tgg ctg gag aag ctg     624
cct cct gaa gtg tgg gct gca ggt gaa cag gaa ttg ctg ctg ctg ctg     672
gag ccc gag gag ttt ctg cag ggc gtc gcc aca ctg acc cag atc tct     720
ggc cca acc cac tgg gtg ccc tgg atc tcc ccc gag acc acc gcc cgg     768
ccc cac ctg gct gtc atc ggg ctg gat gcc tac ctg tgg tac cgc tca     816
ctc tca tgc cca cag cag ggc tgg ctg gga cgg ggg ttc agg gga ggt     864
ggg ctc tgg cag agg cca agc tcg ggc agg gca ggc ccc atg ggg agc     912
ggg gag gaa tgg tca cct ctg ctc agg tct cgc cag cac gtt tcc cgg     960
ggg aca cag cag cca gag agc ccg aag gtg gcc ggt gcc gag gtg gcc    1008
gtc agc tgg ccg gag gtg gaa gag gtg agg gcc tgt ctg agc tgg gcc    1056
ctg gta ctc ctg cag ctc tgg gca aac ctg gac gtg cta ctg gtg gcc    1104
tct tgg cag gag ctg agt cgg cac gtg tgc gcc gtt acc aag gct ctc    1152
gcc cag tat ccc ctc aag tgc gtg atg cca agg ctg aag ggg ggc agg    1200
atc acc tca agg cag tac cgg gaa tcc cag gcc ttc tcc ttc tgc aca    1248
gca ggg cgc tgg gca gcc ggc gag cca gtg gca aga gac ggc gca ggg    1296
ctg cag gcg gcc tgg cgg agg cag atc agg cag ttc agt cgg gtc agc    1344
cca gcc gtg gct gat gca gtt gtc aca gcc ttc ccc tcc ccc cgc ctt    1392
ctg cag cag gcg ctg gag gcc tgc agc acg gag cgg gag cgc atg ggc    1440
ctc ctg gcc gac ctt cct gtg ccg ccc agt gaa ggc ggg cgt ccc cgc    1488
agg gtg ggg cct gac ctc tcc cgc cgc atc tgc ctc ttc ctg acc aca    1536
gcc aac cct gat ctc ctg ctg gac ctg ggc tcc tga                    1572
```

FIG. 7C

Heme2C DNA    SEQ ID NO: 19

```
ctcagactcc gacgctgagg actccgccgg ctcggaggcc gccgcgagag cccgggaccc   60
agcgggtgag cgcagggcgg ctgccgaggc gttgcggctg ctgcggccgg agcaggtcct  120
gaagcgcctc gcggtgtgcg tggacacagc catcctggaa gacgccggtg ccgacgtcct  180
gatggaggcc ctggaggccc tgggctgcga gtgccgcatc gagccccagc gcccggcccg  240
cagcctgcgg tggacccgag cgagtcccga ccctgcccc cgcagcctgc ctcctgaagt  300
gtgggctgca ggtgaacagg aattgctgct gctgctggag cccgaggagt ttctgcaggg  360
cgtcgccaca ctgacccaga tctctggccc aacccactgg gtgccctgga tctcccccga  420
gaccaccgcc cggccccacc tggctgtcat cgggctggat gcctacctgt ggtaccgctc  480
actctcatgc ccacagcagg gctggctggg acggggttc aggggaggtg ggcacacttc  540
tggggttgct gtggcacagc tgatcccact ctccaggtg ggctctggca gaggccaagc  600
tcgggcaggg caggccccat ggggagcggg gaggaatggt caccttgct caggtctcgc  660
cagcacgttt cccggggac acagcagcca gagagcccga aggtggccgg tgccgaggtg  720
gccgtcagct ggccggaggt ggaagaggcc ctggtactcc tgcagctctg ggcaaacctg  780
gacgtgctac tggtggcctc ttggccagga gctgagtcgg cacgtgtgcg ccgttaccaa  840
ggctctcgcc cagtatcccc tcaagcagta ccgggaatcc caggccttct ccttctgcac  900
agcagggcgc tgggcagccg gcgagccagt ggcaagagac ggcgcagggc tgcaggcggc  960
ctggcggagg cagatcaggc agttcagtcg ggtcagccca gccgtggctg atgcagttgt 1020
cacagccttc ccctccccc gccttctgca gcaggcgctg gaggcctgca gcacggagcg 1080
ggagcgcatg ggcctcctgg ccgaccttcc tgtgccgccc agtgaaggcg ggcgtccccg 1140
cagggtgggg cctgacctct cccgccgcat ctgcctcttc ctgaccacag ccaaccctga 1200
tctcctgctg gacctggct cctgaccaca cgtgggacca ccaggacagc atgcagcctt 1260
ggggacagac cagacaccct gggcggtggg ggaggacccc cagccacatg tggaccctca 1320
gcctgggtgg gttctctggc tgagcaggtc tgacctcagg ggagggtgg tggttgcag 1380
gggaagtttt aggtagctgg aggagaaga ggggcttctg gctggcagat ggctggcggt 1440
tcctgtgctg agtcctgaac acgtaggccc caggggaggc ctcagcagca gggctgtgcc 1500
ccccaacac acacacacac tggcaggga ccagaaggca gctccaggc ccccactgcc 1560
acctggaggc ttggggtgtg gcaccctcag ccagaagcag tagggactc caaggatgt 1620
ggaggggcag tgaggcctgg gagaaggccc aggctgctcg caagcccggc ctctgcacgg 1680
atacgtttca gctcacgcca tgtgggtgtt agacatcaac tctacattta ttgcagtcct 1740
ttaagtctat gacggcgggg cagccgctga cagcatgcag agcaagttag gaaaaaccga 1800
ggccctgtgg gaacagcaac gcgggctcca gccaggctct cgtcctcgca gcctcccaca 1860
agacctgggg ctcagggcag ccgcttcccc acccagcaca gcagcagagg ggccctagag 1920
cccccacaga aaggactgtc ccagcctcgg gagcaagaga tggctccctc cggacgggcc 1980
tcatccaact ccgccctgga gtgtggctgg aaggaaggga cagagaaaga agggacagag 2040
gaaaggggct gtcccagccc aagaaggcag ttccactggg aagtcagtca ggtccggcgg 2100
cagcgcttcc tctggcaggg ccgaggctcg cgactgctgg ggtgggcgga ggtcgctgcc 2160
tggggatcgg acactggagc cttcggcgg ctgcaactca tgctcaggac ccagcccagc 2220
ttgttgtgta gcacctgctt gaggcccggc ggcagcggca gaccctccag cgtgtctccc 2280
gagtctggcc gcagctggcg caggcggtgg cagcacaggt actggaggga agtggcgctg 2340
gcacaggagc gggtgacctt catgctgctc cgggccgccg tggagcacac catcgggtag 2400
aatctcttgt tctgcagctt ggtggctgcc acacctggaa gggagggcc cagcctgaac 2460
cccaggcagg aaggggcca gctactgggc gcagcccctc agacctcacg ctacagtcac 2520
ccgggtgggc agctggcaca gctgaggcaa ggcagggtgc acgcgctggc cctgccactc 2580
cagcctggcc tcactgtccc acccctggg acctgggc ctcaggcttc tggaggaac 2640
cctttcagaa aacctcagtg tcccctgggc tggggcgggg tggctgcctc cctcgggtg 2700
acagctgaga ggagctcaag tcctgtgacg gcctcaccta tacacttcct gttcttgaaa 2760
aaggtgagtg tgccgtgcca ggtgtccagg tgcacgccaa tgatggagcc ctggccgaac 2820
cgcgatgaga agctggtctt gtcgcccttg tggtggagga ggctgggggg cagccagggt 2880
cgcagtgagc ccgggagctc caggctcggc ccgccccac cctgggcctc acgcaccgt 2940
gtaggagagg ccccagctgt cctcatccct gcccagcagg ctgcagaacg tgtggcggta 3000
```

FIG. 7D

```
tttgtccagg tccacatccg acgtcccgat gcccaccatc taggaacagg ggccaggcag 3060
agggcgcggg gctgggctgc cggagccagg ttccccagaa gcaccctggg ccgaagcaac 3120
ttaccatgtc ggtgccgtag acgggagagg tcatcttgat ctcccagaag tgctggccct 3180
cccccagctc cttggtgccc cggatggccg ctgtgccgca gctgtactcc atgtggaagc 3240
tgaccttacg gttgtcacag ctcagcaggg tggctgatga cttatttaag tcatcccaga 3300
cccagtcgaa atctgcaaga gaggcccagg ctggggcagc cctgagagct ccatgggct 3360
ctgccctgcc caccccagg cccgcccgca gtgcagtccc agcaggggct gggccccacg 3420
ctcacactcg tcttcctctc cgcagcggca gtccctgccc cggtgggccg agtgcaggct 3480
gctacagaag gaggcctcgc tctgcccagc acagtcacag aaggactcgc cggtcacggg 3540
caccgcactg gggatggatg gcggcagcgt ggagtactcg gggtcggagt ccgagtcgct 3600
gtgctgggag agaagggccg gctgttacta cctgttgccc gctctctacc ctctcaccct 3660
tgccctctgt ccctgtccca ccctgtccct gacccaccca ggaaaggatg ggggtccagg 3720
cctccaggga cttcacagta ccccgagcgc acagcccagg ctccctccca acgggctccg 3780
gctctgcccc attctgcatg accaggaggg ccctggaggc ccagccacag agcagtagcc 3840
aaggctgcct ggcctccaag tggtttctag acggtggata agccccaggt ccaccccacc 3900
tgcccagagc tgagatggtg tggacacctt ccctgctagg ccagccctgc aggggccccc 3960
aggcaaggcc accacccca caccaggccc agctgcagcc acccggcctc agggcagtcc 4020
ccaccacact gtgcccaac gaccttcctg ttacctgagc agacctggct caccacaggg 4080
tcctactgcc cagtgcccac tacaggcccc gcccctcctg gtgcaggttt cagctgtcac 4140
ctccctgagg cttctccagc cccttcaccc ctgttccatt tttcttcttt tgcttcactg 4200
aagttctcct tggtcctgat tcttggcctc ctcccaccag aacgtgagct ccttgtggga 4260
ggcagtgccc ctcccagcct cctccctgtc acagactgtg tgggggccac ccagggctg 4320
aatggaccag ggggtcagca gggagagtgc taagtggtgg cggggggcct gtggcagagg 4380
ccttgtgaca gtgagggttg agggctggtc cagagagatg atgtgatccc caggagaagc 4440
cacaggggac catgacatgg gcgccaccag cttccaggtg aacgtggacc tatcgaaagc 4500
cagcttcagg gcaggacact gtcctttctg gaggggatgg ccccacccca cagacaaggc 4560
aggcccagac aactctaccc cactgcctag aagtgcgggt ccccagagcc agggtagacc 4620
ccctgagtca ggagcccggg cacagaactg agcacctgca ctgcaggccc agggccgggt 4680
tccctggaga aggagaaaga ctgaagccac tgcctacctc ctgcccacaa cagactgcag 4740
gcccatttgg tgacacagga caagcagcac atgtgtcgaa cactccgag cccgcaggca 4800
cgcctgcatc ccacagccac gagcctgtga ggctcaggca tgtgacctgc aggagctgga 4860
ggcggcggg aaggcaggtg ggggcctctc cctggctgga gcagggagct ccaggagacc 4920
tcaggacggc ccccacccgg tgggtaagga ccctgtttcc caatttgccc ccaaggccta 4980
atggacccac cgggcttagg gagtcctcac tcagaggaga ggagcccacc cctcccagga 5040
cacctggctg agccggaaca gcagcgcagg ggagctgtga cagcagagag cagcaccagg 5100
tcacacaagc agccgccccg gaaggacacg gccatggtg acagaggaca agcagcatgc 5160
gtgtgtcaga cactggcctg gcctgtggac acgccgcgt cccacagcca tgaccctgcg 5220
aggccaggag agactgctcc agggcacatg acctgtggta gctggaagtg gggcagggag 5280
gcgcagccac actcctgctc tggtccgagg gagatctcag gaaaccgact gggaaatcac 5340
ccccacagg gaccccacc cctcccagcc tcactgcgcc cgtcaggcca ggcagctgcc 5400
ctcagggtct gccaaggtgg gggtcagggg ccatgggggc aggtagctct gcctgcaaag 5460
cccacaagca tgtcagatca cctgggctgc agacagacaa acacctgagc tgttctgaat 5520
accttcaggt tcctggcctc cctgagcaag tgcagaaatt tttaccttca aggatcaggg 5580
tttttctgtt tgtttgtttt ttaacacaca tatatgtg                       5618
```

FIG. 7D CONT.

Heme2 EST CLONE    SEQ ID NO: 21

```
tct cgc cag cac gtt tcc cgg ggg aca cag cag cca gag agc cag aag    48
gtg gcc ggt gcc gag gtg gcc gtc agc tgg ccg gag gtg gaa gag gcc    96
ctg gta ctc ctg cag ctc tgg gca aac ctg gac gtg cta ctg gtg gcc   144
tct tgg cag gag ctg agt cgg cac gtg tgc gcc gtt acc aag gct ctc   192
gcc cag tat ccc atc aag cag tac cgg gaa tcc cag gcc ttc tcc ttc   240
tgc aca gca ggg cgc tgg gca gcc ggc gag cca gtg gca aga gac ggc   288
gca ggg ctg cag gcg gcc tgg cgg agg cag atc agg cag ttc agt cgg   336
gtc agc cca gcc gtg gct gat gca gtt gtc aca gcc ttc ccc tcc ccc   384
cgc ctt ctg cag cag gcg ctg gag gcc tgc agc acg gag cgg gag cgc   432
atg ggc ctc ctg gcc gac ctt cct gtg ccg ccc agt gaa ggc ggg cgt   480
ccc cgc agg gtg ggg cct gac gtc tcc cgc cgc atc tgc ctc ttc ctg   528
acc aca gcc aac cct gat ctc ctg ctg gac ctg ggc tcc tga           570
```

FIG. 7E

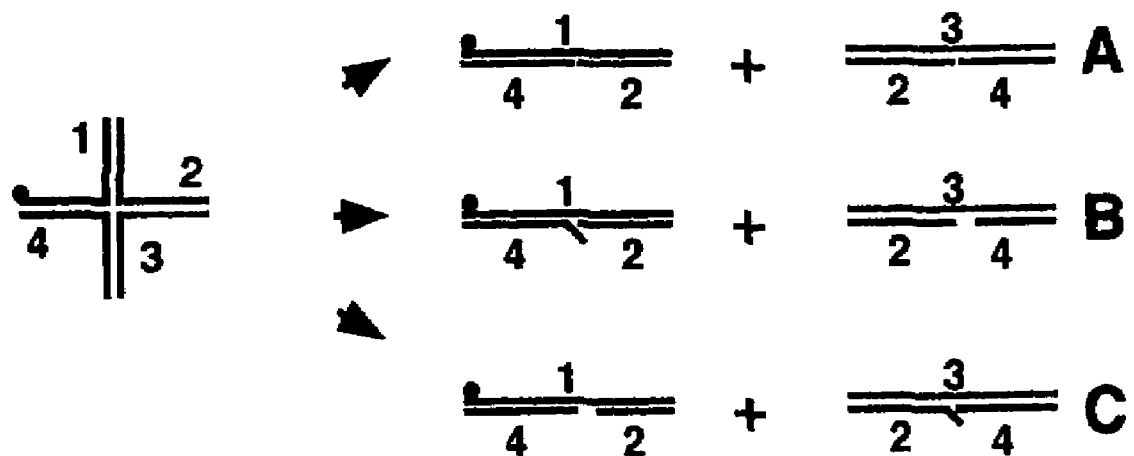
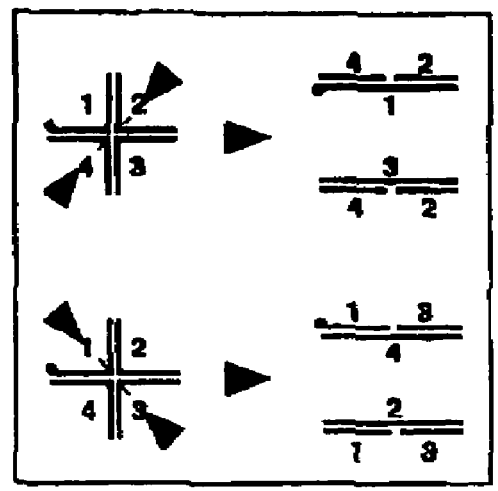
FIG. 9

Mouse Mus81(1)  SEQ ID NO 36

```
gaattcgccc ttgagactct gaaggagcca gtctagttct t atg gcg gag ccg gtc    56
cgc ctg ggc cgg aag cgt ccg ctg ccc gtt tgc ccc aac ccg ctc ttc    104
gtt cgt tgg ctg acc gag tgg cgg gac gag gca gcc agc agg ggg cgc    152
cac acg cgt ttc gtg ttt caa aag gca ttg cgc tcc ctc caa cgg tac    200
ccg cta cca ttg cgc agc ggg aag gaa gcc aag ata ctc cag cac ttc    248
gga gac agg ctc tgc cgc atg ctg gac gaa aag ctg aag cag cac cta    296
gca tca ggc ggt gac cat gcc ccc agc tca cca tct gga aag aag gga    344
gcc agc aaa ggg cca cct gag caa gtc cag gac tct tcc atg cca gtt    392
ccc acc cag cct caa gca gga agc acc agt gtt ggc tat tgg cca gct    440
cag aac tca ggt gct cga gag atc ctg ctg caa ctc tac agg gag cac    488
ctg aat tct gat ggc cac agc ttc cta acc aaa gag gag ctg ctg cag    536
aag tgt gcc cag aag acc ccc agg gta gtg cct gga agt tcg aaa ccc    584
tgg cct gcc ctc cgg agc ctc ctc cat agg aac ctc atc ctt gga acg    632
cat cgg cca gcc agg tat gca ctc aca cca gag ggt ctg gag ctg gct    680
cag aag ctg gcc gag gcg gaa ggc ctg agc act cgg cac gct ggc ttt    728
agg cca gag gaa cat cac gga gag gac tca gca gtt cca gaa gcc ttg    776
tca gaa cct ggc acc acc gag ggg gcc gtc cag cag aga cca ctg gag    824
cta agg cct agc gag tac aga gtg ctg ttg tgt gtg gac att ggc gaa    872
acc aga ggg gca gga cac agg cta gaa atg ctc cga gag tta caa agg    920
ctg cgt gtg ccc cac acc gta cgc aag cta cac gtt gga gac ttt gtg    968
tgg gtg gca cag gag acc agg ccc aga gac cca gaa aga cct ggg gag   1016
ctg gtc ctg gac cac att gtg gaa cgc aag cgg cta gat gac cta tgc   1064
agc agc atc att gac ggc cgc ttt cgg gag cag aag ttc cgc ctg aag   1112
cgc tgt ggc ctg ggg cac cgg gta tac tta gtg gaa gaa cat ggg tct   1160
gtc cac aac ctt agc ctt ccc gag agc acc ttg ctg cag gct gtc aca   1208
aac acc cag gtc att gat ggc ttt ttt gtg aag cga acc atg gat att   1256
```

FIG. 10A

```
aag gag tcg gtt ggc tac ctg gcg ctt ttg aca aag ggc ctg gaa aga    1304
ctg tac cag ggc cac acc cta cgc agc cgc cct tgg ggg gcc cca ggg    1352
gct gct gaa tca gaa gca aag cct tcc aca aac cct ctc tgc tca ctc    1400
ctc acc ttc agt gac ttc aat gca gaa gct gtc aag aac aag gcc cag    1448
tct gtg cga gaa gta ttt gcc cgg cag ctg atg cag gtg cgt gga ctg    1496
agt ggg gag aag gca gca gcc gtg gtg gat cga tac agc acc cct gcc    1544
agt ctc ctg gct gct tat gat gcc tgt gcc acc gcg aag gag cag gag    1592
atg ctc ttg agc acc atc aag tgt ggg cgt ctg cag agg aat ctg gga    1640
ccc gct ctg agc agg acc ctg tac cag ttg tac tgc agc cac agc cct    1688
ctg agc tgagctgtac caggagacgc tcgctcccca gcacccatct tcatctctac    1744
caaggctggc tagccttttta gcaagggcga attctgcaga tatc                  1788
```

Mouse Mus81(1)    SEQ ID NO 37

```
Met Ala Glu Pro Val Arg Leu Gly Arg Lys Arg Pro Leu Pro Val Cys
 1               5                  10                  15
Pro Asn Pro Leu Phe Val Arg Trp Leu Thr Glu Trp Arg Asp Glu Ala
                20                  25                  30
Ala Ser Arg Gly Arg His Thr Arg Phe Val Phe Gln Lys Ala Leu Arg
            35                  40                  45
Ser Leu Gln Arg Tyr Pro Leu Pro Leu Arg Ser Gly Lys Glu Ala Lys
        50                  55                  60
Ile Leu Gln His Phe Gly Asp Arg Leu Cys Arg Met Leu Asp Glu Lys
65                  70                  75                  80
Leu Lys Gln His Leu Ala Ser Gly Gly Asp His Ala Pro Ser Ser Pro
                85                  90                  95
Ser Gly Lys Lys Gly Ala Ser Lys Gly Pro Pro Glu Gln Val Gln Asp
            100                 105                 110
Ser Ser Met Pro Val Pro Thr Gln Pro Gln Ala Gly Ser Thr Ser Val
        115                 120                 125
Gly Tyr Trp Pro Ala Gln Asn Ser Gly Ala Arg Glu Ile Leu Leu Gln
    130                 135                 140
Leu Tyr Arg Glu His Leu Asn Ser Asp Gly His Ser Phe Leu Thr Lys
145                 150                 155                 160
Glu Glu Leu Leu Gln Lys Cys Ala Gln Lys Thr Pro Arg Val Val Pro
                165                 170                 175
Gly Ser Ser Lys Pro Trp Pro Ala Leu Arg Ser Leu Leu His Arg Asn
            180                 185                 190
Leu Ile Leu Gly Thr His Arg Pro Ala Arg Tyr Ala Leu Thr Pro Glu
        195                 200                 205
Gly Leu Glu Leu Ala Gln Lys Leu Ala Glu Ala Glu Gly Leu Ser Thr
    210                 215                 220
Arg His Ala Gly Phe Arg Pro Glu Glu His His Gly Glu Asp Ser Ala
225                 230                 235                 240
Val Pro Glu Ala Leu Ser Glu Pro Gly Thr Thr Glu Gly Ala Val Gln
                245                 250                 255
```

FIG. 10A CONT.

```
Gln Arg Pro Leu Glu Leu Arg Pro Ser Glu Tyr Arg Val Leu Leu Cys
        260                 265                 270
Val Asp Ile Gly Glu Thr Arg Gly Ala Gly His Arg Leu Glu Met Leu
        275                 280                 285
Arg Glu Leu Gln Arg Leu Arg Val Pro His Thr Val Arg Lys Leu His
    290                 295                 300
Val Gly Asp Phe Val Trp Val Ala Gln Glu Thr Arg Pro Arg Asp Pro
305                 310                 315                 320
Glu Arg Pro Gly Glu Leu Val Leu Asp His Ile Val Glu Arg Lys Arg
                325                 330                 335
Leu Asp Asp Leu Cys Ser Ser Ile Ile Asp Gly Arg Phe Arg Glu Gln
            340                 345                 350
Lys Phe Arg Leu Lys Arg Cys Gly Leu Gly His Arg Val Tyr Leu Val
        355                 360                 365
Glu Glu His Gly Ser Val His Asn Leu Ser Leu Pro Glu Ser Thr Leu
    370                 375                 380
Leu Gln Ala Val Thr Asn Thr Gln Val Ile Asp Gly Phe Phe Val Lys
385                 390                 395                 400
Arg Thr Met Asp Ile Lys Glu Ser Val Gly Tyr Leu Ala Leu Leu Thr
                405                 410                 415
Lys Gly Leu Glu Arg Leu Tyr Gln Gly His Thr Leu Arg Ser Arg Pro
            420                 425                 430
Trp Gly Ala Pro Gly Ala Ala Glu Ser Glu Ala Lys Pro Ser Thr Asn
        435                 440                 445
Pro Leu Cys Ser Leu Leu Thr Phe Ser Asp Phe Asn Ala Glu Ala Val
    450                 455                 460
Lys Asn Lys Ala Gln Ser Val Arg Glu Val Phe Ala Arg Gln Leu Met
465                 470                 475                 480
Gln Val Arg Gly Leu Ser Gly Glu Lys Ala Ala Ala Val Val Asp Arg
                485                 490                 495
Tyr Ser Thr Pro Ala Ser Leu Leu Ala Ala Tyr Asp Ala Cys Ala Thr
            500                 505                 510
Ala Lys Glu Gln Glu Met Leu Leu Ser Thr Ile Lys Cys Gly Arg Leu
        515                 520                 525
Gln Arg Asn Leu Gly Pro Ala Leu Ser Arg Thr Leu Tyr Gln Leu Tyr
    530                 535                 540
Cys Ser His Ser Pro Leu Ser
545                 550
```

FIG. 10A CONT.

Mouse Mus81(2)  SEQ ID NO 38

```
gatatctgca gaattcgccc ttgagactct gaaggagcca gtctagttct t atg gcg      57
gag ccg gtc cgc ctg ggc cgg aag cgt ccg ctg ccc gtt tgc ccc aac      105
ccg ctc ttc gtt cgt tgg ctg acc gag tgg cgg gac gag gca gcc agc      153
agg ggg cgc cac acg cgt ttc gtg ttt caa aag gca ttg cgc tcc ctc      201
caa cgg tac ccg cta cca ttg cgc agc ggg aag gaa gcc aag ata ctc      249
cag cac ttc gga gac agg ctc tgc cgc atg ctg gac gaa aag ctg aag      297
cag cac cta gca tca ggc ggt gac cat gcc ccc agc tca cca tct gga      345
aag aag gga gcc agc aaa ggg cca cct gag caa gtc cag gac tct tcc      393
atg cca gtt ccc acc cag cct caa gca gga agc acc agt gtt ggc tat      441
tgg cca gct cag aac tca ggt gct cga gag atc ctg ctg caa ctc tac      489
agg gag cac ctg aat tct gat ggc cac agc ttc cta acc aaa gag gag      537
ctg ctg cag aag tgt gcc cag aag acc ccc agg gta gtg cct gga agt      585
tcg aaa ccc tgg cct gcc ctc cgg agc ctc ctc cat agg aac ctc atc      633
ctt gga acg cat cgg cca gcc agg tat gca ctc aca cca gag ggt ctg      681
gag ctg gct cag aag ctg gcc gag gcg aaa ggc ctg agc act cgg cac      729
gct ggc ttt agg cca gag gaa cat cac gga gag gac tca gca gtt cca      777
gaa gcc ttg tca gaa cct ggc acc acc gag ggg gcc gtc cag cag aga      825
cca ctg gag cta agg cct agc gag tac aga gtg ctg ttg tgt gtg gac      873
att ggc gaa acc aga ggg gca gga cac agg cca gaa atg ctc cga gag      921
tta caa agg ctg cgt gtg ccc cac acc gta cgc aag cta cac gtt gga      969
gac ttt gtg tgg gtg gca cag gag acc agg ccc aga gac cca gaa aga     1017
cct ggg gag ctg gtc ctg gac cac att gtg gaa cgc aag cgg cta gat     1065
gac cta tgc agc agc atc att gac ggc cgc ttt cgg gag cag aag ttc     1113
cgc ctg aag cgc tgt ggc ctg ggc cac cgg gta tac tta gtg gaa gaa     1161
cat ggg tct gtc cac aac ctt agc ctt ccc gag agc acc ttg ctg cag     1209
gct gtc aca aac acc cag gtc att gat ggc ttt ttt gtg aag cga acc     1257
atg gat att aag gag tcg gtt ggc tac ctg gcg ctt ttg aca aag ggc     1305
```

FIG. 10B

```
ctg gaa aga ctg tac cag tgacttcaat gcagaagctg tcaagaacaa      1353
ggtaccaccc ctgcctcacc tctgctcggg tggcctaggc caaggtcacc cttaacacag 1413
gcctacccca accccaggcc cagtctgtgc gagaagtatt tgcccggcag ctgatgcagg 1473
tgcgtggact gagtggggag aaggcagcag ccgtggtgga tcgatacagc accccctgcca 1533
gtctcctggc tgcttatgat gcctgtgcca ccgcgaagga gcaggagatg ctcttgagca 1593
ccatcaagtg tgggcgtctg cagaggaatc tgggacccgc tctgagcagg accctgtacc 1653
agttgtactg cagccacagc cctctgagct gagctgtacc aggagacgct cgctccccag 1713
cacccatctt catctctacc aaggctggct agccttttag caagggcgaa ttc         1766
```

Mouse Mus81(2) SEQ ID NO 39

```
Met Ala Glu Pro Val Arg Leu Gly Arg Lys Arg Pro Leu Pro Val Cys
1               5                   10                  15
Pro Asn Pro Leu Phe Val Arg Trp Leu Thr Glu Trp Arg Asp Glu Ala
            20                  25                  30
Ala Ser Arg Gly Arg His Thr Arg Phe Val Phe Gln Lys Ala Leu Arg
        35                  40                  45
Ser Leu Gln Arg Tyr Pro Leu Pro Leu Arg Ser Gly Lys Glu Ala Lys
    50                  55                  60
Ile Leu Gln His Phe Gly Asp Arg Leu Cys Arg Met Leu Asp Glu Lys
65                  70                  75                  80
Leu Lys Gln His Leu Ala Ser Gly Gly Asp His Ala Pro Ser Ser Pro
                85                  90                  95
Ser Gly Lys Lys Gly Ala Ser Lys Gly Pro Pro Glu Gln Val Gln Asp
            100                 105                 110
Ser Ser Met Pro Val Pro Thr Gln Pro Gln Ala Gly Ser Thr Ser Val
        115                 120                 125
Gly Tyr Trp Pro Ala Gln Asn Ser Gly Ala Arg Glu Ile Leu Leu Gln
    130                 135                 140
Leu Tyr Arg Glu His Leu Asn Ser Asp Gly His Ser Phe Leu Thr Lys
145                 150                 155                 160
Glu Glu Leu Leu Gln Lys Cys Ala Gln Lys Thr Pro Arg Val Val Pro
                165                 170                 175
Gly Ser Ser Lys Pro Trp Pro Ala Leu Arg Ser Leu Leu His Arg Asn
            180                 185                 190
Leu Ile Leu Gly Thr His Arg Pro Ala Arg Tyr Ala Leu Thr Pro Glu
        195                 200                 205
Gly Leu Glu Leu Ala Gln Lys Leu Ala Glu Ala Glu Gly Leu Ser Thr
    210                 215                 220
Arg His Ala Gly Phe Arg Pro Glu Glu His His Gly Glu Asp Ser Ala
225                 230                 235                 240
Val Pro Glu Ala Leu Ser Glu Pro Gly Thr Thr Glu Gly Ala Val Gln
                245                 250                 255
```

FIG. 10B CONT.

```
Gln Arg Pro Leu Glu Leu Arg Pro Ser Glu Tyr Arg Val Leu Leu Cys
            260                 265                 270
Val Asp Ile Gly Glu Thr Arg Gly Ala Gly His Arg Pro Glu Met Leu
        275                 280             285
Arg Glu Leu Gln Arg Leu Arg Val Pro His Thr Val Arg Lys Leu His
    290             295             300
Val Gly Asp Phe Val Trp Val Ala Gln Glu Thr Arg Pro Arg Asp Pro
305             310             315                 320
Glu Arg Pro Gly Glu Leu Val Leu Asp His Ile Val Glu Arg Lys Arg
            325             330             335
Leu Asp Asp Leu Cys Ser Ser Ile Ile Asp Gly Arg Phe Arg Glu Gln
        340             345             350
Lys Phe Arg Leu Lys Arg Cys Gly Leu Gly His Arg Val Tyr Leu Val
        355             360             365
Glu Glu His Gly Ser Val His Asn Leu Ser Leu Pro Glu Ser Thr Leu
    370             375             380
Leu Gln Ala Val Thr Asn Thr Gln Val Ile Asp Gly Phe Phe Val Lys
385             390             395             400
Arg Thr Met Asp Ile Lys Glu Ser Val Gly Tyr Leu Ala Leu Leu Thr
            405             410             415
Lys Gly Leu Glu Arg Leu Tyr Gln
            420
```

FIG. 10B CONT.

Mouse Mus81(3)    SEQ ID NO 40

```
gatatctgca gaattcgccc ttgagactct gaaggagcca gtctagttct t atg gcg      57
gag ccg gtc cgc ctg ggc cgg aag cgt ccg ctg ccc gtt tgc ccc aac     105
ccg ctc ttc gtt cgt tgg ctg acc gag tgg cgg gac gag gca gcc agc     153
agg ggg cgc cac acg cgt ttc gtg ttt caa aag gca ttg cgc tcc ctc     201
caa cgg tac ccg cta cca ttg cgc agc ggg aag gaa gcc aag ata ctc     249
cag cac ttc gga gac agg ctc tgc cgc atg ctg gac gaa aag ctg aag     297
cag cac cta gca tca ggc ggt gac cat gcc ccc agc tca cca tct gga     345
aag aag gga gcc agc aaa ggg cca cct gag caa gtc cag gac tct tcc     393
atg cca gtt ccc acc cag cct caa gca gga agc acc agt gtt ggc tat     441
tgg cca gct cag aac tca ggt gct cga gag atc ctg ctg caa ctc tac     489
agg gag cac ctg aat tct gat ggc cac agc ttc cta acc aaa gag gag     537
ctg ctg cag aag tgt gcc cag aag acc ccc agg gta gtg cct gga agt     585
tcg aaa ccc tgg cct gcc ctc cgg agc ctc ctc cat agg aac ctc atc     633
ctt gga acg cat cgg cca gcc agg tat gca ctc aca cca gag ggt ctg     681
gag ctg gct cag aag ctg gcc gag gcg aaa ggc ctg agc act cgg cac     729
gct ggc ttt agg cca gag gaa cat cac gga gag gac tca gca gtt cca     777
gaa gcc ttg tca gaa cct ggc acc acc gag ggg gcc gtc cag cag aga     825
cca ctg gag cta agg cct agc gag tac aga gtg ctg ttg tgt gtg gac     873
att ggc gaa acc aga ggg gca gga cac agg cca gaa atg ctc cga gag     921
tta caa agg ctg cgt gtg ccc cac acc gta cgc aag cta cac gtt gga     969
gac ttt gtg tgg gtg gca cag gag acc agg ccc aga gac cca gaa aga    1017
cct ggg gag ctg gtc ctg gac cac att gtg gaa cgc aag cgg cta gat    1065
gac cta tgc agc agc atc att gac ggc cgc ttt cgg gag cag aag ttc    1113
cgc ctg aag cgc tgt ggc ctg ggg cac cgg gta tac tta gtg gaa gaa    1161
cat ggg tct gtc cac aac ctt agc ctt ccc gag agc acc ttg ctg cag    1209
gct gtc aca aac acc cag gtc att gat ggc ttt ttt gtg aag cga acc    1257
```

FIG. 10C

```
atg gat att aag gag tcg gtt ggc tac ctg gcg ctt ttg aca aag ggc    1305
ctg gaa aga ctg tac cag cct tcc aca aac cct ctc tgc tca ctc ctc    1353
acc ttc agt gac ttc aat gca gaa gct gtc aag aac aag gcc cag tct    1401
gtg cga gaa gta ttt gcc cgg cag ctg atg cag gtg cgt gga ctg agt    1449
ggg gag aag gca gca gcc gtg gtg gat cga tac agc acc cct gcc agt    1497
ctc ctg gct gct tat gat gcc tgt gcc acc gcg aag gag cag gag atg    1545
ctc ttg agc acc atc aag tgt ggg cgt ctg cag agg aat ctg gga ccc    1593
gct ctg agc agg acc ctg tac cag ttg tac tgc agc cac agc cct ctg    1641
agc tgagctgtac caggagacgc tcgctcccca gcacccatct tcatctctac         1694
caaggctggc tagcctttta gcaagggcga attccagcac actggcggcc gttactagtg  1754
gatccgagct cggtaccaag cttggcgtaa tcatggtcat agctgtttcc tgtgtgaaat  1814
tgttatccgc tcacaattcc acacaacata cgagccggaa gcataaagtg taaagcctgg  1874
ggtgcctaat gagtgagcta actcacatta attgcgttgc gctcactgcc cgctttccag  1934
tcgggaaacc tgtcgtgcca gctgcattaa tgaatcggcc aacgcgcggg gagaggcggt  1994
ttgcgtattg ggcgctcttc cg                                           2016
```

Mouse Mus81(3)    SEQ IS NO 41

```
Met Ala Glu Pro Val Arg Leu Gly Arg Lys Arg Pro Leu Pro Val Cys
 1               5                  10                  15
Pro Asn Pro Leu Phe Val Arg Trp Leu Thr Glu Trp Arg Asp Glu Ala
            20                  25                  30
Ala Ser Arg Gly Arg His Thr Arg Phe Val Phe Gln Lys Ala Leu Arg
        35                  40                  45
Ser Leu Gln Arg Tyr Pro Leu Pro Leu Arg Ser Gly Lys Glu Ala Lys
    50                  55                  60
Ile Leu Gln His Phe Gly Asp Arg Leu Cys Arg Met Leu Asp Glu Lys
65                  70                  75                  80
Leu Lys Gln His Leu Ala Ser Gly Gly Asp His Ala Pro Ser Ser Pro
                85                  90                  95
Ser Gly Lys Lys Gly Ala Ser Lys Gly Pro Pro Glu Gln Val Gln Asp
            100                 105                 110
Ser Ser Met Pro Val Pro Thr Gln Pro Gln Ala Gly Ser Thr Ser Val
        115                 120                 125
Gly Tyr Trp Pro Ala Gln Asn Ser Gly Ala Arg Glu Ile Leu Leu Gln
    130                 135                 140
Leu Tyr Arg Glu His Leu Asn Ser Asp Gly His Ser Phe Leu Thr Lys
145                 150                 155                 160
Glu Glu Leu Leu Gln Lys Cys Ala Gln Lys Thr Pro Arg Val Val Pro
                165                 170                 175
Gly Ser Ser Lys Pro Trp Pro Ala Leu Arg Ser Leu Leu His Arg Asn
```

FIG. 10C CONT.

```
                    180                     185                     190
    Leu Ile Leu Gly Thr His Arg Pro Ala Arg Tyr Ala Leu Thr Pro Glu
            195                     200                     205
    Gly Leu Glu Leu Ala Gln Lys Leu Ala Glu Ala Glu Gly Leu Ser Thr
            210                     215                     220
    Arg His Ala Gly Phe Arg Pro Glu Glu His His Gly Glu Asp Ser Ala
    225                     230                     235                 240
    Val Pro Glu Ala Leu Ser Glu Pro Gly Thr Thr Glu Gly Ala Val Gln
                    245                     250                     255
    Gln Arg Pro Leu Glu Leu Arg Pro Ser Glu Tyr Arg Val Leu Leu Cys
                    260                     265                     270
    Val Asp Ile Gly Glu Thr Arg Gly Ala Gly His Arg Pro Glu Met Leu
                    275                     280                     285
    Arg Glu Leu Gln Arg Leu Arg Val Pro His Thr Val Arg Lys Leu His
            290                     295                     300
    Val Gly Asp Phe Val Trp Val Ala Gln Glu Thr Arg Pro Arg Asp Pro
    305                     310                     315                 320
    Glu Arg Pro Gly Glu Leu Val Leu Asp His Ile Val Glu Arg Lys Arg
                    325                     330                     335
    Leu Asp Asp Leu Cys Ser Ser Ile Ile Asp Gly Arg Phe Arg Glu Gln
                    340                     345                     350
    Lys Phe Arg Leu Lys Arg Cys Gly Leu Gly His Arg Val Tyr Leu Val
            355                     360                     365
    Glu Glu His Gly Ser Val His Asn Leu Ser Leu Pro Glu Ser Thr Leu
            370                     375                     380
    Leu Gln Ala Val Thr Asn Thr Gln Val Ile Asp Gly Phe Phe Val Lys
    385                     390                     395                 400
    Arg Thr Met Asp Ile Lys Glu Ser Val Gly Tyr Leu Ala Leu Leu Thr
                    405                     410                     415
    Lys Gly Leu Glu Arg Leu Tyr Gln Pro Ser Thr Asn Pro Leu Cys Ser
                    420                     425                     430
    Leu Leu Thr Phe Ser Asp Phe Asn Ala Glu Ala Val Lys Asn Lys Ala
            435                     440                     445
    Gln Ser Val Arg Glu Val Phe Ala Arg Gln Leu Met Gln Val Arg Gly
            450                     455                     460
    Leu Ser Gly Glu Lys Ala Ala Ala Val Val Asp Arg Tyr Ser Thr Pro
    465                     470                     475                 480
    Ala Ser Leu Leu Ala Ala Tyr Asp Ala Cys Ala Thr Ala Lys Glu Gln
                    485                     490                     495
    Glu Met Leu Leu Ser Thr Ile Lys Cys Gly Arg Leu Gln Arg Asn Leu
                    500                     505                     510
    Gly Pro Ala Leu Ser Arg Thr Leu Tyr Gln Leu Tyr Cys Ser His Ser
            515                     520                     525
    Pro Leu Ser
            530
```

FIG. 10C CONT.

Mouse Mus81(4)   SEQ ID NO 42

| | | |
|---|---|---|
| gatatctgca gaattcgccc ttgagactct gaaggagcca gtctagttct t atg gcg | 57 |
| gag ccg gtc cgc ctg ggc cgg aag cgt ccg ctg ccc gtt tgc ccc aac | 105 |
| ccg ctc ttc gtt tgt tgg ctg acc gag tgg cgg gac gag gca gcc agc | 153 |
| agg ggg cgc cac acg cgt ttc gtg ttt caa aag gca ttg cgc tcc ctc | 201 |
| caa cgg tac ccg cta cca ttg cgc agc ggg aag gaa gcc aag ata ctc | 249 |
| cag cac ttc gga gac agg ctc tgc cgc atg ctg gac gaa aag ctg aag | 297 |
| cag cac cta gca tca ggc ggt gac cat gcc ccc agc tca cca tct gga | 345 |
| aag aag gga gcc agc aaa ggg cca cct gag caa gtc cag gac tct tcc | 393 |
| atg cca gtt ccc acc cag cct caa gca gga agc acc agt gtt ggc tat | 441 |
| tgg cca gct cag aac tca ggt gct cga gag atc ctg ctg caa ctc tac | 489 |
| agg gag cac ctg aat tct gat ggc cac agc ttc cta acc aaa gag gag | 537 |
| ctg ctg cag aag tgt gcc cag aag acc ccc agg gta gtg cct gga agt | 585 |
| tcg aaa ccc tgg cct gcc ctc cgg agc ctc ctc cat agg aac ctc atc | 633 |
| ctt gga acg cat cgg cca gcc agg tat gca ctc aca cca gag ggt ctg | 681 |
| gag ctg gct cag aag ctg gcc gag gcg gaa ggc ctg agc act cgg cac | 729 |
| gct ggc ttt agg cca gag gaa cat cac gga gag gac tca gca gtt cca | 777 |
| gaa gcc ttg tca gaa cct ggc acc acc gag ggg gcc gtc cag cag aga | 825 |
| cca ctg gag cta agg cct agc gag tac aga gtg ctg ttg tgt gtg gac | 873 |
| att ggc gaa acc aga ggg gca gga cac agg cca gaa atg ctc cga gag | 921 |
| tta caa agg ctg cgt gtg ccc cac acc gta cgc aag cta cac gtt gga | 969 |
| gac ttt gtg tgg gtg gca cag gag acc agg ccc aga gac cca gaa aga | 1017 |
| cct ggg gag ctg gtc ctg gac cac att gtg gaa cgc aag cgg cta gat | 1065 |
| gac cta tgc agc agc atc att gac ggc cgc ttt cgg gag cag aag ttc | 1113 |
| cgc ctg aag cgc tgt ggc ctg ggg cac cgg gta tac tta gtg gaa gaa | 1161 |
| cat ggg tct gtc cac aac ctt agc ctt ccc gag agc acc ttg ctg cag | 1209 |
| gct gtc aca aac acc cag gtc att gat ggc ttt ttt gtg aag cga acc | 1257 |

FIG. 10D

```
atg gat att aag gag tcg gtt ggc tac ctg gcg ctt ttg aca aag ggc    1305 ctg gaa aga ctg tac cag gcc aag gtc acc ctt aac aca ggc cta ccc    1353 caa ccc cag gcc cag tct gtg cga gaa gta ttt gcc cgg cag ctg atg    1401 cag gtg cgt gga ctg agt ggg gag aag gca gca gcc gtg gtg gat cga    1449 tac agc acc cct gcc agt ctc ctg gct gct tat gat gcc tgt gcc acc    1497 gcg aag gag cag gag atg ctc ttg agc acc atc aag tgt ggg cgt ctg    1545 cag agg aat ctg gga ccc gct ctg agc agg acc ctg tac cag ttg tac    1593 tgc agc cac agc cct ctg agc tgagctgtac caggagacgc tcgctcccca       1644
gcacccatct tcatctctac caaggctggc tagccttttta gcaagggcga attc       1698
```

Mouse Mus81(4) SEQ ID NO 43

```
Met Ala Glu Pro Val Arg Leu Gly Arg Lys Arg Pro Leu Pro Val Cys
1               5                   10                  15
Pro Asn Pro Leu Phe Val Cys Trp Leu Thr Glu Trp Arg Asp Glu Ala
            20                  25                  30
Ala Ser Arg Gly Arg His Thr Arg Phe Val Phe Gln Lys Ala Leu Arg
        35                  40                  45
Ser Leu Gln Arg Tyr Pro Leu Pro Leu Arg Ser Gly Lys Glu Ala Lys
    50                  55                  60
Ile Leu Gln His Phe Gly Asp Arg Leu Cys Arg Met Leu Asp Glu Lys
65                  70                  75                  80
Leu Lys Gln His Leu Ala Ser Gly Gly Asp His Ala Pro Ser Ser Pro
                85                  90                  95
Ser Gly Lys Lys Gly Ala Ser Lys Gly Pro Pro Glu Gln Val Gln Asp
            100                 105                 110
Ser Ser Met Pro Val Pro Thr Gln Pro Gln Ala Gly Ser Thr Ser Val
        115                 120                 125
Gly Tyr Trp Pro Ala Gln Asn Ser Gly Ala Arg Glu Ile Leu Leu Gln
    130                 135                 140
Leu Tyr Arg Glu His Leu Asn Ser Asp Gly His Ser Phe Leu Thr Lys
145                 150                 155                 160
Glu Glu Leu Leu Gln Lys Cys Ala Gln Lys Thr Pro Arg Val Val Pro
                165                 170                 175
Gly Ser Ser Lys Pro Trp Pro Ala Leu Arg Ser Leu Leu His Arg Asn
            180                 185                 190
Leu Ile Leu Gly Thr His Arg Pro Ala Arg Tyr Ala Leu Thr Pro Glu
        195                 200                 205
Gly Leu Glu Leu Ala Gln Lys Leu Ala Glu Ala Glu Gly Leu Ser Thr
    210                 215                 220
Arg His Ala Gly Phe Arg Pro Glu Glu His His Gly Glu Asp Ser Ala
225                 230                 235                 240
Val Pro Glu Ala Leu Ser Glu Pro Gly Thr Thr Glu Gly Ala Val Gln
                245                 250                 255
Gln Arg Pro Leu Glu Leu Arg Pro Ser Glu Tyr Arg Val Leu Leu Cys
            260                 265                 270
```

FIG. 10D CONT.

```
Val Asp Ile Gly Glu Thr Arg Gly Ala Gly His Arg Pro Glu Met Leu
    275                 280                 285
Arg Glu Leu Gln Arg Leu Arg Val Pro His Thr Val Arg Lys Leu His
    290                 295                 300
Val Gly Asp Phe Val Trp Val Ala Gln Glu Thr Arg Pro Arg Asp Pro
305                 310                 315                 320
Glu Arg Pro Gly Glu Leu Val Leu Asp His Ile Val Glu Arg Lys Arg
                325                 330                 335
Leu Asp Asp Leu Cys Ser Ser Ile Ile Asp Gly Arg Phe Arg Glu Gln
            340                 345                 350
Lys Phe Arg Leu Lys Arg Cys Gly Leu Gly His Arg Val Tyr Leu Val
        355                 360                 365
Glu Glu His Gly Ser Val His Asn Leu Ser Leu Pro Glu Ser Thr Leu
    370                 375                 380
Leu Gln Ala Val Thr Asn Thr Gln Val Ile Asp Gly Phe Phe Val Lys
385                 390                 395                 400
Arg Thr Met Asp Ile Lys Glu Ser Val Gly Tyr Leu Ala Leu Leu Thr
                405                 410                 415
Lys Gly Leu Glu Arg Leu Tyr Gln Ala Lys Val Thr Leu Asn Thr Gly
            420                 425                 430
Leu Pro Gln Pro Gln Ala Gln Ser Val Arg Glu Val Phe Ala Arg Gln
        435                 440                 445
Leu Met Gln Val Arg Gly Leu Ser Gly Glu Lys Ala Ala Ala Val Val
    450                 455                 460
Asp Arg Tyr Ser Thr Pro Ala Ser Leu Leu Ala Ala Tyr Asp Ala Cys
465                 470                 475                 480
Ala Thr Ala Lys Glu Gln Glu Met Leu Leu Ser Thr Ile Lys Cys Gly
                485                 490                 495
Arg Leu Gln Arg Asn Leu Gly Pro Ala Leu Ser Arg Thr Leu Tyr Gln
                500                 505                 510
Leu Tyr Cys Ser His Ser Pro Leu Ser
            515                 520
```

FIG. 10D CONT.

>Meme1TeA2 SEQ ID NO 44

*GGGGATAGATCTACTTCCGGGT*CTTGCGGACAATTCAAAGAGTGGCGGGAGCAGTAGCAGG
CAGTTCATTTGAGAGCTCTAATGGGTTGATGGCTCTAAGAAGGTTATCCCTGTCTCGCCT
CTCCACGGAGAGTGATTCTGAGGACCTGCCCACATTTGCCTTTTTGAAGAAGGAACCATC
TTCAACCAACAGGAAGCCACCTCAGAGGGCGAAGAACATAGTGGTTGTCACCTCAGATTC
TGAAGCCTCCTGTCCTCCATCACCAGGCCTCAAAGGTCCACCATGTGTCCCCAGTGCAGC
TGGAGCTCCCCCACAAGCAGGGCCAGTCAGAGTGCTAAGCAGTAGCAGTGAGGACGAAGA
TGTATTTGTCCCCCTAGCTGAGAGGATCACATGTAAGCTTTTGACGAGCAAGCAGCTGTG
CCCTGAGCTCTCTAGCTCCTCACTTAAAACAGGTTTGGATGGCCAAAATAATGCCAGCGC
ACCATGTGACTGGAAAAGGCAACCATGGCCAAAGATTCCCGATGTTCCCCTCCACGGTGC
CTTAGAGAAGAGTGCTGCAAATGATGAGGACTCTCTCTTAGACGATCAGTGTCGTCAGCT
TCCAACCTACCAGGCTACCTGCAGGGAGCTGGCAGTCTCCAAAACAAATTCCGACCGACC
TCTACCCAAGAAGAGAACCAAACATATTCAGACGGTCCAGAGCGGAGGCTCTCAGGGATG
CTGGCGACCGGGACAGGCAAGCAGGAAGGAAAACACCCCGAGGCAGCATGAAAGAAAAA
GAAGGCAGAGATGATCAAGAGGCTCAAAGCCCAGAGGCCAGAGGAATGCCTGAAGCACAT
CGTGGTGGTGCTGGATCCAGTGCTTTTACAGATGGAAGGTGGGGGCCAGCTCCTGGGAGC
GCTGCAGGCCATGGAGTGCAGCTGTGTGATTGAAGCCCAGGCCATACCTCGAAGCATCAC
TTGGAGGAGGAGGAGGACAGAGCTGGTAGAGGATGGAGATGACTGGATGGAAGAGCCAAC
AATCCTGGTGTTGGTCCTGGCAGAGGTCTTCATGTCCATGGCCTACAACTTAAAGCAGGC
AAGTCCTAGCAGCACCGAGAAAGGGAAGGAGACCCTTCGGAGCTTTGTAACTGATGTCAC
AGCAAAGACGGGGAAAGCATTGTCACTGGTGATTGTGGACCAGGAGAAATGCTTCAGGCC
TCAGAATCCCCCGAGGAGAAGGAAATCAGGAATGGCAAATAAACAGGCCAAAGCGAAGCA
TCAGCAGAGGCAAGAGTCTAGCACGGGACTCATGGTGTCCAGGGCAGACATGGAGAAGGC
ACTGGTGGATCTGCAGCTTTATACAGAAGCCCAGGCGTGGATGGTGCAGAGCTGGAAGGA
GCTGGCGGACTTCACCTGTGCATTTACAAAGGCTGTGGCTGAAGCACCCTTCAAGAAGCT
CCGGGATCAAGTCACCTTTTCCTTCTTCCTGGAGAAAGACTGGGCTGGAGGGATGAAAGT
GGACCAGTCCGGCAGGGGACTGGCACTGATCTGGAGGCGGCAGATCCAGCAGCTGAACCG
AGTCAGCTCGGAGATGGCCAGTGCTATTGTGGACGCCTATCCCTCACCGCAGCTCCTGGT
GCAGGCTTATCAGCGGTGTTTCTCTGAGCAAGAACGTCAGAATTTGCTGGCTGACATACA
AGTGCGACGTGGGGAAGGTGTGACAGCCACCTCCCGCCGTGTTGGGCCAGAATTATCCAG
GCGGATCTACCTTCAAATGACCACAGCGCAACCAGATCTCATCTTAGACAGTGTTGACTG
ATATCCCACCTTGGCTATTGACAGTAGACAGGCCAGAAGTACCTCCTTGGTACAGTTAGG
GAGCAAGTCTCTCATCTCTGGGAACAGAGAAGGCTGAGTCACTTGAATCTACCTCCACCA
TAGCACTCATGTTCCTCTCCCGGCAAGCGAGATGCCATGGACAGCCATCCACCCCATCC
CAGTTGACCCTCACAGCACAAAGGAGAAAGGCAGACCACTCAGACATGGATTTAATAATT
GTAGAAATCCAAGAAATAAGCATCAAATCTCGAAGTCAGAGTGAACTCTTGCCTGCGGGT
TGGCTTGACTACGCCCAGCCACTGAGCTGCCTCAACCAGCTAGGGAGCTATGATGA*GGCT
GACTCCTGTTTTCATGATG*

>Meme1TeA2 SEQ ID NO 45

MALRRLSLSRLSTESDSEDLPTFAFLKKEPSSTNRKPPQRAKNIVVVTSDSEASCPPSPGLKGPPCVPSAAGAPPQAGPV
RVLSSSSEDEDVFVPLAERITCKLLTSKQLCPELSSSSLKTGLDGQNNASAPCDWKRQPWPKIPDVPLHGALEKSAANDE
DSLLDDQCRQLPTYQATCRELAVSKTNSDRPLPKKRTKHIQTVQSGGSQGCWRPGQASRKENTPRQHERKKKAEMIKRLK
AQRPEECLKHIVVVLDPVLLQMEGGGQLLGALQAMECSCVIEAQAIPRSITWRRRRTELVEDGDDWMEEPTILVLVLAEV
FMSMAYNLKQASPSSTEKGKETLRSFVTDVTAKTGKALSLVIVDQEKCFRPQNPPRRRKSGMANKQAKAKHQQRQESSTG
LMVSRADMEKALVDLQLYTEAQAWMVQSWKELADFTCAFTKAVAEAPFKKLRDQVTFSFFLEKDWAGGMKVDQSGRGLAL
IWRRQIQQLNRVSSEMASAIVDAYPSPQLLVQAYQRCFSEQERQNLLADIQVRRGEGVTATSRRVGPELSRRIYLQMTTA
QPDLILDSVD

FIG. 11A

>MemelTeA4 SEQ ID NO 46

*GGGGATAGATCTACTTCCGGGTCTTGCGGACAATTCAAAGAGTGGCGGGAGCAGTAGCAGT*
GCTTTTACAGATGGAAGGTGGGGGCCAGCTCCTGGGAGCGCTGCAGGCCATGGAGTGCAG
CTGTGTGATTGAAGCCCAGGCCATACCTCGAAGCATCACTTGGAGGAGGAGGAGGACAGA
GCTGGTAGAGTTGCCTGTTGCAGAGAGAGGAGCAACTGGTGGCATCCCTTTCCCCTGCCT
GAATGAGGATGGAGATGACTGGATGGAAGAGCCAACAATCCTGGTGTTGGTCCTGGCAGA
GGTCTTCATGTCCATGGCCTACAACTTAAAGCAGGCAAGTCCTAGCAGCACCGAGAAAGG
GAAGGAGACCCTTCGGAGCTTTGTAACTGATGTCACAGCAAAGACGGGGAAAGCATTGTC
ACTGGTGATTGTGGACCAGGAGAAATGCTTCAGGCCTCAGAATCCCCCGAGGAGAAGGAA
ATCAGGAATGGCAAATAAACAGGCCAAAGCGAAGCATCAGCAGAGGCAAGAGTCTAGCAC
GGGACTCATGGTGTCCAGGGCAGACATGGAGAAGGCACTGGTGGATCTGCAGCTTTATAC
AGAAGCCCAGGCGTGGATGGTGCAGAGCTGGAAGGAGCTGGCGGACTTCACCTGTGCATT
TACAAAGGCTGTGGCTGAAGCACCCTTCAAGAAGCTCCGGGATCAAGTCACCTTTTCCTT
CTTCCTGGAGAAAGACTGGGCTGGAGGGATGAAAGTGGACCAGTCCGGCAGGGACTGGC
ACTGATCTGGAGGCGGCAGATCCAGCAGCTGAACCGAGTCAGCTCGGAGATGGCCAGTGC
TATTGTGGACGCCTATCCCTCACCGCAGCTCCTGGTGCAGGCTTATCAGCGGTGTTTCTC
TGAGCAAGAACGTCAGAATTTGCTGGCTGACATACAAGTGCGACGTGGGGAAGGTGTGAC
AGCCACCTCCCGCCGTGTTGGGCCAGAATTATCCAGGCGGATCTACCTTCAAATGACCAC
AGCGCAACCAGATCTCATCTTAGACAGTGTTGACTGATATCCCACCTTGGCTATTGACAG
TAGACAGGCCAGAAGTACCTCCTTGGTACAGTTAGGGAGCAAGTCTCTCATCTCTGGGAA
CAGAGAAGGCTGAGTCACTTGAATCTACCTCCACCATAGCACTCATGTTCCTCTCCCGGC
AAGCGAGATGCCATGGACAGCCATCCCACCCCATCCCAGTTGACCCTCACAGCACAAAGG
AGAAAGGCAGACCACTCAGACATGGATTTAATAATTGTAGAAATCCAAGAAATAAGCATC
AAATCTCGAAGTCAGAGTGAACTCTTGCCTGCGGGTTGGCTTGACTACGCCCAGCCACTG
AGCTGCCTCAACCAGCTAGGGAGCTATGATGA*GGCTGACTCCTGTTTTCATGATG*

>MemelTeA4 SEQ ID NO 47

MEGGGQLLGALQAMECSCVIEAQAIPRSITWRRRRTELVELPVAERGATGGIPFPCLNEDGDDWMEEPTILVLVLAEVFM
SMAYNLKQASPSSTEKGKETLRSFVTDVTAKTGKALSLVIVDQEKCFRPQNPPRRRKSGMANKQAKAKHQQRQESSTGLM
VSRADMEKALVDLQLYTEAQAWMVQSWKELADFTCAFTKAVAEAPFKKLRDQVTFSFFLEKDWAGGMKVDQSGRGLALIW
RRQIQQLNRVSSEMASAIVDAYPSPQLLVQAYQRCFSEQERQNLLADIQVRRGEGVTATSRRVGPELSRRIYLQMTTAQP
DLILDSVD

FIG. 11B

>Meme1TeA9 SEQ ID NO 48

*GGGGATAGATCTACTTCCGGGT*CTTGCGGACAATTCAAAGAGTGGCGGGAGCAGTAGCAGGCAGTTCA
TTTGAGAGCTCTAATGGGTTGATGGCTCTAAGAAGGTTATCCCTGTCTCGCCTCTCCACGGAGAGTGA
TTCTGAGGACCTGCCCACATTTGCCTTTTTGAAGAAGGAACCATCTTCAACCAACAGGAAGCCACCTC
AGAGGGCGAAGAACATAGTGGTTGTCACCTCAGATTCTGAAGCCTCCTGTCCTCCATCACCAGGCCTC
AAAGGTCCACCATGTGTCCCCAGTGCAGCTGGAGCTCCCCCACAAGCAGGGCCAGTCAGAGTGCTAAG
CAGTAGCAGTGAGGACGAAGATGTATTTGTCCCCCTAGCTGAGAGGATCACATGTAAGCTTTTGACGA
GCAAGCAGCTGTGCCCTGAGCTCTCTAGCTCCTCACTTAAAACAGGTTTGGATGGCCAAAATAATGCC
AGCGCACCATGTGACTGGAAAAGGCAACCATGGCCAAAGATTCCCGATGTTCCCCTCCACGGTGCCTT
AGAGAAGAGTGCTGCAAATGATGAGGACTCTCTCTTAGACGATCAGTGTCGTCAGCTTCCAACCTACC
AGGCTACCTGCAGGGAGCTGGCAGTCTCCAAAACAAATTCCGACCGACCTCTACCCAAGAAGAGAACC
AAGCATATTCAGACGGTCCAGAGCGGAGGCTCTCAGGGATGCTGGCGACCGGGACAGGCAAGCAGGAA
GGAAAACACCCCGAGGCAGCATGAAAGAAAAAGAAGGCAGAGATGATCAAGAGGCTCAAAGCCCAGA
GGCCAGAGGAATGCCTGAAGCACATCGTGGTGGTGCTGGATCCAGTGCTTTTACAGATGGAAGGTGGG
GGCCAGCTCCTGGGAGCGCTGCAGGCCATGGAGTGCAGCTGTGTGATTGAAGCCCAGGCCATACCTCG
AAGCATCACTTGGAGGAGGAGGAGGACAGAGCTGGTAGAGTTGCCTGTTGCAGAGAGAGGAGCAACTG
GTAGCATCCCTTTCCCCTGCCTGAATGAGGATGGAGATGACTGGATGGAAGAGCCAACAATCCTGGTG
TTGGTCCTGGCAGAGGTCTTCATGTCCATGGCCTACAACTTAAAGCAGGCAAGTCCTAGCAGCACCGA
GAAAGGGAAGGAGACCCTTCGGAGCTTTGTAACTGATGTCACAGCAAAGACGGGGAAAGCATTGTCAC
TGGTGATTGTGGACCAGGAGAAATGCTTCAGGCCTCAGAATCCCCCGAGGAGAAGGAAATCAGGAATG
GCAAATAAACAGGCCAAAGCGAAGCATCAGCAGAGGCAAGAGTCTAGCACGGGACTCATGGTGTCCAG
GGCAGACATGGAGAAGGCACTGGTGGATCTGCAGCTTTATACAGAAGCCCAGGCGTGGATGGTGCAGA
GCTGGAAGGAGCTGGCGGACTTCACCTGTGCATTTACAAAGGCTGTGGCTGAAGCACCCTTCAAGAAG
CTCCGGGATCAAGTCACCTTTTCCTTCTTCCTGGAGAAAGACTGGGCTGGAGGGATGAAAGTGGACCA
GTCCGGCAGGGGACTGGCACTGATCTGGAGGCGGCAGATCCAGCAGCTGAACCGAGTCAGCTCGGAGA
TGGCCAGTGCTATTGTGGACGCCTATCCCTCACCGCAGCTCCTGGTGCAGGCTTATCAGCGGTGTTTC
TCTGAGCAAGAACGTCAGAATTTGCTGGCTGACATACAAGTGCGACGTGGGGAAGGTGTGACAGCCAC
CTCCCGCCGTGTTGGGCCAGAATTATCCAGGCGGATCTACCTTCAAATGACCACAGCGCAACCAGATC
TCATCTTAGACAGTGTTGACTGATATCCCACCTTGGCTATTGACAGTAGACAGGCCAGAAGTACCTCC
TTGGTACAGTTAGGGAGCAAGTCTCTCATCTCTGGGAACAGAGAAGGCTGAGTCACTTGAATCTACCT
CCACCATAGCACTCACGTTCCTCTCCCGGCAAGCGAGATGCCATGGACAGCCATCCCACCCCATCCCA
GTTGACCCTCACAGCACAAAGGAGAAAGGCAGACCACTCAGACATGGATTTAATAATTGTAGAAATCC
AAGAAATAAGCATCAAATCTCGAAGTCAGAGTGAACTCTTGCCTGCGGGTTGGCTTGACTACGCCCAG
CCACTGAGCTGCCTCAACCAGCTAGGGAGCTATGATGA*GGCTGACTCCTGTTTTCATGATG*

>Meme1TeA9 SEQ ID NO 49

MALRRLSLSRLSTESDSEDLPTFAFLKKEPSSTNRKPPQRAKNIVVVTSDSEASCPPSPGLKGPPCVPSAA
GAPPQAGPVRVLSSSSEDEDVFVPLAERITCKLLTSKQLCPELSSSSLKTGLDGQNNASAPCDWKRQPWPK
IPDVPLHGALEKSAANDEDSLLDDQCRQLPTYQATCRELAVSKTNSDRPLPKKRTKHIQTVQSGGSQGCWR
PGQASRKENTPRQHERKKKAEMIKRLKAQRPEECLKHIVVVLDPVLLQMEGGGQLLGALQAMECSCVIEAQ
AIPRSITWRRRRTELVELPVAERGATGSIPFPCLNEDGDDWMEEPTILVLVLAEVFMSMAYNLKQASPSST
EKGKETLRSFVTDVTAKTGKALSLVIVDQEKCFRPQNPPRRRKSGMANKQAKAKHQQRQESSTGLMVSRAD
MEKALVDLQLYTEAQAWMVQSWKELADFTCAFTKAVAEAPFKKLRDQVTFSFFLEKDWAGGMKVDQSGRGL
ALIWRRQIQQLNRVSSEMASAIVDAYPSPQLLVQAYQRCFSEQERQNLLADIQVRRGEGVTATSRRVGPEL
SRRIYLQMTTAQPDLILDSVD

FIG. 11C

>Meme1TeB1 SEQ ID NO 50

*GGGGATAGATCTACTTCCGGGT*CTTGCGGACAATTCAAAGAGTGGCGGGAGCAGTAGCAGT
GCTTTTACAGATGGAAGGTGGGGGCCAGCTCCTGGGAGCGCTGCAGGCCATGGAGTGCAG
CTGTGTGATTGAAGCCCAGGCCATACCTCGAAGCATCACTTGGAGGAGGAGGAGGACAGA
GCTGGTAGAGGATGGAGATGACTGGATGGAAGAGCCAACAATCCTGGTGTTGGTCCTGGC
AGAGGTCTTCATGTCCATGGCCTACAACTTAAAGCAGGCAAGTCCTAGCAGCACCGAGAA
AGGGAAGGAGACCCTTCGGAGCTTTGTAACTGATGTCACAGCAAAGACGGGGAAAGCATT
GTCACTGGTGATTGTGGACCAGGAGAAATGCTTCAGGCCTCAGAATCCCCGAGGAGAAG
GAAATCAGGAATGGCAAATAAACAGGCCAAAGCGAAGCATCAGCAGAGGCAAGAGTCTAG
CACGGGACTCATGGTGTCCAGGGCAGACATGGAGAAGGCACTGGTGGATCTGCAGCTTTA
TACAGAAGCCCAGGCGTGGATGGTGCAGAGCTGGAAGGAGCTGGCGGACTTCACCTGTGC
ATTTACAAAGGCTGTGGCTGAAGCACCCTTCAAGAAGCTCCGGGATCAAGTCACCTTTTC
CTTCTTCCTGGAGAAAGACTGGGCTGGAGGGATGAAAGTGGACCAGTCCGGCAGGGGACT
GGCACTGATCTGGAGGCGGCAGATCCAGCAGCTGAACCGAGTCAGCTCGGAGATGGCCAG
TGCTATTGTGGACGCCTATCCCTCACCGCAGCTCCTGGTGCAGGCTTATCAGCGGTGTTT
CTCTGAGCAAGAACGTCAGAATTTGCTGGCTGACATACAAGTGCGACGTGGGGAAGGTGT
GACAGCCACCTCCCGCCGTGTTGGGCCAGAATTATCCAGGCGGATCTACCTTCAAATGAC
CACAGCGCAACCAGATCTCATCTTAGACAGTGTTGACTGATATCCCACCTTGGCTATTGA
CAGTAGACAGGCCAGAAGTACCTCCTTGGTACAGTTAGGGAGCAAGTCTCTCATCTCTGG
GAACAGAGAAGGCTGAGTCACTTGAATCTACCTCCACCATAGCACTCATGTTCCTCTCCC
GGCAAGCGAGATGCCATGGACAGCCATCCTACCCCATCCCAGTTGACCCTCACAGCACAA
AGGAGAAAGGCAGACCACTCAGACATGGATTTAATAATTGTAGAAATCCAAGAAATAAGC
ATCAAATCTCGAAGTCAGAGTGAACTCTTGCCTGCGGGTTGGCTTGACTACGCCCAGCCA
CTGAGCTGCCTCAACCAGCTAGGGAGCTATGATGA*GGCTGACTCCTGTTTTCATGATG*

>Meme1TeB1 SEQ ID NO 51

MEGGGQLLGALQAMECSCVIEAQAIPRSITWRRRRTELVEDGDDWMEEPTILVLVLAEVFMSMAYNLKQASPSSTEKGKE
TLRSFVTDVTAKTGKALSLVIVDQEKCFRPQNPPRRRKSGMANKQAKAKHQQRQESSTGLMVSRADMEKALVDLQLYTEA
QAWMVQSWKELADFTCAFTKAVAE

FIG. 11D

\>Meme1TeB2 SEQ 52

*GGGGATAGATCTACTTCCGGGT*CTTGCGGACAATTCAAAGAGTGGCGGGAGCAGTAGCAGG
ATGGAGATGACTGGATGGAAGAGCCAACAATCCTGGTGTTGGTCCTGGCAGAGGTCTTCA
TGTCCATGGCCTACAACTTAAAGCAGGCAAGTCCTAGCAGCACCGAGAAAGGGAAGGAGA
CCCTTCGGAGCTTTGTAACTGATGTCACAGCAAAGACGGGGAAAGCATTGTCACTGGTGA
TTGTGGACCAGGAGAAATGCTTCAGGCCTCAGAATCCCCCGAGGAGAAGGAAATCAGGAA
TGGCAAATAAACAGGCCAAAGCGAAGCATCAGCAGAGGCAAGAGTCTAGCACGGGACTCA
TGGTGTCCAGGGCAGACATGGAGAAGGCACTGGTGGATCTGCAGCTTTATACAGAAGCCC
AGGCGTGGATGGTGCAGAGCTGGAAGGAGCTGGCGGACTTCACCTGTGCATTTACAAAGG
CTGTGGCTGAAGCACCCTTCAAGAAGCTCCGGGATCAAGTCACCTTTTCCTTCTTCCTGG
AGAAAGACTGGGCTGGAGGGATGAAAGTGGACCAGTCCGGCAGGGGACTGGCACTGATCT
GGAGGCGGCAGATCCAGCAGCTGAACCGAGTCAGCTCGGAGATGGCCAGTGCTATTGTGG
ACGCCTATCCCTCACCGCAGCTCCTGGTGCAGGCTTATCAGCGGTGTTTCTCTGAGCAAG
AACGTCAGAATTTGCTGGCTGACATACAAGTGCGACGTGGGGAAGGTGTGACAGCCACCT
CCCGCCGTGTTGGGCCAGAATTATCCAGGCGGATCTACCTTCAAATGACCACAGCGCAAC
CAGATCTCATCTTAGACAGTGTTGACTGATATCCCACCTTGGCTATTGACAGTAGACAGG
CCAGAAGTACCTCCTTGGTACAGTTAGGGAGCAAGTCTCTCATCTCTGGGAACAGAGAAG
GCTGAGTCACTTGAATCTACCTCCACCATAGCACTCATGTTCCTCTCCCGGCAAGCGAGA
TGCCATGGACAGCCATCCCACCCCATCCCAGTTGACCCTCACAGCACAAAGGAGAAAGGC
AGACCACTCAGACATGGATTTAATAATTGTAGAAATCCAAGAAATAAGCATCAAATCTCG
AAGTCAGAGTGAACTCTTGCCTGCGGGTTGGCTTGACTACGCCCAGCCACTGAGCTGCCT
CAACCAGCTAGGGAGCTATGATGA*GGCTGACTCCTGTTTTCATGATG*

\>Meme1TeB2 SEQ ID NO 53

MEEPTILVLVLAEVFMSMAYNLKQASPSSTEKGKETLRSFVTDVTAKTGKALSLVIVDQEKCFRPQNPPRRRKSGMANKQ
AKAKHQQRQESSTGLMVSRADMEKALVDLQLYTEAQAWMVQSWKELADFTCAFTKAVAEAPFKKLRDQVTFSFFLEKDWA
GGMKVDQSGRGLALIWRRQIQQLNRVSSEMASAIVDAYPSPQLLVQAYQRCFSEQERQNLLADIQVRRGEGVTATSRRVG
PELSRRIYLQMTTAQPDLILDSVD

FIG. 11E

>Meme2Br2 SEQ ID NO 54

*CGAAGGACTTATGGCGGAGGT*TGGTCCCGGGAGAGTCA
CGGTCTCGCGTCTCGGTCGGGGCCTGCGTCTCGGCCATCGGCGACCTCAA
ACCTGGGAGATTTCCGACTCAGACGGTGAAGGTGTCCCCGCTAGGGAGGT
CGGCACGCAAGCCCCGAGTCCAGCAGGAGAGCGCAGAGCTGCAGCCAAGG
CTTTACGGGCAGATCAGTCCGCACTGGAGATGGTGGAATAACTCAATGTT
GCCTGCTGGGATCCAGCTGTCCTGGAAGATGCAGGCTCTGACATCCTGAT
GGAGGCGCTGGGCACGCTAGGCTGTGAATGCCGCATCGAACCGCAGCACC
AGGCCCGCAGCCTGCAGTGGAACGTTGTCAGGCCCGACCCGGCCCCCAGC
AATGTGCCTCTGGAGGCGAAGGCTGAAAATGAGCAGGAACAGTTGCTGCT
GCTGGAACCCCAGGAATTTCTTCAGGGTGCTGCGCAGCTGACCCAGATCA
CAGATCCACCTTGCTCCATCCCCTGGCTTTCTCCAAGAGTCTCACCCGC
TCCCATCTGGCTGTCATTGGACTGGACGCATACCTGTGGTCTCACCAGCT
CAGTTCTCAGAAGACATGGCAACTAAAGAAGTCAAAGGAAGCCCATGCCA
GGGGAGCCATCAGCTGGGCTGAGGTGGAGGAGGCAGCTCCGGGACTCCCA
GGCCTTTTCTTTCTGCACAGCAGGGCACTGGGCCTCAGGCCAGCAAGTGA
CCAGAGATGGCTCTGGGCTCAGAGGAGTGTGGTGGCGACAAATCAGACAG
TTCAACCGGGTCAGCCCAGCTGTGGCTGACGCTGTTGTTACTGCCTTCCC
ATCACCCCGCCTTTTGCAACAGGCTCTCCTGGACTGCAGCACAGAGCAAG
AACGCCTGAGCCTCCTAGCTGATCTCCCTGTGAAGGCCCACAAAGGCAAG
CAGCCTCGCAGAGTGGGGCCTGACCTCACGCAGAATCTGTATCTTCTT
GACAACCACCGACCCTGACCTCCTGCTGGACCTGAGCTCTTGACCTGTGC
CATCCTGGGTCACCTCCTGCCCATCAGTACAACAGGACAAGTCTGCCTAA
GAATCTAATTATTCTGAGAGGCAGGCAAGGAGGTTTGGGTCCAGCCCATA
CCTTTTCAGACTGTGGTAGATAGACTCTGTTGCCTGATGGTCAAATGGAA
ATACCATGGGAGGTGGGTGAGAGGGTAATGGAAGCTGAGGTGAATGGAAG
AGTGGAGGGTAGTGGCCACTTGGTGCAGGAGGCTTAGTAGCAGGCCTGAG
TGCCGAGTTGTACTATTACATCCTCAGAGAGAGGTGCTCAGAGATCCAAG
CCAGGCTCTCTCAAAGCCGCT*GGACAAGACAGATAACCAATAGAC*

>MEme2Br2 SEQ ID NO 55

MEALGTLGCECRIEPQHQARSLQWNVVRPDPAPSNVPLEAKAENEQEQLLLLEPQEFLQG
AAQLTQITDPPCSIPWLSPKSLTRSHLAVIGLDAYLWSHQLSSQKTWQLKKSKEAHARGA
ISWAEVEEAAPGLPGLFFLHSRALGLRPASDQRWLWAQRSVVATNQTVQPGQPSCG

FIG. 12A

>Meme2Br5 SEQ ID NO 56

*CGAAGGACTTATGGCGGAGGTTGGTCCCGGGAGAGCCA*
CGGTCTCGCGTCTCGGTCGGGGCCTGCGTCTCGGCCATCGGCGACCTCAA
ACCTGGGAGATTTCCGACTCAGACGGTGAAGGTGTCCCCGCTAGGGAGGT
CGGCACGCAAGCCCCGAGTCCAGCAGGAGAGCGCAGAGCTGCAGCCAAGG
CTTTACGGGCAGATCAGGTTCTGGGGCGACTGGTGGTGTGCGTGGACCCA
GGTGAGGGGACGGGGGCTGGGAATCTGGGGCCAGCCACCAGACAGGGTAG
CGTTGTCACCCACTAGTCCGCACTGGAGATGGTGGAATAACTCAATGTTG
CCTGCTGGGATCCAGCTGTCCTGGAAGATGCAGGCTCTGACATCCTGATG
GAGGCGCTGGGCACGCTAGGCTGTGAATGCCGCATCGAACCGCAGCACCA
GGCCCGCAGCCTGCAGTGGAACGTTGTCAGGCCCGACCCGGCCCCCAGCA
ATGTGCCTCTGGAGGCGAAGGCTGAAAATGAGCAGGAACAGTTGCTGCTG
CTGGAACCCCAGGAATTTCTTCAGGGTGCTGCGCAGCTGACCCAGATCAC
AGATCCACCTTGCTCCATCCCCTGGCTTTCTCCCAAGAGTCTCACCCGCT
CCCATCTGGCTGTCATTGGACTGGACGCATACCTGTGGTCTCACCAGCTC
AGTTCTCAGAAGACATGGCAACTAAAGAAGTCAAAGGAAGCCCATGCCAG
GGGAGCCATCAGCTGGGCTGAGGTGGAGGAGATCCTGGTGCTGCTGCAGC
TCCATGCAAACCTGGATGTGCTGCTGATGGCTTCGTGGCAGGAGCTGAGT
CAGTACGTGTGTGCCTTCACCAGGGCCCTCTCGCAGCTCCCCTCGAAGCA
GCTCCGGGACTCCCAGGCCTTTTCTTTCTGCACAGCAGGGCACTGGGCCT
CAGGCCAGCAAGTGACCAGAGATGGCTCTGGGCTCAGAGGAGTGTGGTGG
CGACAAATCAGACAGTTCAACCGGGTCAGCCCAGCTGTGGCTGACGCTGT
TGTTACTGCCTTCCCATCACCCCGCCTTTTGCAACAGGCTCTCCTGGACT
GCAGCACAGAGCAAGAACGCCTGAGCCTCCTAGCTGATCTCCCTGTGAAG
GCCCACAAAGGCAAGCAGCCTCGCAGAGTGGGGCCTGACCTCTCACGCAG
AATCTGTATCTTCTTGACAACCACCGACCCTGACCTCCTGCTGGACCTGA
GCTCTTGACCTGTGCCATCCTGGGTCACCTCCTGCCCATCAGTACAACAG
GACAAGTCTGCCTAAGAATCTAATTATTCTGAGAGGCAGGCAAGGAGGTT
TGGGTCCAGCCCATACCTTTTCAGACTGTGGTAGATAGACTCTGTTGCCT
GATGGTCAAATGGAAATACCATGGGAGGTGGGTGAGAGGGTAATGGAAGC
TGAGGTGAATGGAAGAGTGGAGGGTAGTGGCCACTTGGTGCAGGAGGCTT
AGTAGCAGGCCTGAGTGCCGAGTTGTACTATTACATCCTCAGAGAGAGGT
GCTCAGAGATCCAAGCCAGGCTCTCTCAAAGCCGCT*GGACGAGACAGATA*
*ACCAATAGAC*

>Meme2Br5 SEQ ID NO 57

MEALGTLGCECRIEPQHQARSLQWNVVRPDPAPSNVPLEAKAENEQEQLLLLEPQEFLQG
AAQLTQITDPPCSIPWLSPKSLTRSHLAVIGLDAYLWSHQLSSQKTWQLKKSKEAHARGA
ISWAEVEEILVLLQLHANLDVLLMASWQELSQYVCAFTRALSQLPSKQLRDSQAFSFCTA
GHWASGQQVTRDGSLRGVWWRQIRQFNRVSPAVADAVVTAFPSPRLLQQALLDCSTEQE
RLSLLADLPVKAHKGKQPRRVGPDLSRRICIFLTTTDPDLLLDLSS

FIG. 12B

>Meme2Te5 SEQ ID NO 58

```
CGAAGGACTTATGGCGGAGGTTGGTCCCGGGAGAGTCA
CGGTCTCGCGTCTCGGTCGGGGCCTGCGTCTCGGCCATCGGCGACCTCAA
ACCTGGGAGATTTCCGACTCAGACGGTGAAGGTGTCCCCGCTAGGGAGGT
CGGCACGCAAGCCCCGAGTCCAGCAGGAGAGCGCAGAGCTGCAGCCAAGG
CTTTACGGGCAGATCAGGTTCTGGGGCGACTGGTGGTGTGCGTGGACCCA
GCTGTCCTGGAAGATGCAGGCTCTGACATCCTGATGGAGGCGCTGGGCAC
GCTAGGCTGTGAATGCCGCATCGAACCGCAGCACCAGGCCCGCAGCCTGC
AGTGGAACGTTGTCAGGCCCGACCCGGCCCCCAGCAATGTGCCTCTGGAG
GCGAAGGCTGAAAATGAGCAGGAACAGTTGCTGCTGCTGGAACCCCAGGA
ATTTCTTCAGGGTGCTGCGCAGCTGACCCAGATCACAGATCCACCTTGCT
CCATCCCCTGGCTTTCTCCAAGAGTCTCACCCGCTCCCATCTGGCTGTC
ATTGGACTGGACGCATACCTGTGGTACCACTTAACCTCAGTAGGGCTGGC
TTGGGTGGGATTCCAGGAAAGTGGCTTGCCTCTGGTGGCTCTGTCACAGC
TAACCCCACTTGGCCTGATTTGGCTCTGCAGAGGTAGGAGACTCTGGAGC
CCAAAAAATCGTCCCCTCTGTTCAGGTCTCACCAGCTCAGTTCTCAGAAG
ACATGGCAACTAAAGAAGTCAAAGGAAGCCCATGCCAGGGGAGCCATCAG
CTGGGCTGAGGTGGAGGAGATCCTGGTGCTGCTGCAGCTCCATGCAAACC
TGGATGTGCTGCTGATGGCTTCGTGGCAGGAGCTGAGTCAGTACGTGTGT
GCCTTCACCAGGGCCCTCTCGCAGCTCCCCTCGAAGCAGCTCCGGGACTC
CCAGGCCTTTTCTTTCTGCACAGCAGGGCACTGGGCCTCAGGCCAGCAAG
TGACCAGAGATGGCTCTGGGCTCAGAGGAGTGTGGTGGCGACAAATCAGA
CAGTTCAACCGGGTCAGCCCAGCTGTGGCTGACGCTGTTGTTACTGCCTT
CCCATCACCCCGCCTTTTGCAACAGGCTCTCCTGGACTGCAGCACAGAGC
AAGAACGCCTGAGCCTCCTAGCTGATCTCCCTGTGAAGGCCCACAAAGGC
AAGCAGCCTCGCAGAGTGGGGCCTGACCTCTCACGCAGAATCTGTATCTT
CTTGACAACCACCGACCCTGACCTCCTGCTGGACCTGAGCTCTTGACCTG
TGCCATCCTGGGTCACCTCCTGCCCATCAGTACAACAGGACAAGTCTGCC
TAAGAATCTAATTATTCTGAGAGGCAGGCAAGGAGGTTTGGGTCCAGCCC
ATACCTTTTCAGACTGTGGTAGATAGACTCTGTTGCCTGATGGTCAAATG
GAAATACCATGGGAGGTGGGTGAGAGGGTAATGGAAGCTGAGGTGAATGG
AAGAGTGGAGGGTAGTGGCCACTTGGTGCAGGAGGCTTAGTAGCAGGCCT
GAGTGCCGAGTTGTACTATTACATCCTCAGAGAGAGGTGCTCAGAGATCC
AAGCCAGGCTCTCTCAAAGCCGCTGGACGAGACAGATAACCAATAGAC
```

>Meme2Te5 SEQ ID NO 59

```
MAEVGPGRVTVSRLGRGLRLGHRRPQTWEISDSDGEGVPAREVGTQAPSPAGERRAAAKA
LRADQVLGRLVVCVDPAVLEDAGSDILMEALGTLGCECRIEPQHQARSLQWNVVRPDPAP
SNVPLEAKAENEQEQLLLLEPQEFLQGAAQLTQITDPPCSIPWLSPKSLTRSHLAVIGLD
AYLWYHLTSVGLAWVGFQESGLPLVALSQLTPLGLIWLCRGRRLWSPKNRPLCSGLTSSV
LRRHGN
```

FIG. 12C

>Meme2Te6 SEQ ID NO 60

*CGAAGGACTTATGGCGGAGGTTGGTCCCGGGAGAGTCA*
CGGTCTCGCGTCTCGGTCGGGGCCTGCGTCTCGGCCATCGGCGACCTCAA
ACCTGGGAGATTTCCGACTCAGACGGTGAAGGTGTCCCCGCTAGGGAGGT
CGGCACGCAAGCCCCGAGTCCAGCAGGAGAGCGCAGAGCTGCAGCCAAGG
CTTTACGGGCAGATCAGGTTCTGGGGCGACTGGTGGTGTGCGTGGACCCA
GCTGTCCTGGAAGATGCAGGCTCTGACATCCTGATGGAGGCGCTGGGCAC
GCTAGGCTGTGAATGCCGCATCGAACCGCAGCACCAGGCCCGCAGCCTGC
AGTGGAACGTTGTCAGGCCCGACCCGGCCCCAGCAATGTGCCTCTGGAG
GCGAAGGCTGAAAATGAGCAGGAACAGTTGCTGCTGCTGGAACCCCAGGA
ATTTCTTCAGGGTGCTGCGCAGCTGACCCAGATCACAGATCCACCTTGCT
CCATCCCCTGGCTTTCTCCCAAGAGTCTCACCCGCTCCCATCTGGCTGTC
ATTGGACTGGACGCATACCTGTGGTCTCACCAGCTCAGTTCTCAGAAGAC
ATGGCAACTAAAGAAGTCAAAGGAAGCCCATGCCAGGGGAGCCATCAGCT
GGGCTGAGGTGGAGGAGATCCTGGTGCTGCTGCAGCTCCATGCAAACCTG
GATGTGCTGCTGATGGCTTCGTGGCAGGAGCTGAGTCAGTACGTGTGTGC
CTTCACCAGGGCCCTCTCGCAGCTCCCCTCGAAGCAGCTCCGGGACTCCC
AGGCCTTTTCTTTCTGCACAGCAGGGCACTGGGCCTCAGGCCAGCAAGTG
ACCAGAGATGGCTCTGGGCTCAGAGGAGTGTGGTGGCGACAAATCAGACA
GTTCAACCGGGTCAGCCCAGCTGTGGCTGACGCTGTTGTTACTGCCTTCC
CATCACCCCGCCTTTTGCAACAGGCTCTCCTGGACTGCAGCACAGAGCAA
GAACGCCTGAGCCTCCTAGCTGATCTCCCTGTGAAGGCCCACAAAGGCAA
GCAGCCTCGCAGAGTGGGGCCTGACCTCTCACGCAGAATCTGTATCTTCT
TGACAACCACCGACCCTGACCTCCTGCTGGACCTGAGCTCTTGACCTGTG
CCATCCTGGGTCACCTCCTGCCCATCAGTACAACAGGACAAGTCTGCCTA
AGAATCTAATTATTCTGAGAGGCAGGCAAGGAGGTTTGGGTCCAGCCCAT
ACCTTTTCAGACTGTGGTAGATAGACTCTGTTGCCTGATGGTCAAATGGA
AATACCATGGGAGGTGGGTGAGAGGGTAATGGAAGCTGAGGTGAATGGAA
GAGTGGAGGGTAGTGGCCACTTGGTGCAGGAGGCTTAGTAGCAGGCCTGA
GTGCCGAGTTGTACTATTACATCCTCAGAGAGAGGTGCTCAGAGATCCAA
GCCAGGCTCTCTCAAAGCCGCTGGACGAGACAGATAACCAATAGAC

>Meme2Te6    SEQ ID NO 61

MAEVGPGRVTVSRLGRGLRLGHRRPQTWEISDSDGEGVPAREVGTQAPSPAGERRAAAKALRADQVLG
RLVVCVDPAVLEDAGSDILMEALGTLGCECRIEPQHQARSLQWNVVRPDPAPSNVPLEAKAENEQEQLLLL
EPQEFLQGAAQLTQITDPPCSIPWLSPKSLTRSHLAVIGLDAYLWSHQLSSQKTWQLKKSKEAHARGAISW
AEVEEILVLLQLHANLDVLLMASWQELSQYVCAFTRALSQLPSKQLRDSQAFSFCTAGHWASGQQVTRDGS
GLRGVWWRQIRQFNRVSPAVADAVVTAFPSPRLLQQALLDCSTEQERLSLLADLPVKAHKGKQPRRVGPDL
SRRICIFLTTTDPDLLLDLSS

FIG. 12D

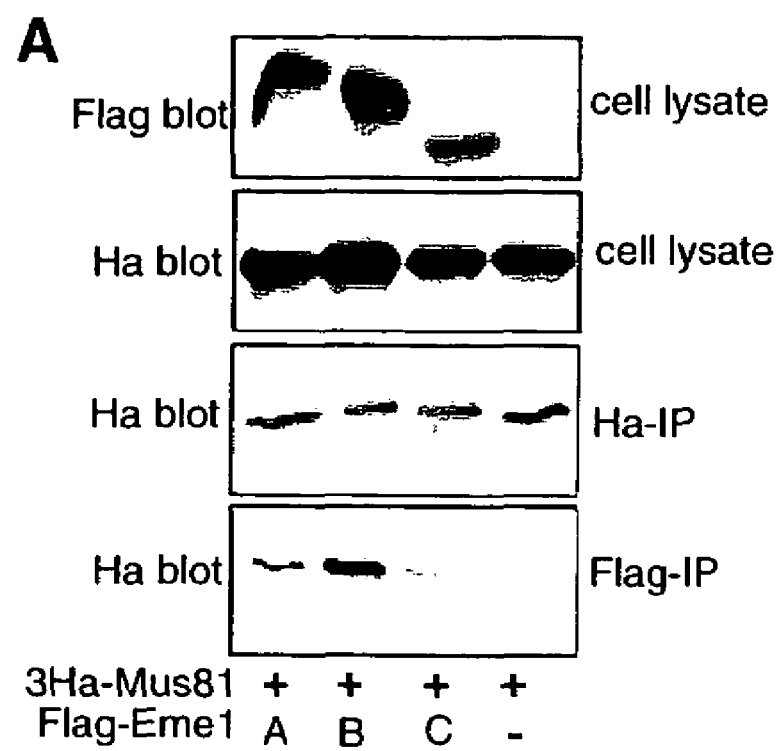
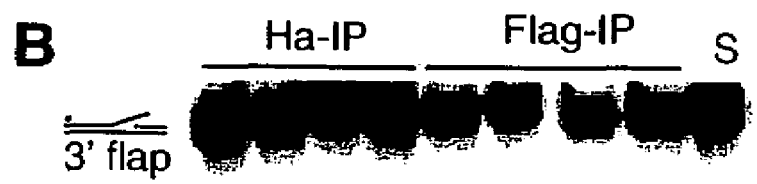
FIG. 13

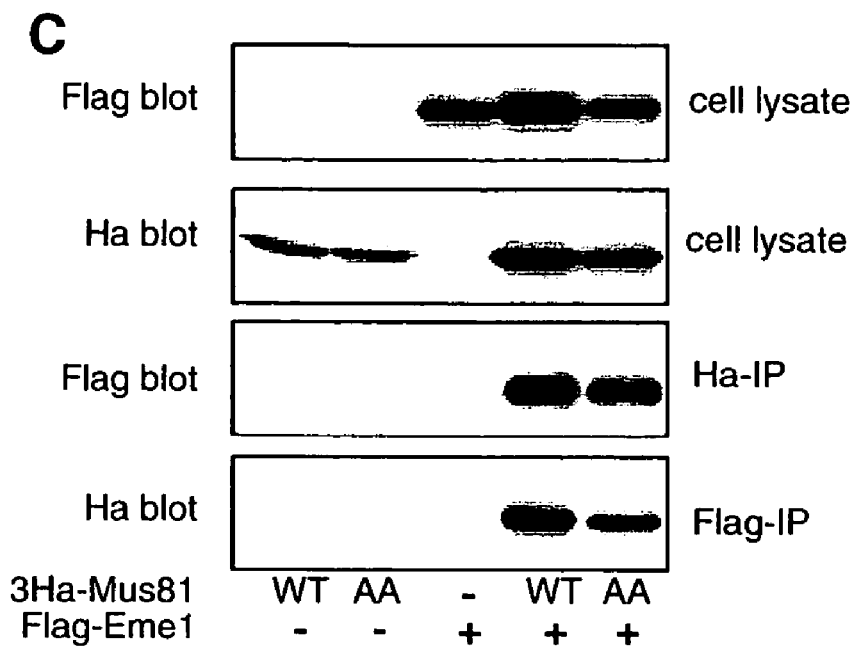
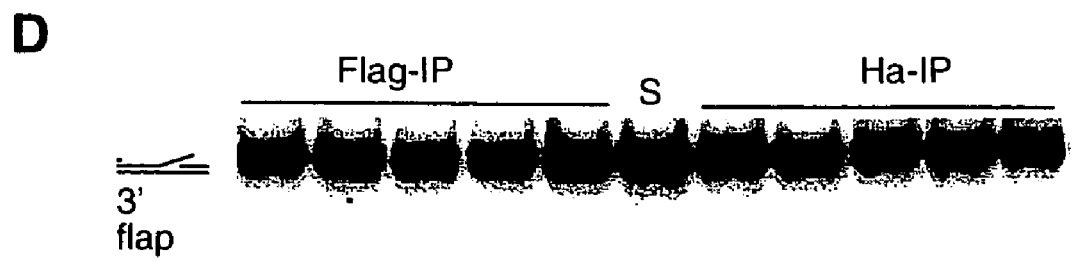
FIG. 13 Cont.

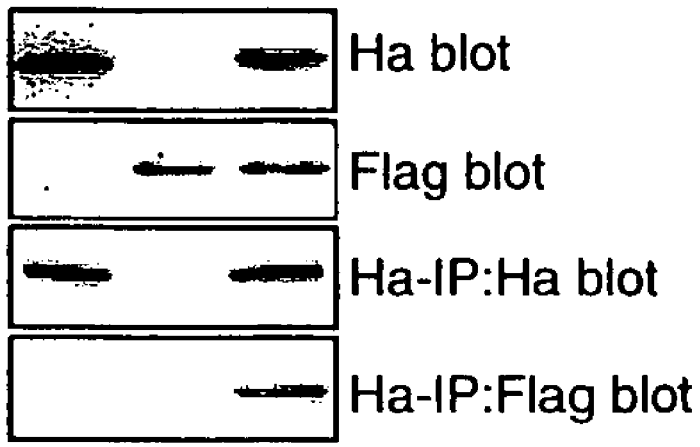
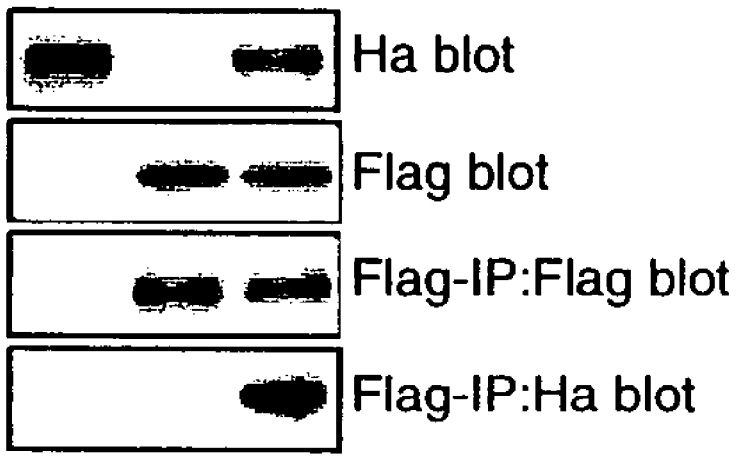
FIG. 15

SEQUENCE LISTING

<160> NUMBER OF SEQ ID NOS: 67

<210> SEQ ID NO 1
<211> LENGTH: 1693
<212> TYPE: DNA
<213> ORGANISM: Homo sapiens
<220> FEATURE:
<221> NAME/KEY: CDS
<222> LOCATION: (23)...(1675)

<400> SEQUENCE: 1

```
gatatctgca gaattcgccc tt atg gcg gcc ccg gtc cgc ctg ggc cgg aag        52
                         Met Ala Ala Pro Val Arg Leu Gly Arg Lys
                          1               5                  10 cgc ccg ctg cct gcc tgt ccc aac ccg ctc ttc gtt cgc tgg ctg acc       100
Arg Pro Leu Pro Ala Cys Pro Asn Pro Leu Phe Val Arg Trp Leu Thr
                15                  20                  25 gag tgg cgg gac gag gcg acc cgc agc agg cac cgc acg cgc ttc gta       148
Glu Trp Arg Asp Glu Ala Thr Arg Ser Arg His Arg Thr Arg Phe Val
            30                  35                  40 ttt cag aag gcg ctg cgt tcc ctc cga cgg tac cca ctg ccg ctg cgc       196
Phe Gln Lys Ala Leu Arg Ser Leu Arg Arg Tyr Pro Leu Pro Leu Arg
        45                  50                  55 agc ggg aag gaa gct aag atc cta cag cac ttc gga gac ggg ctc tgc       244
Ser Gly Lys Glu Ala Lys Ile Leu Gln His Phe Gly Asp Gly Leu Cys
    60                  65                  70 cgg atg ctg gac gag cgg ctg cag cgg cac cga aca tcg ggc ggt gac       292
Arg Met Leu Asp Glu Arg Leu Gln Arg His Arg Thr Ser Gly Gly Asp
75                  80                  85                  90 cat gcc ccg gac tca cca tct gga gag aac agt cca gcc ccg cag ggg       340
His Ala Pro Asp Ser Pro Ser Gly Glu Asn Ser Pro Ala Pro Gln Gly
                95                 100                 105 cga ctt gcg gaa gtc cag gac tct tcc atg cca gtt cct gcc cag ccc       388
Arg Leu Ala Glu Val Gln Asp Ser Ser Met Pro Val Pro Ala Gln Pro
            110                 115                 120 aaa gcg gga ggc tct ggc agc tac tgg cca gct cgg cac tca gga gcc       436
Lys Ala Gly Gly Ser Gly Ser Tyr Trp Pro Ala Arg His Ser Gly Ala
        125                 130                 135 cga gtg ata ctg ctg gtg ctc tac cgg gag cac ctg aat cct aat ggt       484
Arg Val Ile Leu Leu Val Leu Tyr Arg Glu His Leu Asn Pro Asn Gly
    140                 145                 150 cac cac ttc tta acc aag gag gag ctg ctg cag agg tgt gct cag aag       532
His His Phe Leu Thr Lys Glu Glu Leu Leu Gln Arg Cys Ala Gln Lys
155                 160                 165                 170 tcc ccc agg gta gcc cct ggg agt gcc cca ccc tgg cca gcc ctc cgc       580
Ser Pro Arg Val Ala Pro Gly Ser Ala Pro Pro Trp Pro Ala Leu Arg
                175                 180                 185 tcc ctc ctt cac agg aac ctg gtc ctc agg aca cac cag cca gcc agg       628
Ser Leu Leu His Arg Asn Leu Val Leu Arg Thr His Gln Pro Ala Arg
            190                 195                 200
```

| | | |
|---|---|---|
| tac tca ttg acc cca gag ggc ctg gag ctg gcc cag aag ttg gcc gag<br>Tyr Ser Leu Thr Pro Glu Gly Leu Glu Leu Ala Gln Lys Leu Ala Glu<br>205 210 215 | 676 | |
| tca gaa ggc ctg agc ttg ctg aat gtg ggc atc ggg ccc aag gag ccc<br>Ser Glu Gly Leu Ser Leu Leu Asn Val Gly Ile Gly Pro Lys Glu Pro<br>220 225 230 | 724 | |
| cct ggg gag gag aca gca gtg cca gga gca gct tca gca gag ctt gcc<br>Pro Gly Glu Glu Thr Ala Val Pro Gly Ala Ala Ser Ala Glu Leu Ala<br>235 240 245 250 | 772 | |
| agt gaa gca ggg gtc cag cag cag cca ctg gag ctg agg cct gga gag<br>Ser Glu Ala Gly Val Gln Gln Gln Pro Leu Glu Leu Arg Pro Gly Glu<br>255 260 265 | 820 | |
| tac agg gtg ctg ttg tgt gtg gac att ggc gag acc cgg ggc ggg<br>Tyr Arg Val Leu Leu Cys Val Asp Ile Gly Glu Thr Arg Gly Gly Gly<br>270 275 280 | 868 | |
| cac agg ccg gag ctg ctc cga gag cta cag cgg ctg cac gtg acc cac<br>His Arg Pro Glu Leu Leu Arg Glu Leu Gln Arg Leu His Val Thr His<br>285 290 295 | 916 | |
| acg gtg cgc aag ctg cac gtt gga gat ttt gtg tgg gtg gct cag gag<br>Thr Val Arg Lys Leu His Val Gly Asp Phe Val Trp Val Ala Gln Glu<br>300 305 310 | 964 | |
| acc aat cct aga gac cca gca aac cct ggg gag ttg gta ctg gat cac<br>Thr Asn Pro Arg Asp Pro Ala Asn Pro Gly Glu Leu Val Leu Asp His<br>315 320 325 330 | 1012 | |
| att gtg gag cgc aag cga ctg gat gac ctt tgc agc agc atc atc gac<br>Ile Val Glu Arg Lys Arg Leu Asp Asp Leu Cys Ser Ser Ile Ile Asp<br>335 340 345 | 1060 | |
| ggc cgc ttc cgg gag cag aag ttc cga ctg aag cgc tgt ggt ctg gag<br>Gly Arg Phe Arg Glu Gln Lys Phe Arg Leu Lys Arg Cys Gly Leu Glu<br>350 355 360 | 1108 | |
| cgc cgg gta tac ctg gtg gaa gag cat ggt tcc gtc cac aac ctc agc<br>Arg Arg Val Tyr Leu Val Glu Glu His Gly Ser Val His Asn Leu Ser<br>365 370 375 | 1156 | |
| ctt cct gag agc aca ctg ctg cag gct gtc acc aac act cag gtc att<br>Leu Pro Glu Ser Thr Leu Leu Gln Ala Val Thr Asn Thr Gln Val Ile<br>380 385 390 | 1204 | |
| gat ggc ttt ttt gtg aag cgc aca gca gac att aag gag tca gcc gcc<br>Asp Gly Phe Phe Val Lys Arg Thr Ala Asp Ile Lys Glu Ser Ala Ala<br>395 400 405 410 | 1252 | |
| tac ctg gcc ctc ttg act cgg ggc ctg cag aga ctc tac cag ggc cac<br>Tyr Leu Ala Leu Leu Thr Arg Gly Leu Gln Arg Leu Tyr Gln Gly His<br>415 420 425 | 1300 | |
| acc cta cgc agc cgc ccc tgg gga acc cct ggg aac cct gaa tca ggg<br>Thr Leu Arg Ser Arg Pro Trp Gly Thr Pro Gly Asn Pro Glu Ser Gly<br>430 435 440 | 1348 | |
| gcc atg acc tct cca aac cct ctc tgc tca ctc ctc acc ttc agt gac<br>Ala Met Thr Ser Pro Asn Pro Leu Cys Ser Leu Leu Thr Phe Ser Asp<br>445 450 455 | 1396 | |
| ttc aac gca gga gcc atc aag aat aag gcc cag tcg gtg cga gaa gtg<br>Phe Asn Ala Gly Ala Ile Lys Asn Lys Ala Gln Ser Val Arg Glu Val<br>460 465 470 | 1444 | |
| ttt gcc cgg cag ctg atg cag gtg cgc gga gtg agt ggg gag aag gca<br>Phe Ala Arg Gln Leu Met Gln Val Arg Gly Val Ser Gly Glu Lys Ala<br>475 480 485 490 | 1492 | |
| gca gcc ctg gtg gat cga tac agc acc cct gcc agc ctc ctg gcc gcc<br>Ala Ala Leu Val Asp Arg Tyr Ser Thr Pro Ala Ser Leu Leu Ala Ala<br>495 500 505 | 1540 | |
| tat gat gcc tgt gcc acc ccc aag gaa caa gag aca ctg ctg agc acc<br>Tyr Asp Ala Cys Ala Thr Pro Lys Glu Gln Glu Thr Leu Leu Ser Thr<br>510 515 520 | 1588 | |

-continued

```
att aag tgt ggg cgt cta cag agg aat ctg ggg cct gct ctg agc agg    1636
Ile Lys Cys Gly Arg Leu Gln Arg Asn Leu Gly Pro Ala Leu Ser Arg
        525                 530                 535 acc tta tcc cag ctc tac tgc agc tac ggc ccc ttg acc tgagtcaagg    1685
Thr Leu Ser Gln Leu Tyr Cys Ser Tyr Gly Pro Leu Thr
    540                 545                 550 gcgaattc                                                          1693

<210> SEQ ID NO 2
<211> LENGTH: 551
<212> TYPE: PRT
<213> ORGANISM: Homo sapiens

<400> SEQUENCE: 2

Met Ala Ala Pro Val Arg Leu Gly Arg Lys Arg Pro Leu Pro Ala Cys
 1               5                  10                  15

Pro Asn Pro Leu Phe Val Arg Trp Leu Thr Glu Trp Arg Asp Glu Ala
            20                  25                  30

Thr Arg Ser Arg His Arg Thr Arg Phe Val Phe Gln Lys Ala Leu Arg
        35                  40                  45

Ser Leu Arg Arg Tyr Pro Leu Pro Leu Arg Ser Gly Lys Glu Ala Lys
    50                  55                  60

Ile Leu Gln His Phe Gly Asp Gly Leu Cys Arg Met Leu Asp Glu Arg
65                  70                  75                  80

Leu Gln Arg His Arg Thr Ser Gly Gly Asp His Ala Pro Asp Ser Pro
                85                  90                  95

Ser Gly Glu Asn Ser Pro Ala Pro Gln Gly Arg Leu Ala Glu Val Gln
            100                 105                 110

Asp Ser Ser Met Pro Val Pro Ala Gln Pro Lys Ala Gly Gly Ser Gly
        115                 120                 125

Ser Tyr Trp Pro Ala Arg His Ser Gly Ala Arg Val Ile Leu Leu Val
    130                 135                 140

Leu Tyr Arg Glu His Leu Asn Pro Asn Gly His His Phe Leu Thr Lys
145                 150                 155                 160

Glu Glu Leu Leu Gln Arg Cys Ala Gln Lys Ser Pro Arg Val Ala Pro
                165                 170                 175

Gly Ser Ala Pro Pro Trp Pro Ala Leu Arg Ser Leu His Arg Asn
            180                 185                 190

Leu Val Leu Arg Thr His Gln Pro Ala Arg Tyr Ser Leu Thr Pro Glu
        195                 200                 205

Gly Leu Glu Leu Ala Gln Lys Leu Ala Glu Ser Glu Gly Leu Ser Leu
    210                 215                 220

Leu Asn Val Gly Ile Gly Pro Lys Glu Pro Pro Gly Glu Glu Thr Ala
225                 230                 235                 240

Val Pro Gly Ala Ala Ser Ala Glu Leu Ala Ser Glu Ala Gly Val Gln
                245                 250                 255

Gln Gln Pro Leu Glu Leu Arg Pro Gly Glu Tyr Arg Val Leu Leu Cys
            260                 265                 270

Val Asp Ile Gly Glu Thr Arg Gly Gly His Arg Pro Glu Leu Leu
        275                 280                 285

Arg Glu Leu Gln Arg Leu His Val Thr His Thr Val Arg Lys Leu His
    290                 295                 300

Val Gly Asp Phe Val Trp Val Ala Gln Glu Thr Asn Pro Arg Asp Pro
305                 310                 315                 320
```

```
Ala Asn Pro Gly Glu Leu Val Leu Asp His Ile Val Glu Arg Lys Arg
                325                 330                 335

Leu Asp Asp Leu Cys Ser Ser Ile Ile Asp Gly Arg Phe Arg Glu Gln
            340                 345                 350

Lys Phe Arg Leu Lys Arg Cys Gly Leu Glu Arg Val Tyr Leu Val
        355                 360                 365

Glu Glu His Gly Ser Val His Asn Leu Ser Leu Pro Glu Ser Thr Leu
    370                 375                 380

Leu Gln Ala Val Thr Asn Thr Gln Val Ile Asp Gly Phe Phe Val Lys
385                 390                 395                 400

Arg Thr Ala Asp Ile Lys Glu Ser Ala Ala Tyr Leu Ala Leu Leu Thr
                405                 410                 415

Arg Gly Leu Gln Arg Leu Tyr Gln Gly His Thr Leu Arg Ser Arg Pro
            420                 425                 430

Trp Gly Thr Pro Gly Asn Pro Glu Ser Gly Ala Met Thr Ser Pro Asn
        435                 440                 445

Pro Leu Cys Ser Leu Leu Thr Phe Ser Asp Phe Asn Ala Gly Ala Ile
    450                 455                 460

Lys Asn Lys Ala Gln Ser Val Arg Glu Val Phe Ala Arg Gln Leu Met
465                 470                 475                 480

Gln Val Arg Gly Val Ser Gly Glu Lys Ala Ala Ala Leu Val Asp Arg
                485                 490                 495

Tyr Ser Thr Pro Ala Ser Leu Leu Ala Ala Tyr Asp Ala Cys Ala Thr
            500                 505                 510

Pro Lys Glu Gln Glu Thr Leu Leu Ser Thr Ile Lys Cys Gly Arg Leu
        515                 520                 525

Gln Arg Asn Leu Gly Pro Ala Leu Ser Arg Thr Leu Ser Gln Leu Tyr
    530                 535                 540

Cys Ser Tyr Gly Pro Leu Thr
545                 550

<210> SEQ ID NO 3
<211> LENGTH: 2462
<212> TYPE: DNA
<213> ORGANISM: Homo sapiens

<400> SEQUENCE: 3
gcggccgcag gctctcttct cgttagtgcc cctgtgtttt ggggcccccgt gatctcaacg    60 gtcctgccct cggtctccct cttccccccgc ccgccctgg gccaggtgtt cgaatcccga   120
ctccagaact ggcggcgtcc cagtcccgcg ggcgtggagc gcggaggac ccgccctcgg    180 gctcatggcg gccccggtcc gcctgggccg aagcgcccg ctgcctgcct gtcccaaccc    240
gctcttcgtt cgctggctga ccgagtggcg ggacgaggcg acccgcagca ggcaccgcac   300
gcgcttcgta tttcagaagg cgctgcgttc cctccgacgg tacccactgc cgctgcgcag   360
cgggaaggaa gctaagatcc tacagcactt cggagacggg ctctgccgga tgctggacga   420
gcggctgcag cggcaccgaa catcgggcgg tgaccatgcc ccggactcac catctggaga   480
gaacagtcca gccccgcagg ggcgacttgc ggaagtccag gactcttcca tgccagttcc   540
tgcccagccc aaagcgggag gctctggcag ctactggcca gctcggcact caggagcccg   600
agtgatactg ctggtgctct accgggagca cctgaatcct aatggtcacc acttcttaac   660
caaggaggag ctgctgcaga ggtgtgctca gaagtcccccc agggtagccc ctgggagtgc   720
cccaccctgg ccagccctcc gctccctcct tcacaggaac ctggtcctca ggacacacca   780
```

-continued

```
gccagccagg tactcattga ccccagaggg cctggagctg cccagaagt tggccgagtc      840 agaaggcctg agcttgctga atgtgggcat cgggcccaag gagcccctg gggaggagac      900 agcagtgcca ggagcagctt cagcagagct tgccagtgaa gcagggtcc agcagcagcc      960 actggagctg aggcctggag agtacagggt gctgttgtgt gtggacattg gcgagacccg     1020
ggggggcggg cacaggccgg agctgctccg agagctacag cggctgcacg tgacccacac     1080
ggtgcgcaag ctgcacgttg agattttgt gtgggtggct caggagacca atcctagaga     1140
cccagcaaac cctggggagt tggtactgga tcacattgtg gagcgcaagc gactggatga     1200
cctttgcagc agcatcatcg acggccgctt ccgggagcag aagttccgac tgaagcgctg     1260
tggtctggag cgccgggtat acctggtgga agagcatggt tccgtccaca acctcagctt     1320
tcttgagagc acacttgtgc aggctgtcac caacactcag gtcattgatg cttttttgt      1380 gaagcgcaca gcagacatta aggagtcagc cgcctacctg gccctcttga ctcggggcct     1440
gcagagactc taccaggtga gcagaggccc ctttcccagt gtcgggacag agcccacaag     1500
gaattcacct tgcctgggcc ctgtgcatcc ccaaaagaag caaggtgggt gagatcccca     1560
tttctcaggc tggccccca aggctgagga ctgggcaggg gctggctgga gttgttcctt      1620
cgagctccag cctggcctca gtccttcttc cctcagggc cacaccctac gcagccgccc     1680
ctggggaacc cctgggaacc ctgaatcagg ggccatgacc tctccaaacc ctctctgctc     1740
actcctcacc ttcagtgact tcaacgcagg agccatcaag aataaggccc agtcggtgcg     1800
agaagtgttt gccggcagc tgatgcaggt gcgcggagtg agtggggaga aggcagcagc      1860
cctggtggat cgatacagca cccctgccag cctcctggcc gcctatgatg cctgtgccac     1920
ccccaaggaa caagagacac tgctgagcac cattaagtgt gggcgtctac agaggaatct     1980
ggggcctgct ctgagcagga ccttatccca gctctactgc agctacggcc ccttgacctg     2040
agcttatgcc gtgaaacagc ccccagcccc cgtctgtccc ccaacccagg ctagccagcc     2100 tttttaacaac atctttggg gtacaattag aatctaagtg tttgcagcca tatgtgtcat     2160
gtagaagatg cctagccctg ggaccttgt gaaatacgca ggaaccaggg ataccatctg      2220
gtccagtggt ttttaaacaa agctgcttag cacctggaat tccctggtca gggagatgga     2280
gtcagtgggg cattgcagct tggaatctat tttatgtcac cagttggtcc tcatcaaata     2340
aaatttcctt aggagtgcag agggctcatt gggaaaataa aaataataaa aataaataaa     2400
acttcctaaa agaaaagatt gaaaaccaaa aaaaaaaaa aaaaaaacct cgtgccgaat      2460
tc                                                                    2462
```

<210> SEQ ID NO 4
<211> LENGTH: 455
<212> TYPE: PRT
<213> ORGANISM: Homo sapiens

<400> SEQUENCE: 4

```
Met Ala Ala Pro Val Arg Leu Gly Arg Lys Arg Pro Leu Pro Ala Cys
 1               5                  10                  15

Pro Asn Pro Leu Phe Val Arg Trp Leu Thr Glu Trp Arg Asp Glu Ala
                20                  25                  30

Thr Arg Ser Arg His Arg Thr Arg Phe Val Phe Gln Lys Ala Leu Arg
            35                  40                  45

Ser Leu Arg Arg Tyr Pro Leu Pro Leu Arg Ser Gly Lys Glu Ala Lys
        50                  55                  60

Ile Leu Gln His Phe Gly Asp Gly Leu Cys Arg Met Leu Asp Glu Arg
```

```
                 65                  70                  75                  80
Leu Gln Arg His Arg Thr Ser Gly Gly Asp His Ala Pro Asp Ser Pro
                 85                  90                  95
Ser Gly Glu Asn Ser Pro Ala Pro Gln Gly Arg Leu Ala Glu Val Gln
                100                 105                 110
Asp Ser Ser Met Pro Val Pro Ala Gln Pro Lys Ala Gly Ser Gly
            115                 120                 125
Ser Tyr Trp Pro Ala Arg His Ser Gly Ala Arg Val Ile Leu Leu Val
        130                 135                 140
Leu Tyr Arg Glu His Leu Asn Pro Asn Gly His His Phe Leu Thr Lys
145                 150                 155                 160
Glu Glu Leu Leu Gln Arg Cys Ala Gln Lys Ser Pro Arg Val Ala Pro
                165                 170                 175
Gly Ser Ala Pro Pro Trp Pro Ala Leu Arg Ser Leu Leu His Arg Asn
            180                 185                 190
Leu Val Leu Arg Thr His Gln Pro Ala Arg Tyr Ser Leu Thr Pro Glu
        195                 200                 205
Gly Leu Glu Leu Ala Gln Lys Leu Ala Glu Ser Glu Gly Leu Ser Leu
    210                 215                 220
Leu Asn Val Gly Ile Gly Pro Lys Glu Pro Gly Glu Glu Thr Ala
225                 230                 235                 240
Val Pro Gly Ala Ala Ser Ala Glu Leu Ala Ser Glu Ala Gly Val Gln
                245                 250                 255
Gln Gln Pro Leu Glu Leu Arg Pro Gly Glu Tyr Arg Val Leu Leu Cys
            260                 265                 270
Val Asp Ile Gly Glu Thr Arg Gly Gly His Arg Pro Glu Leu Leu
        275                 280                 285
Arg Glu Leu Gln Arg Leu His Val Thr His Thr Val Arg Lys Leu His
    290                 295                 300
Val Gly Asp Phe Val Trp Val Ala Gln Glu Thr Asn Pro Arg Asp Pro
305                 310                 315                 320
Ala Asn Pro Gly Glu Leu Val Leu Asp His Ile Val Glu Arg Lys Arg
                325                 330                 335
Leu Asp Asp Leu Cys Ser Ser Ile Ile Asp Gly Arg Phe Arg Glu Gln
            340                 345                 350
Lys Phe Arg Leu Lys Arg Cys Gly Leu Glu Arg Arg Val Tyr Leu Val
        355                 360                 365
Glu Glu His Gly Ser Val His Asn Leu Ser Phe Leu Glu Ser Thr Leu
    370                 375                 380
Val Gln Ala Val Thr Asn Thr Gln Val Ile Asp Gly Phe Phe Val Lys
385                 390                 395                 400
Arg Thr Ala Asp Ile Lys Glu Ser Ala Ala Tyr Leu Ala Leu Leu Thr
                405                 410                 415
Arg Gly Leu Gln Arg Leu Tyr Gln Val Ser Arg Gly Pro Phe Pro Ser
            420                 425                 430
Val Gly Thr Glu Pro Thr Arg Asn Ser Pro Cys Leu Gly Pro Val His
        435                 440                 445
Pro Gln Lys Lys Gln Gly Gly
    450                 455

<210> SEQ ID NO 5
<211> LENGTH: 1598
<212> TYPE: DNA
<213> ORGANISM: Homo sapiens
```

<400> SEQUENCE: 5

```
gatatctgca gaattcgccc ttgacatggc ggccccggtc cgcctgggcc ggaagcgccc      60
gctgcctgcc tgtcccaacc cgctcttcgt tcgctggctg accgagtggc gggacgaggc     120
gacccgcagc aggcgccgca cgcgcttcgt atttcagaag gcgctgcgtt ccctccgacg     180
gtacccactg ccgctgcgca gcgggaagga agctaagatc ctacagcact cggagacgg      240
gctctgccgg atgctggacg agcggctgca gcggaccga acatcgggcg gtgaccatgc     300
cccggactca ccatctggag agaacagtcc agccccgcag gggcgacttg cggaagtcca     360
ggactcttcc atgccagttc ctgcccagcc caaagcggga ggctctggca gctactggcc     420
agctcggcac tcaggagccc gagtgatact gctggtgctc taccgggagc acctgaatcc     480
taatggtcac cacttcttaa ccaaggagga gctgctgcag aggtgtgctc agaagtcccc     540
cagggtagcc cctgggagtg ctcgaccctg ccagccctc cgctccctcc ttcacaggaa      600
cctggtcctc aggacacacc agccagccag gtactcattg accccagagg gcctggagct     660
ggcccagaag ttggccgagt cagaaggcct gagcttgctg aatgtgggca tcggccccaa     720
ggagccccct ggggaggaga cagcagtgcc aggagcagct tcagcagagc ttgccagtga     780
agcaggggtc cagcagcagc cactggagct gaggcctgga gagtacaggg tgctgttgtg     840
tgtggacatt ggcgagaccc ggggggggcgg gcacaggccg gagctgctcc gagagctaca     900
gcggctgcac gtgacccaca cggtgcgcaa gctgcacgtt ggagattttg tgtgggtggc     960
ccaggagacc aatcctagag acccagcaaa ccctggggag ttggtactgg atcacattgt    1020
ggagcgcaag cgactggatg acctttgcag cagcatcatc gacggccgct tccgggagca    1080
gaagttccgg ctgaagcgct gtggtctgga gcgccgggta tacctggtgg aagagcatgg    1140
ttccgtccac aacctcagcc ttcctgagag cacactgctg caggctgtca ccaacactca    1200
ggtcattgat ggcttttttg tgaagcgcac agcagacatt aaggagtcag ccgcctacct    1260
ggccctcttg acgcgggggcc tgcagagact ctaccagtga cttcaacgca ggagccatca    1320
agaataaggc ccagtcggtg cgagaagtgt ttgcccggca gctgatgcag gtgcgcggag    1380
tgagtgggga gaaggcagca gcccctggtgg atcgatacag caccccctgcc agcctcctgg    1440
ccgcctatga tgcctgtgcc accccccaagg aacaagagac actgctgagc accattaagt    1500
gtgggcgtct acagaggaat ctggggcctg ctctgagcag gaccttatcc cagctctact    1560
gcagctacgg ccccttgacc tgagtcaagg gcgaattc                            1598
```

<210> SEQ ID NO 6
<211> LENGTH: 424
<212> TYPE: PRT
<213> ORGANISM: Homo sapiens

<400> SEQUENCE: 6

```
Met Ala Ala Pro Val Arg Leu Gly Arg Lys Arg Pro Leu Pro Ala Cys
  1               5                  10                  15

Pro Asn Pro Leu Phe Val Arg Trp Leu Thr Glu Trp Arg Asp Glu Ala
             20                  25                  30

Thr Arg Ser Arg Arg Arg Thr Arg Phe Val Phe Gln Lys Ala Leu Arg
         35                  40                  45

Ser Leu Arg Arg Tyr Pro Leu Pro Leu Arg Ser Gly Lys Glu Ala Lys
     50                  55                  60

Ile Leu Gln His Phe Gly Asp Gly Leu Cys Arg Met Leu Asp Glu Arg
 65                  70                  75                  80
```

```
Leu Gln Arg His Arg Thr Ser Gly Gly Asp His Ala Pro Asp Ser Pro
                85                  90                  95

Ser Gly Glu Asn Ser Pro Ala Pro Gln Gly Arg Leu Ala Glu Val Gln
            100                 105                 110

Asp Ser Ser Met Pro Val Pro Ala Gln Pro Lys Ala Gly Ser Gly
        115                 120                 125

Ser Tyr Trp Pro Ala Arg His Ser Gly Ala Arg Val Ile Leu Leu Val
130                 135                 140

Leu Tyr Arg Glu His Leu Asn Pro Asn Gly His His Phe Leu Thr Lys
145                 150                 155                 160

Glu Glu Leu Leu Gln Arg Cys Ala Gln Lys Ser Pro Arg Val Ala Pro
                165                 170                 175

Gly Ser Ala Arg Pro Trp Pro Ala Leu Arg Ser Leu Leu His Arg Asn
            180                 185                 190

Leu Val Leu Arg Thr His Gln Pro Ala Arg Tyr Ser Leu Thr Pro Glu
        195                 200                 205

Gly Leu Glu Leu Ala Gln Lys Leu Ala Glu Ser Glu Gly Leu Ser Leu
210                 215                 220

Leu Asn Val Gly Ile Gly Pro Lys Glu Pro Pro Gly Glu Glu Thr Ala
225                 230                 235                 240

Val Pro Gly Ala Ala Ser Ala Glu Leu Ala Ser Glu Ala Gly Val Gln
                245                 250                 255

Gln Gln Pro Leu Glu Leu Arg Pro Gly Glu Tyr Arg Val Leu Leu Cys
            260                 265                 270

Val Asp Ile Gly Glu Thr Arg Gly Gly His Arg Pro Glu Leu Leu
        275                 280                 285

Arg Glu Leu Gln Arg Leu His Val Thr His Thr Val Arg Lys Leu His
290                 295                 300

Val Gly Asp Phe Val Trp Val Ala Gln Glu Thr Asn Pro Arg Asp Pro
305                 310                 315                 320

Ala Asn Pro Gly Glu Leu Val Leu Asp His Ile Val Glu Arg Lys Arg
                325                 330                 335

Leu Asp Asp Leu Cys Ser Ser Ile Ile Asp Gly Arg Phe Arg Glu Gln
            340                 345                 350

Lys Phe Arg Leu Lys Arg Cys Gly Leu Glu Arg Arg Val Tyr Leu Val
        355                 360                 365

Glu Glu His Gly Ser Val His Asn Leu Ser Leu Pro Glu Ser Thr Leu
370                 375                 380

Leu Gln Ala Val Thr Asn Thr Gln Val Ile Asp Gly Phe Phe Val Lys
385                 390                 395                 400

Arg Thr Ala Asp Ile Lys Glu Ser Ala Ala Tyr Leu Ala Leu Leu Thr
                405                 410                 415

Arg Gly Leu Gln Arg Leu Tyr Gln
            420

<210> SEQ ID NO 7
<211> LENGTH: 1699
<212> TYPE: DNA
<213> ORGANISM: Homo sapiens

<400> SEQUENCE: 7
gatatctgca gaattcgccc ttgacatggc ggccccggtc cgcctgggcc ggaagcgccc        60
gctgcctgcc tgtcccaacc cgctcttcgt tcgctggctg accgagtggc gggacgaggc       120
```

```
gacccgcagc aggcgccgca cgcgcttcgt atttcagaag gcgctgcgtt ccctccgacg      180
gtacccactg ccgctgcgca gcgggaagga agctaagatc ctacagcact tcggagacgg      240
gctctgccgg atgctggacg agcggctgca gcggcaccga catcgggcg gtgaccatgc       300
cccggactca ccatctggag agaacagtcc agccccgcag gggcgacttg cggaagtcca      360
ggactcttcc atgccagttc ctgcccagcc caaagcggga ggctctggca gctactggcc      420
agctcggcac tcaggagccc gagtgatact gctggtgctc taccgggagc acctgaatcc      480
taatggtcac cacttcttaa ccaaggagga gctgctgcag aggtgtgctc agaagtcccc      540
cagggtagcc cctgggagtg ctcgaccctg ccagccctc cgctccctcc ttcacaggaa       600
cctggtcctc aggacacacc agccagccag gtactcattg accccagagg gcctggagct      660
ggcccagaag ttggccgagt cagaaggcct gagcttgctg aatgtgggca tcgggcccaa      720
ggagcccccct ggggaggaga cagcagtgcc aggagcagct tcagcagagc ttgccagtga    780
agcaggggtc cagcagcagc cactggagct gaggcctgga gagtacaggg tgctgttgtg      840
tgtggacatt ggcgagaccc gggggggcgg gcacaggccg gagctgctcc gagagctaca     900
gcggctgcac gtgacccaca cggtgcgcaa gctgcacgtt ggagattttg tgtgggtggc      960
ccaggagacc aatcctagag acccagcagc aaaccctggg gagttggtac tggatcacat    1020
tgtggagcgc aagcgactgg atgacctttg cagcagcatc atcgacggcc gcttccggga    1080
gcagaagttc cggctgaagc gctgtggtct ggagcgccgg gtatacctgg tggaagagca    1140
tggttccgtc cacaacctca gccttcctga gagcacactg ctgcaggctg tcaccaacac    1200
tcaggtcatt gatggctttt tgtgaagcg cacagcagac attaaggagt cagccgccta     1260
cctggccctc ttgacgcggg gcctgcagag actctaccag gccacaccc tacgcagccg      1320
cccctgggga acccctggga acctgaatc aggggccatg acctctccaa accctctctg     1380
ctcactcctc accttcagtg acttcaacgc aggagccatc aagaataagg cccagtcggt    1440
gcgagaagtg tttgcccggc agctgatgca ggtgcgcgga gtgagtgggg agaaggcagc    1500
agccctggtg gatcgataca gcaccccctgc cagcctcctg gccgcctatg atgcctgtgc    1560
cacccccaag gaacaagaga cactgctgag caccattaag tgtgggcgtc tacagaggaa    1620
tctggggcct gctctgagca ggaccttatc ccagctctac tgcagctacg gccccttgac    1680
ctgagtcaag ggcgaattc                                                  1699
```

<210> SEQ ID NO 8
<211> LENGTH: 552
<212> TYPE: PRT
<213> ORGANISM: Homo sapiens

<400> SEQUENCE: 8

```
Met Ala Ala Pro Val Arg Leu Gly Arg Lys Arg Pro Leu Pro Ala Cys
 1               5                  10                  15

Pro Asn Pro Leu Phe Val Arg Trp Leu Thr Glu Trp Arg Asp Glu Ala
                20                  25                  30

Thr Arg Ser Arg Arg Thr Arg Phe Val Phe Gln Lys Ala Leu Arg
            35                  40                  45

Ser Leu Arg Arg Tyr Pro Leu Pro Leu Arg Ser Gly Lys Glu Ala Lys
        50                  55                  60

Ile Leu Gln His Phe Gly Asp Gly Leu Cys Arg Met Leu Asp Glu Arg
65                  70                  75                  80

Leu Gln Arg His Arg Thr Ser Gly Gly Asp His Ala Pro Asp Ser Pro
                85                  90                  95
```

```
Ser Gly Glu Asn Ser Pro Ala Pro Gln Gly Arg Leu Ala Glu Val Gln
            100                 105                 110

Asp Ser Ser Met Pro Val Pro Ala Gln Pro Lys Ala Gly Gly Ser Gly
            115                 120                 125

Ser Tyr Trp Pro Ala Arg His Ser Gly Ala Arg Val Ile Leu Leu Val
            130                 135                 140

Leu Tyr Arg Glu His Leu Asn Pro Asn Gly His His Phe Leu Thr Lys
145                 150                 155                 160

Glu Glu Leu Leu Gln Arg Cys Ala Gln Lys Ser Pro Arg Val Ala Pro
                165                 170                 175

Gly Ser Ala Arg Pro Trp Pro Ala Leu Arg Ser Leu Leu His Arg Asn
            180                 185                 190

Leu Val Leu Arg Thr His Gln Pro Ala Arg Tyr Ser Leu Thr Pro Glu
            195                 200                 205

Gly Leu Glu Leu Ala Gln Lys Leu Ala Glu Ser Glu Gly Leu Ser Leu
        210                 215                 220

Leu Asn Val Gly Ile Gly Pro Lys Glu Pro Pro Gly Glu Glu Thr Ala
225                 230                 235                 240

Val Pro Gly Ala Ala Ser Ala Glu Leu Ala Ser Glu Ala Gly Val Gln
                245                 250                 255

Gln Gln Pro Leu Glu Leu Arg Pro Gly Glu Tyr Arg Val Leu Leu Cys
            260                 265                 270

Val Asp Ile Gly Glu Thr Arg Gly Gly His Arg Pro Glu Leu Leu
            275                 280                 285

Arg Glu Leu Gln Arg Leu His Val Thr His Thr Val Arg Lys Leu His
        290                 295                 300

Val Gly Asp Phe Val Trp Val Ala Gln Glu Thr Asn Pro Arg Asp Pro
305                 310                 315                 320

Ala Ala Asn Pro Gly Glu Leu Val Leu Asp His Ile Val Glu Arg Lys
                325                 330                 335

Arg Leu Asp Asp Leu Cys Ser Ser Ile Ile Asp Gly Arg Phe Arg Glu
            340                 345                 350

Gln Lys Phe Arg Leu Lys Arg Cys Gly Leu Glu Arg Arg Val Tyr Leu
        355                 360                 365

Val Glu Glu His Gly Ser Val His Asn Leu Ser Leu Pro Glu Ser Thr
370                 375                 380

Leu Leu Gln Ala Val Thr Asn Thr Gln Val Ile Asp Gly Phe Phe Val
385                 390                 395                 400

Lys Arg Thr Ala Asp Ile Lys Glu Ser Ala Ala Tyr Leu Ala Leu Leu
                405                 410                 415

Thr Arg Gly Leu Gln Arg Leu Tyr Gln Gly His Thr Leu Arg Ser Arg
            420                 425                 430

Pro Trp Gly Thr Pro Gly Asn Pro Glu Ser Gly Ala Met Thr Ser Pro
        435                 440                 445

Asn Pro Leu Cys Ser Leu Leu Thr Phe Ser Asp Phe Asn Ala Gly Ala
        450                 455                 460

Ile Lys Asn Lys Ala Gln Ser Val Arg Glu Val Phe Ala Arg Gln Leu
465                 470                 475                 480

Met Gln Val Arg Gly Val Ser Gly Glu Lys Ala Ala Leu Val Asp
                485                 490                 495

Arg Tyr Ser Thr Pro Ala Ser Leu Leu Ala Ala Tyr Asp Ala Cys Ala
            500                 505                 510
```

```
                Thr Pro Lys Glu Gln Glu Thr Leu Leu Ser Thr Ile Lys Cys Gly Arg
                        515                 520                 525

Leu Gln Arg Asn Leu Gly Pro Ala Leu Ser Arg Thr Leu Ser Gln Leu
                        530                 535                 540

Tyr Cys Ser Tyr Gly Pro Leu Thr
                545                 550

<210> SEQ ID NO 9
<211> LENGTH: 2343
<212> TYPE: DNA
<213> ORGANISM: Homo sapiens
<220> FEATURE:
<221> NAME/KEY: CDS
<222> LOCATION: (74)...(1825)

<400> SEQUENCE: 9
acttccgggc cctgcgtggc agttgaaaga gtggcgggag aagttgcagg gaattatttg        60
atagcacata ctg atg gct cta aag aag tca tca ccc tca ctg gat tct         109
            Met Ala Leu Lys Lys Ser Ser Pro Ser Leu Asp Ser
              1               5                  10 ggt gat agt gac tct gag gag ttg cca aca ttt gcc ttt ctg aag aag        157
Gly Asp Ser Asp Ser Glu Glu Leu Pro Thr Phe Ala Phe Leu Lys Lys
         15                  20                  25 gaa cca tct tca aca aag agg aga cag cct gaa agg gaa gag aag att        205
Glu Pro Ser Ser Thr Lys Arg Arg Gln Pro Glu Arg Glu Glu Lys Ile
 30                  35                  40 gta gtg gtt gac atc tca gat tgt gaa gcc tcc tgt cct cca gca cca        253
Val Val Val Asp Ile Ser Asp Cys Glu Ala Ser Cys Pro Pro Ala Pro
 45                  50                  55                  60 gag tta ttt tca cca cct gtc cca gac ata gct gaa act gtc aca caa        301
Glu Leu Phe Ser Pro Pro Val Pro Asp Ile Ala Glu Thr Val Thr Gln
                 65                  70                  75 aca cag cca gtc agg ttg cta agc agt gaa agt gaa gat gaa gaa gaa        349
Thr Gln Pro Val Arg Leu Leu Ser Ser Glu Ser Glu Asp Glu Glu Glu
             80                  85                  90 ttt att cct ctg gct caa agg ctt aca tgt aag ttt ctg acc cac aag        397
Phe Ile Pro Leu Ala Gln Arg Leu Thr Cys Lys Phe Leu Thr His Lys
         95                 100                 105 caa ctg agc cct gag gac tct agc tcc cca gtt aaa agt gtt ttg gat        445
Gln Leu Ser Pro Glu Asp Ser Ser Ser Pro Val Lys Ser Val Leu Asp
110                 115                 120 cat caa aat aat gaa ggt gca tca tgt gac tgg aaa aag ccc ttt cca        493
His Gln Asn Asn Glu Gly Ala Ser Cys Asp Trp Lys Lys Pro Phe Pro
125                 130                 135                 140 aag atc cct gaa gtt ccc ctc cat gat acc cca gag agg agt gca gca        541
Lys Ile Pro Glu Val Pro Leu His Asp Thr Pro Glu Arg Ser Ala Ala
                145                 150                 155 gat aac aag gac ctg atc tta gat cca tgc tgt cag ctt cca gcc tac        589
Asp Asn Lys Asp Leu Ile Leu Asp Pro Cys Cys Gln Leu Pro Ala Tyr
            160                 165                 170 ctg tct acc tgc cct ggc cag agc agc agc ttg gca gta acc aaa aca        637
Leu Ser Thr Cys Pro Gly Gln Ser Ser Ser Leu Ala Val Thr Lys Thr
        175                 180                 185 aat tct gac atc ctt cca ccc cag aag aaa acc aag ccg agt cag aag        685
Asn Ser Asp Ile Leu Pro Pro Gln Lys Lys Thr Lys Pro Ser Gln Lys
    190                 195                 200 gtc cag gga aga ggt tca cac gga tgc cgg cag cag aga caa gca agg        733
Val Gln Gly Arg Gly Ser His Gly Cys Arg Gln Gln Arg Gln Ala Arg
205                 210                 215                 220 cag aag gaa agc acc ctg aga aga cag gaa aga aag aat gca gca ctg        781
```

```
Gln Lys Glu Ser Thr Leu Arg Arg Gln Glu Arg Lys Asn Ala Ala Leu
            225                 230                 235 gtt acc agg atg aaa gcc cag agg cca gag gaa tgc tta aaa cac atc      829
Val Thr Arg Met Lys Ala Gln Arg Pro Glu Glu Cys Leu Lys His Ile
            240                 245                 250 att gta gtg ctg gat cca gtg ctc tta cag atg gaa ggt ggg ggc cag      877
Ile Val Val Leu Asp Pro Val Leu Leu Gln Met Glu Gly Gly Gly Gln
            255                 260                 265 ctc cta gga gca ctg cag acc atg gag tgc cgc tgt gtg att gag gcg      925
Leu Leu Gly Ala Leu Gln Thr Met Glu Cys Arg Cys Val Ile Glu Ala
            270                 275                 280 cag gct gtg cct tgc agt gtc act tgg agg aga agg gct ggg ccg tct      973
Gln Ala Val Pro Cys Ser Val Thr Trp Arg Arg Arg Ala Gly Pro Ser
285                 290                 295                 300 gag gac aga gag gac tgg gtg gag gag cca aca gta ctg gtg ttg ctc     1021
Glu Asp Arg Glu Asp Trp Val Glu Glu Pro Thr Val Leu Val Leu Leu
                305                 310                 315 cgg gca gag gca ttt gtg tcc atg atc gac aat gga aag cag gga agc     1069
Arg Ala Glu Ala Phe Val Ser Met Ile Asp Asn Gly Lys Gln Gly Ser
            320                 325                 330 ctg gac agc act atg aaa ggg aag gaa acg ctt cag ggc ttt gta act     1117
Leu Asp Ser Thr Met Lys Gly Lys Glu Thr Leu Gln Gly Phe Val Thr
            335                 340                 345 gac atc aca gca aag aca gca ggg aaa gct ctg tca ctg gtg att gtg     1165
Asp Ile Thr Ala Lys Thr Ala Gly Lys Ala Leu Ser Leu Val Ile Val
350                 355                 360 gat cag gag aaa tgc ttc agc ctg gag ctg ctg ttc ttt gat ttc ctc     1213
Asp Gln Glu Lys Cys Phe Ser Leu Glu Leu Leu Phe Phe Asp Phe Leu
365                 370                 375                 380 ccc tgc acc agt gct cag aat cct cca aga aga ggg aaa cag gga gca     1261
Pro Cys Thr Ser Ala Gln Asn Pro Pro Arg Arg Gly Lys Gln Gly Ala
                385                 390                 395 aat aaa cag acc aag aag cag cag cag aga caa cca gag gcc agc ata     1309
Asn Lys Gln Thr Lys Lys Gln Gln Gln Arg Gln Pro Glu Ala Ser Ile
            400                 405                 410 ggg tcc atg gta tcc agg gta gac gct gaa gag gca ttg gtg gat ctg     1357
Gly Ser Met Val Ser Arg Val Asp Ala Glu Glu Ala Leu Val Asp Leu
            415                 420                 425 cag cta cac aca gaa gcc cag gct caa att gtg cag agc tgg aaa gag     1405
Gln Leu His Thr Glu Ala Gln Ala Gln Ile Val Gln Ser Trp Lys Glu
            430                 435                 440 ctg gcc gac ttc aca tgc gca ttc aca aag gct gtg gct gag gcg ccc     1453
Leu Ala Asp Phe Thr Cys Ala Phe Thr Lys Ala Val Ala Glu Ala Pro
445                 450                 455                 460 ttc aag aag ctc cga gat gaa act acc ttc tcc ttc tgt ctg gag agt     1501
Phe Lys Lys Leu Arg Asp Glu Thr Thr Phe Ser Phe Cys Leu Glu Ser
                465                 470                 475 gac tgg gct gga ggg gtg aag gtg gac ctt gct ggc agg gga ctc gca     1549
Asp Trp Ala Gly Gly Val Lys Val Asp Leu Ala Gly Arg Gly Leu Ala
            480                 485                 490 cta gtc tgg agg aga cag att cag cag ctg aac cga gtc agc ctg gaa     1597
Leu Val Trp Arg Arg Gln Ile Gln Gln Leu Asn Arg Val Ser Leu Glu
            495                 500                 505 atg gcc agt gca gtt gtg aat gcc tat ccc tcc cca cag ctc ctg gta     1645
Met Ala Ser Ala Val Val Asn Ala Tyr Pro Ser Pro Gln Leu Leu Val
            510                 515                 520 cag gct tat cag cag tgt ttt tcg gat aaa gaa cgc cag aat ttg ctc     1693
Gln Ala Tyr Gln Gln Cys Phe Ser Asp Lys Glu Arg Gln Asn Leu Leu
525                 530                 535                 540
```

-continued

```
gca gac ata cag gtg cgc cgt ggg gaa ggt gtg aca tcc act tct cgc    1741
Ala Asp Ile Gln Val Arg Arg Gly Glu Gly Val Thr Ser Thr Ser Arg
            545                 550                 555 cgc att gga cca gaa cta tcc agg cgt atc tac ctt cag atg acc act    1789
Arg Ile Gly Pro Glu Leu Ser Arg Arg Ile Tyr Leu Gln Met Thr Thr
            560                 565                 570 tta cag cca cat ctc tct tta gat agt gct gac tga ttctagccct         1835
Leu Gln Pro His Leu Ser Leu Asp Ser Ala Asp *
            575                 580 cagggatgag gatgaaaagc tggaaacttc cacttcccca acctcagagc ctgactgtaa   1895
tgaagagact ggcagcacct cctggaacac aagcctaggt gaggcccagt ctttcttggg   1955
tcttattatt tgtgaaggtc tctctgcctg tcggctgggg cagagactga aatactgcca   2015
cctacctttg gcattaatg ttcctctcct ggcaaaaatt cactgccaca gacaaaccac    2075
ccccactcct acccagccag ccctcaaaac acaaggaac aaagacagtc cactcagaca    2135
cttatttaat aactgtagaa atccaaaaga attagcatca aatcttgaag tcgtgagtga   2195
agctgcgggt tggcttgact gggctcagcc actgagctgc ctcaaccggc caaggaacgg   2255
gattatgatg actatgcgga cttctatatt gtcttcatct cattgtgtgt attatgtatt   2315
tagtttcaat aaagcatttg taccaatg                                     2343
```

<210> SEQ ID NO 10
<211> LENGTH: 583
<212> TYPE: PRT
<213> ORGANISM: Homo sapiens

<400> SEQUENCE: 10

```
Met Ala Leu Lys Lys Ser Ser Pro Ser Leu Asp Ser Gly Asp Ser Asp
1               5                   10                  15

Ser Glu Glu Leu Pro Thr Phe Ala Phe Leu Lys Lys Glu Pro Ser Ser
                20                  25                  30

Thr Lys Arg Arg Gln Pro Glu Arg Glu Lys Ile Val Val Asp
            35                  40                  45

Ile Ser Asp Cys Glu Ala Ser Cys Pro Pro Ala Pro Glu Leu Phe Ser
        50                  55                  60

Pro Pro Val Pro Asp Ile Ala Glu Thr Val Thr Gln Thr Gln Pro Val
65                  70                  75                  80

Arg Leu Leu Ser Ser Glu Ser Glu Asp Glu Glu Phe Ile Pro Leu
                85                  90                  95

Ala Gln Arg Leu Thr Cys Lys Phe Leu Thr His Lys Gln Leu Ser Pro
                100                 105                 110

Glu Asp Ser Ser Pro Val Lys Ser Val Leu Asp His Gln Asn Asn
            115                 120                 125

Glu Gly Ala Ser Cys Asp Trp Lys Lys Pro Phe Pro Lys Ile Pro Glu
    130                 135                 140

Val Pro Leu His Asp Thr Pro Glu Arg Ser Ala Ala Asp Asn Lys Asp
145                 150                 155                 160

Leu Ile Leu Asp Pro Cys Cys Gln Leu Pro Ala Tyr Leu Ser Thr Cys
                165                 170                 175

Pro Gly Gln Ser Ser Leu Ala Val Thr Lys Thr Asn Ser Asp Ile
            180                 185                 190

Leu Pro Pro Gln Lys Lys Thr Lys Pro Ser Gln Lys Val Gln Gly Arg
        195                 200                 205

Gly Ser His Gly Cys Arg Gln Gln Arg Gln Ala Arg Gln Lys Glu Ser
    210                 215                 220
```

Thr Leu Arg Arg Gln Glu Arg Lys Asn Ala Ala Leu Val Thr Arg Met
225                 230                 235                 240

Lys Ala Gln Arg Pro Glu Glu Cys Leu Lys His Ile Ile Val Val Leu
            245                 250                 255

Asp Pro Val Leu Leu Gln Met Glu Gly Gly Gln Leu Leu Gly Ala
        260                 265                 270

Leu Gln Thr Met Glu Cys Arg Cys Val Ile Glu Ala Gln Ala Val Pro
    275                 280                 285

Cys Ser Val Thr Trp Arg Arg Ala Gly Pro Ser Glu Asp Arg Glu
    290                 295                 300

Asp Trp Val Glu Pro Thr Val Leu Val Leu Arg Ala Glu Ala
305                 310                 315                 320

Phe Val Ser Met Ile Asp Asn Gly Lys Gln Gly Ser Leu Asp Ser Thr
                325                 330                 335

Met Lys Gly Lys Glu Thr Leu Gln Gly Phe Val Thr Asp Ile Thr Ala
            340                 345                 350

Lys Thr Ala Gly Lys Ala Leu Ser Leu Val Ile Val Asp Gln Glu Lys
        355                 360                 365

Cys Phe Ser Leu Glu Leu Leu Phe Phe Asp Phe Leu Pro Cys Thr Ser
370                 375                 380

Ala Gln Asn Pro Pro Arg Arg Gly Lys Gln Gly Ala Asn Lys Gln Thr
385                 390                 395                 400

Lys Lys Gln Gln Gln Arg Gln Pro Glu Ala Ser Ile Gly Ser Met Val
                405                 410                 415

Ser Arg Val Asp Ala Glu Glu Ala Leu Val Asp Leu Gln Leu His Thr
            420                 425                 430

Glu Ala Gln Ala Gln Ile Val Gln Ser Trp Lys Glu Leu Ala Asp Phe
        435                 440                 445

Thr Cys Ala Phe Thr Lys Ala Val Ala Glu Ala Pro Phe Lys Lys Leu
450                 455                 460

Arg Asp Glu Thr Thr Phe Ser Phe Cys Leu Glu Ser Asp Trp Ala Gly
465                 470                 475                 480

Gly Val Lys Val Asp Leu Ala Gly Arg Gly Leu Ala Leu Val Trp Arg
                485                 490                 495

Arg Gln Ile Gln Gln Leu Asn Arg Val Ser Leu Glu Met Ala Ser Ala
            500                 505                 510

Val Val Asn Ala Tyr Pro Ser Pro Gln Leu Leu Val Gln Ala Tyr Gln
        515                 520                 525

Gln Cys Phe Ser Asp Lys Glu Arg Gln Asn Leu Leu Ala Asp Ile Gln
530                 535                 540

Val Arg Arg Gly Glu Gly Val Thr Ser Thr Ser Arg Arg Ile Gly Pro
545                 550                 555                 560

Glu Leu Ser Arg Arg Ile Tyr Leu Gln Met Thr Thr Leu Gln Pro His
                565                 570                 575

Leu Ser Leu Asp Ser Ala Asp
            580

<210> SEQ ID NO 11
<211> LENGTH: 2307
<212> TYPE: DNA
<213> ORGANISM: Homo sapiens
<220> FEATURE:
<221> NAME/KEY: CDS
<222> LOCATION: (74)...(1786)

<400> SEQUENCE: 11

```
acttccgggc cctgcgtggc agttgaaaga gtggcgggag aagttgcagg gaattatttg         60
atagcacata ctg atg gct cta aag aag tca tca ccc tca ctg gat tct        109
           Met Ala Leu Lys Lys Ser Ser Pro Ser Leu Asp Ser
             1               5                  10 ggt gat agt gac tct gag gag ttg cca aca ttt gcc ttt ctg aag aag        157
Gly Asp Ser Asp Ser Glu Glu Leu Pro Thr Phe Ala Phe Leu Lys Lys
         15                  20                  25 gaa cca tct tca aca aag agg aga cag cct gaa agg gaa gag aag att        205
Glu Pro Ser Ser Thr Lys Arg Arg Gln Pro Glu Arg Glu Glu Lys Ile
     30                  35                  40 gta gtg gtt gac atc tca gat tgt gaa gcc tcc tgt cct cca gca cca        253
Val Val Val Asp Ile Ser Asp Cys Glu Ala Ser Cys Pro Pro Ala Pro
 45                  50                  55                  60 gag tta ttt tca cca cct gtc cca gac ata gct gaa act gtc aca caa        301
Glu Leu Phe Ser Pro Pro Val Pro Asp Ile Ala Glu Thr Val Thr Gln
                 65                  70                  75 aca cag cca gtc agg ttg cta agc agt gaa agt gaa gat gaa gaa gaa        349
Thr Gln Pro Val Arg Leu Leu Ser Ser Glu Ser Glu Asp Glu Glu Glu
             80                  85                  90 ttt att cct ctg gct caa agg ctt aca tgt aag ttt ctg acc cac aag        397
Phe Ile Pro Leu Ala Gln Arg Leu Thr Cys Lys Phe Leu Thr His Lys
         95                  100                 105 caa ctg agc cct gag gac tct agc tcc cca gtt aaa agt gtt ttg gat        445
Gln Leu Ser Pro Glu Asp Ser Ser Ser Pro Val Lys Ser Val Leu Asp
     110                 115                 120 cat caa aat aat gaa ggt gca tca tgt gac tgg aaa aag cag ccc ttt        493
His Gln Asn Asn Glu Gly Ala Ser Cys Asp Trp Lys Lys Gln Pro Phe
125                 130                 135                 140 cca aag atc cct gaa gtt ccc ctc cat gat acc cca gag agg agt gca        541
Pro Lys Ile Pro Glu Val Pro Leu His Asp Thr Pro Glu Arg Ser Ala
                 145                 150                 155 gca gat aac aag gac ctg atc tta gat cca tgc tgt cag ctt cca gcc        589
Ala Asp Asn Lys Asp Leu Ile Leu Asp Pro Cys Cys Gln Leu Pro Ala
             160                 165                 170 tac ctg tct acc tgc cct ggc cag agc agc agc ttg gca gta acc aaa        637
Tyr Leu Ser Thr Cys Pro Gly Gln Ser Ser Ser Leu Ala Val Thr Lys
         175                 180                 185 aca aat tct gac atc ctt cca ccc cag aag aaa acc aag ccg agt cag        685
Thr Asn Ser Asp Ile Leu Pro Pro Gln Lys Lys Thr Lys Pro Ser Gln
     190                 195                 200 aag gtc cag gga aga ggc tca cac gga tgc cgg cag cag aga caa gca        733
Lys Val Gln Gly Arg Gly Ser His Gly Cys Arg Gln Gln Arg Gln Ala
205                 210                 215                 220 agg cag aag gaa agc acc ctg aga aga cag gaa aga aag aat gca gca        781
Arg Gln Lys Glu Ser Thr Leu Arg Arg Gln Glu Arg Lys Asn Ala Ala
                 225                 230                 235 ctg gtt acc agg atg aaa gcc cag agg cca gag gaa tgc tta aaa cac        829
Leu Val Thr Arg Met Lys Ala Gln Arg Pro Glu Glu Cys Leu Lys His
             240                 245                 250 atc att gta gtg ctg gat cca gtg ctc tta cag atg gaa ggt ggg ggc        877
Ile Ile Val Val Leu Asp Pro Val Leu Leu Gln Met Glu Gly Gly Gly
         255                 260                 265 cag ctc cta gga gca ctg cag acc atg gag tgc cgc tgt gtg att gag        925
Gln Leu Leu Gly Ala Leu Gln Thr Met Glu Cys Arg Cys Val Ile Glu
     270                 275                 280 gcg cag gct gtg cct tgc agt gtc act tgg agg aga agg gct ggg ccg        973
Ala Gln Ala Val Pro Cys Ser Val Thr Trp Arg Arg Arg Ala Gly Pro
285                 290                 295                 300
```

```
tct gag gac aga gag gac tgg gtg gag gag cca aca gta ctg gtg ttg      1021
Ser Glu Asp Arg Glu Asp Trp Val Glu Glu Pro Thr Val Leu Val Leu
                305                 310                 315 ctc cgg gca gag gca ttt gtg tcc atg atc gac aat gga aag cag gga      1069
Leu Arg Ala Glu Ala Phe Val Ser Met Ile Asp Asn Gly Lys Gln Gly
            320                 325                 330 agc ctg gac agc act atg aaa ggg aag gaa acg ctt cag ggc ttt gta      1117
Ser Leu Asp Ser Thr Met Lys Gly Lys Glu Thr Leu Gln Gly Phe Val
        335                 340                 345 act gac atc aca gca aag aca gca ggg aaa gct ctg tca ctg gtg att      1165
Thr Asp Ile Thr Ala Lys Thr Ala Gly Lys Ala Leu Ser Leu Val Ile
    350                 355                 360 gtg gat cag gag aaa tgc ttc agt gct cag aat cct cca aga aga ggg      1213
Val Asp Gln Glu Lys Cys Phe Ser Ala Gln Asn Pro Pro Arg Arg Gly
365                 370                 375                 380 aaa cag gga gca aat aaa cag acc aag aag cag cag cag aga caa cca      1261
Lys Gln Gly Ala Asn Lys Gln Thr Lys Lys Gln Gln Gln Arg Gln Pro
                385                 390                 395 gag gcc agc ata ggg tcc atg gta tcc agg gta gac gct gaa gag gca      1309
Glu Ala Ser Ile Gly Ser Met Val Ser Arg Val Asp Ala Glu Glu Ala
            400                 405                 410 ttg gtg gat ctg cag cta cac aca gaa gcc cag gct caa att gtg cag      1357
Leu Val Asp Leu Gln Leu His Thr Glu Ala Gln Ala Gln Ile Val Gln
        415                 420                 425 agc tgg aaa gag ctg gcc gac ttc aca tgc gca ttc aca aag gct gtg      1405
Ser Trp Lys Glu Leu Ala Asp Phe Thr Cys Ala Phe Thr Lys Ala Val
    430                 435                 440 gct gag gcg ccc ttc aag aag ctc cga gat gaa act acc ttc tcc ttc      1453
Ala Glu Ala Pro Phe Lys Lys Leu Arg Asp Glu Thr Thr Phe Ser Phe
445                 450                 455                 460 tgt ctg gag agt gac tgg gct gga ggg gtg aag gtg gac ctt gct ggc      1501
Cys Leu Glu Ser Asp Trp Ala Gly Gly Val Lys Val Asp Leu Ala Gly
                465                 470                 475 agg gga ctc gca cta gtc tgg agg aga cag att cag cag ctg aac cga      1549
Arg Gly Leu Ala Leu Val Trp Arg Arg Gln Ile Gln Gln Leu Asn Arg
            480                 485                 490 gtc agc ctg gaa atg gcc agt gca gtt gtg aat gcc tat ccc tcc cca      1597
Val Ser Leu Glu Met Ala Ser Ala Val Val Asn Ala Tyr Pro Ser Pro
        495                 500                 505 cag ctc ctg gta cag gct tat cag cag tgt ttt tcg gat aaa gaa cgc      1645
Gln Leu Leu Val Gln Ala Tyr Gln Gln Cys Phe Ser Asp Lys Glu Arg
    510                 515                 520 cag aat ttg ctc gca gac ata cag gtg cgc cgt ggg gaa ggt gtg aca      1693
Gln Asn Leu Leu Ala Asp Ile Gln Val Arg Arg Gly Glu Gly Val Thr
525                 530                 535                 540 tcc act tct cgc cgc att gga cca gaa cta tcc agg cgt atc tac ctt      1741
Ser Thr Ser Arg Arg Ile Gly Pro Glu Leu Ser Arg Arg Ile Tyr Leu
                545                 550                 555 cag atg acc act tta cag cca cat ctc tct tta gat agt gct gac           1786
Gln Met Thr Thr Leu Gln Pro His Leu Ser Leu Asp Ser Ala Asp
            560                 565                 570 tgattctagc cctcagggat gaggatgaaa agctggaaac ttccacttcc ccaacctcag    1846
agcctgactg taatgaagag actggcagca cctcctggaa cacaagccta ggtgaggccc    1906
agtctttctt gggtcttatt atttgtgaag gtctctctgc ctgtcggctg gggcagagac    1966
tgaaatactg ccacctacct ttggcattta atgttcctct cctggcaaaa attcactgcc    2026
acagacaaac caccccact cctacccagc cagccctcaa aacacaaagg aacaaagaca     2086
```

```
gtccactcag acacttattt aataactgta gaaatccaaa agaattagca tcaaatcttg    2146
aagtcgtgag tgaagctgcg ggttggcttg actgggctca gccactgagc tgcctcaacc    2206
ggccaaggaa cgggattatg atgactatgc ggacttctat attgtcttca tctcattgtg    2266
tgtattatgt atttagtttc aataaagcat ttgtaccaat g                        2307
```

<210> SEQ ID NO 12
<211> LENGTH: 571
<212> TYPE: PRT
<213> ORGANISM: Homo sapiens

<400> SEQUENCE: 12

```
Met Ala Leu Lys Lys Ser Ser Pro Ser Leu Asp Ser Gly Asp Ser Asp
 1               5                  10                  15

Ser Glu Glu Leu Pro Thr Phe Ala Phe Leu Lys Lys Glu Pro Ser Ser
                20                  25                  30

Thr Lys Arg Arg Gln Pro Glu Arg Glu Lys Ile Val Val Val Asp
         35                  40                  45

Ile Ser Asp Cys Glu Ala Ser Cys Pro Pro Ala Pro Glu Leu Phe Ser
     50                  55                  60

Pro Pro Val Pro Asp Ile Ala Glu Thr Val Thr Gln Thr Gln Pro Val
 65                  70                  75                  80

Arg Leu Leu Ser Ser Glu Ser Glu Asp Glu Glu Phe Ile Pro Leu
                 85                  90                  95

Ala Gln Arg Leu Thr Cys Lys Phe Leu Thr His Lys Gln Leu Ser Pro
            100                 105                 110

Glu Asp Ser Ser Ser Pro Val Lys Ser Val Leu Asp His Gln Asn Asn
        115                 120                 125

Glu Gly Ala Ser Cys Asp Trp Lys Lys Gln Pro Phe Pro Lys Ile Pro
    130                 135                 140

Glu Val Pro Leu His Asp Thr Pro Glu Arg Ser Ala Ala Asp Asn Lys
145                 150                 155                 160

Asp Leu Ile Leu Asp Pro Cys Cys Gln Leu Pro Ala Tyr Leu Ser Thr
                165                 170                 175

Cys Pro Gly Gln Ser Ser Leu Ala Val Thr Lys Thr Asn Ser Asp
            180                 185                 190

Ile Leu Pro Pro Gln Lys Lys Thr Lys Pro Ser Gln Lys Val Gln Gly
        195                 200                 205

Arg Gly Ser His Gly Cys Arg Gln Gln Arg Gln Ala Arg Gln Lys Glu
    210                 215                 220

Ser Thr Leu Arg Arg Gln Glu Arg Lys Asn Ala Ala Leu Val Thr Arg
225                 230                 235                 240

Met Lys Ala Gln Arg Pro Glu Glu Cys Leu Lys His Ile Ile Val Val
                245                 250                 255

Leu Asp Pro Val Leu Leu Gln Met Glu Gly Gly Gly Gln Leu Leu Gly
            260                 265                 270

Ala Leu Gln Thr Met Glu Cys Arg Cys Val Ile Glu Ala Gln Ala Val
        275                 280                 285

Pro Cys Ser Val Thr Trp Arg Arg Arg Ala Gly Pro Ser Glu Asp Arg
    290                 295                 300

Glu Asp Trp Val Glu Glu Pro Thr Val Leu Val Leu Arg Ala Glu
305                 310                 315                 320

Ala Phe Val Ser Met Ile Asp Asn Gly Lys Gln Gly Ser Leu Asp Ser
                325                 330                 335
```

```
Thr Met Lys Gly Lys Glu Thr Leu Gln Gly Phe Val Thr Asp Ile Thr
            340                 345                 350
Ala Lys Thr Ala Gly Lys Ala Leu Ser Leu Val Ile Val Asp Gln Glu
            355                 360                 365
Lys Cys Phe Ser Ala Gln Asn Pro Arg Arg Gly Lys Gln Gly Ala
370                 375                 380
Asn Lys Gln Thr Lys Gln Gln Gln Arg Gln Pro Glu Ala Ser Ile
385                 390                 395                 400
Gly Ser Met Val Ser Arg Val Asp Ala Glu Glu Ala Leu Val Asp Leu
            405                 410                 415
Gln Leu His Thr Glu Ala Gln Ala Gln Ile Val Gln Ser Trp Lys Glu
            420                 425                 430
Leu Ala Asp Phe Thr Cys Ala Phe Thr Lys Ala Val Ala Glu Ala Pro
            435                 440                 445
Phe Lys Lys Leu Arg Asp Glu Thr Thr Phe Ser Phe Cys Leu Glu Ser
            450                 455                 460
Asp Trp Ala Gly Gly Val Lys Val Asp Leu Ala Gly Arg Gly Leu Ala
465                 470                 475                 480
Leu Val Trp Arg Arg Gln Ile Gln Gln Leu Asn Arg Val Ser Leu Glu
            485                 490                 495
Met Ala Ser Ala Val Val Asn Ala Tyr Pro Ser Pro Gln Leu Leu Val
            500                 505                 510
Gln Ala Tyr Gln Gln Cys Phe Ser Asp Lys Glu Arg Gln Asn Leu Leu
            515                 520                 525
Ala Asp Ile Gln Val Arg Arg Gly Glu Gly Val Thr Ser Thr Ser Arg
            530                 535                 540
Arg Ile Gly Pro Glu Leu Ser Arg Arg Ile Tyr Leu Gln Met Thr Thr
545                 550                 555                 560
Leu Gln Pro His Leu Ser Leu Asp Ser Ala Asp
            565                 570

<210> SEQ ID NO 13
<211> LENGTH: 2219
<212> TYPE: DNA
<213> ORGANISM: Homo sapiens
<220> FEATURE:
<221> NAME/KEY: CDS
<222> LOCATION: (73)...(1698)

<400> SEQUENCE: 13
cttccgggcc ctgcgtggca gttgaaagag tggcgggaga agttgcaggg aattatttga      60
tagcacatac tg atg gct cta aag aag tca tca ccc tca ctg gat tct ggt     111
              Met Ala Leu Lys Lys Ser Ser Pro Ser Leu Asp Ser Gly
                1               5                   10 gat agt gac tct gag gag ttg cca aca ttt gcc ttt ctg aag aag gaa       159
Asp Ser Asp Ser Glu Glu Leu Pro Thr Phe Ala Phe Leu Lys Lys Glu
    15                  20                  25 cca tct tca aca aag agg aga cag cct gaa agg gaa gag aag att gta       207
Pro Ser Ser Thr Lys Arg Arg Gln Pro Glu Arg Glu Glu Lys Ile Val
30                  35                  40                  45 gtg gtt gac atc tca gat tgt gaa gcc tcc tgt cct cca gca cca gag       255
Val Val Asp Ile Ser Asp Cys Glu Ala Ser Cys Pro Pro Ala Pro Glu
                50                  55                  60 tta ttt tca cca cct gtc cca gac ata gct gaa act gtc aca caa aca       303
Leu Phe Ser Pro Pro Val Pro Asp Ile Ala Glu Thr Val Thr Gln Thr
            65                  70                  75 cag cca gtc agg ttg cta agc agt gaa agt gaa gat gaa gaa gaa ttt       351
```

```
                                                         -continued

Gln Pro Val Arg Leu Leu Ser Ser Glu Ser Glu Asp Glu Glu Phe
         80                  85                  90 att cct ctg gct caa agg ctt aca tgt aag ttt ctg acc cac aag caa          399
Ile Pro Leu Ala Gln Arg Leu Thr Cys Lys Phe Leu Thr His Lys Gln
         95                  100                 105 ctg agc cct gag gac tct agc tcc cca gtt aaa agt gtt ttg gat cat          447
Leu Ser Pro Glu Asp Ser Ser Ser Pro Val Lys Ser Val Leu Asp His
110                 115                 120                 125 caa aat aat gaa ggt gca tca tgt gac tgg aaa aag cag ccc ttt cca          495
Gln Asn Asn Glu Gly Ala Ser Cys Asp Trp Lys Lys Gln Pro Phe Pro
                130                 135                 140 aag atc cct gaa gtt ccc ctc cat gat acc cca gag agg agt gca gca          543
Lys Ile Pro Glu Val Pro Leu His Asp Thr Pro Glu Arg Ser Ala Ala
        145                 150                 155 gat aac aag gac ctg atc tta gat cca tgc tgt cag ctt cca gcc tac          591
Asp Asn Lys Asp Leu Ile Leu Asp Pro Cys Cys Gln Leu Pro Ala Tyr
        160                 165                 170 ctg tct acc tgc cct ggc cag agc agc agc ttg gca gta acc aaa aca          639
Leu Ser Thr Cys Pro Gly Gln Ser Ser Ser Leu Ala Val Thr Lys Thr
        175                 180                 185 aat tct gac atc ctt cca ccc cag aag aaa acc aag ccg agt cag aag          687
Asn Ser Asp Ile Leu Pro Pro Gln Lys Lys Thr Lys Pro Ser Gln Lys
190                 195                 200                 205 gtc cag gga aga ggc tca cac gga tgc cgg cag cag aga caa gca agg          735
Val Gln Gly Arg Gly Ser His Gly Cys Arg Gln Gln Arg Gln Ala Arg
                210                 215                 220 cag aag gaa agc acc ctg aga aga cag gaa aga aag aat gca gca ctg          783
Gln Lys Glu Ser Thr Leu Arg Arg Gln Glu Arg Lys Asn Ala Ala Leu
        225                 230                 235 gtt acc agg atg aaa gcc cag agg cca gag gaa tgc tta aaa cac atc          831
Val Thr Arg Met Lys Ala Gln Arg Pro Glu Glu Cys Leu Lys His Ile
        240                 245                 250 att gta gtg ctg gat cca gtg ctc tta cag atg gaa ggt ggg ggc cag          879
Ile Val Val Leu Asp Pro Val Leu Leu Gln Met Glu Gly Gly Gly Gln
        255                 260                 265 ctc cta gga gca ctg cag acc atg gag tgc cgc tgt gtg att gag gcg          927
Leu Leu Gly Ala Leu Gln Thr Met Glu Cys Arg Cys Val Ile Glu Ala
270                 275                 280                 285 cag gct gtg cct tgc agt gtc act tgg agg aga agg gct ggg ccg tct          975
Gln Ala Val Pro Cys Ser Val Thr Trp Arg Arg Arg Ala Gly Pro Ser
                290                 295                 300 gag gga agc ctg gac agc act atg aaa ggg aag gaa acg ctt cag ggc         1023
Glu Gly Ser Leu Asp Ser Thr Met Lys Gly Lys Glu Thr Leu Gln Gly
        305                 310                 315 ttt gta act gac atc aca gca aag aca gca ggg aaa gct ctg tca ctg         1071
Phe Val Thr Asp Ile Thr Ala Lys Thr Ala Gly Lys Ala Leu Ser Leu
        320                 325                 330 gtg att gtg gat cag gag aaa tgc ttc agt gct cag aat cct cca aga         1119
Val Ile Val Asp Gln Glu Lys Cys Phe Ser Ala Gln Asn Pro Pro Arg
        335                 340                 345 aga ggg aaa cag gga gca aat aaa cag acc aag aag cag cag aga            1167
Arg Gly Lys Gln Gly Ala Asn Lys Gln Thr Lys Lys Gln Gln Arg
350                 355                 360                 365 caa cca gag gcc agc ata ggg tcc atg gta tcc agg gta gac gct gaa         1215
Gln Pro Glu Ala Ser Ile Gly Ser Met Val Ser Arg Val Asp Ala Glu
                370                 375                 380 gag gca ttg gtg gat ctg cag cta cac aca gaa gcc cag gct caa att         1263
Glu Ala Leu Val Asp Leu Gln Leu His Thr Glu Ala Gln Ala Gln Ile
        385                 390                 395
```

-continued

```
gtg cag agc tgg aaa gag ctg gcc gac ttc aca tgc gca ttc aca aag    1311
Val Gln Ser Trp Lys Glu Leu Ala Asp Phe Thr Cys Ala Phe Thr Lys
        400                 405                 410 gct gtg gct gag gcg ccc ttc aag aag ctc cga gat gaa act acc ttc    1359
Ala Val Ala Glu Ala Pro Phe Lys Lys Leu Arg Asp Glu Thr Thr Phe
    415                 420                 425 tcc ttc tgt ctg gag agt gac tgg gct gga ggg gtg aag gtg gac ctt    1407
Ser Phe Cys Leu Glu Ser Asp Trp Ala Gly Gly Val Lys Val Asp Leu
430                 435                 440                 445 gct ggc agg gga ctc gca cta gtc tgg agg aga cag att cag cag ctg    1455
Ala Gly Arg Gly Leu Ala Leu Val Trp Arg Arg Gln Ile Gln Gln Leu
                450                 455                 460 aac cga gtc agc ctg gaa atg gcc agt gca gtt gtg aat gcc tat ccc    1503
Asn Arg Val Ser Leu Glu Met Ala Ser Ala Val Val Asn Ala Tyr Pro
            465                 470                 475 tcc cca cag ctc ctg gta cag gct tat cag cag tgt ttt tcg gat aaa    1551
Ser Pro Gln Leu Leu Val Gln Ala Tyr Gln Gln Cys Phe Ser Asp Lys
        480                 485                 490 gaa cgc cag aat ttg ctc gca gac ata cag gtg cgc cgt ggg gaa ggt    1599
Glu Arg Gln Asn Leu Leu Ala Asp Ile Gln Val Arg Arg Gly Glu Gly
    495                 500                 505 gtg aca tcc act tct cgc cgc att gga cca gaa cta tcc agg tgt atc    1647
Val Thr Ser Thr Ser Arg Arg Ile Gly Pro Glu Leu Ser Arg Cys Ile
510                 515                 520                 525 tac ctt cag atg acc act tta cag cca cat ctc tct tta gat agt gct    1695
Tyr Leu Gln Met Thr Thr Leu Gln Pro His Leu Ser Leu Asp Ser Ala
                530                 535                 540 gac                                                                1698
Asp gattctagc cctcagggat gaggatgaaa agctggaaac ttccacttcc              1748
ccaacctcag agcctgactg taatgaagag actggcagca cctcctggaa cacaagccta  1808
ggtgaggccc agtctttctt gggtcttatt atttgtgaag gtctctctgc ctgtcggctg  1868
gggcagagac tgaaatactg ccacctacct ttggcattta atgttcctct cctggcaaaa  1928
attcactgcc acagacaaac cacccccact cctacccagc cagccctcaa aacacaaagg  1988
aacaaagaca gtccactcag acacttattt aataactgta gaaatccaaa agaattagca  2048
tcaaatcttg aagtcgtgag tgaagctgcg ggttggcttg actgggctca gccactgagc  2108
tgcctcaacc ggccaaggaa cgggattatg atgactatgc ggacttctat attgtcttca  2168
tctcattgtg tgtattatgt atttagtttc aataaagcat ttgtaccaat g          2219

<210> SEQ ID NO 14
<211> LENGTH: 542
<212> TYPE: PRT
<213> ORGANISM: Homo sapiens

<400> SEQUENCE: 14

Met Ala Leu Lys Lys Ser Ser Pro Ser Leu Asp Ser Gly Asp Ser Asp
1               5                   10                  15

Ser Glu Glu Leu Pro Thr Phe Ala Phe Leu Lys Lys Glu Pro Ser Ser
            20                  25                  30

Thr Lys Arg Arg Gln Pro Glu Arg Glu Glu Lys Ile Val Val Val Asp
        35                  40                  45

Ile Ser Asp Cys Glu Ala Ser Cys Pro Pro Ala Pro Glu Leu Phe Ser
    50                  55                  60

Pro Pro Val Pro Asp Ile Ala Glu Thr Val Thr Gln Thr Gln Pro Val
65                  70                  75                  80

Arg Leu Leu Ser Ser Glu Ser Glu Asp Glu Glu Glu Phe Ile Pro Leu
```

```
                       85                  90                  95
Ala Gln Arg Leu Thr Cys Lys Phe Leu Thr His Lys Gln Leu Ser Pro
                100                 105                 110

Glu Asp Ser Ser Pro Val Lys Ser Val Leu Asp His Gln Asn Asn
            115                 120                 125

Glu Gly Ala Ser Cys Asp Trp Lys Lys Gln Phe Pro Lys Ile Pro
        130                 135                 140

Glu Val Pro Leu His Asp Thr Pro Glu Arg Ser Ala Ala Asp Asn Lys
145                 150                 155                 160

Asp Leu Ile Leu Asp Pro Cys Cys Gln Leu Pro Ala Tyr Leu Ser Thr
                165                 170                 175

Cys Pro Gly Gln Ser Ser Leu Ala Val Thr Lys Thr Asn Ser Asp
                180                 185                 190

Ile Leu Pro Pro Gln Lys Lys Thr Lys Pro Ser Gln Lys Val Gln Gly
                195                 200                 205

Arg Gly Ser His Gly Cys Arg Gln Gln Arg Ala Arg Gln Lys Glu
    210                 215                 220

Ser Thr Leu Arg Arg Gln Glu Arg Lys Asn Ala Ala Leu Val Thr Arg
225                 230                 235                 240

Met Lys Ala Gln Arg Pro Glu Glu Cys Leu Lys His Ile Ile Val Val
                245                 250                 255

Leu Asp Pro Val Leu Leu Gln Met Glu Gly Gly Gln Leu Leu Gly
                260                 265                 270

Ala Leu Gln Thr Met Glu Cys Arg Cys Val Ile Glu Ala Gln Ala Val
                275                 280                 285

Pro Cys Ser Val Thr Trp Arg Arg Arg Ala Gly Pro Ser Glu Gly Ser
    290                 295                 300

Leu Asp Ser Thr Met Lys Gly Lys Glu Thr Leu Gln Gly Phe Val Thr
305                 310                 315                 320

Asp Ile Thr Ala Lys Thr Ala Gly Lys Ala Leu Ser Leu Val Ile Val
                325                 330                 335

Asp Gln Glu Lys Cys Phe Ser Ala Gln Asn Pro Pro Arg Arg Gly Lys
            340                 345                 350

Gln Gly Ala Asn Lys Gln Thr Lys Lys Gln Gln Arg Gln Pro Glu
    355                 360                 365

Ala Ser Ile Gly Ser Met Val Ser Arg Val Asp Ala Glu Glu Ala Leu
    370                 375                 380

Val Asp Leu Gln Leu His Thr Glu Ala Gln Ala Gln Ile Val Gln Ser
385                 390                 395                 400

Trp Lys Glu Leu Ala Asp Phe Thr Cys Ala Phe Thr Lys Ala Val Ala
                405                 410                 415

Glu Ala Pro Phe Lys Lys Leu Arg Asp Glu Thr Thr Phe Ser Phe Cys
            420                 425                 430

Leu Glu Ser Asp Trp Ala Gly Val Lys Val Asp Leu Ala Gly Arg
        435                 440                 445

Gly Leu Ala Leu Val Trp Arg Arg Gln Ile Gln Gln Leu Asn Arg Val
    450                 455                 460

Ser Leu Glu Met Ala Ser Ala Val Val Asn Ala Tyr Pro Ser Pro Gln
465                 470                 475                 480

Leu Leu Val Gln Ala Tyr Gln Gln Cys Phe Ser Asp Lys Glu Arg Gln
                485                 490                 495

Asn Leu Leu Ala Asp Ile Gln Val Arg Arg Gly Glu Gly Val Thr Ser
                500                 505                 510
```

```
Thr Ser Arg Arg Ile Gly Pro Glu Leu Ser Arg Cys Ile Tyr Leu Gln
        515                 520                 525

Met Thr Thr Leu Gln Pro His Leu Ser Leu Asp Ser Ala Asp
        530                 535                 540
```

<210> SEQ ID NO 15
<211> LENGTH: 1335
<212> TYPE: DNA
<213> ORGANISM: Homo sapiens

<400> SEQUENCE: 15

```
atggcgcggg ttggacccgg gagggcgggg gtctcttgcc agggccgggg ccggggacgg      60
ggcgggagcg gtcagcggcg acctccaacc tgggagatct cagactccga cgctgaggac     120
tccgccggct cggaggccgc cgcgagagcc cgggacccag cgggtgagcg cagggcggct     180
gccgaggcgt tgcggctgct gcggccggag caggtgctga agcgcctcgc ggtgtgcgtg     240
gacacagcca tcctggaaga cgccggtgcc gacgtcctga tggaggccct ggaggccctg     300
ggctgcgagt gccgcatcga gccccagcgc cggcccgca gcctgcggtg acccgagcg      360
agtcccgacc cctgccccg cagcctgcct cctgaagtgt gggctgcagg tgaacaggaa     420
ttgctgctgc tgctggagcc cgaggagttt ctgcagggcg tcgccacact gacccagatc     480
tctggcccaa cccactgggt gccctggatc tcccccgaga ccaccgcccg gccccacctg     540
gctgtcatcg gctggatgc ctacctgtgg taccgctcac tctcatgccc acagcagggc     600
tggctgggac gggggttcag ggaggtgggg ctctggcaga ggccaagctc gggcagggca     660
ggccccatgg ggagcgggga ggaatggtca cctctgctca ggtctcgcca gcacgtttcc     720
cggggacac agcagccaga gagcccgaag gtggccggtg ccgaggtggc cgtcagctgg     780
ccggaggtgg aagaggtgag ggcctgtctg agctgggccc tggtactcct gcagctctgg     840
gcaaacctgg acgtgctact ggtggcctct tggcaggagc tgagtcggca cgtgtgcgcc     900
gttaccaagg ctctcgccca gtatcccctc aagtgcgtga tgccaaggct gaagggggggc     960
aggatcacct caaggcagta ccgggaatcc caggccttct ccttctgcac agcagggcgc    1020
tgggcagccg gcgagccagt ggcaagagac ggcgcagggc tgcaggcggc ctggcggagg    1080
cagatcaggc agttcagtcg ggtcagccca gccgtggctg atgcagttgt cacagccttc    1140
ccctccccc gccttctgca gcaggcgctg gaggcctgca gcacggagcg ggagcgcatg    1200
ggcctcctgg ccgaccttcc tgtgccgccc agtgaaggcg ggcgtccccg cagggtgggg    1260
cctgacctct cccgccgcat ctgcctcttc ctgaccacag ccaaccctga tctcctgctg    1320
gacctgggct cctga                                                    1335
```

<210> SEQ ID NO 16
<211> LENGTH: 444
<212> TYPE: PRT
<213> ORGANISM: Homo sapiens

<400> SEQUENCE: 16

```
Met Ala Arg Val Gly Pro Gly Arg Ala Gly Val Ser Cys Gln Gly Arg
  1               5                  10                  15

Gly Arg Gly Arg Gly Gly Ser Gly Gln Arg Arg Pro Pro Thr Trp Glu
            20                  25                  30

Ile Ser Asp Ser Asp Ala Glu Asp Ser Ala Gly Ser Glu Ala Ala Ala
        35                  40                  45

Arg Ala Arg Asp Pro Ala Gly Glu Arg Arg Ala Ala Ala Glu Ala Leu
```

```
            50                  55                  60
Arg Leu Leu Arg Pro Glu Gln Val Leu Lys Arg Leu Ala Val Cys Val
 65                  70                  75                  80

Asp Thr Ala Ile Leu Glu Asp Ala Gly Ala Asp Val Leu Met Glu Ala
                 85                  90                  95

Leu Glu Ala Leu Gly Cys Glu Cys Arg Ile Glu Pro Gln Arg Pro Ala
                100                 105                 110

Arg Ser Leu Arg Trp Thr Arg Ala Ser Pro Asp Pro Cys Pro Arg Ser
            115                 120                 125

Leu Pro Pro Glu Val Trp Ala Ala Gly Glu Gln Glu Leu Leu Leu Leu
130                 135                 140

Leu Glu Pro Glu Glu Phe Leu Gln Gly Val Ala Thr Leu Thr Gln Ile
145                 150                 155                 160

Ser Gly Pro Thr His Trp Val Pro Trp Ile Ser Pro Glu Thr Thr Ala
                165                 170                 175

Arg Pro His Leu Ala Val Ile Gly Leu Asp Ala Tyr Leu Trp Tyr Arg
            180                 185                 190

Ser Leu Ser Cys Pro Gln Gln Gly Trp Leu Gly Arg Gly Phe Arg Gly
            195                 200                 205

Gly Gly Leu Trp Gln Arg Pro Ser Ser Gly Arg Ala Gly Pro Met Gly
210                 215                 220

Ser Gly Glu Glu Trp Ser Pro Leu Leu Arg Ser Arg Gln His Val Ser
225                 230                 235                 240

Arg Gly Thr Gln Gln Pro Glu Ser Pro Lys Val Ala Gly Ala Glu Val
                245                 250                 255

Ala Val Ser Trp Pro Glu Val Glu Val Arg Ala Cys Leu Ser Trp
                260                 265                 270

Ala Leu Val Leu Gln Leu Trp Ala Asn Leu Asp Val Leu Leu Val
            275                 280                 285

Ala Ser Trp Gln Glu Leu Ser Arg His Val Cys Ala Val Thr Lys Ala
            290                 295                 300

Leu Ala Gln Tyr Pro Leu Lys Cys Val Met Pro Arg Leu Lys Gly Gly
305                 310                 315                 320

Arg Ile Thr Ser Arg Gln Tyr Arg Glu Ser Gln Ala Phe Ser Phe Cys
                325                 330                 335

Thr Ala Gly Arg Trp Ala Ala Gly Glu Pro Val Ala Arg Asp Gly Ala
                340                 345                 350

Gly Leu Gln Ala Ala Trp Arg Arg Gln Ile Arg Gln Phe Ser Arg Val
            355                 360                 365

Ser Pro Ala Val Ala Asp Ala Val Val Thr Ala Phe Pro Ser Pro Arg
370                 375                 380

Leu Leu Gln Gln Ala Leu Glu Ala Cys Ser Thr Glu Arg Glu Arg Met
385                 390                 395                 400

Gly Leu Leu Ala Asp Leu Pro Val Pro Pro Ser Glu Gly Gly Arg Pro
                405                 410                 415

Arg Arg Val Gly Pro Asp Leu Ser Arg Arg Ile Cys Leu Phe Leu Thr
            420                 425                 430

Thr Ala Asn Pro Asp Leu Leu Leu Asp Leu Gly Ser
            435                 440

<210> SEQ ID NO 17
<211> LENGTH: 1572
<212> TYPE: DNA
<213> ORGANISM: Homo sapiens
```

```
-continued

<220> FEATURE:
<221> NAME/KEY: CDS
<222> LOCATION: (1)...(1572)

<400> SEQUENCE: 17 atg gcg cgg gtt gga ccc ggg agg gcg ggg gtc tct tgc cag ggc cgg        48
Met Ala Arg Val Gly Pro Gly Arg Ala Gly Val Ser Cys Gln Gly Arg
 1               5                  10                  15 ggc cgg gga cgg ggc ggg agc ggt cag cgg cga cct cca acc tgg gag        96
Gly Arg Gly Arg Gly Gly Ser Gly Gln Arg Arg Pro Pro Thr Trp Glu
             20                  25                  30 atc tca gac tcc gac gct gag gac tcc gcc ggc tcg gag gcc gcc gcg       144
Ile Ser Asp Ser Asp Ala Glu Asp Ser Ala Gly Ser Glu Ala Ala Ala
         35                  40                  45 aga gcc cgg gac cca gcg ggt gag cgc agg gcg gct gcc gag gcg ttg       192
Arg Ala Arg Asp Pro Ala Gly Glu Arg Arg Ala Ala Ala Glu Ala Leu
     50                  55                  60 cgg ctg ctg cgg ccg gag cag gtg ctg aag cgc ctc gcg gta ggg cgc       240
Arg Leu Leu Arg Pro Glu Gln Val Leu Lys Arg Leu Ala Val Gly Arg
 65                  70                  75                  80 tcg cga ggg tgg aag gaa gca gtg acc gcg ctc ctc tcc ccc ggt ccc       288
Ser Arg Gly Trp Lys Glu Ala Val Thr Ala Leu Leu Ser Pro Gly Pro
                 85                  90                  95 agc cat cct gga aga cgc cgg tgc cga cgt cct gat gga ggc cct gga       336
Ser His Pro Gly Arg Arg Arg Cys Arg Arg Pro Asp Gly Gly Pro Gly
            100                 105                 110 ggc cct ggg ctg cga gtg ccg cat cga gcc cca gcg ccc ggc ccg cag       384
Gly Pro Gly Leu Arg Val Pro His Arg Ala Pro Ala Pro Gly Pro Gln
        115                 120                 125 cct gcg gtg gac ccg agc gag tcc cga ccc ctg ccc ccg cag cgt gag       432
Pro Ala Val Asp Pro Ser Glu Ser Arg Pro Leu Pro Pro Gln Arg Glu
    130                 135                 140 tgg tcg cgg gtt ccc gag ggc cag ccg cga gtt ggc tgt ttt gct tcc       480
Trp Ser Arg Val Pro Glu Gly Gln Pro Arg Val Gly Cys Phe Ala Ser
145                 150                 155                 160 atg att tca gcc ctg gag ctg tcc ctg agg cag ctg ccc tgg gcc gtg       528
Met Ile Ser Ala Leu Glu Leu Ser Leu Arg Gln Leu Pro Trp Ala Val
                165                 170                 175 cgc gtc tcg cgg atg ggt aaa gca agg atg gag aac ggg aag tgg agg       576
Arg Val Ser Arg Met Gly Lys Ala Arg Met Glu Asn Gly Lys Trp Arg
            180                 185                 190 tgc cca agc cgt tct gct ggt ata gag ccg agc tgg ctg gag aag ctg       624
Cys Pro Ser Arg Ser Ala Gly Ile Glu Pro Ser Trp Leu Glu Lys Leu
        195                 200                 205 cct cct gaa gtg tgg gct gca ggt gaa cag gaa ttg ctg ctg ctg ctg       672
Pro Pro Glu Val Trp Ala Ala Gly Glu Gln Glu Leu Leu Leu Leu Leu
    210                 215                 220 gag ccc gag gag ttt ctg cag ggc gtc gcc aca ctg acc cag atc tct       720
Glu Pro Glu Glu Phe Leu Gln Gly Val Ala Thr Leu Thr Gln Ile Ser
225                 230                 235                 240 ggc cca acc cac tgg gtg ccc tgg atc tcc ccc gag acc acc gcc cgg       768
Gly Pro Thr His Trp Val Pro Trp Ile Ser Pro Glu Thr Thr Ala Arg
                245                 250                 255 ccc cac ctg gct gtc atc ggg ctg gat gcc tac ctg tgg tac cgc tca       816
Pro His Leu Ala Val Ile Gly Leu Asp Ala Tyr Leu Trp Tyr Arg Ser
            260                 265                 270 ctc tca tgc cca cag cag ggc tgg ctg gga cgg ggg ttc agg gga ggt       864
Leu Ser Cys Pro Gln Gln Gly Trp Leu Gly Arg Gly Phe Arg Gly Gly
        275                 280                 285 ggg ctc tgg cag agg cca agc tcg ggc agg gca ggc ccc atg ggg agc       912
```

```
                Gly Leu Trp Gln Arg Pro Ser Ser Gly Arg Ala Gly Pro Met Gly Ser
                    290                 295                 300 ggg gag gaa tgg tca cct ctg ctc agg tct cgc cag cac gtt tcc cgg       960
Gly Glu Glu Trp Ser Pro Leu Leu Arg Ser Arg Gln His Val Ser Arg
305                 310                 315                 320 ggg aca cag cag cca gag agc ccg aag gtg gcc ggt gcc gag gtg gcc      1008
Gly Thr Gln Gln Pro Glu Ser Pro Lys Val Ala Gly Ala Glu Val Ala
                325                 330                 335 gtc agc tgg ccg gag gtg gaa gag gtg agg gcc tgt ctg agc tgg gcc      1056
Val Ser Trp Pro Glu Val Glu Glu Val Arg Ala Cys Leu Ser Trp Ala
            340                 345                 350 ctg gta ctc ctg cag ctc tgg gca aac ctg gac gtg cta ctg gtg gcc      1104
Leu Val Leu Leu Gln Leu Trp Ala Asn Leu Asp Val Leu Leu Val Ala
        355                 360                 365 tct tgg cag gag ctg agt cgg cac gtg tgc gcc gtt acc aag gct ctc      1152
Ser Trp Gln Glu Leu Ser Arg His Val Cys Ala Val Thr Lys Ala Leu
    370                 375                 380 gcc cag tat ccc ctc aag tgc gtg atg cca agg ctg aag ggg ggc agg      1200
Ala Gln Tyr Pro Leu Lys Cys Val Met Pro Arg Leu Lys Gly Gly Arg
385                 390                 395                 400 atc acc tca agg cag tac cgg gaa tcc cag gcc ttc tcc ttc tgc aca      1248
Ile Thr Ser Arg Gln Tyr Arg Glu Ser Gln Ala Phe Ser Phe Cys Thr
                405                 410                 415 gca ggg cgc tgg gca gcc ggc gag cca gtg gca aga gac ggc gca ggg      1296
Ala Gly Arg Trp Ala Ala Gly Glu Pro Val Ala Arg Asp Gly Ala Gly
            420                 425                 430 ctg cag gcg gcc tgg cgg agg cag atc agg cag ttc agt cgg gtc agc      1344
Leu Gln Ala Ala Trp Arg Arg Gln Ile Arg Gln Phe Ser Arg Val Ser
        435                 440                 445 cca gcc gtg gct gat gca gtt gtc aca gcc ttc ccc tcc ccc cgc ctt      1392
Pro Ala Val Ala Asp Ala Val Val Thr Ala Phe Pro Ser Pro Arg Leu
    450                 455                 460 ctg cag cag gcg ctg gag gcc tgc agc acg gag cgg gag cgc atg ggc      1440
Leu Gln Gln Ala Leu Glu Ala Cys Ser Thr Glu Arg Glu Arg Met Gly
465                 470                 475                 480 ctc ctg gcc gac ctt cct gtg ccg ccc agt gaa ggc ggg cgt ccc cgc      1488
Leu Leu Ala Asp Leu Pro Val Pro Pro Ser Glu Gly Gly Arg Pro Arg
                485                 490                 495 agg gtg ggg cct gac ctc tcc cgc cgc atc tgc ctc ttc ctg acc aca      1536
Arg Val Gly Pro Asp Leu Ser Arg Arg Ile Cys Leu Phe Leu Thr Thr
            500                 505                 510 gcc aac cct gat ctc ctg ctg gac ctg ggc tcc tga                      1572
Ala Asn Pro Asp Leu Leu Leu Asp Leu Gly Ser  *
        515                 520

<210> SEQ ID NO 18
<211> LENGTH: 523
<212> TYPE: PRT
<213> ORGANISM: Homo sapiens

<400> SEQUENCE: 18

Met Ala Arg Val Gly Pro Gly Arg Ala Gly Val Ser Cys Gln Gly Arg
1               5                   10                  15

Gly Arg Gly Arg Gly Gly Ser Gly Gln Arg Arg Pro Pro Thr Trp Glu
            20                  25                  30

Ile Ser Asp Ser Asp Ala Glu Asp Ser Ala Gly Ser Glu Ala Ala Ala
        35                  40                  45

Arg Ala Arg Asp Pro Ala Gly Glu Arg Arg Ala Ala Glu Ala Leu
    50                  55                  60
```

```
Arg Leu Leu Arg Pro Glu Gln Val Leu Lys Arg Leu Ala Val Gly Arg
 65                  70                  75                  80

Ser Arg Gly Trp Lys Glu Ala Val Thr Ala Leu Leu Ser Pro Gly Pro
                 85                  90                  95

Ser His Pro Gly Arg Arg Cys Arg Arg Pro Asp Gly Gly Pro Gly Gly
            100                 105                 110

Gly Pro Gly Leu Arg Val Pro His Arg Ala Pro Ala Pro Gly Pro Gln
        115                 120                 125

Pro Ala Val Asp Pro Ser Glu Ser Arg Pro Leu Pro Pro Gln Arg Glu
    130                 135                 140

Trp Ser Arg Val Pro Glu Gly Gln Pro Arg Val Gly Cys Phe Ala Ser
145                 150                 155                 160

Met Ile Ser Ala Leu Glu Leu Ser Leu Arg Gln Leu Pro Trp Ala Val
                165                 170                 175

Arg Val Ser Arg Met Gly Lys Ala Arg Met Glu Asn Gly Lys Trp Arg
            180                 185                 190

Cys Pro Ser Arg Ser Ala Gly Ile Glu Pro Ser Trp Leu Glu Lys Leu
        195                 200                 205

Pro Pro Glu Val Trp Ala Ala Gly Glu Gln Leu Leu Leu Leu Leu Leu
    210                 215                 220

Glu Pro Glu Glu Phe Leu Gln Gly Val Ala Thr Leu Thr Gln Ile Ser
225                 230                 235                 240

Gly Pro Thr His Trp Val Pro Trp Ile Ser Pro Glu Thr Thr Ala Arg
                245                 250                 255

Pro His Leu Ala Val Ile Gly Leu Asp Ala Tyr Leu Trp Tyr Arg Ser
            260                 265                 270

Leu Ser Cys Pro Gln Gln Gly Trp Leu Gly Arg Gly Phe Arg Gly Gly
        275                 280                 285

Gly Leu Trp Gln Arg Pro Ser Ser Gly Arg Ala Gly Pro Met Gly Ser
    290                 295                 300

Gly Glu Glu Trp Ser Pro Leu Leu Arg Ser Arg Gln His Val Ser Arg
305                 310                 315                 320

Gly Thr Gln Gln Pro Glu Ser Pro Lys Val Ala Gly Ala Glu Val Ala
                325                 330                 335

Val Ser Trp Pro Glu Val Glu Glu Val Arg Ala Cys Leu Ser Trp Ala
            340                 345                 350

Leu Val Leu Leu Gln Leu Trp Ala Asn Leu Asp Val Leu Leu Val Ala
        355                 360                 365

Ser Trp Gln Glu Leu Ser Arg His Val Cys Ala Val Thr Lys Ala Leu
    370                 375                 380

Ala Gln Tyr Pro Leu Lys Cys Val Met Pro Arg Leu Lys Gly Gly Arg
385                 390                 395                 400

Ile Thr Ser Arg Gln Tyr Arg Glu Ser Gln Ala Phe Ser Phe Cys Thr
                405                 410                 415

Ala Gly Arg Trp Ala Ala Gly Glu Pro Val Ala Arg Asp Gly Ala Gly
            420                 425                 430

Leu Gln Ala Ala Trp Arg Arg Gln Ile Arg Gln Phe Ser Arg Val Ser
        435                 440                 445

Pro Ala Val Ala Asp Ala Val Val Thr Ala Phe Pro Ser Pro Arg Leu
    450                 455                 460

Leu Gln Gln Ala Leu Glu Ala Cys Ser Thr Glu Arg Glu Arg Met Gly
465                 470                 475                 480

Leu Leu Ala Asp Leu Pro Val Pro Pro Ser Glu Gly Gly Arg Pro Arg
```

485                 490                 495
        Arg Val Gly Pro Asp Leu Ser Arg Arg Ile Cys Leu Phe Leu Thr Thr
                500                 505                 510

Ala Asn Pro Asp Leu Leu Leu Asp Leu Gly Ser
                515                 520

<210> SEQ ID NO 19
<211> LENGTH: 5618
<212> TYPE: DNA
<213> ORGANISM: Homo sapiens

<400> SEQUENCE: 19

| | | | | |
|---|---|---|---|---|
| ctcagactcc | gacgctgagg | actccgccgg | ctcggaggcc | gccgcgagag | cccgggaccc | 60 |
| agcgggtgag | cgcagggcgg | ctgccgaggc | gttgcggctg | ctgcggccgg | agcaggtcct | 120 |
| gaagcgcctc | gcggtgtgcg | tggacacagc | catcctggaa | gacgccggtg | ccgacgtcct | 180 |
| gatggaggcc | ctggaggccc | tgggctgcga | gtgccgcatc | gagccccagc | gcccggcccg | 240 |
| cagcctgcgg | tggacccgag | cgagtcccga | ccctgcccc | cgcagcctgc | ctcctgaagt | 300 |
| gtgggctgca | ggtgaacagg | aattgctgct | gctgctggag | cccgaggagt | ttctgcaggg | 360 |
| cgtcgccaca | ctgacccaga | tctctggccc | aaccccactgg | gtgccctgga | tctccccga | 420 |
| gaccaccgcc | cggccccacc | tggctgtcat | cgggctggat | gcctacctgt | ggtaccgctc | 480 |
| actctcatgc | ccacagcagg | gctggctggg | acggggttc | agggaggtg | ggcacacttc | 540 |
| tggggttgct | gtggcacagc | tgatcccact | tctccaggtg | ggctctggca | gaggccaagc | 600 |
| tcgggcaggg | caggccccat | ggggagcggg | gaggaatggt | cacctctgct | caggtctcgc | 660 |
| cagcacgttt | cccgggggac | acagcagcca | gagagcccga | aggtggccgg | tgccgaggtg | 720 |
| gccgtcagct | ggccggaggt | ggaagaggcc | ctggtactcc | tgcagctctg | ggcaaacctg | 780 |
| gacgtgctac | tggtggcctc | ttggccagga | gctgagtcgg | cacgtgtgcg | ccgttaccaa | 840 |
| ggctctcgcc | cagtatcccc | tcaagcagta | ccgggaatcc | caggccttct | ccttctgcac | 900 |
| agcagggcgc | tgggcagccg | gcgagccagt | ggcaagagac | ggcgcagggc | tgcaggcggc | 960 |
| ctggcggagg | cagatcaggc | agttcagtcg | ggtcagccca | gccgtggctg | atgcagttgt | 1020 |
| cacagccttc | ccctcccccc | gccttctgca | gcaggcgctg | gaggcctgca | gcacggagcg | 1080 |
| ggagcgcatg | ggcctcctgg | ccgaccttcc | tgtgccgccc | agtgaaggcg | ggcgtccccg | 1140 |
| cagggtgggg | cctgacctct | cccgccgcat | ctgcctcttc | ctgaccacag | ccaaccctga | 1200 |
| tctcctgctg | gacctgggct | cctgaccaca | cgtgggacca | ccaggacagc | atgcagcctt | 1260 |
| ggggacagac | cagacaccct | gggcggtggg | ggaggacccc | cagccacatg | tggaccctca | 1320 |
| gcctgggtgg | gttctctggc | tgagcaggtc | tgacctcagg | ggagggtgg | gtggttgcag | 1380 |
| gggaagtttt | aggtagctgg | gaggagaaga | ggggcttctg | gctggcagat | ggctggcggt | 1440 |
| tcctgtgctg | agtcctgaac | acgtaggccc | aggggaggc | ctcagcagca | gggctgtgcc | 1500 |
| cccccaacac | acacacacac | tcggcaggga | ccagaaggca | gctccagggc | cccactgcc | 1560 |
| acctggaggc | ttggggtgtg | gcaccctcag | ccagaagcag | tagggactc | caaggatgt | 1620 |
| ggaggggcag | tgaggcctgg | gagaaggccc | aggctgctcg | caagcccggc | ctctgcacgg | 1680 |
| atacgtttca | gctcacgcca | tgtgggtgtt | agacatcaac | tctacattta | ttgcagtcct | 1740 |
| ttaagtctat | gacggcgggg | cagccgctga | cagcatgcag | agcaagttag | gaaaaaccga | 1800 |
| ggccctgtgg | gaacagcaac | gcgggctcca | gccaggctct | cgtcctcgca | gcctcccaca | 1860 |
| agacctgggg | ctcagggcag | ccgcttcccc | acccagcaca | gcagcagagg | ggccctagag | 1920 |

-continued

```
cccccacaga aaggactgtc ccagcctcgg gagcaagaga tggctccctc cggacgggcc    1980
tcatccaact ccgccctgga gtgtggctgg aaggaaggga cagagaaaga agggacagag    2040
gaaaggggct gtcccagccc aagaaggcag ttccactggg aagtcagtca ggtccggcgg    2100
cagcgcttcc tctggcaggg ccgaggctcg cgactgctgg ggtgggcgga ggtcgctgcc    2160
tggggatcgg acactggagc cttgcggcgg ctgcaactca tgctcaggac ccagcccagc    2220
ttgttgtgta gcacctgctt gaggcccggc ggcagcggca gaccctccag cgtgtctccc    2280
gagtctggcc gcagctggcg caggcggtgg cagcacaggt actggaggga gtggcgctg     2340 gcacaggagc gggtgacctt catgctgctc cgggccgccg tggagcacac catcgggtag    2400
aatctcttgt tctgcagctt ggtggctgcc acacctggaa gggaggggcc cagcctgaac    2460
cccaggcagg aaggggcca gctactgggc gcagcccctc agacctcacg ctacagtcac     2520
ccgggtgggc agctggcaca gctgaggcaa ggcagggtgc acgcgctggc cctgccactc    2580
cagcctggcc tcactgtccc accccctggg accctggggc ctcaggcttc tgggaggaac    2640
cctttcagaa aacctcagtg tcccctgggc tggggcgggg tggctgcctc cctcggggtg    2700
acagctgaga ggagctcaag tcctgtgacg gcctcaccta tacacttcct gttcttgaaa    2760
aaggtgagtg tgccgtgcca ggtgtccagg tgcacgccaa tgatggagcc ctggccgaac    2820
cgcgatgaga agctggtctt gtcgcccttg tggtggagga ggcctggggg cagccagggt    2880
cgcagtgagc ccgggagctc caggctcggc cccgccccac cctgggcctc acgcacccgt    2940
gtaggagagg ccccagctgt cctcatccct gcccagcagg ctgcagaacg tgtggcggta    3000
tttgtccagg tccacatccg acgtcccgat gcccaccatc taggaacagg ggccaggcag    3060
agggcgcggg gctgggctgc cggagccagg ttccccagaa gcaccctggg ccgaagcaac    3120
ttaccatgtc ggtgccgtag acgggagagg tcatcttgat ctcccagaag tgctggccct    3180
cccccagctc cttggtgccc cggatggccg ctgtgccgca gctgtactcc atgtggaagc    3240
tgaccttacg gttgtcacag ctcagcaggg tggctgatga cttatttaag tcatcccaga    3300
cccagtcgaa atctgcaaga gaggcccagg ctggggcagc cctgagagct ccatggggct    3360
ctgccctgcc cacccccagg cccgcccgca gtgcagtccc agcaggggct gggccccacg    3420
ctcacactcg tcttcctctc cgcagcggca gtccctgccc cggtgggccg agtgcaggct    3480
gctacagaag gaggcctcgc tctgcccagc acagtcacag aaggactcgc cggtcacggg    3540
caccgcactg gggatggatg gcggcagcgt ggagtactcg gggtcggagt ccgagtcgct    3600
gtgctgggag agaagggccg gctgttacta cctgttgccc gctctctacc ctctcaccct    3660
tgccctctgt ccctgtccca ccctgtccct gacccaccca ggaaaggatg ggggtccagg    3720
cctccaggga cttcacagta ccccgagcgc acagcccagg ctccctccca acgggctccg    3780
gctctgcccc attctgcatg accaggaggg ccctggaggc ccagccacag agcagtagcc    3840
aaggctgcct ggcctccaag tggtttctag acggtggata agccccaggt ccaccccacc    3900
tgcccagagc tgagatggtg tggacacctt ccctgctagg ccagccctgc aggggccccc    3960
aggcaaggcc accaccccca caccaggccc agctgcagcc accggcctc agggcagtcc     4020 ccaccacact gtggcccaac gaccttcctg ttacctgagc agacctggct caccacaggg    4080
tcctactgcc cagtgcccac tacaggcccc gcccctcctg gtgcaggttt cagctgtcac    4140
ctccctgagg cttctccagc cccttcaccc ctgttccatt tttcttcttt tgcttcactg    4200
aagttctcct tggtcctgat tcttggcctc ctcccaccag aacgtgagct ccttgtggga    4260
```

-continued

```
ggcagtgccc ctcccagcct cctccctgtc acagactgtg tgggggccac ccagggggctg    4320 aatggaccag ggggtcagca gggagagtgc taagtggtgg cggggggcct gtggcagagg    4380
ccttgtgaca gtgagggttg agggctggtc cagagagatg atgtgatccc caggagaagc    4440 cacagggggac catgacatgg gcgccaccag cttccaggtg aacgtggacc tatcgaaagc    4500
cagcttcagg gcaggacact gtcctttctg gagggggatgg ccccacccca cagacaaggc    4560
aggcccagac aactctaccc cactgcctag aagtgcgggt cccagagcc agggtagacc    4620 ccctgagtca ggagcccggg cacagaactg agcacctgca ctgcaggccc agggccgggt    4680
tccctggaga aggagaaaga ctgaagccac tgcctacctc ctgccacaa cagactgcag    4740 gcccatttgg tgacacagga caagcagcac atgtgtcgaa cactgccgag cccgcaggca    4800
cgcctgcatc ccacagccac gagcctgtga ggctcaggca tgtgacctgc aggagctgga    4860
ggcgggcggg aaggcaggtg ggggcctctc cctggctgga gcagggagct ccaggagacc    4920
tcaggacggc ccccaccccgg tgggtaagga ccctgtttcc caatttgccc ccaaggccta    4980
atggacccac cgggcttagg gagtcctcac tcagaggaga ggagcccacc cctcccagga    5040
cacctggctg agccggaaca gcagcgcagg ggagctgtga cagcagagag cagcaccagg    5100
tcacacaagc agccgccccg gaaggacacg gcccatggtg acagaggaca agcagcatgc    5160
gtgtgtcaga cactggcctg gcctgtggac acgcccgcgt cccacagcca tgaccctgcg    5220
aggccaggag agactgctcc agggcacatg acctgtggta gctggaagtg gggcagggag    5280
gcgcagccac actcctgctc tggtccgagg gagatctcag gaaaccgact gggaaatcac    5340
cccccacagg gaccccccacc cctcccagcc tcactgcgcc cgtcaggcca ggcagctgcc    5400
ctcagggtct gccaaggtgg gggtcagggg ccatgggggc aggtagctct gcctgcaaag    5460
cccacaagca tgtcagatca cctgggctgc agacagacaa acacctgagc tgttctgaat    5520
accttcaggt tcctggcctc cctgagcaag tgcagaaatt tttaccttca aggatcaggg    5580
tttttctgtt tgtttgtttt ttaacacaca tatatgtg                            5618
```

```
<210> SEQ ID NO 20
<211> LENGTH: 351
<212> TYPE: PRT
<213> ORGANISM: Homo sapiens

<400> SEQUENCE: 20
```

```
Met Glu Ala Leu Glu Ala Leu Gly Cys Glu Cys Arg Ile Glu Pro Gln
  1               5                  10                  15

Arg Pro Ala Arg Ser Leu Arg Trp Thr Arg Ala Ser Pro Asp Pro Cys
             20                  25                  30

Pro Arg Ser Leu Pro Pro Glu Val Trp Ala Ala Gly Glu Gln Glu Leu
         35                  40                  45

Leu Leu Leu Leu Glu Pro Glu Glu Phe Leu Gln Gly Val Ala Thr Leu
     50                  55                  60

Thr Gln Ile Ser Gly Pro Thr His Trp Val Pro Trp Ile Ser Pro Glu
 65                  70                  75                  80

Thr Thr Ala Arg Pro His Leu Ala Val Ile Gly Leu Asp Ala Tyr Leu
                 85                  90                  95

Trp Tyr Arg Ser Leu Ser Cys Pro Gln Gln Gly Trp Leu Gly Arg Gly
            100                 105                 110

Phe Arg Gly Gly Gly Leu Trp Gln Arg Pro Ser Ser Gly Arg Ala Gly
        115                 120                 125

Pro Met Gly Ser Gly Glu Glu Trp Ser Pro Leu Leu Arg Ser Arg Gln
```

```
            130                 135                 140
His Val Ser Arg Gly Thr Gln Gln Pro Glu Ser Pro Lys Val Ala Gly
145                 150                 155                 160

Ala Glu Val Ala Val Ser Trp Pro Glu Val Glu Glu Val Arg Ala Cys
                165                 170                 175

Leu Ser Trp Ala Leu Val Leu Gln Leu Trp Ala Asn Leu Asp Val
            180                 185                 190

Leu Leu Val Ala Ser Trp Gln Glu Leu Ser Arg His Val Cys Ala Val
            195                 200                 205

Thr Lys Ala Leu Ala Gln Tyr Pro Leu Lys Cys Val Met Pro Arg Leu
210                 215                 220

Lys Gly Gly Arg Ile Thr Ser Arg Gln Tyr Arg Glu Ser Gln Ala Phe
225                 230                 235                 240

Ser Phe Cys Thr Ala Gly Arg Trp Ala Ala Gly Glu Pro Val Ala Arg
                245                 250                 255

Asp Gly Ala Gly Leu Gln Ala Ala Trp Arg Arg Gln Ile Arg Gln Phe
                260                 265                 270

Ser Arg Val Ser Pro Ala Val Ala Asp Ala Val Val Thr Ala Phe Pro
            275                 280                 285

Ser Pro Arg Leu Leu Gln Gln Ala Leu Glu Ala Cys Ser Thr Glu Arg
290                 295                 300

Glu Arg Met Gly Leu Leu Ala Asp Leu Pro Val Pro Pro Ser Glu Gly
305                 310                 315                 320

Gly Arg Pro Arg Arg Val Gly Pro Asp Leu Ser Arg Arg Ile Cys Leu
                325                 330                 335

Phe Leu Thr Thr Ala Asn Pro Asp Leu Leu Leu Asp Leu Gly Ser
            340                 345                 350

<210> SEQ ID NO 21
<211> LENGTH: 570
<212> TYPE: DNA
<213> ORGANISM: Homo sapiens
<220> FEATURE:
<221> NAME/KEY: CDS
<222> LOCATION: (1)...(570)

<400> SEQUENCE: 21 tct cgc cag cac gtt tcc cgg ggg aca cag cag cca gag agc cag aag    48
Ser Arg Gln His Val Ser Arg Gly Thr Gln Gln Pro Glu Ser Gln Lys
 1               5                  10                  15 gtg gcc ggt gcc gag gtg gcc gtc agc tgg ccg gag gtg gaa gag gcc    96
Val Ala Gly Ala Glu Val Ala Val Ser Trp Pro Glu Val Glu Glu Ala
            20                  25                  30 ctg gta ctc ctg cag ctc tgg gca aac ctg gac gtg cta ctg gtg gcc   144
Leu Val Leu Leu Gln Leu Trp Ala Asn Leu Asp Val Leu Leu Val Ala
        35                  40                  45 tct tgg cag gag ctg agt cgg cac gtg tgc gcc gtt acc aag gct ctc   192
Ser Trp Gln Glu Leu Ser Arg His Val Cys Ala Val Thr Lys Ala Leu
    50                  55                  60 gcc cag tat ccc atc aag cag tac cgg gaa tcc cag gcc ttc tcc ttc   240
Ala Gln Tyr Pro Ile Lys Gln Tyr Arg Glu Ser Gln Ala Phe Ser Phe
65                  70                  75                  80 tgc aca gca ggg cgc tgg gca gcc ggc gag cca gtg gca aga gac ggc   288
Cys Thr Ala Gly Arg Trp Ala Ala Gly Glu Pro Val Ala Arg Asp Gly
                85                  90                  95 gca ggg ctg cag gcg gcc tgg cgg agg cag atc agg cag ttc agt cgg   336
Ala Gly Leu Gln Ala Ala Trp Arg Arg Gln Ile Arg Gln Phe Ser Arg
            100                 105                 110
```

```
gtc agc cca gcc gtg gct gat gca gtt gtc aca gcc ttc ccc tcc ccc       384
Val Ser Pro Ala Val Ala Asp Ala Val Val Thr Ala Phe Pro Ser Pro
        115                 120                 125 cgc ctt ctg cag cag gcg ctg gag gcc tgc agc acg gag cgg gag cgc       432
Arg Leu Leu Gln Gln Ala Leu Glu Ala Cys Ser Thr Glu Arg Glu Arg
    130                 135                 140 atg ggc ctc ctg gcc gac ctt cct gtg ccg ccc agt gaa ggc ggg cgt       480
Met Gly Leu Leu Ala Asp Leu Pro Val Pro Pro Ser Glu Gly Gly Arg
145                 150                 155                 160 ccc cgc agg gtg ggg cct gac gtc tcc cgc cgc atc tgc ctc ttc ctg       528
Pro Arg Arg Val Gly Pro Asp Val Ser Arg Arg Ile Cys Leu Phe Leu
                165                 170                 175 acc aca gcc aac cct gat ctc ctg ctg gac ctg ggc tcc tga               570
Thr Thr Ala Asn Pro Asp Leu Leu Leu Asp Leu Gly Ser  *
            180                 185

<210> SEQ ID NO 22
<211> LENGTH: 189
<212> TYPE: PRT
<213> ORGANISM: Homo sapiens

<400> SEQUENCE: 22

Ser Arg Gln His Val Ser Arg Gly Thr Gln Gln Pro Glu Ser Gln Lys
1               5                   10                  15

Val Ala Gly Ala Glu Val Ala Val Ser Trp Pro Glu Val Glu Glu Ala
                20                  25                  30

Leu Val Leu Leu Gln Leu Trp Ala Asn Leu Asp Val Leu Leu Val Ala
            35                  40                  45

Ser Trp Gln Glu Leu Ser Arg His Val Cys Ala Val Thr Lys Ala Leu
        50                  55                  60

Ala Gln Tyr Pro Ile Lys Gln Tyr Arg Glu Ser Gln Ala Phe Ser Phe
65                  70                  75                  80

Cys Thr Ala Gly Arg Trp Ala Ala Gly Glu Pro Val Ala Arg Asp Gly
                85                  90                  95

Ala Gly Leu Gln Ala Ala Trp Arg Arg Gln Ile Arg Gln Phe Ser Arg
            100                 105                 110

Val Ser Pro Ala Val Ala Asp Ala Val Val Thr Ala Phe Pro Ser Pro
        115                 120                 125

Arg Leu Leu Gln Gln Ala Leu Glu Ala Cys Ser Thr Glu Arg Glu Arg
    130                 135                 140

Met Gly Leu Leu Ala Asp Leu Pro Val Pro Pro Ser Glu Gly Gly Arg
145                 150                 155                 160

Pro Arg Arg Val Gly Pro Asp Val Ser Arg Arg Ile Cys Leu Phe Leu
                165                 170                 175

Thr Thr Ala Asn Pro Asp Leu Leu Leu Asp Leu Gly Ser
            180                 185

<210> SEQ ID NO 23
<211> LENGTH: 738
<212> TYPE: PRT
<213> ORGANISM: Schizosaccharomyces pombe

<400> SEQUENCE: 23

Met Thr Leu Gln Ser Thr Asp Ser Ala Ile Val Ile Asp Ser Glu Ala
1               5                   10                  15

Asp Val Asp Ile Ser Ser Ser Gln Ala Ser Pro Ser Lys Val Cys Arg
                20                  25                  30
```

-continued

```
Asp Asn Ile Ala Leu Ser Glu His Asn Val Ile Thr Val Leu Asp Thr
         35                  40                  45

Pro Gln Arg Ser Thr Gln Cys Asp Ser Leu Leu Lys Ser Phe Ser Thr
 50                  55                  60

Pro Leu Val Ser Gly Ser Glu Asp Val Leu Pro Ser Pro Arg Asp Ala
 65                  70                  75                  80

Leu Asn Ile Thr Asn Lys Lys Ser Val Thr Asp Asn Leu Leu Leu Ser
                 85                  90                  95

Leu Thr Ser Ser Asn Gln Ser Thr Asn Thr Asn Leu Asn Pro Ser Ser
                100                 105                 110

Arg Val Glu Ile Ile Asn Leu Asn Ser Ser Pro Asn Ser Leu Ser
             115                 120                 125

Ser Gln Pro Lys His Gln Glu Phe His Leu Phe His Thr Pro Thr Ile
     130                 135                 140

Pro Arg Thr Thr Gln Leu Ser Ser Lys Thr Ser Ser Pro Ile Val Ile
145                 150                 155                 160

Pro Asp Asp Asn Glu Gln Val Ala Ser Pro Leu Ser Lys Lys Ala Ala
                165                 170                 175

Ser Leu Thr Ser Ser Pro Leu Lys Asp Phe Gln Ser Ser Pro Pro Leu
            180                 185                 190

Ser Thr Val Leu Gln Lys Ser His Ser Leu His Asp Ile Leu Leu Asp
            195                 200                 205

Thr Asn Asp Asp Asp His Phe Pro Phe Thr Gln Ser Pro Leu Thr Lys
            210                 215                 220

Thr Lys Ser Phe Asn Asp Ala Leu Thr Ser Ser Ser Ile Leu Lys
225                 230                 235                 240

Pro Cys Met Pro Ser Ile Ala Ser Pro Thr Ser Asn Arg Leu Ser His
                245                 250                 255

Ala Pro Ser Thr Pro Asn Leu Phe Pro Asn Gln Asp Ser Ser Asn Thr
            260                 265                 270

Ile Asp Leu Ile Asn Asn Arg Ser Lys Thr Ser Val Glu Asn Gln Glu
            275                 280                 285

Arg Thr Phe Asn Leu Thr Ser Asp Val His Leu Asp Ser Pro Thr Ser
            290                 295                 300

Pro Ser Lys His Ser Ser Ile Glu Pro Asn Thr Ser Gln Glu Asp Ser
305                 310                 315                 320

Phe Gln Glu Leu Pro Ser Leu Asn Lys Leu Ser Ile Gln Ser Arg Ala
                325                 330                 335

Phe Lys Lys Met Arg Leu Pro Lys Ile Ser Arg Thr Thr Asp Thr Pro
            340                 345                 350

Pro Ala Ser Thr Ser Asn Ser Asn Lys Lys Asn Leu Asp Lys Leu Lys
            355                 360                 365

Lys Met Arg Lys Leu Cys Ser Arg Ser Leu Glu Pro Tyr Glu Leu Asp
            370                 375                 380

Ser Asn Thr Gln Arg Lys Arg Lys Tyr Glu Asp Ser Leu Lys Lys
385                 390                 395                 400

Ser Lys Thr Leu Asp Lys Val Asp Ser Leu Asn Arg Lys Met Ala Lys
                405                 410                 415

Glu Leu Asp Arg Lys Asn Ser Lys Glu Leu Gln Lys Ile Asn Lys Val
            420                 425                 430

Lys Arg Thr Lys Glu Glu Cys Leu Ser Glu Ile Ile Leu Leu Ser Pro
            435                 440                 445

Asp Asp Trp Ala Ser Ser Trp Tyr Ser Thr Val Arg Ser Gln Leu Asp
```

-continued

```
                450                 455                 460
Ser Tyr Asn Cys Gln Phe Val Val Asn Ser Asn Gln Pro Lys Asp Ser
465                 470                 475                 480

Ile Met Trp Lys Arg Lys Val Asn Asn Val Phe Asn Ser Ser Thr Asn
                485                 490                 495

Arg Phe Glu Leu Ser Ile Glu His Glu Gln Ile Glu Pro Phe Ala Leu
            500                 505                 510

Leu Arg Leu Lys Cys Arg Asp Phe Ile Lys Tyr Ile Glu Glu Asp Gln
        515                 520                 525

Ala Asp Thr Phe Phe His Glu Met Ser Glu Lys Phe Lys Gly Cys Lys
530                 535                 540

Leu Ile Leu Leu Leu Glu Gly Ile Pro Asn Tyr Phe Lys Ser Leu Lys
545                 550                 555                 560

Ala Glu Leu Asn Arg Gln Tyr Ala Ala Ala Val Asn Ser Gly Thr Arg
                565                 570                 575

Pro Leu Leu Phe Gly Ser Leu Ser Lys Tyr Gln Asn Phe Thr Lys Glu
            580                 585                 590

Lys Leu Glu Ser Glu Ile Val Arg Phe Ser Phe Glu His Ser Ile Leu
        595                 600                 605

Ile Asn Thr Ser Asn Asp Glu Lys Glu Thr Ala Gln Trp Ile Val Ser
610                 615                 620

Phe Thr Gly Asp Ile Ala Leu Ser Arg Tyr Lys His Phe Ser Lys Phe
625                 630                 635                 640

Ser Ala Arg Ala Ser Thr Thr Glu Ile Gly His Val Lys Ser Ala Asp
                645                 650                 655

Arg Ile Glu Asn Ser Leu Asn Phe Met Leu Arg Gln Ile Leu Arg Val
            660                 665                 670

Thr Pro Asn Ile Ala Asn Ala Ile Cys Asp Gln Phe Asp Ser Ile Pro
        675                 680                 685

Ser Leu Ile His His Leu Lys Thr His Gly Glu Glu Ser Leu Thr Asn
690                 695                 700

Val Val Ile Gln Ser Ser Ile Ser Glu Arg Asn Leu Gly Pro Val Leu
705                 710                 715                 720

Ser Arg Arg Ile Tyr Asn Thr Phe Leu Cys Lys Glu Ala Ser Ser Asp
                725                 730                 735

Ala Pro

<210> SEQ ID NO 24
<211> LENGTH: 20
<212> TYPE: DNA
<213> ORGANISM: Artificial Sequence
<220> FEATURE:
<223> OTHER INFORMATION: PCR primer

<400> SEQUENCE: 24
gacatggcgg ccccggtccg                                              20

<210> SEQ ID NO 25
<211> LENGTH: 22
<212> TYPE: DNA
<213> ORGANISM: Artificial Sequence
<220> FEATURE:
<223> OTHER INFORMATION: PCR primer

<400> SEQUENCE: 25
gactcaggtc aagggggccgt ag                                          22
```

```
<210> SEQ ID NO 26
<211> LENGTH: 17
<212> TYPE: DNA
<213> ORGANISM: Homo sapiens

<400> SEQUENCE: 26
atggcggccc cggtccg                                                    17

<210> SEQ ID NO 27
<211> LENGTH: 19
<212> TYPE: DNA
<213> ORGANISM: Homo sapiens

<400> SEQUENCE: 27
ctacggcccc ttgacctga                                                  19

<210> SEQ ID NO 28
<211> LENGTH: 50
<212> TYPE: DNA
<213> ORGANISM: Artificial Sequence
<220> FEATURE:
<223> OTHER INFORMATION: Holliday junction segment

<400> SEQUENCE: 28
gacgctgccg aattctggct tgctaggaca tctttgccca cgttgacccg                50

<210> SEQ ID NO 29
<211> LENGTH: 50
<212> TYPE: DNA
<213> ORGANISM: Artificial Sequence
<220> FEATURE:
<223> OTHER INFORMATION: Holliday junction segment

<400> SEQUENCE: 29
cgggtcaacg tgggcaaaga tgtcctagca atgtaatcgt ctatgacgtc                50

<210> SEQ ID NO 30
<211> LENGTH: 50
<212> TYPE: DNA
<213> ORGANISM: Artificial Sequence
<220> FEATURE:
<223> OTHER INFORMATION: Holliday junction segment

<400> SEQUENCE: 30
gacgtcatag acgattacat tgctaggaca tgctgtctag agactatcgc                50

<210> SEQ ID NO 31
<211> LENGTH: 50
<212> TYPE: DNA
<213> ORGANISM: Artificial Sequence
<220> FEATURE:
<223> OTHER INFORMATION: Holliday junction segment

<400> SEQUENCE: 31
gcgatagtct ctagacagca tgtcctagca agccagaatt cggcagcgtc                50

<210> SEQ ID NO 32
<211> LENGTH: 50
<212> TYPE: DNA
<213> ORGANISM: Artificial Sequence
<220> FEATURE:
<223> OTHER INFORMATION: Holliday junction segment

<400> SEQUENCE: 32
caacgtcata gacgattaca ttgctacatg gagctgtcta gaggatccga                50
```

<210> SEQ ID NO 33
<211> LENGTH: 50
<212> TYPE: DNA
<213> ORGANISM: Artificial Sequence
<220> FEATURE:
<223> OTHER INFORMATION: Holliday junction segment

<400> SEQUENCE: 33
gtcggatcct ctagacagct ccatgatcac tggcactggt agaattcggc        50

<210> SEQ ID NO 34
<211> LENGTH: 50
<212> TYPE: DNA
<213> ORGANISM: Artificial Sequence
<220> FEATURE:
<223> OTHER INFORMATION: Holliday junction segment

<400> SEQUENCE: 34
tgccgaattc taccagtgcc agtgatggac atctttgccc acgttgaccc        50

<210> SEQ ID NO 35
<211> LENGTH: 50
<212> TYPE: DNA
<213> ORGANISM: Artificial Sequence
<220> FEATURE:
<223> OTHER INFORMATION: Holliday junction segment

<400> SEQUENCE: 35
tgggtcaacg tgggcaaaga tgtcctagca atgtaatcgt ctatgacgtt        50

<210> SEQ ID NO 36
<211> LENGTH: 1788
<212> TYPE: DNA
<213> ORGANISM: Mus musculus

<400> SEQUENCE: 36
gaattcgccc ttgagactct gaaggagcca gtctagttct tatggcggag ccggtccgcc        60
tgggccggaa gcgtccgctg cccgtttgcc caacccgct cttcgttcgt tggctgaccg       120
agtggcggga cgaggcagcc agcagggggc gccacacgcg tttcgtgttt caaaaggcat       180
tgcgctccct ccaacggtac ccgctaccat tgcgcagcgg gaaggaagcc aagatactcc       240
agcacttcgg agacaggctc tgccgcatgc tggacgaaaa gctgaagcag cacctagcat       300
caggcggtga ccatgccccc agctcaccat ctggaaagaa gggagccagc aaagggccac       360
ctgagcaagt ccaggactct tccatgccag ttcccaccca gcctcaagca ggaagcacca       420
gtgttggcta ttggccagct cagaactcag gtgctcgaga gatcctgctg caactctaca       480
gggagcacct gaattctgat ggccacagct tcctaaccaa agaggagctg ctgcagaagt       540
gtgcccagaa gaccccagg gtagtgcctg gaagttcgaa accctggcct gcctccgga       600
gcctcctcca taggaacctc atccttggaa cgcatcggcc agccaggtat gcactcacac       660
cagagggtct ggagctggct cagaagctgg ccgaggcgga aggcctgagc actcggcacg       720
ctggctttag gccagaggaa catcacggag aggactcagc agttccagaa gccttgtcag       780
aacctggcac caccgagggg gccgtccagc agagaccact ggagctaagg cctagcgagt       840
acagagtgct gttgtgtgtg acattggcg aaaccagagg ggcaggacac aggctagaaa       900
tgctccgaga gttacaaagg ctgcgtgtgc cccacaccgt acgcaagcta cacgttggag       960
actttgtgtg ggtggcacag agaccaggc ccagagaccc agaaagacct ggggagctgg      1020

-continued

```
tcctggacca cattgtggaa cgcaagcggc tagatgacct atgcagcagc atcattgacg    1080
gccgctttcg ggagcagaag ttccgcctga agcgctgtgg cctggggcac cgggtatact    1140
tagtggaaga acatgggtct gtccacaacc ttagccttcc cgagagcacc ttgctgcagg    1200
ctgtcacaaa cacccaggtc attgatggct tttttgtgaa gcgaaccatg gatattaagg    1260
agtcggttgg ctacctggcg cttttgacaa agggcctgga agactgtac cagggccaca    1320 ccctacgcag ccgcccttgg ggggcccag gggctgctga atcagaagca aagccttcca    1380
caaaccctct ctgctcactc ctcaccttca gtgacttcaa tgcagaagct gtcaagaaca    1440
aggcccagtc tgtgcgagaa gtatttgccc ggcagctgat gcaggtgcgt ggactgagtg    1500
gggagaaggc agcagccgtg gtggatcgat acagcacccc tgccagtctc ctggctgctt    1560
atgatgcctg tgccaccgcg aaggagcagg agatgctctt gagcaccatc aagtgtgggc    1620
gtctgcagag gaatctggga cccgctctga gcaggaccct gtaccagttg tactgcagcc    1680
acagccctct gagctgagct gtaccaggag acgctcgctc cccagcaccc atcttcatct    1740
ctaccaaggc tggctagcct tttagcaagg gcgaattctg cagatatc                 1788
```

<210> SEQ ID NO 37
<211> LENGTH: 551
<212> TYPE: PRT
<213> ORGANISM: Mus musculus

<400> SEQUENCE: 37

```
Met Ala Glu Pro Val Arg Leu Gly Arg Lys Arg Pro Leu Pro Val Cys
  1               5                   10                  15

Pro Asn Pro Leu Phe Val Arg Trp Leu Thr Glu Trp Arg Asp Glu Ala
                 20                  25                  30

Ala Ser Arg Gly Arg His Thr Arg Phe Val Phe Gln Lys Ala Leu Arg
             35                  40                  45

Ser Leu Gln Arg Tyr Pro Leu Pro Leu Arg Ser Gly Lys Glu Ala Lys
 50                  55                  60

Ile Leu Gln His Phe Gly Asp Arg Leu Cys Arg Met Leu Asp Glu Lys
 65                  70                  75                  80

Leu Lys Gln His Leu Ala Ser Gly Gly Asp His Ala Pro Ser Ser Pro
                 85                  90                  95

Ser Gly Lys Lys Gly Ala Ser Lys Gly Pro Pro Glu Gln Val Gln Asp
            100                 105                 110

Ser Ser Met Pro Val Pro Thr Gln Pro Gln Ala Gly Ser Thr Ser Val
        115                 120                 125

Gly Tyr Trp Pro Ala Gln Asn Ser Gly Ala Arg Glu Ile Leu Leu Gln
    130                 135                 140

Leu Tyr Arg Glu His Leu Asn Ser Asp Gly His Ser Phe Leu Thr Lys
145                 150                 155                 160

Glu Glu Leu Leu Gln Lys Cys Ala Gln Lys Thr Pro Arg Val Val Pro
                165                 170                 175

Gly Ser Ser Lys Pro Trp Pro Ala Leu Arg Ser Leu His Arg Asn
            180                 185                 190

Leu Ile Leu Gly Thr His Arg Pro Ala Arg Tyr Ala Leu Thr Pro Glu
        195                 200                 205

Gly Leu Glu Leu Ala Gln Lys Leu Ala Glu Ala Glu Gly Leu Ser Thr
    210                 215                 220

Arg His Ala Gly Phe Arg Pro Glu Glu His His Gly Glu Asp Ser Ala
225                 230                 235                 240
```

```
Val Pro Glu Ala Leu Ser Glu Pro Gly Thr Thr Gly Ala Val Gln
            245                 250                 255

Gln Arg Pro Leu Glu Leu Arg Pro Ser Glu Tyr Arg Val Leu Leu Cys
        260                 265                 270

Val Asp Ile Gly Glu Thr Arg Gly Ala Gly His Arg Leu Glu Met Leu
            275                 280                 285

Arg Glu Leu Gln Arg Leu Arg Val Pro His Thr Val Arg Lys Leu His
        290                 295                 300

Val Gly Asp Phe Val Trp Val Ala Gln Glu Thr Arg Pro Arg Asp Pro
305                 310                 315                 320

Glu Arg Pro Gly Glu Leu Val Leu Asp His Ile Val Glu Arg Lys Arg
                325                 330                 335

Leu Asp Asp Leu Cys Ser Ser Ile Ile Asp Gly Arg Phe Arg Glu Gln
            340                 345                 350

Lys Phe Arg Leu Lys Arg Cys Gly Leu Gly His Arg Val Tyr Leu Val
        355                 360                 365

Glu Glu His Gly Ser Val His Asn Leu Ser Leu Pro Glu Ser Thr Leu
    370                 375                 380

Leu Gln Ala Val Thr Asn Thr Gln Val Ile Asp Gly Phe Phe Val Lys
385                 390                 395                 400

Arg Thr Met Asp Ile Lys Glu Ser Val Gly Tyr Leu Ala Leu Leu Thr
                405                 410                 415

Lys Gly Leu Glu Arg Leu Tyr Gln Gly His Thr Leu Arg Ser Arg Pro
            420                 425                 430

Trp Gly Ala Pro Gly Ala Ala Glu Ser Glu Ala Lys Pro Ser Thr Asn
        435                 440                 445

Pro Leu Cys Ser Leu Leu Thr Phe Ser Asp Phe Asn Ala Glu Ala Val
    450                 455                 460

Lys Asn Lys Ala Gln Ser Val Arg Glu Val Phe Ala Arg Gln Leu Met
465                 470                 475                 480

Gln Val Arg Gly Leu Ser Gly Glu Lys Ala Ala Ala Val Val Asp Arg
                485                 490                 495

Tyr Ser Thr Pro Ala Ser Leu Leu Ala Ala Tyr Asp Ala Cys Ala Thr
            500                 505                 510

Ala Lys Glu Gln Glu Met Leu Leu Ser Thr Ile Lys Cys Gly Arg Leu
        515                 520                 525

Gln Arg Asn Leu Gly Pro Ala Leu Ser Arg Thr Leu Tyr Gln Leu Tyr
    530                 535                 540

Cys Ser His Ser Pro Leu Ser
545                 550

<210> SEQ ID NO 38
<211> LENGTH: 1766
<212> TYPE: DNA
<213> ORGANISM: Mus musculus

<400> SEQUENCE: 38
gatatctgca gaattcgccc ttgagactct gaaggagcca gtctagttct tatggcggag      60
ccggtccgcc tgggccggaa gcgtccgctg cccgtttgcc ccaacccgct cttcgttcgt     120
tggctgaccg agtggcggga cgaggcagcc agcagggggc gccacacgcg tttcgtgttt     180
caaaaggcat tgcgctccct ccaacggtac ccgctaccat tgcgcagcgg gaaggaagcc     240
aagatactcc agcacttcgg agacaggctc tgccgcatgc tggacgaaaa gctgaagcag     300
cacctagcat caggcggtga ccatgccccc agctcaccat ctggaaagaa gggagccagc     360
```

-continued

```
aaagggccac ctgagcaagt ccaggactct tccatgccag ttcccaccca gcctcaagca    420
ggaagcacca gtgttggcta ttggccagct cagaactcag gtgctcgaga gatcctgctg    480
caactctaca gggagcacct gaattctgat ggccacagct tcctaaccaa agaggagctg    540
ctgcagaagt gtgcccagaa daccccccagg gtagtgcctg gaagttcgaa accctggcct    600
gccctccgga gcctcctcca taggaacctc atccttggaa cgcatcggcc agccaggtat    660
gcactcacac cagagggtct ggagctggct cagaagctgg ccgaggcgga aggcctgagc    720
actcggcacg ctggctttag gccagaggaa catcacggag aggactcagc agttccagaa    780
gccttgtcag aacctggcac caccgagggg gccgtccagc agagaccact ggagctaagg    840
cctagcgagt acagagtgct gttgtgtgtg gacattggcg aaaccagagg ggcaggacac    900
aggccagaaa tgctccgaga gttacaaagg ctgcgtgtgc cccacaccgt acgcaagcta    960
cacgttggag actttgtgtg ggtggcacag gagaccaggc ccagagaccc agaaagacct   1020
ggggagctgg tcctggacca cattgtggaa cgcaagcggc tagatgacct atgcagcagc   1080
atcattgacg gccgcctttcg ggagcagaag ttccgcctga gcgctgtgg cctggggcac    1140 cgggtatact tagtggaaga acatgggtct gtccacaacc ttagccttcc cgagagcacc   1200
ttgctgcagg ctgtcacaaa cacccaggtc attgatggct tttttgtgaa gcgaaccatg   1260
gatattaagg agtcggttgg ctacctggcg cttttgacaa agggcctgga aagactgtac   1320
cagtgacttc aatgcagaag ctgtcaagaa caaggtacca cccctgcctc acctctgctc   1380
gggtggccta ggccaaggtc acccttaaca caggcctacc caaccccag cccagtctg    1440 tgcgagaagt atttgcccgg cagctgatgc aggtgcgtgg actgagtggg gagaaggcag   1500
cagccgtggt ggatcgatac agcacccctg ccagtctcct ggctgcttat gatgcctgtg   1560
ccaccgcgaa ggagcaggag atgctcttga gcaccatcaa gtgtgggcgt ctgcagagga   1620
atctgggacc cgctctgagc aggacccgtt accagttgta ctgcagccac agccctctga   1680
gctgagctgt accaggagac gctcgctccc cagcacccat cttcatctct accaaggctg   1740
gctagccttt tagcaagggc gaattc                                        1766
```

<210> SEQ ID NO 39
<211> LENGTH: 424
<212> TYPE: PRT
<213> ORGANISM: Mus musculus

<400> SEQUENCE: 39

```
Met Ala Glu Pro Val Arg Leu Gly Arg Lys Arg Pro Leu Pro Val Cys
 1               5                  10                  15

Pro Asn Pro Leu Phe Val Arg Trp Leu Thr Glu Trp Arg Asp Glu Ala
            20                  25                  30

Ala Ser Arg Gly Arg His Thr Arg Phe Val Phe Gln Lys Ala Leu Arg
        35                  40                  45

Ser Leu Gln Arg Tyr Pro Leu Pro Leu Arg Ser Gly Lys Glu Ala Lys
    50                  55                  60

Ile Leu Gln His Phe Gly Asp Arg Leu Cys Arg Met Leu Asp Glu Lys
65                  70                  75                  80

Leu Lys Gln His Leu Ala Ser Gly Gly Asp His Ala Pro Ser Ser Pro
                85                  90                  95

Ser Gly Lys Lys Gly Ala Ser Lys Gly Pro Pro Glu Gln Val Gln Asp
            100                 105                 110

Ser Ser Met Pro Val Pro Thr Gln Pro Gln Ala Gly Ser Thr Ser Val
```

```
                115                 120                     125
Gly Tyr Trp Pro Ala Gln Asn Ser Gly Ala Arg Glu Ile Leu Leu Gln
    130                 135                 140

Leu Tyr Arg Glu His Leu Asn Ser Asp Gly His Ser Phe Leu Thr Lys
145                 150                 155                 160

Glu Glu Leu Leu Gln Lys Cys Ala Gln Lys Thr Pro Arg Val Val Pro
                165                 170                 175

Gly Ser Ser Lys Pro Trp Pro Ala Leu Arg Ser Leu Leu His Arg Asn
            180                 185                 190

Leu Ile Leu Gly Thr His Arg Pro Ala Arg Tyr Ala Leu Thr Pro Glu
        195                 200                 205

Gly Leu Glu Leu Ala Gln Lys Leu Ala Glu Ala Glu Gly Leu Ser Thr
    210                 215                 220

Arg His Ala Gly Phe Arg Pro Glu Glu His His Gly Glu Asp Ser Ala
225                 230                 235                 240

Val Pro Glu Ala Leu Ser Glu Pro Gly Thr Thr Glu Gly Ala Val Gln
                245                 250                 255

Gln Arg Pro Leu Glu Leu Arg Pro Ser Glu Tyr Arg Val Leu Leu Cys
            260                 265                 270

Val Asp Ile Gly Glu Thr Arg Gly Ala Gly His Arg Pro Glu Met Leu
        275                 280                 285

Arg Glu Leu Gln Arg Leu Arg Val Pro His Thr Val Arg Lys Leu His
    290                 295                 300

Val Gly Asp Phe Val Trp Val Ala Gln Glu Thr Arg Pro Arg Asp Pro
305                 310                 315                 320

Glu Arg Pro Gly Glu Leu Val Leu Asp His Ile Val Glu Arg Lys Arg
                325                 330                 335

Leu Asp Asp Leu Cys Ser Ser Ile Ile Asp Gly Arg Phe Arg Glu Gln
            340                 345                 350

Lys Phe Arg Leu Lys Arg Cys Gly Leu Gly His Arg Val Tyr Leu Val
        355                 360                 365

Glu Glu His Gly Ser Val His Asn Leu Ser Leu Pro Glu Ser Thr Leu
    370                 375                 380

Leu Gln Ala Val Thr Asn Thr Gln Val Ile Asp Gly Phe Phe Val Lys
385                 390                 395                 400

Arg Thr Met Asp Ile Lys Glu Ser Val Gly Tyr Leu Ala Leu Leu Thr
                405                 410                 415

Lys Gly Leu Glu Arg Leu Tyr Gln
            420

<210> SEQ ID NO 40
<211> LENGTH: 2016
<212> TYPE: DNA
<213> ORGANISM: Mus musculus

<400> SEQUENCE: 40
gatatctgca gaattcgccc ttgagactct gaaggagcca gtctagttct tatggcggag      60
ccggtccgcc tgggccggaa gcgtccgctg ccgtttgcc ccaacccgct cttcgttcgt     120
tggctgaccg agtggcggga cgaggcagcc agcaggggc gccacacgcg tttcgtgttt     180
caaaaggcat tgcgctccct ccaacggtac ccgctaccat tgcgcagcgg gaaggaagcc     240
aagatactcc agcacttcgg agacaggctc tgccgcatgc tggacgaaaa gctgaagcag     300
cacctagcat caggcggtga ccatgccccc agctcaccat ctggaaagaa gggagccagc     360
```

```
aaagggccac ctgagcaagt ccaggactct tccatgccag ttcccaccca gcctcaagca    420
ggaagcacca gtgttggcta ttggccagct cagaactcag gtgctcgaga gatcctgctg    480
caactctaca gggagcacct gaattctgat ggccacagct tcctaaccaa agaggagctg    540
ctgcagaagt gtgcccagaa gaccccccagg gtagtgcctg aagttcgaa  accctggcct    600 gccctccgga gcctcctcca taggaacctc atccttggaa cgcatcggcc agccaggtat    660
gcactcacac cagagggtct ggagctggct cagaagctgg ccgaggcgga aggcctgagc    720
actcggcacg ctggctttag gccagaggaa catcacggag aggactcagc agttccagaa    780
gccttgtcag aacctggcac caccgagggg gccgtccagc agagaccact ggagctaagg    840
cctagcgagt acagagtgct gttgtgtgtg gacattggcg aaaccagagg ggcaggacac    900
aggccagaaa tgctccgaga gttacaaagg ctgcgtgtgc cccacaccgt acgcaagcta    960
cacgttggag actttgtgtg ggtggcacag gagaccaggc ccagagaccc agaaagacct   1020
ggggagctgg tcctggacca cattgtggaa cgcaagcggc tagatgacct atgcagcagc   1080
atcattgacg gccgcttccg ggagcagaag ttccgcctga agcgctgtgg cctggggcac   1140
cgggtatact tagtggaaga acatgggtct gtccacaacc ttagccttcc cgagagcacc   1200
ttgctgcagg ctgtcacaaa cacccaggtc attgatggct tttttgtgaa gcgaaccatg   1260
gatattaagg agtcggttgg ctacctggcg cttttgacaa agggcctgga agactgtac    1320 cagccttcca caaaccctct ctgctcactc ctcaccttca gtgacttcaa tgcagaagct   1380
gtcaagaaca aggcccagtc tgtgcgagaa gtatttgccc ggcagctgat gcaggtgcgt   1440
ggactgagtg gggagaaggc agcagccgtg gtggatcgat acagcacccc tgccagtctc   1500
ctggctgctt atgatgcctg tgccaccgcg aaggagcagg agatgctctt gagcaccatc   1560
aagtgtgggc gtctgcagag gaatctggga cccgctctga gcaggaccct gtaccagttg   1620
tactgcagcc acagccctct gagctgagct gtaccaggag acgctcgctc ccagcaccc    1680 atcttcatct ctaccaaggc tggctagcct tttagcaagg gcgaattcca gcacactggc   1740
ggccgttact agtggatccg agctcggtac caagcttggc gtaatcatgg tcatagctgt   1800
ttcctgtgtg aaattgttat ccgctcacaa ttccacacaa catacgagcc ggaagcataa   1860
agtgtaaagc ctggggtgcc taatgagtga gctaactcac attaattgcg ttgcgctcac   1920
tgcccgcttt ccagtcggga aacctgtcgt gccagctgca ttaatgaatc ggccaacgcg   1980
cggggagagg cggtttgcgt attgggcgct cttccg                             2016
```

<210> SEQ ID NO 41
<211> LENGTH: 531
<212> TYPE: PRT
<213> ORGANISM: Mus musculus

<400> SEQUENCE: 41

```
Met Ala Glu Pro Val Arg Leu Gly Arg Lys Arg Pro Leu Pro Val Cys
 1               5                  10                  15

Pro Asn Pro Leu Phe Val Arg Trp Leu Thr Glu Trp Arg Asp Glu Ala
             20                  25                  30

Ala Ser Arg Gly Arg His Thr Arg Phe Val Phe Gln Lys Ala Leu Arg
         35                  40                  45

Ser Leu Gln Arg Tyr Pro Leu Pro Leu Arg Ser Gly Lys Glu Ala Lys
     50                  55                  60

Ile Leu Gln His Phe Gly Asp Arg Leu Cys Arg Met Leu Asp Glu Lys
65                  70                  75                  80
```

-continued

```
Leu Lys Gln His Leu Ala Ser Gly Gly Asp His Ala Pro Ser Ser Pro
                85                  90                  95

Ser Gly Lys Lys Gly Ala Ser Lys Gly Pro Pro Glu Gln Val Gln Asp
            100                 105                 110

Ser Ser Met Pro Val Pro Thr Gln Pro Gln Ala Gly Ser Thr Ser Val
        115                 120                 125

Gly Tyr Trp Pro Ala Gln Asn Ser Gly Ala Arg Glu Ile Leu Leu Gln
    130                 135                 140

Leu Tyr Arg Glu His Leu Asn Ser Asp Gly His Ser Phe Leu Thr Lys
145                 150                 155                 160

Glu Glu Leu Leu Gln Lys Cys Ala Gln Lys Thr Pro Arg Val Val Pro
                165                 170                 175

Gly Ser Ser Lys Pro Trp Pro Ala Leu Arg Ser Leu Leu His Arg Asn
            180                 185                 190

Leu Ile Leu Gly Thr His Arg Pro Ala Arg Tyr Ala Leu Thr Pro Glu
        195                 200                 205

Gly Leu Glu Leu Ala Gln Lys Leu Ala Glu Ala Glu Gly Leu Ser Thr
    210                 215                 220

Arg His Ala Gly Phe Arg Pro Glu Glu His Gly Glu Asp Ser Ala
225                 230                 235                 240

Val Pro Glu Ala Leu Ser Glu Pro Gly Thr Thr Glu Gly Ala Val Gln
                245                 250                 255

Gln Arg Pro Leu Glu Leu Arg Pro Ser Glu Tyr Arg Val Leu Leu Cys
            260                 265                 270

Val Asp Ile Gly Glu Thr Arg Gly Ala Gly His Arg Pro Glu Met Leu
        275                 280                 285

Arg Glu Leu Gln Arg Leu Arg Val Pro His Thr Val Arg Lys Leu His
    290                 295                 300

Val Gly Asp Phe Val Trp Val Ala Gln Glu Thr Arg Pro Arg Asp Pro
305                 310                 315                 320

Glu Arg Pro Gly Glu Leu Val Leu Asp His Ile Val Glu Arg Lys Arg
                325                 330                 335

Leu Asp Asp Leu Cys Ser Ser Ile Ile Asp Gly Arg Phe Arg Glu Gln
            340                 345                 350

Lys Phe Arg Leu Lys Arg Cys Gly Leu Gly His Arg Val Tyr Leu Val
        355                 360                 365

Glu Glu His Gly Ser Val His Asn Leu Ser Leu Pro Glu Ser Thr Leu
    370                 375                 380

Leu Gln Ala Val Thr Asn Thr Gln Val Ile Asp Gly Phe Phe Val Lys
385                 390                 395                 400

Arg Thr Met Asp Ile Lys Glu Ser Val Gly Tyr Leu Ala Leu Leu Thr
                405                 410                 415

Lys Gly Leu Glu Arg Leu Tyr Gln Pro Ser Thr Asn Pro Leu Cys Ser
            420                 425                 430

Leu Leu Thr Phe Ser Asp Phe Asn Ala Glu Ala Val Lys Asn Lys Ala
        435                 440                 445

Gln Ser Val Arg Glu Val Phe Ala Arg Gln Leu Met Gln Val Arg Gly
    450                 455                 460

Leu Ser Gly Glu Lys Ala Ala Val Val Asp Arg Tyr Ser Thr Pro
465                 470                 475                 480

Ala Ser Leu Leu Ala Ala Tyr Asp Ala Cys Ala Thr Ala Lys Glu Gln
                485                 490                 495

Glu Met Leu Leu Ser Thr Ile Lys Cys Gly Arg Leu Gln Arg Asn Leu
```

```
                  500             505             510
Gly Pro Ala Leu Ser Arg Thr Leu Tyr Gln Leu Tyr Cys Ser His Ser
        515                 520                 525
Pro Leu Ser
    530

<210> SEQ ID NO 42
<211> LENGTH: 1698
<212> TYPE: DNA
<213> ORGANISM: Mus musculus

<400> SEQUENCE: 42
gatatctgca gaattcgccc ttgagactct gaaggagcca gtctagttct tatggcggag    60
ccggtccgcc tgggccggaa gcgtccgctg cccgtttgcc ccaacccgct cttcgtttgt   120
tggctgaccg agtggcggga cgaggcagcc agcaggggc gccacacgcg tttcgtgttt    180
caaaaggcat tgcgctccct ccaacggtac ccgctaccat tgcgcagcgg gaaggaagcc   240
aagatactcc agcacttcgg agacaggctc tgccgcatgc tggacgaaaa gctgaagcag   300
cacctagcat caggcggtga ccatgccccc agctcaccat ctggaaagaa gggagccagc   360
aaagggccac ctgagcaagt ccaggactct tccatgccag ttcccaccca gcctcaagca   420
ggaagcacca gtgttggcta ttggccagct cagaactcag gtgctcgaga gatcctgctg   480
caactctaca gggagcacct gaattctgat ggccacagct cctaaccaa agaggagctg     540 ctgcagaagt gtgcccagaa gacccccagg gtagtgcctg gaagttcgaa ccctggcct    600 gccctccgga gcctcctcca taggaacctc atccttggaa cgcatcggcc agccaggtat   660
gcactcacac cagagggtct ggagctggct cagaagctgg ccgaggcgga aggcctgagc   720
actcggcacg ctggctttag gccagaggaa catcacggag aggactcagc agttccagaa   780
gccttgtcag aacctggcac caccgagggg ccgtccagc agagaccact ggagctaagg    840
cctagcgagt acagagtgct gttgtgtgtg gacattggcg aaaccagagg ggcaggacac   900
aggccagaaa tgctccgaga gttacaaagg ctgcgtgtgc cccacaccgt acgcaagcta   960
cacgttggag actttgtgtg ggtggcacag gagaccaggc ccagagaccc agaaagacct  1020
ggggagctgg tcctggacca cattgtggaa cgcaagcggc tagatgacct atgcagcagc  1080
atcattgacg gccgctttcg ggagcagaag ttccgcctga gcgctgtgg cctggggcac   1140 cgggtatact tagtggaaga acatgggtct gtccacaacc ttagccttcc cgagagcacc   1200
ttgctgcagg ctgtcacaaa cacccaggtc attgatggct ttttttgtgaa gcgaaccatg  1260 gatattaagg agtcggttgg ctacctggcg cttttgacaa agggcctgga aagactgtac   1320
caggccaagg tcacccttaa cacaggccta ccccaacccc aggcccagtc tgtgcgagaa   1380
gtatttgccc ggcagctgat gcaggtgcgt ggactgagtg gggagaaggc agcagccgtg   1440
gtggatcgat acagcacccc tgccagtctc ctggctgctt atgatgcctg tgccaccgcg   1500
aaggagcagg agatgctctt gagcaccatc aagtgtgggc gtctgcagag gaatctggga  1560
cccgctctga gcaggaccct gtaccagttg tactgcagcc acagccctct gagctgagct   1620
gtaccaggag acgctcgctc cccagcaccc atcttcatct ctaccaaggc tggctagcct   1680
tttagcaagg gcgaattc                                                 1698

<210> SEQ ID NO 43
<211> LENGTH: 521
<212> TYPE: PRT
<213> ORGANISM: Mus musculus
```

<400> SEQUENCE: 43

```
Met Ala Glu Pro Val Arg Leu Gly Arg Lys Arg Pro Leu Pro Val Cys
  1               5                  10                  15
Pro Asn Pro Leu Phe Val Cys Trp Leu Thr Glu Trp Arg Asp Glu Ala
             20                  25                  30
Ala Ser Arg Gly Arg His Thr Arg Phe Val Phe Gln Lys Ala Leu Arg
         35                  40                  45
Ser Leu Gln Arg Tyr Pro Leu Pro Leu Arg Ser Gly Lys Glu Ala Lys
     50                  55                  60
Ile Leu Gln His Phe Gly Asp Arg Leu Cys Arg Met Leu Asp Glu Lys
 65                  70                  75                  80
Leu Lys Gln His Leu Ala Ser Gly Gly Asp His Ala Pro Ser Ser Pro
                 85                  90                  95
Ser Gly Lys Lys Gly Ala Ser Lys Gly Pro Pro Glu Gln Val Gln Asp
            100                 105                 110
Ser Ser Met Pro Val Pro Thr Gln Pro Gln Ala Gly Ser Thr Ser Val
            115                 120                 125
Gly Tyr Trp Pro Ala Gln Asn Ser Gly Ala Arg Glu Ile Leu Leu Gln
        130                 135                 140
Leu Tyr Arg Glu His Leu Asn Ser Asp Gly His Ser Phe Leu Thr Lys
145                 150                 155                 160
Glu Glu Leu Leu Gln Lys Cys Ala Gln Lys Thr Pro Arg Val Val Pro
                165                 170                 175
Gly Ser Ser Lys Pro Trp Pro Ala Leu Arg Ser Leu Leu His Arg Asn
            180                 185                 190
Leu Ile Leu Gly Thr His Arg Pro Ala Arg Tyr Ala Leu Thr Pro Glu
        195                 200                 205
Gly Leu Glu Leu Ala Gln Lys Leu Ala Glu Ala Glu Gly Leu Ser Thr
    210                 215                 220
Arg His Ala Gly Phe Arg Pro Glu Glu His His Gly Glu Asp Ser Ala
225                 230                 235                 240
Val Pro Glu Ala Leu Ser Glu Pro Gly Thr Thr Glu Gly Ala Val Gln
                245                 250                 255
Gln Arg Pro Leu Glu Leu Arg Pro Ser Glu Tyr Arg Val Leu Leu Cys
            260                 265                 270
Val Asp Ile Gly Glu Thr Arg Gly Ala Gly His Arg Pro Glu Met Leu
        275                 280                 285
Arg Glu Leu Gln Arg Leu Arg Val Pro His Thr Val Arg Lys Leu His
    290                 295                 300
Val Gly Asp Phe Val Trp Val Ala Gln Glu Thr Arg Pro Arg Asp Pro
305                 310                 315                 320
Glu Arg Pro Gly Glu Leu Val Leu Asp His Ile Val Glu Arg Lys Arg
                325                 330                 335
Leu Asp Asp Leu Cys Ser Ser Ile Ile Asp Gly Arg Phe Arg Glu Gln
            340                 345                 350
Lys Phe Arg Leu Lys Arg Cys Gly Leu Gly His Arg Val Tyr Leu Val
        355                 360                 365
Glu Glu His Gly Ser Val His Asn Leu Ser Leu Pro Glu Ser Thr Leu
    370                 375                 380
Leu Gln Ala Val Thr Asn Thr Gln Val Ile Asp Gly Phe Phe Val Lys
385                 390                 395                 400
Arg Thr Met Asp Ile Lys Glu Ser Val Gly Tyr Leu Ala Leu Leu Thr
```

```
                    405                 410                 415
Lys Gly Leu Glu Arg Leu Tyr Gln Ala Lys Val Thr Leu Asn Thr Gly
                420                 425                 430

Leu Pro Gln Pro Gln Ala Gln Ser Val Arg Glu Val Phe Ala Arg Gln
            435                 440                 445

Leu Met Gln Val Arg Gly Leu Ser Gly Glu Lys Ala Ala Val Val
        450                 455                 460

Asp Arg Tyr Ser Thr Pro Ala Ser Leu Leu Ala Ala Tyr Asp Ala Cys
465                 470                 475                 480

Ala Thr Ala Lys Glu Gln Glu Met Leu Leu Ser Thr Ile Lys Cys Gly
                485                 490                 495

Arg Leu Gln Arg Asn Leu Gly Pro Ala Leu Ser Arg Thr Leu Tyr Gln
            500                 505                 510

Leu Tyr Cys Ser His Ser Pro Leu Ser
        515                 520

<210> SEQ ID NO 44
<211> LENGTH: 2180
<212> TYPE: DNA
<213> ORGANISM: Mus musculus

<400> SEQUENCE: 44
```

| | | | | | |
|---|---|---|---|---|---|
| ggggatagat | ctacttccgg | gtcttgcgga | caattcaaag | agtggcggga | gcagtagcag | 60 |
| gcagttcatt | tgagagctct | aatgggttga | tggctctaag | aaggttatcc | ctgtctcgcc | 120 |
| tctccacgga | gagtgattct | gaggacctgc | ccacatttgc | cttttttgaag | aaggaaccat | 180 |
| cttcaaccaa | caggaagcca | cctcagaggg | cgaagaacat | agtggttgtc | acctcagatt | 240 |
| ctgaagcctc | ctgtcctcca | tcaccaggcc | tcaaaggtcc | accatgtgtc | cccagtgcag | 300 |
| ctggagctcc | cccacaagca | gggccagtca | gagtgctaag | cagtagcagt | gaggacgaag | 360 |
| atgtatttgt | cccctagct | gagaggatca | catgtaagct | tttgacgagc | aagcagctgt | 420 |
| gccctgagct | ctctagctcc | tcacttaaaa | caggtttgga | tggccaaaat | aatgccagcg | 480 |
| caccatgtga | ctggaaaagg | caaccatggc | caaagattcc | cgatgttccc | ctccacggtg | 540 |
| ccttagagaa | gagtgctgca | aatgatgagg | actctctctt | agacgatcag | tgtcgtcagc | 600 |
| ttccaaccta | ccaggctacc | tgcagggagc | tggcagtctc | caaaacaaat | tccgaccgac | 660 |
| ctctacccaa | gaagagaacc | aaacatattc | agacggtcca | gagcggaggc | tctcagggat | 720 |
| gctggcgacc | gggacaggca | agcaggaagg | aaaacacccc | gaggcagcat | gaaagaaaaa | 780 |
| agaaggcaga | gatgatcaag | aggctcaaag | cccagaggcc | agaggaatgc | ctgaagcaca | 840 |
| tcgtggtggt | gctggatcca | gtgctttttac | agatggaagg | tgggggccag | ctcctgggag | 900 |
| cgctgcaggc | catggagtgc | agctgtgtga | ttgaagccca | ggccatacct | cgaagcatca | 960 |
| cttggaggag | gaggaggaca | gagctggtag | aggatgagag | tgactggatg | gaagagccaa | 1020 |
| caatcctggt | gttggtcctg | gcagaggtct | tcatgtccat | ggcctacaac | ttaaagcagg | 1080 |
| caagtcctag | cagcaccgag | aaagggaagg | agacccttcg | gagctttgta | actgatgtca | 1140 |
| cagcaaagac | ggggaaagca | ttgtcactgg | tgattgtgga | ccaggagaaa | tgcttcaggc | 1200 |
| ctcagaatcc | cccgaggaga | aggaaatcag | gaatggcaaa | taacaggcc | aaagcgaagc | 1260 |
| atcagcagag | gcaagagtct | agcacgggac | tcatggtgtc | cagggcagac | atggagaagg | 1320 |
| cactggtgga | tctgcagctt | tatacagaag | cccaggcgtg | gatggtgcag | agctggaagg | 1380 |
| agctggcgga | cttcacctgt | gcatttacaa | aggctgtggc | tgaagcaccc | ttcaagaagc | 1440 |

-continued

```
tccgggatca agtcaccttt tccttcttcc tggagaaaga ctgggctgga gggatgaaag   1500
tggaccagtc cggcagggga ctggcactga tctggaggcg gcagatccag cagctgaacc   1560
gagtcagctc ggagatggcc agtgctattg tggacgccta tccctcaccg cagctcctgg   1620
tgcaggctta tcagcggtgt ttctctgagc aagaacgtca gaatttgctg ctgacatac    1680 aagtgcgacg tggggaaggt gtgacagcca cctcccgccg tgttgggcca gaattatcca   1740
ggcggatcta ccttcaaatg accacagcgc aaccagatct catcttagac agtgttgact   1800
gatatcccac cttggctatt gacagtagac aggccagaag tacctccttg gtacagttag   1860
ggagcaagtc tctcatctct gggaacagag aaggctgagt cacttgaatc tacctccacc   1920
atagcactca tgttcctctc ccggcaagcg agatgccatg gacagccatc ccacccatc    1980 ccagttgacc ctcacagcac aaaggagaaa ggcagaccac tcagacatgg atttaataat   2040
tgtagaaatc caagaaataa gcatcaaatc tcgaagtcag agtgaactct gcctgcggg    2100 ttggcttgac tacgcccagc cactgagctg cctcaaccag ctagggagct atgatgaggc   2160
tgactcctgt tttcatgatg                                              2180
```

<210> SEQ ID NO 45
<211> LENGTH: 570
<212> TYPE: PRT
<213> ORGANISM: Mus musculus

<400> SEQUENCE: 45

```
Met Ala Leu Arg Arg Leu Ser Leu Ser Arg Leu Ser Thr Glu Ser Asp
 1               5                  10                  15

Ser Glu Asp Leu Pro Thr Phe Ala Phe Leu Lys Lys Glu Pro Ser Ser
            20                  25                  30

Thr Asn Arg Lys Pro Pro Gln Arg Ala Lys Asn Ile Val Val Val Thr
        35                  40                  45

Ser Asp Ser Glu Ala Ser Cys Pro Pro Ser Pro Gly Leu Lys Gly Pro
    50                  55                  60

Pro Cys Val Pro Ser Ala Ala Gly Ala Pro Pro Gln Ala Gly Pro Val
65                  70                  75                  80

Arg Val Leu Ser Ser Ser Glu Asp Glu Asp Val Phe Val Pro Leu
                85                  90                  95

Ala Glu Arg Ile Thr Cys Lys Leu Leu Thr Ser Lys Gln Leu Cys Pro
            100                 105                 110

Glu Leu Ser Ser Ser Ser Leu Lys Thr Gly Leu Asp Gly Gln Asn Asn
        115                 120                 125

Ala Ser Ala Pro Cys Asp Trp Lys Arg Gln Pro Trp Pro Lys Ile Pro
    130                 135                 140

Asp Val Pro Leu His Gly Ala Leu Glu Lys Ser Ala Ala Asn Asp Glu
145                 150                 155                 160

Asp Ser Leu Leu Asp Asp Gln Cys Arg Gln Leu Pro Thr Tyr Gln Ala
                165                 170                 175

Thr Cys Arg Glu Leu Ala Val Ser Lys Thr Asn Ser Asp Arg Pro Leu
            180                 185                 190

Pro Lys Lys Arg Thr Lys His Ile Gln Thr Val Gln Ser Gly Gly Ser
        195                 200                 205

Gln Gly Cys Trp Arg Pro Gly Gln Ala Ser Arg Lys Glu Asn Thr Pro
    210                 215                 220

Arg Gln His Glu Arg Lys Lys Lys Ala Glu Met Ile Lys Arg Leu Lys
225                 230                 235                 240
```

-continued

| | | | | | | | | | | | |
|---|---|---|---|---|---|---|---|---|---|---|---|
|Ala|Gln|Arg|Pro|Glu|Glu|Cys|Leu|Lys|His|Ile|Val|Val|Leu|Asp|
| | |245| | | |250| | | |255| | | | |

Pro Val Leu Leu Gln Met Glu Gly Gly Gly Gln Leu Leu Gly Ala Leu
          260             265             270

Gln Ala Met Glu Cys Ser Cys Val Ile Glu Ala Gln Ala Ile Pro Arg
          275             280             285

Ser Ile Thr Trp Arg Arg Arg Thr Glu Leu Val Glu Asp Gly Asp
      290             295             300

Asp Trp Met Glu Glu Pro Thr Ile Leu Val Leu Val Leu Ala Glu Val
305             310             315             320

Phe Met Ser Met Ala Tyr Asn Leu Lys Gln Ala Ser Pro Ser Ser Thr
              325             330             335

Glu Lys Gly Lys Glu Thr Leu Arg Ser Phe Val Thr Asp Val Thr Ala
          340             345             350

Lys Thr Gly Lys Ala Leu Ser Leu Val Ile Val Asp Gln Glu Lys Cys
          355             360             365

Phe Arg Pro Gln Asn Pro Pro Arg Arg Lys Ser Gly Met Ala Asn
      370             375             380

Lys Gln Ala Lys Ala Lys His Gln Gln Arg Gln Glu Ser Ser Thr Gly
385             390             395             400

Leu Met Val Ser Arg Ala Asp Met Glu Lys Ala Leu Val Asp Leu Gln
          405             410             415

Leu Tyr Thr Glu Ala Gln Ala Trp Met Val Gln Ser Trp Lys Glu Leu
          420             425             430

Ala Asp Phe Thr Cys Ala Phe Thr Lys Ala Val Ala Glu Ala Pro Phe
          435             440             445

Lys Lys Leu Arg Asp Gln Val Thr Phe Ser Phe Phe Leu Glu Lys Asp
      450             455             460

Trp Ala Gly Gly Met Lys Val Asp Gln Ser Gly Arg Gly Leu Ala Leu
465             470             475             480

Ile Trp Arg Arg Gln Ile Gln Gln Leu Asn Arg Val Ser Ser Glu Met
              485             490             495

Ala Ser Ala Ile Val Asp Ala Tyr Pro Ser Pro Gln Leu Leu Val Gln
          500             505             510

Ala Tyr Gln Arg Cys Phe Ser Glu Gln Glu Arg Gln Asn Leu Leu Ala
          515             520             525

Asp Ile Gln Val Arg Arg Gly Glu Gly Val Thr Ala Thr Ser Arg Arg
      530             535             540

Val Gly Pro Glu Leu Ser Arg Arg Ile Tyr Leu Gln Met Thr Thr Ala
545             550             555             560

Gln Pro Asp Leu Ile Leu Asp Ser Val Asp
              565             570

<210> SEQ ID NO 46
<211> LENGTH: 1436
<212> TYPE: DNA
<213> ORGANISM: Mus musculus

<400> SEQUENCE: 46
ggggatagat ctacttccgg gtcttgcgga caattcaaag agtggcggga gcagtagcag     60
tgcttttaca gatggaaggt gggggccagc tcctgggagc gctgcaggcc atggagtgca    120
gctgtgtgat tgaagcccag gccataccto gaagcatcac ttggaggagg aggaggacag    180
agctggtaga gttgcctgtt gcagagagag gagcaactgg tggcatccct ttccctgcc     240

```
tgaatgagga tggagatgac tggatggaag agccaacaat cctggtgttg gtcctggcag    300
aggtcttcat gtccatggcc tacaacttaa agcaggcaag tcctagcagc accgagaaag    360
ggaaggagac ccttcggagc tttgtaactg atgtcacagc aaagacgggg aaagcattgt    420
cactggtgat tgtggaccag gagaaatgct tcaggcctca gaatccccg aggagaagga    480 aatcaggaat ggcaaataaa caggccaaag cgaagcatca gcagaggcaa gagtctagca    540
cgggactcat ggtgtccagg gcagacatgg agaaggcact ggtggatctg cagctttata    600
cagaagccca ggcgtggatg gtgcagagct ggaaggagct ggcggacttc acctgtgcat    660
ttacaaaggc tgtggctgaa gcaccttca agaagctccg ggatcaagtc accttttcct    720
tcttcctgga gaaagactgg gctggaggga tgaaagtgga ccagtccggc aggggactgg    780
cactgatctg gaggcggcag atccagcagc tgaaccgagt cagctcggag atggccagtg    840
ctattgtgga cgcctatccc tcaccgcagc tcctggtgca ggcttatcag cggtgtttct    900
ctgagcaaga acgtcagaat ttgctggctg acatacaagt gcgacgtggg gaaggtgtga    960
cagccacctc ccgccgtgtt gggccagaat tatccaggcg gatctaccct caaatgacca   1020
cagcgcaacc agatctcatc ttagacagtg ttgactgata tcccaccttg gctattgaca   1080
gtagacaggc cagaagtacc tccttggtac agttagggag caagtctctc atctctggga   1140
acagagaagg ctgagtcact tgaatctacc tccaccatag cactcatgtt cctctcccgg   1200
caagcgagat gccatggaca gccatccac cccatcccag ttgaccctca cagcacaaag    1260
gagaaaggca gaccactcag acatggattt aataattgta gaaatccaag aaataagcat   1320
caaatctcga agtcagagtg aactcttgcc tgcgggttgg cttgactacg cccagccact   1380
gagctgcctc aaccagctag ggagctatga tgaggctgac tcctgttttc atgatg       1436
```

<210> SEQ ID NO 47
<211> LENGTH: 328
<212> TYPE: PRT
<213> ORGANISM: Mus musculus

<400> SEQUENCE: 47

```
Met Glu Gly Gly Gly Gln Leu Leu Gly Ala Leu Gln Ala Met Glu Cys
 1               5                  10                  15

Ser Cys Val Ile Glu Ala Gln Ala Ile Pro Arg Ser Ile Thr Trp Arg
                20                  25                  30

Arg Arg Arg Thr Glu Leu Val Glu Leu Pro Val Ala Glu Arg Gly Ala
            35                  40                  45

Thr Gly Gly Ile Pro Phe Pro Cys Leu Asn Glu Asp Gly Asp Asp Trp
        50                  55                  60

Met Glu Glu Pro Thr Ile Leu Val Leu Val Leu Ala Glu Val Phe Met
65                  70                  75                  80

Ser Met Ala Tyr Asn Leu Lys Gln Ala Ser Pro Ser Thr Glu Lys
                85                  90                  95

Gly Lys Glu Thr Leu Arg Ser Phe Val Thr Asp Val Thr Ala Lys Thr
            100                 105                 110

Gly Lys Ala Leu Ser Leu Val Ile Val Asp Gln Glu Lys Cys Phe Arg
        115                 120                 125

Pro Gln Asn Pro Pro Arg Arg Lys Ser Gly Met Ala Asn Lys Gln
    130                 135                 140

Ala Lys Ala Lys His Gln Gln Arg Gln Glu Ser Ser Thr Gly Leu Met
145                 150                 155                 160

Val Ser Arg Ala Asp Met Glu Lys Ala Leu Val Asp Leu Gln Leu Tyr
```

|  | 165 |  |  |  |  | 170 |  |  |  |  | 175 |  |
|---|---|---|---|---|---|---|---|---|---|---|---|---|
Thr Glu Ala Gln Ala Trp Met Val Gln Ser Trp Lys Glu Leu Ala Asp
                180                 185                 190

Phe Thr Cys Ala Phe Thr Lys Ala Val Ala Glu Ala Pro Phe Lys Lys
            195                 200                 205

Leu Arg Asp Gln Val Thr Phe Ser Phe Phe Leu Glu Lys Asp Trp Ala
        210                 215                 220

Gly Gly Met Lys Val Asp Gln Ser Gly Arg Gly Leu Ala Leu Ile Trp
225                 230                 235                 240

Arg Arg Gln Ile Gln Gln Leu Asn Arg Val Ser Ser Glu Met Ala Ser
                245                 250                 255

Ala Ile Val Asp Ala Tyr Pro Ser Pro Gln Leu Leu Val Gln Ala Tyr
            260                 265                 270

Gln Arg Cys Phe Ser Glu Gln Glu Arg Gln Asn Leu Leu Ala Asp Ile
        275                 280                 285

Gln Val Arg Arg Gly Glu Gly Val Thr Ala Thr Ser Arg Arg Val Gly
    290                 295                 300

Pro Glu Leu Ser Arg Arg Ile Tyr Leu Gln Met Thr Thr Ala Gln Pro
305                 310                 315                 320

Asp Leu Ile Leu Asp Ser Val Asp
                325

<210> SEQ ID NO 48
<211> LENGTH: 2237
<212> TYPE: DNA
<213> ORGANISM: Mus musculus

<400> SEQUENCE: 48

```
gggatagat ctacttccgg gtcttgcgga caattcaaag agtggcggga gcagtagcag        60
gcagttcatt tgagagctct aatgggttga tggctctaag aaggttatcc ctgtctcgcc       120
tctccacgga gagtgattct gaggacctgc ccacatttgc cttttttgaag aaggaaccat      180 cttcaaccaa caggaagcca cctcagaggg cgaagaacat agtggttgtc acctcagatt       240
ctgaagcctc ctgtcctcca tcaccaggcc tcaaggtcc accatgtgtc cccagtgcag        300
ctggagctcc cccacaagca gggccagtca gagtgctaag cagtagcagt gaggacgaag       360
atgtatttgt cccccctagct gagaggatca catgtaagct tttgacgagc aagcagctgt      420
gccctgagct ctctagctcc tcacttaaaa caggtttgga tggccaaaat aatgccagcg       480
caccatgtga ctggaaaagg caaccatggc caaagattcc cgatgttccc ctccacggtg       540
ccttagagaa gagtgctgca atgatgagg actctctctt agacgatcag tgtcgtcagc       600
ttccaaccta ccaggctacc tgcagggagc tggcagtctc caaaacaaat tccgaccgac       660
ctctacccaa gaagagaacc aagcatattc agacggtcca gagcggaggc tctcagggat       720
gctggcgacc gggacaggca agcaggaagg aaaacacccc gaggcagcat gaaagaaaaa       780
agaaggcaga gatgatcaag aggctcaaag cccagaggcc agaggaatgc ctgaagcaca       840
tcgtggtggt gctggatcca gtgcttttac agatggaagg tggggccag ctcctgggag       900 cgctgcaggc catggagtgc agctgtgtga ttgaagccca ggccatacct cgaagcatca       960
cttggaggag gaggaggaca gagctggtag agttgcctgt tgcagagaga ggagcaactg      1020
gtagcatccc ttttccctgc ctgaatgagg atggagatga ctggatggaa gagccaacaa      1080
tcctggtgtt ggtcctggca gaggtcttca gtgtccatgg ctacaactta aagcaggcaa      1140
gtcctagcag caccgagaaa gggaaggaga cccttcggag cttttgtaact gatgtcacag     1200
```

```
caaagacggg gaaagcattg tcactggtga ttgtggacca ggagaaatgc ttcaggcctc    1260
agaatccccc gaggagaagg aaatcaggaa tggcaaataa acaggccaaa gcgaagcatc    1320
agcagaggca agagtctagc acgggactca tggtgtccag ggcagacatg gagaaggcac    1380
tggtggatct gcagctttat acagaagccc aggcgtggat ggtgcagagc tggaaggagc    1440
tggcggactt cacctgtgca tttacaaagg ctgtggctga agcacccttc aagaagctcc    1500
gggatcaagt caccttttcc ttcttcctgg agaaagactg ggctggaggg atgaaagtgg    1560
accagtccgg caggggactg gcactgatct ggaggcggca gatccagcag ctgaaccgag    1620
tcagctcgga gatggccagt gctattgtgg acgcctatcc ctcaccgcag ctcctggtgc    1680
aggcttatca gcggtgtttc tctgagcaag aacgtcagaa tttgctggct gacatacaag    1740
tgcgacgtgg ggaaggtgtg acagccacct cccgccgtgt gggccagaa ttatccaggc     1800 ggatctacct tcaaatgacc acagcgcaac cagatctcat cttagacagt gttgactgat    1860
atcccacctt ggctattgac agtagacagg ccagaagtac ctccttggta cagttaggga    1920
gcaagtctct catctctggg aacagagaag gctgagtcac ttgaatctac ctccaccata    1980
gcactcacgt tcctctcccg gcaagcgaga tgccatggac agccatccca ccccatccca    2040
gttgaccctc acagcacaaa ggagaaaggc agaccactca gacatggatt taataattgt    2100
agaaatccaa gaaataagca tcaaatctcg aagtcagagt gaactcttgc ctgcgggttg    2160
gcttgactac gcccagccac tgagctgcct caaccagcta gggagctatg atgaggctga    2220
ctcctgtttt catgatg                                                   2237
```

<210> SEQ ID NO 49
<211> LENGTH: 589
<212> TYPE: PRT
<213> ORGANISM: Mus musculus

<400> SEQUENCE: 49

```
Met Ala Leu Arg Arg Leu Ser Leu Ser Arg Leu Ser Thr Glu Ser Asp
 1               5                  10                  15

Ser Glu Asp Leu Pro Thr Phe Ala Phe Leu Lys Lys Glu Pro Ser Ser
            20                  25                  30

Thr Asn Arg Lys Pro Pro Gln Arg Ala Lys Asn Ile Val Val Val Thr
        35                  40                  45

Ser Asp Ser Glu Ala Ser Cys Pro Ser Pro Gly Leu Lys Gly Pro
    50                  55                  60

Pro Cys Val Pro Ser Ala Ala Gly Ala Pro Gln Ala Gly Pro Val
65                  70                  75                  80

Arg Val Leu Ser Ser Ser Glu Asp Glu Asp Val Phe Val Pro Leu
                85                  90                  95

Ala Glu Arg Ile Thr Cys Lys Leu Leu Thr Ser Lys Gln Leu Cys Pro
            100                 105                 110

Glu Leu Ser Ser Ser Ser Leu Lys Thr Gly Leu Asp Gly Gln Asn Asn
        115                 120                 125

Ala Ser Ala Pro Cys Asp Trp Lys Arg Gln Pro Trp Pro Lys Ile Pro
    130                 135                 140

Asp Val Pro Leu His Gly Ala Leu Glu Lys Ser Ala Ala Asn Asp Glu
145                 150                 155                 160

Asp Ser Leu Leu Asp Asp Gln Cys Arg Gln Leu Pro Thr Tyr Gln Ala
                165                 170                 175

Thr Cys Arg Glu Leu Ala Val Ser Lys Thr Asn Ser Asp Arg Pro Leu
```

```
                180                 185                 190
Pro Lys Lys Arg Thr Lys His Ile Gln Thr Val Gln Ser Gly Gly Ser
            195                 200                 205
Gln Gly Cys Trp Arg Pro Gly Gln Ala Ser Arg Lys Glu Asn Thr Pro
        210                 215                 220
Arg Gln His Glu Arg Lys Lys Ala Glu Met Ile Lys Arg Leu Lys
225                 230                 235                 240
Ala Gln Arg Pro Glu Glu Cys Leu Lys His Ile Val Val Leu Asp
                245                 250                 255
Pro Val Leu Leu Gln Met Glu Gly Gly Gln Leu Leu Gly Ala Leu
            260                 265                 270
Gln Ala Met Glu Cys Ser Cys Val Ile Glu Ala Gln Ala Ile Pro Arg
        275                 280                 285
Ser Ile Thr Trp Arg Arg Arg Thr Glu Leu Val Glu Leu Pro Val
        290                 295                 300
Ala Glu Arg Gly Ala Thr Gly Ser Ile Pro Phe Pro Cys Leu Asn Glu
305                 310                 315                 320
Asp Gly Asp Asp Trp Met Glu Pro Thr Ile Leu Val Leu Val Leu
                325                 330                 335
Ala Glu Val Phe Met Ser Met Ala Tyr Asn Leu Lys Gln Ala Ser Pro
            340                 345                 350
Ser Ser Thr Glu Lys Gly Lys Glu Thr Leu Arg Ser Phe Val Thr Asp
        355                 360                 365
Val Thr Ala Lys Thr Gly Lys Ala Leu Ser Leu Ile Val Asp Gln
        370                 375                 380
Glu Lys Cys Phe Arg Pro Gln Asn Pro Pro Arg Arg Lys Ser Gly
385                 390                 395                 400
Met Ala Asn Lys Gln Ala Lys Ala Lys His Gln Arg Gln Glu Ser
                405                 410                 415
Ser Thr Gly Leu Met Val Ser Arg Ala Asp Met Glu Lys Ala Leu Val
            420                 425                 430
Asp Leu Gln Leu Tyr Thr Glu Ala Gln Ala Trp Met Val Gln Ser Trp
        435                 440                 445
Lys Glu Leu Ala Asp Phe Thr Cys Ala Phe Thr Lys Ala Val Ala Glu
    450                 455                 460
Ala Pro Phe Lys Lys Leu Arg Asp Gln Val Thr Phe Ser Phe Phe Leu
465                 470                 475                 480
Glu Lys Asp Trp Ala Gly Gly Met Lys Val Asp Gln Ser Gly Arg Gly
                485                 490                 495
Leu Ala Leu Ile Trp Arg Arg Gln Ile Gln Gln Leu Asn Arg Val Ser
            500                 505                 510
Ser Glu Met Ala Ser Ala Ile Val Asp Ala Tyr Pro Ser Pro Gln Leu
        515                 520                 525
Leu Val Gln Ala Tyr Gln Arg Cys Phe Ser Glu Gln Glu Arg Gln Asn
        530                 535                 540
Leu Leu Ala Asp Ile Gln Val Arg Arg Gly Glu Gly Val Thr Ala Thr
545                 550                 555                 560
Ser Arg Arg Val Gly Pro Glu Leu Ser Arg Arg Ile Tyr Leu Gln Met
                565                 570                 575
Thr Thr Ala Gln Pro Asp Leu Ile Leu Asp Ser Val Asp
            580                 585

<210> SEQ ID NO 50
```

<211> LENGTH: 1379
<212> TYPE: DNA
<213> ORGANISM: Mus musculus

<400> SEQUENCE: 50

```
ggggatagat ctacttccgg gtcttgcgga caattcaaag agtggcggga gcagtagcag      60
tgcttttaca gatggaaggt gggggccagc tcctgggagc gctgcaggcc atggagtgca     120
gctgtgtgat tgaagcccag gccatacctc gaagcatcac ttggaggagg aggaggacag     180
agctggtaga ggatggagat gactggatgg aagagccaac aatcctggtg ttggtcctgg     240
cagaggtctt catgtccatg gcctacaact taaagcaggc aagtcctagc agcaccgaga     300
aagggaagga gacccttcgg agctttgtaa ctgatgtcac agcaaagacg gggaaagcat     360
tgtcactggt gattgtggac caggagaaat gcttcaggcc tcagaatccc cgaggagaa      420
ggaaatcagg aatggcaaat aaacaggcca agcgaagca tcagcagagg caagagtcta      480
gcacgggact catggtgtcc agggcagaca tggagaaggc actggtggat ctgcagcttt     540
atacagaagc ccaggcgtgg atggtgcaga gctggaagga gctggcggac ttcacctgtg     600
catttacaaa ggctgtggct gaagcaccct caagaagct ccgggatcaa gtcacctttt      660
ccttcttcct ggagaaagac tgggctggag ggatgaaagt ggaccagtcc ggcaggggac     720
tggcactgat ctggaggcgg cagatccagc agctgaaccg agtcagctcg gagatggcca     780
gtgctattgt ggacgcctat ccctcaccgc agctcctggt gcaggcttat cagcggtgtt     840
tctctgagca agaacgtcag aatttgctgg ctgacataca agtgcgacgt ggggaaggtg     900
tgacagccac ctcccgccgt gttgggccag aattatccag gcggatctac cttcaaatga     960
ccacagcgca accagatctc atcttagaca gtgttgactg atatcccacc ttggctattg    1020
acagtagaca ggccagaagt acctccttgg tacagttagg gagcaagtct ctcatctctg    1080
ggaacagaga aggctgagtc acttgaatct acctccacca tagcactcat gttcctctcc    1140
cggcaagcga gatgccatgg acagccatcc taccccatcc cagttgaccc tcacagcaca    1200
aaggagaaag gcagaccact cagacatgga tttaataatt gtagaaatcc aagaaataag    1260
catcaaatct cgaagtcaga gtgaactctt gcctgcgggt tggcttgact acgcccagcc    1320
actgagctgc ctcaaccagc tagggagcta tgatgaggct gactcctgtt ttcatgatg    1379
```

<210> SEQ ID NO 51
<211> LENGTH: 309
<212> TYPE: PRT
<213> ORGANISM: Mus musculus

<400> SEQUENCE: 51

```
Met Glu Gly Gly Gly Gln Leu Leu Gly Ala Leu Gln Ala Met Glu Cys
 1               5                  10                  15

Ser Cys Val Ile Glu Ala Gln Ala Ile Pro Arg Ser Ile Thr Trp Arg
            20                  25                  30

Arg Arg Arg Thr Glu Leu Val Glu Asp Gly Asp Asp Trp Met Glu Glu
        35                  40                  45

Pro Thr Ile Leu Val Leu Val Leu Ala Glu Val Phe Met Ser Met Ala
    50                  55                  60

Tyr Asn Leu Lys Gln Ala Ser Pro Ser Ser Thr Glu Lys Gly Lys Glu
65                  70                  75                  80

Thr Leu Arg Ser Phe Val Thr Asp Val Thr Ala Lys Thr Gly Lys Ala
                85                  90                  95

Leu Ser Leu Val Ile Val Asp Gln Glu Lys Cys Phe Arg Pro Gln Asn
```

|   |   |   | 100 |   |   |   |   | 105 |   |   |   |   | 110 |   |
|---|---|---|---|---|---|---|---|---|---|---|---|---|---|---|

Pro Pro Arg Arg Arg Lys Ser Gly Met Ala Asn Lys Gln Ala Lys Ala
    115              120              125

Lys His Gln Gln Arg Gln Glu Ser Ser Thr Gly Leu Met Val Ser Arg
    130              135              140

Ala Asp Met Glu Lys Ala Leu Val Asp Leu Gln Leu Tyr Thr Glu Ala
145            150              155              160

Gln Ala Trp Met Val Gln Ser Trp Lys Glu Leu Ala Asp Phe Thr Cys
            165            170              175

Ala Phe Thr Lys Ala Val Ala Glu Ala Pro Phe Lys Lys Leu Arg Asp
    180              185              190

Gln Val Thr Phe Ser Phe Phe Leu Glu Lys Asp Trp Ala Gly Gly Met
    195              200              205

Lys Val Asp Gln Ser Gly Arg Gly Leu Ala Leu Ile Trp Arg Arg Gln
210            215              220

Ile Gln Gln Leu Asn Arg Val Ser Ser Glu Met Ala Ser Ala Ile Val
225            230              235              240

Asp Ala Tyr Pro Ser Pro Gln Leu Leu Val Gln Ala Tyr Gln Arg Cys
            245            250              255

Phe Ser Glu Gln Glu Arg Gln Asn Leu Leu Ala Asp Ile Gln Val Arg
    260              265              270

Arg Gly Glu Gly Val Thr Ala Thr Ser Arg Arg Val Gly Pro Glu Leu
    275              280              285

Ser Arg Arg Ile Tyr Leu Gln Met Thr Thr Ala Gln Pro Asp Leu Ile
    290              295              300

Leu Asp Ser Val Asp
305

<210> SEQ ID NO 52
<211> LENGTH: 1248
<212> TYPE: DNA
<213> ORGANISM: Mus musculus

<400> SEQUENCE: 52

| gggatagat | ctacttccgg | gtcttgcgga | caattcaaag | agtggcggga | gcagtagcag | 60 |
|---|---|---|---|---|---|---|
| gatggagatg | actggatgga | agagccaaca | atcctggtgt | tggtcctggc | agaggtcttc | 120 |
| atgtccatgg | cctacaactt | aaagcaggca | agtcctagca | gcaccgagaa | agggaaggag | 180 |
| acccttcgga | gctttgtaac | tgatgtcaca | gcaaagacgg | ggaaagcatt | gtcactggtg | 240 |
| attgtggacc | aggagaaatg | cttcaggcct | cagaatcccc | cgaggagaag | gaaatcagga | 300 |
| atggcaaata | acaggccaa | agcgaagcat | cagcagaggc | aagagtctag | cacgggactc | 360 |
| atggtgtcca | gggcagacat | ggagaaggca | ctggtggatc | tgcagcttta | tacagaagcc | 420 |
| caggcgtgga | tggtgcagag | ctggaaggag | ctggcggact | tcacctgtgc | atttacaaag | 480 |
| gctgtggctg | aagcacccctt | caagaagctc | cgggatcaag | tcacctttc | cttcttcctg | 540 |
| gagaaagact | gggctggagg | gatgaaagtg | gaccagtccg | gcaggggact | ggcactgatc | 600 |
| tggaggcggc | agatccagca | gctgaaccga | gtcagctcgg | agatggccag | tgctattgtg | 660 |
| gacgcctatc | cctcaccgca | gctcctggtg | caggcttatc | agcggtgttt | ctctgagcaa | 720 |
| gaacgtcaga | atttgctggc | tgacatacaa | gtgcgacgtg | ggaaggtgt | gacagccacc | 780 |
| tcccgccgtg | ttgggccaga | attatccagg | cggatctacc | ttcaaatgac | cacagcgcaa | 840 |
| ccagatctca | tcttagacag | tgttgactga | tatcccacct | tggctattga | cagtagacag | 900 |

| | |
|---|---:|
| gccagaagta cctccttggt acagttaggg agcaagtctc tcatctctgg gaacagagaa | 960 |
| ggctgagtca cttgaatcta cctccaccat agcactcatg ttcctctccc ggcaagcgag | 1020 |
| atgccatgga cagccatccc acccatccc agttgaccct cacagcacaa aggagaaagg | 1080 |
| cagaccactc agacatggat ttaataattg tagaaatcca agaataagc atcaaatctc | 1140 |
| gaagtcagag tgaactcttg cctgcgggtt ggcttgacta cgcccagcca ctgagctgcc | 1200 |
| tcaaccagct agggagctat gatgaggctg actcctgttt tcatgatg | 1248 |

```
<210> SEQ ID NO 53
<211> LENGTH: 264
<212> TYPE: PRT
<213> ORGANISM: Mus musculus

<400> SEQUENCE: 53

Met Glu Glu Pro Thr Ile Leu Val Leu Val Leu Ala Glu Val Phe Met
1               5                   10                  15

Ser Met Ala Tyr Asn Leu Lys Gln Ala Ser Pro Ser Ser Thr Glu Lys
            20                  25                  30

Gly Lys Glu Thr Leu Arg Ser Phe Val Thr Asp Val Thr Ala Lys Thr
        35                  40                  45

Gly Lys Ala Leu Ser Leu Val Ile Val Asp Gln Glu Lys Cys Phe Arg
    50                  55                  60

Pro Gln Asn Pro Pro Arg Arg Lys Ser Gly Met Ala Asn Lys Gln
65                  70                  75                  80

Ala Lys Ala Lys His Gln Gln Arg Gln Glu Ser Ser Thr Gly Leu Met
                85                  90                  95

Val Ser Arg Ala Asp Met Glu Lys Ala Leu Val Asp Leu Gln Leu Tyr
            100                 105                 110

Thr Glu Ala Gln Ala Trp Met Val Gln Ser Trp Lys Glu Leu Ala Asp
        115                 120                 125

Phe Thr Cys Ala Phe Thr Lys Ala Val Ala Glu Ala Pro Phe Lys Lys
    130                 135                 140

Leu Arg Asp Gln Val Thr Phe Ser Phe Phe Leu Glu Lys Asp Trp Ala
145                 150                 155                 160

Gly Gly Met Lys Val Asp Gln Ser Gly Arg Gly Leu Ala Leu Ile Trp
                165                 170                 175

Arg Arg Gln Ile Gln Gln Leu Asn Arg Val Ser Ser Glu Met Ala Ser
            180                 185                 190

Ala Ile Val Asp Ala Tyr Pro Ser Pro Gln Leu Val Gln Ala Tyr
        195                 200                 205

Gln Arg Cys Phe Ser Glu Gln Glu Arg Gln Asn Leu Leu Ala Asp Ile
    210                 215                 220

Gln Val Arg Arg Gly Glu Gly Val Thr Ala Thr Ser Arg Arg Val Gly
225                 230                 235                 240

Pro Glu Leu Ser Arg Arg Ile Tyr Leu Gln Met Thr Thr Ala Gln Pro
                245                 250                 255

Asp Leu Ile Leu Asp Ser Val Asp
            260

<210> SEQ ID NO 54
<211> LENGTH: 1383
<212> TYPE: DNA
<213> ORGANISM: Mus musculus

<400> SEQUENCE: 54
```

-continued

```
cgaaggactt atggcggagg ttggtcccgg gagagtcacg gtctcgcgtc tcggtcgggg      60
cctgcgtctc ggccatcggc gacctcaaac ctgggagatt tccgactcag acggtgaagg     120
tgtccccgct agggaggtcg gcacgcaagc cccgagtcca gcaggagagc gcagagctgc     180
agccaaggct ttacgggcag atcagtccgc actggagatg tggaataac tcaatgttgc      240
ctgctgggat ccagctgtcc tggaagatgc aggctctgac atcctgatgg aggcgctggg     300
cacgctaggc tgtgaatgcc gcatcgaacc gcagcaccag gcccgcagcc tgcagtggaa     360
cgttgtcagg cccgacccgg cccccagcaa tgtgcctctg gaggcgaagg ctgaaaatga     420
gcaggaacag ttgctgctgc tggaacccca ggaatttctt cagggtgctg cgcagctgac     480
ccagatcaca gatccacctt gctccatccc ctggctttct cccaagagtc tcacccgctc     540
ccatctggct gtcattggac tggacgcata cctgtggtct caccagctca gttctcagaa     600
gacatggcaa ctaaagaagt caaaggaagc ccatgccagg ggagccatca gctgggctga     660
ggtggaggag gcagctccgg gactcccagg ccttttcttt ctgcacagca gggcactggg     720
cctcaggcca gcaagtgacc agagatggct ctgggctcag aggagtgtgg tggcgacaaa     780
tcagacagtt caaccgggtc agcccagctg tggctgacgc tgttgttact gccttcccat     840
caccccgcct tttgcaacag gctctcctgg actgcagcac agagcaagaa cgcctgagcc     900
tcctagctga tctccctgtg aaggcccaca aaggcaagca gcctcgcaga gtggggcctg     960
acctctcacg cagaatctgt atcttcttga caaccaccga ccctgacctc ctgctggacc    1020
tgagctcttg acctgtgcca tcctgggtca cctcctgccc atcagtacaa caggacaagt    1080
ctgcctaaga atctaattat tctgagaggc aggcaaggag gtttgggtcc agcccatacc    1140
ttttcagact gtggtagata gactctgttg cctgatggtc aaatggaaat accatgggag    1200
gtgggtgaga gggtaatgga agctgaggtg aatggaagag tggagggtag tggccacttg    1260
gtgcaggagg cttagtagca ggcctgagtg ccgagttgta ctattacatc ctcagagaga    1320
ggtgctcaga gatccaagcc aggctctctc aaagccgctg gacaagacag ataaccaata    1380
gac                                                                 1383
```

<210> SEQ ID NO 55
<211> LENGTH: 176
<212> TYPE: PRT
<213> ORGANISM: Mus musculus

<400> SEQUENCE: 55

```
Met Glu Ala Leu Gly Thr Leu Gly Cys Glu Cys Arg Ile Glu Pro Gln
  1               5                  10                  15

His Gln Ala Arg Ser Leu Gln Trp Asn Val Val Arg Pro Asp Pro Ala
             20                  25                  30

Pro Ser Asn Val Pro Leu Glu Ala Lys Ala Glu Asn Glu Gln Glu Gln
         35                  40                  45

Leu Leu Leu Leu Glu Pro Gln Glu Phe Leu Gln Gly Ala Ala Gln Leu
     50                  55                  60

Thr Gln Ile Thr Asp Pro Pro Cys Ser Ile Pro Trp Leu Ser Pro Lys
 65                  70                  75                  80

Ser Leu Thr Arg Ser His Leu Ala Val Ile Gly Leu Asp Ala Tyr Leu
                 85                  90                  95

Trp Ser His Gln Leu Ser Ser Gln Lys Thr Trp Gln Leu Lys Lys Ser
            100                 105                 110

Lys Glu Ala His Ala Arg Gly Ala Ile Ser Trp Ala Glu Val Glu Glu
        115                 120                 125
```

Ala Ala Pro Gly Leu Pro Gly Leu Phe Phe Leu His Ser Arg Ala Leu
    130                 135                 140

Gly Leu Arg Pro Ala Ser Asp Gln Arg Trp Leu Trp Ala Gln Arg Ser
145                 150                 155                 160

Val Val Ala Thr Asn Gln Thr Val Gln Pro Gly Gln Pro Ser Cys Gly
                165                 170                 175

<210> SEQ ID NO 56
<211> LENGTH: 1598
<212> TYPE: DNA
<213> ORGANISM: Mus musculus

<400> SEQUENCE: 56

| | | | | | |
|---|---|---|---|---|---|
| cgaaggactt | atggcggagg | ttggtcccgg | gagagccacg | gtctcgcgtc | tcggtcgggg | 60 |
| cctgcgtctc | ggccatcggc | gacctcaaac | ctgggagatt | tccgactcag | acggtgaagg | 120 |
| tgtccccgct | agggaggtcg | gcacgcaagc | cccgagtcca | gcaggagagc | gcagagctgc | 180 |
| agccaaggct | ttacgggcag | atcaggttct | ggggcgactg | gtggtgtgcg | tggacccagg | 240 |
| tgaggggacg | gggctgggga | atctgggggcc | agccaccaga | cagggtagcg | ttgtcaccca | 300 |
| ctagtccgca | ctggagatgg | tggaataact | caatgttgcc | tgctgggatc | cagctgtcct | 360 |
| ggaagatgca | ggctctgaca | tcctgatgga | ggcgctgggc | acgctaggct | gtgaatgccg | 420 |
| catcgaaccg | cagcaccagg | cccgcagcct | gcagtggaac | gttgtcaggc | ccgacccggc | 480 |
| ccccagcaat | gtgcctctgg | aggcgaaggc | tgaaaatgag | caggaacagt | tgctgctgct | 540 |
| ggaaccccag | gaatttcttc | agggtgctgc | gcagctgacc | cagatcacag | atccaccttg | 600 |
| ctccatcccc | tggctttctc | caagagtct | cacccgctcc | catctggctg | tcattggact | 660 |
| ggacgcatac | ctgtggtctc | accagctcag | ttctcagaag | acatggcaac | taaagaagtc | 720 |
| aaaggaagcc | catgccaggg | gagccatcag | ctgggctgag | gtggaggaga | tcctggtgct | 780 |
| gctgcagctc | catgcaaacc | tggatgtgct | gctgatggct | tcgtggcagg | agctgagtca | 840 |
| gtacgtgtgt | gccttcacca | gggccctctc | gcagctcccc | tcgaagcagc | tccgggactc | 900 |
| ccaggccttt | tctttctgca | cagcagggca | ctgggcctca | ggccagcaag | tgaccagaga | 960 |
| tggctctggg | ctcagaggag | tgtggtggcg | acaaatcaga | cagttcaacc | gggtcagccc | 1020 |
| agctgtggct | gacgctgttg | ttactgcctt | cccatcaccc | cgccttttgc | aacaggctct | 1080 |
| cctggactgc | agcacagagc | aagaacgcct | gagcctccta | gctgatctcc | ctgtgaaggc | 1140 |
| ccacaaaggc | aagcagcctc | gcagagtggg | gcctgacctc | tcacgcagaa | tctgtatctt | 1200 |
| cttgacaacc | accgaccctg | acctcctgct | ggacctgagc | tcttgacctg | tgccatcctg | 1260 |
| ggtcacctcc | tgcccatcag | tacaacagga | caagtctgcc | taagaatcta | attattctga | 1320 |
| gaggcaggca | aggaggtttg | ggtccagccc | atacctttc | agactgtggt | agatagactc | 1380 |
| tgttgcctga | tggtcaaatg | gaaataccat | gggaggtggg | tgagggta | atggaagctg | 1440 |
| aggtgaatgg | aagagtggag | ggtagtggcc | acttggtgca | ggaggcttag | tagcaggcct | 1500 |
| gagtgccgag | ttgtactatt | acatcctcag | agagaggtgc | tcagagatcc | aagccaggct | 1560 |
| ctctcaaagc | cgctggacga | gacagataac | caatagac | | | 1598 |

<210> SEQ ID NO 57
<211> LENGTH: 286
<212> TYPE: PRT
<213> ORGANISM: Mus musculus

<400> SEQUENCE: 57

```
Met Glu Ala Leu Gly Thr Leu Gly Cys Glu Cys Arg Ile Glu Pro Gln
 1               5                  10                  15

His Gln Ala Arg Ser Leu Gln Trp Asn Val Val Arg Pro Asp Pro Ala
             20                  25                  30

Pro Ser Asn Val Pro Leu Glu Ala Lys Ala Glu Asn Glu Gln Glu Gln
             35                  40                  45

Leu Leu Leu Leu Glu Pro Gln Glu Phe Leu Gln Gly Ala Ala Gln Leu
         50                  55                  60

Thr Gln Ile Thr Asp Pro Pro Cys Ser Ile Pro Trp Leu Ser Pro Lys
65                  70                  75                  80

Ser Leu Thr Arg Ser His Leu Ala Val Ile Gly Leu Asp Ala Tyr Leu
                 85                  90                  95

Trp Ser His Gln Leu Ser Ser Gln Lys Thr Trp Gln Leu Lys Lys Ser
            100                 105                 110

Lys Glu Ala His Ala Arg Gly Ala Ile Ser Trp Ala Glu Val Glu Glu
            115                 120                 125

Ile Leu Val Leu Gln Leu His Ala Asn Leu Asp Val Leu Leu Met
            130                 135                 140

Ala Ser Trp Gln Glu Leu Ser Gln Tyr Val Cys Ala Phe Thr Arg Ala
145                 150                 155                 160

Leu Ser Gln Leu Pro Ser Lys Gln Leu Arg Asp Ser Gln Ala Phe Ser
                165                 170                 175

Phe Cys Thr Ala Gly His Trp Ala Ser Gly Gln Gln Val Thr Arg Asp
            180                 185                 190

Gly Ser Gly Leu Arg Gly Val Trp Trp Arg Gln Ile Arg Gln Phe Asn
            195                 200                 205

Arg Val Ser Pro Ala Val Ala Asp Ala Val Val Thr Ala Phe Pro Ser
            210                 215                 220

Pro Arg Leu Leu Gln Gln Ala Leu Leu Asp Cys Ser Thr Glu Gln Glu
225                 230                 235                 240

Arg Leu Ser Leu Leu Ala Asp Leu Pro Val Lys Ala His Lys Gly Lys
                245                 250                 255

Gln Pro Arg Arg Val Gly Pro Asp Leu Ser Arg Arg Ile Cys Ile Phe
            260                 265                 270

Leu Thr Thr Thr Asp Pro Asp Leu Leu Asp Leu Ser Ser
            275                 280                 285

<210> SEQ ID NO 58
<211> LENGTH: 1636
<212> TYPE: DNA
<213> ORGANISM: Mus musculus

<400> SEQUENCE: 58
cgaaggactt atggcggagg ttggtcccgg gagagtcacg gtctcgcgtc tcggtcgggg    60
cctgcgtctc ggccatcggc gacctcaaac ctgggagatt tccgactcag acggtgaagg   120
tgtccccgct agggaggtcg gcacgcaagc cccgagtcca gcaggagagc gcagagctgc   180
agccaaggct ttacgggcag atcaggttct ggggcgactg gtggtgtgcg tggacccagc   240
tgtcctggaa gatgcaggct ctgacatcct gatggaggcg ctgggcacgc taggctgtga   300
atgccgcatc gaaccgcagc accaggcccg cagcctgcag tggaacgttg tcaggcccga   360
cccggccccc agcaatgtgc ctctggaggc gaaggctgaa aatgagcagg aacagttgct   420
gctgctggaa ccccaggaat tcttcagggg tgctgcgcag ctgacccaga tcacagatcc   480
```

-continued

```
accttgctcc atcccctggc tttctcccaa gagtctcacc cgctcccatc tggctgtcat    540
tggactggac gcatacctgt ggtaccactt aacctcagta gggctggctt gggtgggatt    600
ccaggaaagt ggcttgcctc tggtggctct gtcacagcta accccacttg gcctgatttg    660
gctctgcaga ggtaggagac tctggagccc aaaaaatcgt cccctctgtt caggtctcac    720
cagctcagtt ctcagaagac atggcaacta agaagtcaa aggaagccca tgccagggga     780
gccatcagct gggctgaggt ggaggagatc ctggtgctgc tgcagctcca tgcaaacctg    840
gatgtgctgc tgatggcttc gtggcaggag ctgagtcagt acgtgtgtgc cttcaccagg    900
gccctctcgc agctccccte gaagcagctc cgggactccc aggccttttc tttctgcaca    960
gcagggcact gggcctcagg ccagcaagtg accagagatg gctctgggct cagaggagtg    1020
tggtggcgac aaatcagaca gttcaaccgg gtcagcccag ctgtggctga cgctgttgtt    1080
actgccttcc catcaccccg ccttttgcaa caggctctcc tggactgcag cacagagcaa    1140
gaacgcctga gctcctagc tgatctccct gtgaaggccc acaaaggcaa gcagcctcgc     1200
agagtggggc ctgacctctc acgcagaatc tgtatcttct tgacaaccac cgaccctgac    1260
ctcctgctgg acctgagctc ttgacctgtg ccatcctggg tcacctcctg cccatcagta    1320
caacaggaca agtctgccta agaatctaat tattctgaga ggcaggcaag gaggtttggg    1380
tccagcccat acctttcag actgtggtag atagactctg ttgcctgatg gtcaaatgga    1440
aataccatgg gaggtgggtg agagggtaat ggaagctgag gtgaatggaa gagtggaggg    1500
tagtggccac ttggtgcagg aggcttagta gcaggcctga gtgccgagtt gtactattac    1560
atcctcagag agaggtgctc agagatccaa gccaggctct ctcaaagccg ctggacgaga    1620
cagataacca atagac                                                    1636
```

<210> SEQ ID NO 59
<211> LENGTH: 246
<212> TYPE: PRT
<213> ORGANISM: Mus musculus

<400> SEQUENCE: 59

```
Met Ala Glu Val Gly Pro Gly Arg Val Thr Val Ser Arg Leu Gly Arg
1               5                   10                  15

Gly Leu Arg Leu Gly His Arg Arg Pro Gln Thr Trp Glu Ile Ser Asp
            20                  25                  30

Ser Asp Gly Glu Gly Val Pro Ala Arg Glu Val Gly Thr Gln Ala Pro
        35                  40                  45

Ser Pro Ala Gly Glu Arg Arg Ala Ala Lys Ala Leu Arg Ala Asp
    50                  55                  60

Gln Val Leu Gly Arg Leu Val Val Cys Val Asp Pro Ala Val Leu Glu
65                  70                  75                  80

Asp Ala Gly Ser Asp Ile Leu Met Glu Ala Leu Gly Thr Leu Gly Cys
                85                  90                  95

Glu Cys Arg Ile Glu Pro Gln His Gln Ala Arg Ser Leu Gln Trp Asn
            100                 105                 110

Val Val Arg Pro Asp Pro Ala Pro Ser Asn Val Pro Leu Glu Ala Lys
        115                 120                 125

Ala Glu Asn Glu Gln Glu Gln Leu Leu Leu Glu Pro Gln Glu Phe
    130                 135                 140

Leu Gln Gly Ala Ala Gln Leu Thr Gln Ile Thr Asp Pro Pro Cys Ser
145                 150                 155                 160

Ile Pro Trp Leu Ser Pro Lys Ser Leu Thr Arg Ser His Leu Ala Val
```

|     |     | 165 |     |     |     | 170 |     |     |     | 175 |     |
| --- | --- | --- | --- | --- | --- | --- | --- | --- | --- | --- | --- |
| Ile | Gly | Leu | Asp | Ala | Tyr | Leu | Trp | Tyr | His | Leu | Thr | Ser | Val | Gly | Leu |
|     |     |     | 180 |     |     |     |     | 185 |     |     |     |     | 190 |     |     |
| Ala | Trp | Val | Gly | Phe | Gln | Glu | Ser | Gly | Leu | Pro | Leu | Val | Ala | Leu | Ser |
|     |     |     | 195 |     |     |     |     | 200 |     |     |     |     | 205 |     |     |
| Gln | Leu | Thr | Pro | Leu | Gly | Leu | Ile | Trp | Leu | Cys | Arg | Gly | Arg | Arg | Leu |
|     |     |     | 210 |     |     |     |     | 215 |     |     |     |     | 220 |     |     |
| Trp | Ser | Pro | Lys | Asn | Arg | Pro | Leu | Cys | Ser | Gly | Leu | Thr | Ser | Ser | Val |
| 225 |     |     |     |     | 230 |     |     |     |     | 235 |     |     |     |     | 240 |
| Leu | Arg | Arg | His | Gly | Asn |
|     |     |     |     |     | 245 |

```
<210> SEQ ID NO 60
<211> LENGTH: 1484
<212> TYPE: DNA
<213> ORGANISM: Mus musculus

<400> SEQUENCE: 60
cgaaggactt atggcggagg ttggtcccgg gagagtcacg gtctcgcgtc tcggtcgggg    60
cctgcgtctc ggccatcggc gacctcaaac ctgggagatt tccgactcag acggtgaagg   120
tgtccccgct agggaggtcg gcacgcaagc cccgagtcca gcaggagagc gcagagctgc   180
agccaaggct ttacgggcag atcaggttct ggggcgactg gtggtgtgcg tggacccagc   240
tgtcctggaa gatgcaggct ctgacatcct gatggaggcg ctgggcacgc taggctgtga   300
atgccgcatc gaaccgcagc accaggcccg cagcctgcag tggaacgttg tcaggcccga   360
cccggccccc agcaatgtgc ctctggaggc gaaggctgaa aatgagcagg aacagttgct   420
gctgctggaa cccaggaat tcttcaggg tgctgcgcag ctgacccaga tcacagatcc   480
accttgctcc atcccctggc tttctcccaa gagtctcacc cgctcccatc tggctgtcat   540
tggactggac gcatacctgt ggtctcacca gctcagttct cagaagacat ggcaactaaa   600
gaagtcaaag gaagcccatg ccaggggagc catcagctgg gctgaggtgg aggagatcct   660
ggtgctgctg cagctccatg caaacctgga tgtgctgctg atggcttcgt ggcaggagct   720
gagtcagtac gtgtgtgcct tcaccagggc cctctcgcag ctcccctcga gcagctccg   780
ggactcccag gcctttttctt tctgcacagc agggcactgg gcctcaggcc agcaagtgac   840
cagagatggc tctgggctca gaggagtgtg gtggcgacaa atcagacagt tcaaccgggt   900
cagcccagct gtggctgacg ctgttgttac tgccttccca tcaccccgcc ttttgcaaca   960
ggctctcctg gactgcagca cagagcaaga acgcctgagc ctcctagctg atctcccgt   1020
gaaggcccac aaaggcaagc agcctcgcag agtgggggcct gacctctcac gcagaatctg  1080
tatcttcttg acaaccaccg accctgacct cctgctggac ctgagctctt gacctgtgcc  1140
atcctgggtc acctcctgcc catcagtaca acaggacaag tctgcctaag aatctaatta  1200
ttctgagagg caggcaagga ggtttgggtc cagcccatac cttttcagac tgtggtagat  1260
agactctgtt gcctgatggt caaatggaaa taccatggga ggtgggtgag agggtaatgg  1320
aagctgaggt gaatggaaga gtggagggta gtggccactt ggtgcaggag cttagtagc   1380
aggcctgagt gccgagttgt actattacat cctcagagag aggtgctcag agatccaagc  1440
caggctctct caaagccgct ggacgagaca gataaccaat agac                   1484

<210> SEQ ID NO 61
<211> LENGTH: 373
<212> TYPE: PRT
```

<213> ORGANISM: Mus musculus

<400> SEQUENCE: 61

```
Met Ala Glu Val Gly Pro Gly Arg Val Thr Val Ser Arg Leu Gly Arg
1               5                   10                  15

Gly Leu Arg Leu Gly His Arg Arg Pro Gln Thr Trp Glu Ile Ser Asp
            20                  25                  30

Ser Asp Gly Glu Gly Val Pro Ala Arg Glu Val Gly Thr Gln Ala Pro
        35                  40                  45

Ser Pro Ala Gly Glu Arg Arg Ala Ala Lys Ala Leu Arg Ala Asp
    50                  55                  60

Gln Val Leu Gly Arg Leu Val Val Cys Val Asp Pro Ala Val Leu Glu
65              70                  75                  80

Asp Ala Gly Ser Asp Ile Leu Met Glu Ala Leu Gly Thr Leu Gly Cys
                85                  90                  95

Glu Cys Arg Ile Glu Pro Gln His Gln Ala Arg Ser Leu Gln Trp Asn
            100                 105                 110

Val Val Arg Pro Asp Pro Ala Pro Ser Asn Val Pro Leu Glu Ala Lys
        115                 120                 125

Ala Glu Asn Glu Gln Glu Gln Leu Leu Leu Glu Pro Gln Glu Phe
    130                 135                 140

Leu Gln Gly Ala Ala Gln Leu Thr Gln Ile Thr Asp Pro Pro Cys Ser
145                 150                 155                 160

Ile Pro Trp Leu Ser Pro Lys Ser Leu Thr Arg Ser His Leu Ala Val
                165                 170                 175

Ile Gly Leu Asp Ala Tyr Leu Trp Ser His Gln Leu Ser Ser Gln Lys
            180                 185                 190

Thr Trp Gln Leu Lys Lys Ser Lys Glu Ala His Ala Arg Gly Ala Ile
        195                 200                 205

Ser Trp Ala Glu Val Glu Glu Ile Leu Val Leu Leu Gln Leu His Ala
    210                 215                 220

Asn Leu Asp Val Leu Leu Met Ala Ser Trp Gln Glu Leu Ser Gln Tyr
225                 230                 235                 240

Val Cys Ala Phe Thr Arg Ala Leu Ser Gln Leu Pro Ser Lys Gln Leu
                245                 250                 255

Arg Asp Ser Gln Ala Phe Ser Phe Cys Thr Ala Gly His Trp Ala Ser
            260                 265                 270

Gly Gln Gln Val Thr Arg Asp Gly Ser Gly Leu Arg Gly Val Trp Trp
        275                 280                 285

Arg Gln Ile Arg Gln Phe Asn Arg Val Ser Pro Ala Val Ala Asp Ala
    290                 295                 300

Val Val Thr Ala Phe Pro Ser Pro Arg Leu Leu Gln Gln Ala Leu Leu
305                 310                 315                 320

Asp Cys Ser Thr Glu Gln Glu Arg Leu Ser Leu Ala Asp Leu Pro
                325                 330                 335

Val Lys Ala His Lys Gly Lys Gln Pro Arg Arg Val Gly Pro Asp Leu
            340                 345                 350

Ser Arg Arg Ile Cys Ile Phe Leu Thr Thr Thr Asp Pro Asp Leu Leu
        355                 360                 365

Leu Asp Leu Ser Ser
    370
```

<210> SEQ ID NO 62
<211> LENGTH: 34

```
<212> TYPE: DNA
<213> ORGANISM: Artificial Sequence
<220> FEATURE:
<223> OTHER INFORMATION: PCR primer

<400> SEQUENCE: 62
cggaattcac catggctcta aagaagtcat cacc                          34

<210> SEQ ID NO 63
<211> LENGTH: 56
<212> TYPE: DNA
<213> ORGANISM: Artificial Sequence
<220> FEATURE:
<223> OTHER INFORMATION: PCR primer

<400> SEQUENCE: 63
gcccgctcga gtcacttgtc atcgtcgtcc ttgtagtcag cactatctaa agagag   56

<210> SEQ ID NO 64
<211> LENGTH: 53
<212> TYPE: DNA
<213> ORGANISM: Artificial Sequence
<220> FEATURE:
<223> OTHER INFORMATION: PCR Primer

<400> SEQUENCE: 64
gcccgctcga gtcacttgtc atcgtcgtcc ttgtagtcag cactatctaa aga      53

<210> SEQ ID NO 65
<211> LENGTH: 50
<212> TYPE: DNA
<213> ORGANISM: Artificial Sequence
<220> FEATURE:
<223> OTHER INFORMATION: PCR Primer

<400> SEQUENCE: 65
ctcgagtcac ttgtcatcgt cgtccttgta gtcggtcaag gggccgtagc          50

<210> SEQ ID NO 66
<211> LENGTH: 34
<212> TYPE: DNA
<213> ORGANISM: Artificial Sequence
<220> FEATURE:
<223> OTHER INFORMATION: PCR Primer

<400> SEQUENCE: 66
cggaattcac catggctcta aagaagtcat cacc                          34

<210> SEQ ID NO 67
<211> LENGTH: 35
<212> TYPE: DNA
<213> ORGANISM: Artificial Sequence
<220> FEATURE:
<223> OTHER INFORMATION: PCR Primer

<400> SEQUENCE: 67
gcccgctcga gtcagtcagc actatctaaa gagag                         35
```

MAMMALIAN ENDONUCLEASES AND METHODS OF USE

GOVERNMENT RIGHTS

This invention was made with government support under contract No. NIH CA 69112-01 by the National Institutes of Health. The government has certain rights to this invention.

FIELD OF THE INVENTION

The present invention relates generally to the field of medicine, and relates specifically to mammalian endonucleases and methods of use thereof for identifying chemical compounds that modulate cellular response to DNA damage.

BACKGROUND OF THE INVENTION

The integrity of the genome is of prime importance to a dividing cell. Together, DNA repair and checkpoint responses ensure the integrity of the genome. Coordination of cell cycle checkpoints and DNA repair is especially important when unusually high loads of DNA damage are sustained following radiation or genotoxic chemotherapy. Mammalian Cds1 (also known as Chk2) is a checkpoint kinase that is activated in an ATM/ATR-dependent manner in response to DNA damage. In addition to delaying cell cycle progression, Cds1 homologs (Cds1 in fission yeast and Rad53 in budding yeast) have non-cell cycle functions that are important for survival following treatments that interrupt DNA replication or that damage DNA. Cds1 associates with a damage tolerance protein, Mus81, in fission yeast, implicating a direct role for Cds1 in DNA repair (Boddy et al., 2000, *Molecular Cell Biol.* 20:8758-66; hereinafter Boddy et al., 2000). In budding yeast, Mus81 mutants are reported to be sensitive to methyl methane sulfonate and to UV but not to agents that induce double-strand breaks (Interthal et al., 2000, *Mol. Gen. Genet.*, 263:812-27; hereinafter Interthal, et al., 2000). Mus81 is important for survival following exposure to agents that block DNA replication, when DNA-polymerase function is compromised, and in the absence of the Bloom's syndrome helicase homologs (Rqh1 in fission yeast and Sgs1 in budding yeast, Boddy et al., 2000). These observations suggest a direct role for Mus81 in promoting recovery from problems encountered during replication.

In prokaryotes, reactivation of blocked replication forks is thought to proceed through a nonmutagenic pathway of homologous recombination. Several of the genes required for homologous recombination in vertebrate cells are essential for chromosomal stability. A number of genetic and physical observations suggest that Holliday junctions are intermediates in this recombination process (reviewed in Paques, et al., 1999, *Microbiol. Mol. Biol. Rev.*, 63:349-404). Holliday junctions (HJs) are 4-stranded DNA crossover structures postulated as transient intermediates during genetic recombination and repair. Cleavage of the X-shaped HJs across an axis, performed by an HJ resolvase, is required to disentangle homologous duplexes. Recent studies suggest that HJs also arise at stalled replication forks (Seigneur et al., 1998, *Cell*, 95:419-30; hereinafter Seigneur et al., 1998). Thus, uncovering how HJs are resolved is vital for understanding mechanisms of genetic recombination, chromosomal replication, and genome maintenance.

Physical and genetic evidence for HJ formation exists from a number of different experimental systems. X-structures formed during meiosis have been observed in the budding yeast *Saccharomyces cerevisiae* (Collins, et al., 1994, *Cell*, 76:65-75). Evidence for replication-associated HJs was originally obtained with *E. coli* (Seigneur et al., 1998). These HJs are thought to form by the annealing of nascent strands at a stalled replication fork (known as fork regression). Evidence is mounting that HJs are an integral part of replication in eukaryotes. HJs accumulate at the rDNA locus during normal replication in *S. cerevisiae*, and this accumulation is enhanced by mutations in DNA replication polymerases α and δ (Zou et al., 1997, *Cell*, 90:87-96). X-structures were reported to form between sister chromatids during DNA replication in *Physarum* (Benard et al., 2001, *Cell*, 7:971-80; hereinafter Benard et al., 2001). Mutants of the fission yeast *Schizosaccharomyces pombe* that lack Rqh1 DNA helicase display enhanced mitotic recombination and are unable to segregate chromosomes when grown with the replication inhibitor hydroxyurea (Stewart et al., 1997, *EMBO J*, 16:2682-92). These phenotypes are partially rescued by expression of RusA, a bacterial HJ resolvase, indicating that Rqh1 may be involved in branch migration of HJs that arise at regressed replication forks (Doe et al., 2000, *EMBO J*, 19:2751-62; hereinafter Doe et al., 2000).

The best characterized HJ resolvase is RuvC of *E. coli*, which is part of the RuvABC complex that branch migrates and cleaves HJs (Bennett et al., 1993, *Cell*, 74: 1021-1031). Interestingly, there are no known eukaryotic sequence counterparts of bacterial resolvases, although eukaryotes have mitochondrial HJ resolvases that may be ancestrally related to RuvC (Lilley et al., 2001, *Nat. Rev. Mol. Cell Biol.*, 2:433-43 hereinafter Lilley et al., 2001). Recent studies suggest that HJ branch migration and resolvase activities may associate in calf testes and mammalian cell lines (Constantinou et al., 2001, *EMBO Rep.*, 1:80-84), but eukaryotic nuclear HJ resolvases have thus far eluded identification.

The ERCC1-XPF family of heterodimeric enzymes constitute another interesting class of structure-specific endonucleases. ERCC1-XPF, which has no bacterial orthologs, cuts duplex DNA with a defined polarity on the 5' side of a junction between double-strand and single-strand DNA (Sijbers et al., 1996, *Cell*, 86:811-22). ERCC1-XPF is essential for nucleotide excision repair (NER), where it incises the damaged strand on the 5' side of the lesion. The ERCC1-XPF nuclease family also appears to participate in various recombination pathways (Paques, et al., 1999, *Microbiol. Mol. Biol. Rev.*, 63: 349-404). For example, in *Drosophilia melanogaster*, MEI-9, an XPF homolog, is required for normal levels of meiotic recombination (Sekelsky et al., 1995, *Genetics*, 141:619-27).

Mus81, a novel XPF-related protein, was recently discovered through its association with the replication checkpoint kinase Cds1 in fission yeast and the recombination repair protein Rad54 in budding yeast (Boddy et al., 2000; Interthal et al., 2000). Strikingly, fission yeast Mus81 cells exhibit phenotypes expected of an HJ resolvase mutant (Boddy et al., 2000). Mus81 is important for cell viability in a variety of circumstances that impede replication fork progression, such as unrepaired thymine dimers, nucleotide starvation, and compromised DNA polymerase alleles. Mus81 is essential in Rqh1 cells of fission yeast, which are thought to accumulate HJs during DNA replication (Doe et al., 2000). Moreover, Mus81 is required for production of viable spores, a process that is thought to depend on HJ resolution prior to meiosis I (Boddy et al., 2000; Interthal et al., 2000). Mus81 is also involved in resolution of HJs (Boddy et al., 2000).

Boddy et al., 2001, *Cell* 107: 537-548 (hereinafter Boddy et al., 2001), have reported that the endonuclease activity of Mus81 in fission yeast depends upon the presence of a particular binding partner, essential meiotic endonuclease 1 (Eme1). Thus both Mus81 and Eme1 are subunits of an endonuclease complex, which is analogous to the well characterized endonuclease ERCC1-XPF. Boddy et al. also reported that Eme1 has no sequence homology with ERCC1, whereas Mus81 shares homology with the C-terminus of XPF (Boddy et al., 2001). Mus81 and Eme1 are reported to interact through their C-termini.

Chen et al. have reported that the human homolog of Mus81 (Hmus81) has endonuclease activity and cleaves Holliday Junctions in vivo (Chen et al., 2001, *Molecular Cell*, 8:1117-1127; hereinafter Chen et al., 2001). A number of murine homologs of Mus81 (Mmus81) are disclosed in U.S. Pat. No. 6,440,732 to Russell et al.

In humans, excision repair is an important defense mechanism against two major carcinogens: sunlight and cigarette smoke. It has been found that individuals defective in excision repair exhibit a high incidence of cancer (Sancar, 1996, "DNA Excision Repair" *Ann. Rev. Biochem.* 65:43-81). Other mechanisms are also available for DNA repair, such as mismatch repair, which stabilizes the cellular genome by correcting DNA replication errors and by blocking recombination events between divergent DNA sequences. Inactivation of genes encoding enzymes involved in these repair mechanisms reportedly result in a large increase in spontaneous mutability and a predisposition to tumor development. (Modrich et al., 1996, "Mismatch Repair in Replication Fidelity, Genetic Recombination and Cancer Biology" *Ann. Rev. Biochem.* 65:101-33). The importance of maintaining genomic fidelity is amply illustrated by the many available mechanisms for repair, and if unrepairable, by the arrest of cell division. (Wood, 1996, "DNA Repair in Eukaryotes" *Ann. Rev. Biochem.* 65:135-67).

Many chemotherapeutic agents are designed to disrupt or otherwise cause damage to the DNA of targeted malignant cells. Antineoplastic agents such as alkylating agents, antimetabolites, and other chemical analogs and substances typically act by inhibiting nucleotide biosynthesis or protein synthesis, cross-linking DNA, or intercalating with DNA to inhibit replication or gene expression. Bleomycin and etoposide, for example, specifically damage DNA and prevent repair.

The inhibition of DNA damage repair activity amplifies the potency of antineoplastic agents, and enhances the efficacy of their use as chemotherapeutic agents. For example, the targeted cells are relatively more susceptible to damage caused by chemotherapeutic agents when repair mechanisms are inhibited, so that reduced dosages of the chemotherapeutic agents can be used, in proportion to the increased efficacy, thus reducing unwanted side effects.

Diseases can also result from defective DNA repair mechanisms, including, for example, hereditary nonpolyposis colorectal cancer (defect in mismatch repair), Nijmegen breakage syndrome (defect in double strand break repair), *Xeroderma pigmentosum*, *Cockayne* syndrome, and *Trocothiodystrophy* (defects in nuclear excision repair), and the like (Lengauer et al., 1998, "Genetic instabilities in human cancers" *Nature*, 396(6712):643-649; Kanaar et al., 1998, "Molecular mechanisms of DNA double stranded repair" *Trends Cell Biol.* 8(12):483489).

It is further envisioned that the transient inhibition of DNA checkpoint and DNA damage arrest in dividing cells may allow the use of relatively lower doses of chemotherapeutic agents to effect relatively greater damage to targeted cells in the treatment of diseases such as cancer.

SUMMARY OF THE INVENTION

Novel, isolated mammalian endonucleases (e.g., human or murine endonucleases), and methods of utilizing the endonucleases for identifying chemical compounds that modulate mammalian cellular response to DNA damage are described herein.

The human endonucleases of the present invention are isolated complexes of a human Mus81 (Hmus81) protein and a human Eme (Heme) protein. The isolated human Mus81-Eme (Hmus81-Eme) endonucleases can comprise recombinant proteins, isolated natural proteins, or a combination thereof. The human Mus81 and human Eme proteins are believed to interact at their C-terminal ends. The isolated Hmus81-Eme endonucleases preferably comprise (a) an Hmus81 protein having an amino acid sequence that is at least 50% homologous to any of the amino acid sequences set forth in SEQ ID NO: 2, SEQ ID NO: 4, SEQ ID NO: 6, or SEQ ID NO: 8; and (b) an Heme1 or Heme2 protein having an amino acid sequence that is at least about 50% homologous to any of the amino acid sequences set forth in SEQ ID NO: 10, SEQ ID NO: 12, SEQ ID NO: 14, SEQ ID NO: 16, SEQ ID NO: 18, or SEQ ID NO: 20.

The murine endonucleases of the present invention are isolated complexes of a murine Mus81 (Mmus81) protein and a murine Eme (Meme) protein. The isolated murine Mus81-Eme (Mmus81-Eme) endonucleases can comprise recombinant proteins, isolated natural proteins, or a combination thereof. The murine Mus81 and murine Eme proteins are believed to interact at their C-terminal ends. The isolated Mmus81-Eme endonucleases preferably comprise (a) an Mmus81 protein having an amino acid sequence that is at least 50% homologous to any of the amino acid sequences set forth in SEQ ID NO: 37, SEQ ID NO: 39, SEQ ID NO: 41, or SEQ ID NO: 43; and (b) an Meme1 or Meme2 protein having an amino acid sequence that is at least about 50% homologous to any of the amino acid sequences set forth in SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, or SEQ ID NO: 61.

Preferably, a human or murine Mus81 protein useful in the compositions and methods of the present invention has an intact VERK domain as described in detail hereinbelow. Useful human and murine Mus81 proteins are described in detail in U.S. Pat. No. 6,440,732 B1 to Russell et al., incorporated herein by reference to the extent relevant.

One method aspect for identifying chemical compounds that modulate mammalian cellular response to DNA damage, such as identifying potential DNA repair-modulating pharmaceutical agents, comprises individually contacting one or more chemical compounds to be evaluated or tested (i.e., a test compound) as a DNA repair-modulating pharmaceutical agent with an aqueous biochemical mixture containing an isolated mammalian (e.g., human or murine) Mus81-Eme endonuclease complex, a source of magnesium ion, and a DNA test substrate. The activity level of the Mus81-Eme endonuclease complex in the mixture is determined and the so-determined activity is compared with the activity of a substantially similar Mus81-Eme complex-containing a control material that does not contain the test compound.

A difference in activity between mixtures containing a test compound relative to the control indicates that the test compound modulates Mus81-Eme endonuclease activity, and thus modulates cellular response to DNA damage. Such identified compounds can then be utilized as pharmaceutical agents or can be selected for additional evaluation in a cell-based assay or in vivo assay, for example, to further characterize the DNA damage response-modulating activity of the identified active compounds.

A test compound that exhibits an enhancement of Mus81-Eme endonuclease activity indicates that the test compound is a potential pharmaceutical agent for repairing DNA damage. Such compounds have applications in the treatment of UV radiation damaged tissues, for example.

In contrast, a test compound that exhibits a suppression of Mus81-Eme endonuclease activity indicates that the test compound is a potential pharmaceutical agent for inhibiting DNA damage repair. DNA damage repair inhibitors are useful, for example, in combination with chemotherapeutic agents to enhance the potency of the chemotherapeutic agent by temporarily inhibiting cellular DNA repair mechanisms.

In another embodiment, the present invention provides a kit for identifying chemical compounds that modulate mammalian cellular response to DNA damage according to the methods described herein. The kit comprises a first component, which is an isolated mammalian (e.g., human or murine) Mus81-Eme endonuclease complex, a second component, which is a source of magnesium ion, and a third component, which is a DNA test substrate for the endonuclease. The kit also includes instructions for testing chemical compounds, preferably according to the methods of the present invention. Each component of the kit preferably is sealed in an individual container, and each component preferably is included in a quantity sufficient to test at least one chemical compound for DNA damage-repair-modulating activity.

BRIEF DESCRIPTION OF THE DRAWINGS

The invention may be better understood by reference to one or more of the following drawings in combination with the detailed description of specific embodiments and claims presented herein.

FIG. 1 depicts nucleotide sequences of human Mus81 cDNA molecules and amino acid sequences of their translation products. FIG. 1A depicts the nucleotide sequence and amino acid sequence of Hmus81(1) (SEQ ID NO: 1 and 2, respectively); FIG. 1B depicts the nucleotide sequence and amino acid sequence of Hmus81(2) (SEQ ID NO: 3 and 4, respectively); FIG. 1C depicts the nucleotide sequence and amino acid sequence of Hmus81(3) (SEQ ID NO: 5 and 6, respectively); and FIG. 1D depicts a nucleotide sequence and amino acid sequence of Hmus81(4) (SEQ ID NO: 7 and 8, respectively).

FIG. 3 includes a comparison of the amino acid sequences of S. pombe Eme1 (SEQ ID NO: 23) and human Eme1A (SEQ ID NO: 10); identical residues are shown black boxes.

FIG. 4 depicts the amino acid sequences and homologies of human Eme1A (SEQ ID NO: 10) and human Eme2A (SEQ ID NO:16); identical residues are shown in black boxes, and conservative substitutions are shown in gray boxes.

FIG. 5 compares the amino acid sequences of human Mus81(1) (SEQ ID NO: 2), human Eme1A (SEQ ID NO: 10), and human Eme2A (SEQ ID NO: 16); identical residues are shown in black boxes, and conservative substitutions are shown in gray boxes.

FIG. 6 compares the amino acid sequences of human Eme1A, human Eme1B, and human Eme1C (SEQ ID NO: 10, 12, and 14; respectively); identical residues are shown in black boxes (FIG. 6A). FIG. 6B shows the nucleic acid sequence of Heme1A (SEQ ID NO: 9). FIG. 6C shows the nucleic acid sequence of Heme1B (SEQ ID NO: 11). FIG. 6D shows the nucleic acid sequence of Heme1C (SEQ ID NO: 13).

FIG. 7 compares the amino acid sequences of human Eme2A, human Eme2B, human Eme2C, and an EST clone of human Eme2 (SEQ ID NO: 16, 18, 20, and 22; respectively); identical residues are shown in black boxes (FIG. 7A). FIG. 7B shows the nucleic acid sequence of Heme2A (SEQ ID NO: 15). FIG. 7C shows the nucleic acid sequence of Heme2B (SEQ ID NO: 17). FIG. 7D shows the nucleic acid sequence of Heme2C (SEQ ID NO: 19). FIG. 7E shows the nucleic acid sequence of an EST clone of human Heme2 (SEQ ID NO: 21).

FIG. 9 schematically illustrates possible cleavage patterns for the resolution of Holliday junctions in X-shaped quadruplex DNA.

FIG. 10 depicts nucleotide sequences of murine Mus81 cDNA molecules and amino acid sequences of their translation products. FIG. 10A depicts the nucleotide sequence and amino acid sequence of Mmus81(1) (SEQ ID NO: 36 and 37, respectively); FIG. 10B depicts the nucleotide sequence and amino acid sequence of Mmus81 (2) (SEQ ID NO: 38 and 39, respectively); FIG. 10C depicts the nucleotide sequence and amino acid sequence of Mmus81(3) (SEQ ID NO: 40 and 41, respectively); and FIG. 10D depicts a nucleotide sequence and amino acid sequence of Mmus81(4) (SEQ ID NO: 42 and 43, respectively).

FIG. 11 depicts nucleotide sequences of murine Eme1 cDNA molecules and amino acid sequences of their translation products. FIG. 11A depicts the nucleotide sequence and amino acid sequence of Meme1TeA2 (SEQ ID NO: 44 and 45, respectively); FIG. 11B depicts the nucleotide sequence and amino acid sequence of Meme1TeA4 (SEQ ID NO: 46 and 47, respectively); FIG. 11C depicts the nucleotide sequence and amino acid sequence of Meme1TeA9 (SEQ ID NO: 48 and 49, respectively); FIG. 11D depicts a nucleotide sequence and amino acid sequence of Meme1TeB1 (SEQ ID NO: 50 and 51, respectively); and FIG. 11E depicts a nucleotide sequence and amino acid sequence of Meme1TeB2 (SEQ ID NO: 52 and 53, respectively).

FIG. 12 depicts nucleotide sequences of murine Eme2 cDNA molecules and amino acid sequences of their translation products. FIG. 12A depicts the nucleotide sequence and amino acid sequence of Meme2Br2 (SEQ ID NO: 54 and 55, respectively); FIG. 12B depicts the nucleotide sequence and amino acid sequence of Meme2Br5 (SEQ ID NO: 56 and 57, respectively); FIG. 12C depicts the nucleotide sequence and amino acid sequence of Meme2Te5 (SEQ ID NO: 58 and 59, respectively); and FIG. 12D depicts a nucleotide sequence and amino acid sequence of Meme2Te6 (SEQ ID NO: 60 and 61, respectively).

FIG. 13 depicts Eme1 interactions with Mus81. FIG. 13A depicts FLAG immune-precipitates from HeLa cells transiently transfected with 3HaMus81 in the presence or absence of FLAG-Eme1. Forty-eight hours following transfection lysates and immune-precipitates were probed for the presence of 3HaMus81 and FLAG-Eme1. 3HaMus81 was detected in FLAG immune-precipitates from cells that express FLAG-Eme1. FIG. 13B depicts Ha and FLAG immune-precipitates assayed for associated endonuclease activity using a 3' flap substrate. Co-expression of 3HaMus81 and FLAG-Eme1B resulted in highest activity. FIG. 13C depicts FLAG-Eme1 detection in Ha immune-precipitates from cells that express wild type 3HaMus81 (WT) and an endonuclease-inactive version of Mus81 (AA). FIG. 13D depicts FLAG-Eme1 immune-precipitates from cells that were co-transfected with wild type but not endonuclease inactive 3HaMus81 cleave 3' flap structures. 3HaMus81WT immune-precipitates have associated endonuclease activity that was increased when cells were co-transfected with FLAG-Eme1. S indicates substrate alone.

FIG. 14A shows Mus81 immune-precipitates probed for the presence of Gst-Mus81 and FLAG-Eme1. FIG. 14B shows recombinant Mus81-Eme1 cleaves 3' flaps, replication forks and Holliday junction (X12) structures in vitro. The activity associated with Mus 81 immune-precipitates from HeLa cells is shown for comparison (En). S indicates substrate alone.

FIG. 15 depicts Mus81 and Eme1 self-association. FIG. 15A shows 293 cells transfected with 3HaMus81, FLAG-Mus81 or both. Forty hours after transfection, the lysates and Ha immune-precipitates were probed for the presence of 3HaMus81 and FLAG Mus81. FLAG-Mus81 was detected in Ha immune-precipitates from cells that express 3HaMus81. FIG. 13B shows 293 cells transfected with 3HaEme1, FLAG-Eme1, or both. Forty hours after transfection the lysates and FLAG immune-precipitates were probed for the presence of 3HaEme1 and FLAG-Eme1. 3Ha-Eme1 was detected in FLAG immune-precipitates from cells that express FLAG-Eme1.

FIG. 16A shows transfection with pSuper-178, pSuper 292 but not empty pSuper results in reducing Mus81 protein. Non-Tx indicates untransfected cells. FIG. 16B shows pLrec contains a direct repeat of two inactive LacZ genes separated by the neomycin resistance gene (black box). Expression is under the control of the SV40 promoter (grey box). 693 base pairs of identical sequence in the two LacZ alleles are indicated by arrows. L×2 is inactive due to an insertion at a site indicated by X. The cell-line GM847L22 contains a single intact copy of pLrec . FIG. 16C shows incidence of LacZ cells. About $5 \times 10^5$ cells were plated in G418 free medium 16 hours prior to transfection with the indicated plasmid. The amount of DNA transfected was kept constant by use of empty vector. 2 mM thymidine was added to the culture medium and cells were grown for 16 hours. Cells were cultured in normal growth medium for a further 24 hours, prior to staining for β-galactosidase activity. Duplicate dishes were used to monitor cell number and expression of Mus81 and RusA. Error bars represent data from 4 separate experiments.

DETAILED DESCRIPTION OF PREFERRED EMBODIMENTS

Figure 2:
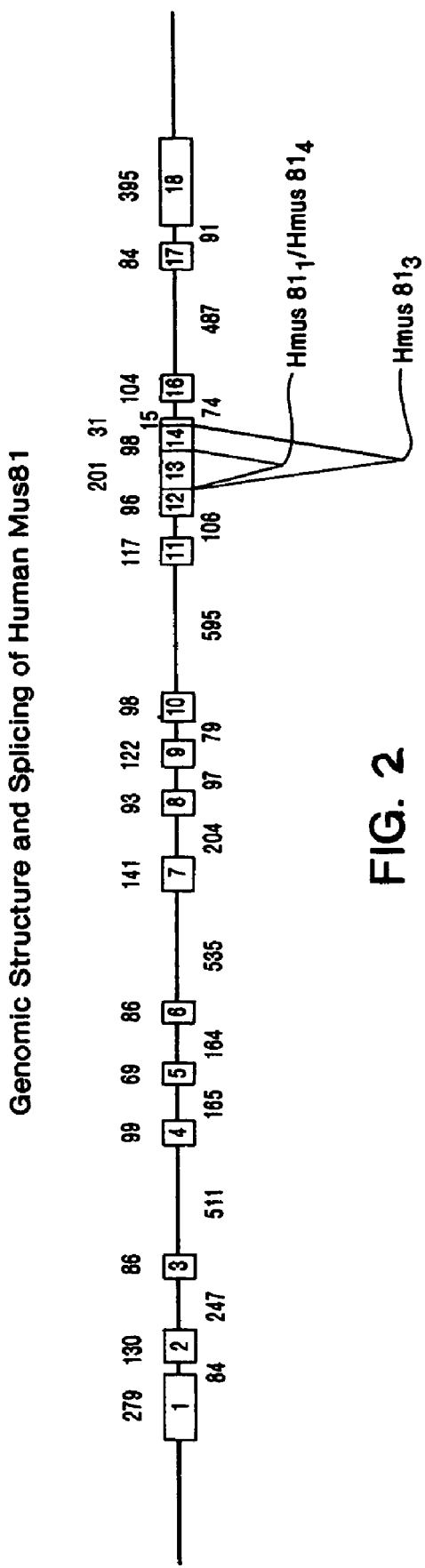
FIG. 2 schematically depicts the genomic structure and splicing variations of human Mus81; the solid line represents genomic sequence and boxes indicate positions of exons; the sizes of exons and introns (in bp) are indicated above and below the genomic fragment, respectively. Alternative splicing that occurs around exons 13 and 14 corresponds to human Mus81(1), Mus81(4), and Mus81(3), is shown by thin lines; Hmus81(2) utilizes all the identified exons.

As used herein, "checkpoint gene" means a gene that encodes a protein that acts in the checkpoint/repair regulation of cell division. Such protein can effect both replication and DNA damage checkpoint activity, i.e., having checkpoint/repair activity.

The terms "human Mus81 gene", "Hmus81 encoding gene," "Hmus81 gene", and any grammatical variations thereof as used herein and in the appended claims encompass genes that encode human variants of Mus81, including the allelic variants of the gene, which can occur in a human population, but still encode the same protein, splice variants of the gene, as well as the transcripts from such genomic genes, cDNA encoding for the transcript, and other nucleic acids that encode an Hmus81 protein.

As used herein and in the appended claims, the terms "human Mus81 protein", "Hmus81", "Hmus81 protein", and any grammatical variations thereof refer generally to a protein expressed from a human Mus81 encoding gene, and include splice variants and glycosylation variants of the protein that are generated by the translation and processing of a protein encoded by an Hmus81 gene, and in particular to proteins that are at least about 50% homologous to a human Mus81 protein having an amino acid sequence corresponding to SEQ ID NO: 2, 4, 6, or 8.

The terms "human Eme gene", "Heme encoding gene" and "Heme gene", and grammatical variations thereof as used herein and in the appended claims encompass genes that encode human Eme1 and human Eme2 proteins, including allelic variants of the genes that can occur in a human population, but still encode for the same protein, splice variants of the gene, as well as the transcripts from such genes, cDNA encoding for the transcript, and other nucleic acids that encode a human Eme1 or Eme2 protein. In a preferred embodiment, the isolated nucleic acids of the invention correspond to a cDNA that encodes a human Eme1 or Eme2 protein. Any particular isolated nucleic acid of the invention preferably encodes for only one form of a human Eme protein.

As used herein and in the appended claims, the terms "human Eme protein", "Heme1", "Heme2", "Heme protein", and grammatical variations thereof refer generally to a protein expressed from a human Eme encoding gene, and include splice variants and glycosylation variants of the protein that are generated by the translation and processing of the protein encoded by a human Eme gene, and in particular to Heme1, Heme2, and related proteins having an amino acid sequence that is at least about 50% homologous to SEQ ID NO: 10, 12, 14, 16, 18, or 20.

The terms "murine Mus81 gene", "Mmus81 encoding gene", "Mmus81 gene", and grammatical variations thereof, as used herein and in the appended claims encompass genes that encode murine variants of Mus81, including the allelic variants of the gene, which can occur in a murine population, but still encode for the same protein, splice variants of the gene, as well as the transcripts from such genomic genes, cDNA encoding for the transcript, and other nucleic acids that will encode an Mmus81 protein.

As used herein and in the appended claims, the terms "murine Mus81 protein", "Mmus81", "Mmus81 protein", and grammatical variations thereof refer generally to a protein expressed from a murine Mus81 encoding gene, and include splice variants and glycosylation variants of the protein that are generated by the translation and processing of the protein encoded by an Mmus81 gene, and in particular to proteins that are at least about 50% homologous to a murine Mus81 protein having an amino acid sequence corresponding to SEQ ID NO: 37, 39, 41, or 43.

The terms "murine Eme gene", "Meme encoding gene", "Meme gene", and grammatical variations thereof as used herein and in the appended claims encompass genes that encode murine Eme1 and murine Eme2 proteins, including allelic variants of the genes that can occur in a murine population, but still encode for the same protein, splice variants of the gene, as well as the transcripts from such genes, cDNA encoding for the transcript, and other nucleic acids that encode a murine Eme1 or Eme2 protein. In a preferred embodiment, the isolated nucleic acids of the invention correspond to a cDNA that encodes a murine Eme1 or Eme2 protein. Any particular isolated nucleic acid of the invention preferably encodes only one form of a murine Eme protein.

As used herein and in the appended claims, the terms "murine Eme protein", "Meme1", "Meme2", "Meme protein", and grammatical variations thereof refer generally to proteins expressed from a murine Eme encoding gene, and include splice variants and glycosylation variants of the protein that are generated by the translation and processing of the protein encoded by a murine Eme gene, and in particular to Meme1, Meme2, and related proteins having an amino acid sequence that is at least about 50% homologous to SEQ ID NO: 45, 47, 49, 51, 53, 55, 57, 59, or 61.

The term "biologically active protein" and grammatical variations thereof as used herein refers to a fusion product, fragment, digestion fragment, segment, domain, and the like, of a mammalian Mus81, Eme1, or Eme2 protein having at least a portion of the protein activity exhibited by whole Mus81, Eme1 or Eme2 protein, respectively. A biologically active protein thus contains at least a biologically functional portion of a mammalian (e.g., human or murine) Mus81, Eme1, or Eme2 protein.

The useful homologous variants of mammalian Mus81, Eme1, and Eme2 protein sequences contain amino acid substitutions at one or more positions in the sequences of the proteins. Such amino acid substitutions include conservative substitutions of similar amino acid residues that are reasonably predictable as providing equivalent function, or semi-conservative substitutions that have a reasonably predictable effect on solubility, glycosylation, or protein expression. For example, non-polar (hydrophobic side-chain) amino acids such as alanine, valine, leucine, isoleucine, proline, phenylalanine, tryptophan, methionine; uncharged polar amino acids such as glycine, serine, threonine, cysteine, tyrosine, asparagine, glutamine; charged polar amino acids such as aspartic acid, glutamic acid; and basic amino acids such as lysine, arginine, and histidine, are understood by those in the art to have functionally predictable effects when substituted in the protein sequence. Amino acid substitutions also include replacement of amino acid residues with modified amino acid residues or chemically altered substitutes.

Advantageously, the mammalian Mus81 and Eme proteins useful in the compositions and methods of the present invention can be produced using recombinant or synthetic techniques. For example, a nucleic acid encoding the Mus81 or Eme protein can be synthesized using PCR cloning mechanisms, which generally involve making a pair of primers, having approximately 15 to 50 nucleotides corresponding to a region of the gene that is to be cloned, bringing the primers into contact with mRNA, cDNA, or genomic DNA from a human cell, performing a polymerase chain reaction (PCR) under conditions that bring about amplification of the desired region of the gene (and where necessary, first performing a reverse transcription step), isolating the amplified region or fragment of the gene, and then recovering the amplified genomic DNA.

Advantageously, mammalian allelic variants of the nucleic acids encoding the Mus81 and Eme proteins can be obtained, for example, by probing genomic DNA libraries from a range of individuals, e.g., from different mammal populations, such as human or murine populations, and other genotyping techniques. Furthermore, nucleic acids and probes may be used to sequence genomic DNA from mammalian subjects using techniques well known in the art, for example, the Sanger dideoxy chain termination method, which can advantageously ascertain predispositions of a patient to certain proliferative disorders. The nucleic acids can then be incorporated into an expression vector and introduced into an appropriate host, optionally encoding a fusion protein or with a suitable tag sequence, for example, to facilitate isolation of the expressed proteins.

Nucleic acid sequences encoding Hmus81 variants Hmus81(1), Hmus81(2), Hmus81(3), and Hmus81(4) are shown in FIG. 1 (SEQ ID NO: 1, 3, 5, and 7, respectively). FIG. 10 shows nucleic acid sequences encoding Mmus81 variants Mmus81(1), Mmus81(2), Mmus81(3), and Mmus81(4) (SEQ ID NO: 36, 38, 40, and 42, respectively). Such sequences can be modified by utilizing codons preferred by the target host cell, while still encoding for the human or murine Mus81 protein. The nucleic acids encoding the human and murine Mus81 proteins can also encompass modified nucleic acids that incorporate, for example, internucleotide linkage modifications, base modifications, sugar modifications, radioactive and nonradioactive labels, nucleic acid cross-linking, and altered backbones including PNAs (polypeptide nucleic acids), as well as codon substitutions to reduce the number of less-preferred codons and/or an increase in the number of preferred codons used by the target host cell (see Zhang et al., 1991, "Graphic analysis of codon usage strategy in 1490 human proteins" *Gene* 105(1):61-72; hereinafter Zhang et al., 1996; Zhang et al., 1993, "Low-usage codons in *Escherichia coli*, yeast, fruit fly and primates" *J. Protein Chemistry* 12(3):329-335, hereinafter Zhang et al., 1993). Biologically active fragments representing the C-terminal region of the human and murine Mus81 proteins can also be utilized.

The mammalian Mus81 and Eme proteins useful in the methods of the present invention can be utilized in a substantially purified form, in any degree of purity that is suitable for the intended use of the proteins, which one of ordinary skill in the art can determine by methods well known in the art. The proteins also can be modified, for example, by the addition of histidine residues to assist their purification (His-tag), or by the addition of a signal sequence to promote their secretion from a cell.

Human Mus81 proteins having at least about 50% homology (sequence identity), preferably at least about 80% homology, more preferably at least about 90% homology to a protein depicted in SEQ ID NO: 2, 4, 6 or 8, (FIG. 1) including proteins that are amino acid sequence variants, alleles, derivatives, or mutants of a protein depicted in SEQ ID NO: 2, 4, 6, or 8, are also useful in the methods of the present invention. Murine Mus81 proteins having at least about 50% homology, preferably at least about 80% homology, more preferably at least about 90% homology to a protein depicted in SEQ ID NO: 37, 39, 41, or 43, (FIG. 10) including proteins that are amino acid sequence variants, alleles, derivatives, or mutants of a protein depicted in SEQ ID NO: 37, 39, 41, or 43, are also useful in the methods of the present invention.

Preferably the mammalian Mus81 protein (e.g., human or murine Mus81 protein) includes an intact VERK domain. The VERK domain of Mus81 is located in the C-terminal end of the protein and encompasses the folding region, which includes the valine-glutamic acid-arginine-lysine (VERK) segment from which the name derives. The VERK domain is a sequence motif (V/IERKX3D), which is believed to contribute to a conserved overall fold needed for endonuclease activity of Mus81 and related proteins. Specific residues within the VERK domain of Mus81 are known to be required for activity. The VERK domain of Mus81 is included within residues 300-368 of Hmus81(1) and murine Mmus81(1) sequences (i.e., SEQ ID NO: 2 in FIG. 1A and SEQ ID NO: 37 in FIG. 10A, respectively).

Figure 7A:
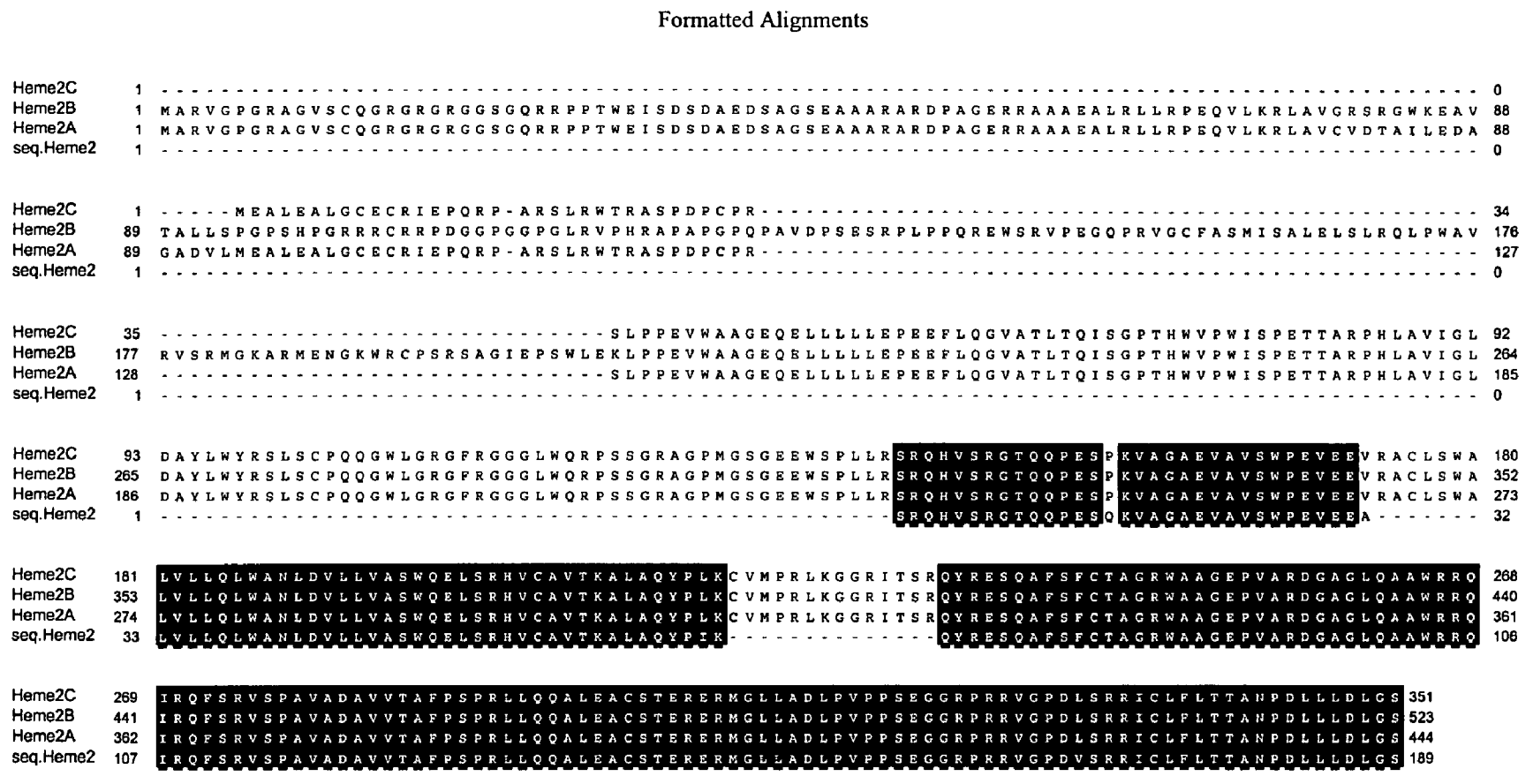

Human Eme proteins having at least about 50% homology, preferably at least about 80% homology, more preferably at least about 90% homology to a human Eme1 protein variant Heme1A, Heme1B and Heme1C, having an amino acid sequence corresponding to SEQ ID NO: 10, 12, and 14, respectively (FIG. 6), or to a human Eme2 protein variant Meme2A, Heme2B and Heme 2C, having an amino acid sequence corresponding to SEQ ID NO 16, 18, and 20 (FIG. 7), including proteins that are amino acid sequence variants, alleles, derivatives, or mutants of the protein having an amino acid sequence corresponding to SEQ ID NO: 10, 12, 14, 16, 18, or 20, are useful in the methods of the present invention.

Murine Eme proteins having at least about 50% homology, preferably at least about 80% homology, more preferably at least about 90% homology to a murine Eme1 protein variant Meme1TeA2, Meme1TeA4, Meme1TeA9, Meme1TeB 1, and Meme1TeB2, having an amino acid sequence corresponding to SEQ ID NO: 45, 47, 49, 51, and 53, respectively (FIG. 11); or to a murine Eme2 protein variant Meme2Br2, Meme2Br5, Meme2Te5, and Meme2Te6, having an amino acid sequence corresponding to SEQ ID NO: 55, 57, 59, and 61, respectively (FIG. 12); including proteins that are amino acid sequence variants, alleles, derivatives, or mutants of the protein having an amino acid sequence corresponding to SEQ ID NO: 45, 47, 49, 51, 53, 55, 57, 59, or 61, are also useful in the methods of the present invention.

The percentage homology of amino acid residue sequences can be calculated by using commercially available algorithms that compare a reference protein sequence (e.g., SEQ ID NO: 2, 4, 6, 8, 10, 12, 14, 16, 18, 20, 45, 47, 49, 51, 53, 55, 57, 59, or 61) with a query amino acid sequence. The percentage homology of nucleic acid sequences can be calculated by using commercially available algorithms that compare a reference nucleic acid sequence (e.g., SEQ ID NO: 1, 3, 5, 7, 9, 11, 13, 15, 17, 19, 44, 46, 48, 50, 52, 56, 58, or 60) with a query polynucleotide sequence.

The following programs (provided by the National Center for Biotechnology Information, NCBI) may be used to determine homologies: BLAST, BLAST2, gapped BLAST, BLASTP, BLASTN, and psi-BLAST, for example, which may be used with default parameters or with user specified parameters. Use of either of the terms "homology" or "homologous" herein does not imply any necessary evolutionary relationship between compared sequences, in keeping with standard use of such terms as "homologous recombination," which merely requires that two nucleotide sequence are sufficiently similar to recombine under the appropriate conditions.

Another method for determining the best overall match between a nucleotide sequence or portion thereof, and a query sequence is the use of the FASTDB computer program based on the algorithm of Brutlag et al., 1990, "Improved sensitivity of biological sequence database searches" *Compt. Appl. Biosci.,* 6:237-245. The FASTDB program provides a global sequence alignment. The result of such a global sequence alignment is expressed as percent identity. Suitable parameters used in a FASTDB search of a nucleotide sequence to calculate the degree of identity (homology) are known to those of ordinary skill in the art.

The present invention also advantageously provides for nucleotide sequences of about 15 to about 50 nucleotides that are complementary to a contiguous portion of a nucleic acid encoding a mammalian Eme protein according to the invention. These complementary sequences can be used as probes or primers to initiate replication, to detect the presence of nucleic acids encoding a mammalian Eme protein, or to specifically amplify segments of the desired nucleic acid from a sample. Such complementary nucleotide sequences can be produced according to techniques well known in the art, such as by recombinant or synthetic means. The prepared primers, properly coordinated to specifically amplify a portion of a target nucleic acid in a sample may be used in diagnostic kits, or the like, for detecting the presence of a nucleic acid according to the invention. These tests generally comprise contacting the probe nucleotide with the sample under hybridizing conditions and detecting for the presence of any duplex or triplex formation between the probe and any nucleic acid in the sample.

Specific modification of codons used in the nucleic acids corresponding to SEQ ID NO: 1, 3, 5, and 7 can be such that the modified nucleic acids utilize codons preferred by the target host cell, while still encoding for the Hmus81 protein. Similarly, the present invention encompasses specific modification of codons used in the nucleic acids corresponding to SEQ ID NO: 9, 11, 13, 15, 17, and 19, such that the modified nucleic acids utilize codons preferred by the target host cell, while still encoding for a Heme protein. Specific modification of codons used in the nucleic acids corresponding to SEQ ID NO: 36, 38, 40, and 42 can be such that the modified nucleic acids utilize codons preferred by the target host cell, while still encoding for the Mmus81 protein. Similarly, the present invention encompasses specific modification of codons used in the nucleic acids corresponding to SEQ ID NO: 44, 46, 48, 50, 52, 56, 58, and 60, such that the modified nucleic acids utilize codons preferred by the target host cell, while still encoding for a Meme protein.

The present invention also provides isolated nucleic acids encoding (a) a Heme protein having an amino acid sequence corresponding to SEQ ID NO: 10, 12, 14, 16, 18, or 20, or encoding a biologically active or equivalent fragment, or bioprecursor of the Heme protein; and (b) a Meme protein having an amino acid sequence corresponding to SEQ ID NO: 45, 47, 49, 51, 53, 55, 57, 59, or 61, or encoding a biologically active or equivalent fragment, or bioprecursor of the Meme protein.

The present invention also encompasses modifications of these nucleic acids that incorporate, for example, internucleotide linkage modifications, base modifications, sugar modification, nonradioactive labels, nucleic acid cross-linking, and altered backbones including PNAs (polypeptide nucleic acids), as well as codon substitutions to reduce the number of less preferred codons and/or an increase in the number of preferred codons used by the target host cell (see Zhang et al., 1991, Zhang et al., 1993).

Preferably, a nucleic acid utilized in the present invention is a DNA molecule such as a genomic DNA molecule, and even more preferably a cDNA molecule. However, the nucleic acid may also be an RNA molecule. As is well known to those of ordinary skill in the art, the present nucleotide sequences can include substitutions therein, yet still encode the same amino acid residue sequence due to the degeneracy of the triplet codon genetic code.

The present nucleic acids can be incorporated into an expression vector and subsequently used to transform, transfect, or infect a suitable host cell. In such an expression vector the nucleic acid according to the invention preferably is operably linked to a control sequence, such as a suitable promoter or the like, ensuring expression of the proteins according to the invention in a suitable host cell. The expression vector can be a plasmid, cosmid, virus, or any other suitable vector. The expression vector and the host cell that has been transfected, transformed, or infected with the vector also form part of the present invention. Preferably, the host cell is a eukaryotic cell or a bacterial cell, and even more preferably a mammalian cell or and insect cell. Mammalian host cells are particularly advantageous because they provide the necessary post-translational modifications to the expressed proteins according to the invention, such as glycosylation or the like, which modifications continue to confer at least some of the biological activity of the Heme proteins, which when isolated can advantageously be used in diagnostic kits, and the like.

The recombinant vectors of the invention generally comprise a mammalian Heme gene operatively positioned downstream from a promoter. The promoter is capable of directing expression of human or murine Eme proteins, for example, from the genes in a mammalian cell such as a human or murine cell. Such promoters are thus "operative" in mammalian cells. In one preferred embodiment the vector comprises both an Hmus81 gene and an Heme gene and expresses an Hmus81-Eme endonuclease complex. In another preferred embodiment the vector comprises both an Mmus81 gene and an Meme gene and expresses a murine Mus81-Eme endonuclease complex.

Expression vectors and plasmids embodying the present invention preferably comprise one or more constitutive promoters, such as viral promoters or promoters from mammalian genes that are generally active in promoting transcription. Examples of constitutive viral promoters include the HSV, TK, RSV, SV40 and CMV promoters, of which the CMV promoter is a currently preferred example. Examples of constitutive mammalian promoters include various housekeeping gene promoters, as exemplified by the β-actin promoter.

Inducible promoters and/or regulatory elements are also contemplated for use with the expression vectors of the invention. Examples of suitable inducible promoters include promoters from genes such as cytochrome P450 genes, heat shock protein genes, metallothionein genes, hormone-inducible genes, such as the estrogen gene promoter, and the like. Promoters that are activated in response to exposure to ionizing radiation, such as fos, jun, and erg-1, are also contemplated. The tetVP16 promoter that is responsive to tetracycline is a currently preferred example.

Tissue-specific promoters and/or regulatory elements can be useful in certain embodiments. Examples of such promoters that can be used with the expression vectors of the invention include promoters from the liver fatty acid binding (FAB) protein gene, specific for colon epithelial cells; the insulin gene, specific for pancreatic cells; the transphyretin, α1-antitrypsin, plasminogen activator inhibitor type 1 (PAI-1), apolipoprotein AI, and LDL receptor genes, specific for liver cells; the myelin basic protein (MBP) gene, specific for oligodendrocytes; the glial fibrillary acidic protein (GFAP) gene, specific for glial cells; the opsin gene, specific for targeting to the eye; and the neural-specific enolase (NSE) promoter, which is specific for nerve cells.

The construction and use of expression vectors and plasmids is well known to those of skill in the art. Any mammalian suitable cell expression vector can be used in connection with the genes disclosed herein.

Preferred vectors and plasmids are constructed with at least one multiple cloning site. In certain embodiments, the expression vector will comprise a multiple cloning site that is operatively positioned between a promoter and a mammalian Mus81 or mammalian Eme encoding gene sequence. Such vectors can be used, in addition to uses in other embodiments, to create N-terminal or C-terminal fusion proteins by cloning a second protein-encoding DNA segment into the multiple cloning site so that it is contiguous and in-frame with the mammalian Mus81 and Eme encoding nucleotide sequences.

In other embodiments, expression vectors comprise a multiple cloning site that is operatively positioned downstream from the expressible Mus81 or Eme encoding sequence. These vectors are useful in creating C-terminal fusion proteins by cloning a second protein-encoding DNA segment into the cloning site, so that it is contiguous and in-frame with the Mus81 or Eme encoding sequence.

Vectors and plasmids in which one or more protein- or RNA-encoding nucleic acid segment are present, in addition to the Mus81 and Eme genes, are also encompassed by the invention, irrespective of the nature of the nucleic acid segment itself.

A reporter gene can be included within an expression vector of the present invention. The reporter gene can be included within a second transcriptional unit. Suitable reporter genes include those that confer resistance to agents such as neomycin, hygromycin, puromycin, zeocin, mycophenolic acid, histidinol, methotrexate, and the like and genes to aid in detecting such as green fluorescent protein (GFP), β-galactosidase, and the like.

Expression vectors can also contain other nucleotide sequences, such as internal ribosome entry sequence (IRES) elements, polyadenylation signals, splice donor/splice acceptor signals, and the like.

Particular examples of suitable expression vectors are those adapted for expression using a recombinant adenoviral, recombinant adeno-associated viral (AAV), or recombinant retroviral system. Vaccinia virus, herpes simplex virus, cytomegalovirus, and defective hepatitis B viruses, for example, can also be used.

In one embodiment, the present invention encompasses isolated nucleic acids that encode for mammalian Eme proteins, which associate with Mus81 proteins to form a mammalian Mus81-Eme endonuclease complexes. Other embodiments of the present invention include isolated mammalian Eme proteins nucleic acids having nucleic acid sequences corresponding to SEQ ID NO: 9, 11, 13, 15, 17, 19, 44, 46, 48, 50, 52, 54, 56, 58, and 60 (FIG. 6, FIG. 7, FIG. 11 and FIG. 12) and to codon substitution variations thereof, which encode proteins having an amino acid sequence corresponding to any of SEQ ID NO: 9, 11, 13, 15, 17, 19, 44, 46, 48, 50, 52, 54, 56, 58, or 60.

Also provided by the present invention are isolated mammalian Eme proteins having an amino acid sequence corresponding to SEQ ID NO: 10, 12, 14, 16, 18, 20, 45, 47, 49, 51, 53, 55, 57, 59, and 61 (FIG. 6, FIG. 7, FIG. 11 and FIG. 12), or the amino acid sequence of a biologically active or functionally equivalent fusion protein product, fragment or biofractorsor of said protein, or a protein that is at least about 50% homologous to a protein having an amino acid sequence corresponding to SEQ ID NO: 10, 12, 14, 16, 18, 20, 5, 47, 49, 51, 53, 55, 57, 59, or 61.

A protein of the invention can be utilized in a substantially purified form at any level of purity that is convenient and useful for the intended purpose of the protein. Proteins of the invention can be modified, for example by the addition of histidine residues to assist their purification or by the addition of a signal sequence to promote their secretion from a cell, if desired.

In one preferred embodiment, the present invention provides an isolated human Mus81-Eme endonuclease, which is a complex of a human Mus81 protein and a human Eme protein, such as human Eme1 or human Eme2, as described above.

In another preferred embodiment, the present invention provides an isolated murine Mus81-Eme endonuclease, which is a complex of a murine Mus81 protein and a murine Eme protein, such as murine Eme1 or murine Eme2, as described above.

The present invention also encompasses a method for identifying a chemical compound that modulates mammalian cellular response to DNA damage. The method comprises the steps of: contacting a chemical compound to be tested with a biochemical mixture containing an isolated mammalian (e.g., human or murine) Mus81-Eme endonuclease complex, a source of magnesium ion, and a DNA test substrate; measuring the activity level of Mus81-Eme endonuclease complex in the mixture; comparing the measured activity level to the activity level of a substantially similar control mixture of isolated Mus81-Eme1 endonuclease, magnesium ion, and the DNA substrate in the absence of the chemical compound to be tested; and selecting a chemical compound that increases or decreases the endonuclease activity.

A difference in activity between mixtures containing a test compound relative to the control indicates that the test compound modulates Mus81-Eme endonuclease activity, and thus modulates cellular response to DNA damage. Such identified compounds can then be utilized as pharmaceutical agents or can be selected for additional evaluation in a cell-based assay or in vivo assay, for example, to further evaluate the DNA damage response-modulating activity of the identified compounds.

A cell-based assay can include the use of a cell line that has been co-transfected with a mammalian Mus81 gene and a mammalian Eme gene from the same species of mammal, such as an Eme1 gene or an Eme2 gene, and which expresses a mammalian Mus81-Eme endonuclease complex, such as a human or murine Mus81-Eme1 or Mus81-Eme2 endonuclease complex. In the cell-based assay, the isolated Mus81-Eme complex is replaced by a transformed cell that expresses a mammalian Mus81-Eme complex of the invention.

The present invention also encompasses chemical compounds identified by the methods of the present invention. A test compound that exhibits an enhancement of mammalian Mus81-Eme endonuclease activity is a potential pharmaceutical agent for repairing DNA damage. Such compounds have applications in the treatment of UV radiation damaged tissues, and other types of cellular damage, for example.

In contrast, a test compound that exhibits a suppression or inhibition of Mus81-Eme endonuclease activity is a potential pharmaceutical agent for inhibiting DNA damage repair. DNA damage repair inhibitors are useful, for example, in combination therapies with chemotherapeutic agents to enhance the potency of the chemotherapy by temporarily delaying cellular DNA repair mechanisms.

Preferably, the magnesium ion is present in the biochemical test medium in a concentration in the range of about 0.5 mM to about 20 mM, more preferably in the range of about 1 mM to about 3 mM.

Preferably the DNA test substrate includes a Holliday junction or a related branched DNA substrate. Preferred DNA test substrates include, without limitation, oligonucleotides containing Holliday junctions described in Boddy, et al., *Cell*, 2001; 107:537-548, the relevant disclosures of which are incorporated herein by reference. Particularly preferred DNA test substrates include synthetic oligonucleotides designed to give branched multiplex DNA, and naturally occurring or engineered four-way X junctions in cruciform DNA of a supercoiled plasmid. The substrates to be assayed include, without limitation, Holliday junctions, X-structures, partial X, nicked-X, cruciforms, duplex Y, flaps, branched duplex, replication forks and the like. The branched shape of the substrate, and not the sequence of the nucleotides within the structure, is the important parameter in selecting a suitable substrate. Particularly preferred substrates are X-structures, replication forks, and flap structures.

DNA test substrates containing Holliday junctions can be prepared as described in Example 6, below, and as described by Boddy et al., *Cell*, 2001; 107:537-548, the relevant disclosure of which is incorporated herein by reference. Four oglionucleotides having complementary and homologous regions are prepared and annealed to form the X-structure of a Holliday junction. The oglionucleotides can be of different lengths or equal lengths. Preferably, the oligonucleotides are prepared in a 5' $^{32}$P-radiolabeled form and a "cold" form. A radiolabeled oligonucleotide preferably is annealed with 3 cold oligonucleotides to prepare the Holliday junction substrate (X-structure). Preferably each of the four possible radiolabeled X-structures are prepared.

The oligonucleotides are typically annealed by incubating the oligonucleotides in a suitable buffer and purifying the resulting "X-structures" by gel electrophoresis. See, for example, Parsons, et al., 1990, *J. Biol. Chem.*, 265: 9285-89 (hereinafter Parsons, et al., 1990).

Plasmid substrates can also be assayed. Super-coiled plasmids from bacteria are purified by standard cesium chloride gradient or column chromatography, and the plasmid is incubated with Mus81-Eme1 endonuclease in the presence of a divalent cation, such as magnesium. A product is resolved from the starting plasmid by standard gel electrophoresis techniques. See Giraud-Panis et al., 1997, *EMBO J.*, 16(9): 2528-34 for a discussion of near-simultaneous DNA cleavage by the subunits of the junction-resolving enzyme T4 endonuclease VII.

When the X-structure oligonucleotides and like branched DNA structures are contacted with an endonuclease of the present invention in a buffer containing magnesium ion, the branched structures are cleaved to form linear duplex DNA products. When X-structures are utilized, cleavage products from all four radiolabeled X-structures are examined, e.g., by electrophoresis, and the cleavage sites of the X-structures can be determined from the resultant cleavage products. Generally, cleavage occurs symmetrically at the central junction site in the X-structure, however, cleavage can be asymmetric, as described in Boddy et al., 2001.

Figure 8:
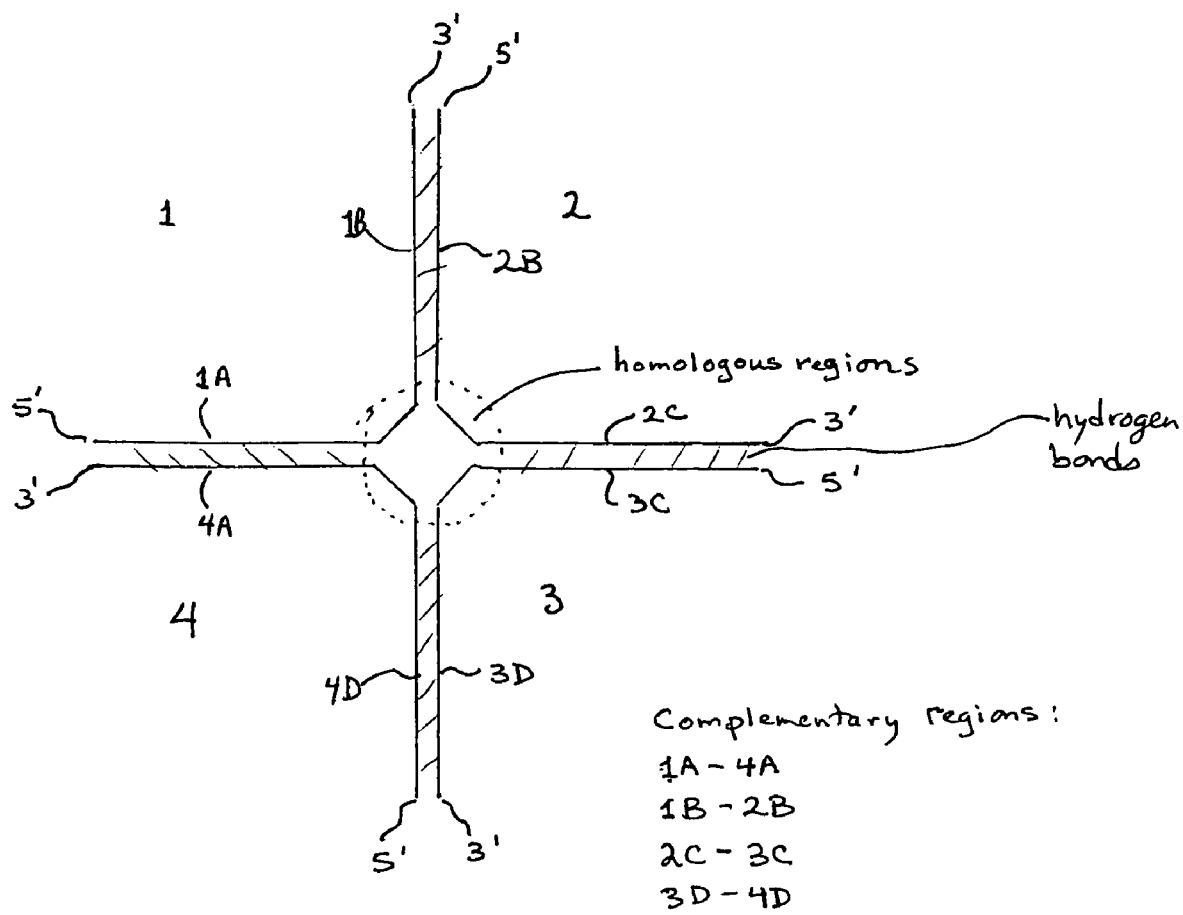
FIG. 8 schematically illustrates the regions of complementarity and homology of oligonucleotides comprising a Holliday Junction-containing DNA structure.

FIG. 8 schematically illustrates the structure of a Holliday junction. Four DNA strands have pairs of 5'-3' complementary regions and central regions that are homologous to each other. DNA strand 1 has a 5' region 1A that is complementary to the 3' region of strand 4 (i.e. 4A). The 3' region of strand 1 (1B) is complementary to the 5' region of strand 2 (2B). The 3' region of strand 2 (2C) is complementary to the 5' region of strand 3 (3C). Finally, the 3' region of strand 3 (3D) is complementary to the 5' region of strand 4 (4D). The resulting quadruplex DNA structure has a generally X-like shape (X-structure). The central regions of the strands are homologous to each other and therefore do not bind to each other.

FIG. 9 illustrates a variety of cleavage patterns for resolution of a Holliday junction. FIG. 9A illustrates a cleavage pattern in which strands 2 and 4 are both cut symmetrically (i.e. at the same position relative to the junction). FIG. 9B depicts cleavage of strands 2 relatively closer to the junction than the cleavage of strand 4. FIG. 9C illustrates cleavage of strand 4 relatively closer to the junction than strand 2. FIG. 9D illustrates two alternative symmetric cleavage patterns, i.e., cleavage of strands 2 and 4 or stands 1 and 3.

Preferably, the activity that is measured in the method of the present invention is formation of linear duplex DNA from a quadruplex, Holliday junction-containing DNA, a replication fork, or a flap structure, e.g., as described in Boddy et al., 2001. The activity is determined by analyzing the DNA that has been exposed to the endonuclease and test compound for the presence of linear duplex DNA corresponding to strands cleaved from the branched DNA of the substrate. The presence of linear duplex DNA can be determined by methods well known in the biochemical arts, such as by gel electrophoresis, and like techniques.

Preferably, the isolated mammalian Mus81-Eme endonucleases used in the methods of the present invention comprise a human or murine Mus81 protein, as described above and having an intact VERK domain. The isolated mammalian Mus81-Eme endonuclease most preferably comprises a human or murine version of an Eme1 protein, preferably human Eme1B or human Eme1A, most preferably human Eme1B. Alternatively an Eme2 protein can be utilized.

Another preferred method aspect of the present invention is a method of identifying a DNA repair-enhancing pharmaceutical agent. The method comprises the steps of: contacting a potential pharmaceutical agent with a biochemical mixture of an isolated mammalian Mus81-Eme endonuclease and a DNA substrate including a branched DNA substrate such as a Holliday junction, replication fork, or flap under conditions suitable for endonuclease resolution of Holliday junctions; measuring the activity of Mus81-Eme endonuclease in the presence and absence of the potential pharmaceutical agent; and selecting potential pharmaceutical agents which increase Mus81-Eme endonuclease activity, as determined by an increase in linear duplex DNA formation in mixtures containing the potential pharmaceutical agent relative to mixtures that do not contain the pharmaceutical agent.

The pharmaceutical agents identified as enhancing DNA repair are particularly useful for repair of cellular damage due to UV exposure, for example.

Yet another preferred method aspect of the present invention is a method of identifying a DNA repair-inhibiting pharmaceutical agent. The method comprises the steps of: contacting a potential pharmaceutical agent with an isolated mammalian Mus81-Eme endonuclease and a DNA substrate including a branched DNA substrate such as a Holliday junction replication fork, flap, and the like, and under conditions suitable for endonuclease resolution of such branched DNA structures; measuring the activity of Mus81-Eme endonuclease in the presence and absence of the potential pharmaceutical agent; and selecting potential pharmaceutical agents which inhibit or suppress Mus81-Eme endonuclease activity, as determined by a decrease in linear duplex DNA formation in mixtures containing the potential pharmaceutical agent relative to mixtures that do not contain the pharmaceutical agent.

The pharmaceutical agents identified as suppressing or inhibiting DNA damage repair are particularly useful, for example, in combination with chemotherapeutic agents to enhance the potency of the chemotherapies by temporarily delaying cellular DNA repair mechanisms.

Another aspect of the present invention is a kit for identifying a chemical compound that modulates cellular response to DNA damage. The kit comprises a first component, which is an isolated mammalian Mus81-Eme endonuclease complex, a second component, which is a source of magnesium ion, and a third component, which is a DNA test substrate preferably including a branched DNA substrate such as a Holliday junction replication fork structure, flap structure, and the like. The kit also includes instructional materials for testing at least one chemical compound. Each component is individually packaged in a separate container, such as a vial, ampule, packet, and the like, and each component is included in an amount sufficient to test one or more chemical compounds. Preferably, the instructional materials provide instructions for testing a chemical compound according to the methods of the present invention. Any mammalian Mus81-Eme endonuclease, such as a human or murine Mus81-Eme endonuclease complex, as described herein, can be utilized in the kits of the present invention. Preferably the endonuclease is an Hmus81-Eme1 endonuclease, most preferably an Hmus81-Eme1B endonuclease.

As would be understood by one of ordinary skill in the art, many variations and equivalents to the compositions of the present invention are easily obtained and generated through the application of routine methods known in the art using the teachings of the present invention.

Many of the methods and materials for carrying out the basic molecular biology manipulations as described in the examples below are known in the art, and can be found in such references as Sambrook et al., *Molecular Cloning*, 3rd edition, Cold Spring Harbor Laboratory Press (2001); Berger et al., *Guide to Molecular Cloning Techniques, Methods in Enzymology*, Vol. 152, Academic Press, Inc., (1987); Davis et al., *Basic Methods in Molecular Biology*, Elsevier Science Publishing Co., Inc. (1986); Ausubel et al., *Short Protocols in Molecular Biology*, 2nd ed., John Wiley & Sons, (1992); Goeddel *Gene Expression Technology, Methods in Enzymology*, Vol. 185, Academic Press, Inc., (1991); Guthrie et al., *Guide to Yeast Genetics and Molecular Biology, Methods in Enzymology*, Vol. 194, Academic Press, Inc., (1991); McPherson et al., *PCR Volume* 1, Oxford University Press, (1991); McPherson et al., *PCR Volume* 2, Oxford University Press, (1995); Richardson, C. D. ed., *Baculovirus Expression Protocols, Methods in Molecular Biology*, Vol. 39, Humana Press, Inc. (1995); and the like.

The invention in its several aspects is further illustrated by the following non-limiting examples.

EXAMPLE 1

Human Mus81 (Hmus81) Cloning

Oligonucleotide primers Hmus81(1) forward (GACATG-GCGGCCCCGGTCCG) (SEQ ID NO: 24) and Hmus81(1) reverse (GACTCAGGTCAAGGGGCCGTAG) (SEQ ID NO: 25), corresponding to the 5' (ATGGCGGCCCCG-GTCCG) (SEQ ID NO: 26) and 3' (CTACGGCCCCTTGAC-CTGA) (SEQ ID NO: 27) ends of the putative human Mus81 (1) opening reading frame (ORF) were used to amplify DNA products from a Marathon-Ready human cerebellum cDNA library (Clontech, Palo Alto, Calif.) by polymerase chain reaction (PCR). PCR was performed using Pfu polymerase and the heating of the reaction mixture under the following reaction conditions: about 95° C. for about 30 seconds, about 68° C. for about 30 seconds, about 72° C. for about 1 to about 30 seconds (35×). The resulting DNA products were cloned into the pCR2.1-TOPO plasmid as recommended by the manufacturer (Invitrogen, Carlsbad Calif.) and the DNA was sequenced by standard methods well known in the art.

Oligonucleotide primers corresponding to the 5' and 3' ends of Hmus81(1), from a putative ORF constructed using the identified yeast sequences were used to amplify a sequence (SEQ ID NO: 1) from a human cerebellum cDNA library. A 1653 nucleotide sequence was obtained, which encodes a 551 amino acid protein (SEQ ID NO:2). A longer 1857 nucleotide sequence (SEQ ID NO: 3) encodes a shorter variant, Hmus81, which is a 455 amino acid protein (SEQ ID NO:4). FIGS. 1A-1D depict the sequences of Hmus81 genes (SEQ ID NO: 1, 3, 5 and 7) encoding proteins Hmus81(1), Hmus81(2), Hmus81(3) and Hmus81(4), (SEQ ID NO: 2, 4, 6, and 8 respectively).

EXAMPLE 2

Genomic Structure and Chromosomal Localization of Human Mus81

The human cDNAs were used to identify contiguous genomic sequences containing Mus81 in the public databases. Comparison of the genomic sequence confirmed that the various cDNA forms corresponded to different splice variants of Mus81. Examination of the results identified 18 exons encoding Mus81 sequences within a 5.8 kb genomic region (FIG. 2). The splicing differences in the identified cDNAs occurred in the region encompassing exons 13 and 14. The nucleic acid encoding for human Mus81(2) (SEQ ID NO: 3) was composed of all of the exons identified. The nucleic acid encoding for human Mus81(1) (SEQ ID NO: 1) did not contain exon 13 and the nucleic acid encoding for human Mus81(3) (SEQ ID NO: 5) was lacking exons 13 and 14. Splicing of the nucleic acid encoding for human Mus81 (4) (SEQ ID NO: 7) was nearly identical to that found in the nucleic acid encoding for human Mus81(1) (SEQ ID NO: 1) except that it contained three additional nucleotides (CAG) at the 5' end of exon 14, likely due to utilization of an alternative splice acceptor site. Splicing of all introns utilized the consensus donor and acceptor sites.

Fluorescence in situ Hybridisation (FISH) analysis was carried out using standard procedures. Briefly, human lymphocytes isolated from blood were synchronized by culturing in the presence of about 0.18 mg/mL bromodeoxyuridine (BrdU). The BrdU was washed off to release the block and the cells were cultured for 6 hours prior to harvesting and fixation. FISH detection was carried out with an Mus81 cDNA probe labeled with biotinylated dATP. Chromosomal localization was determined by comparison of FISH signals to DAPI banding pattern.

FISH analysis using human Mus81 cDNA as a probe resulted in staining of a single pair of chromosomes at 11q13 in 70 out of 100 mitotic spreads. This localization was confirmed by the previous assignment of a public express sequence tag (EST) (WI-18484), which is identical to part of the Mus81 sequence, to chromosome 11 on the WICGR radiation hybrid map.

EXAMPLE 3

Expression and Intracellular Localization of Human Mus81

The human Mus81(1) cDNA was cloned downstream and in frame with the green fluorescent protein (GFP) encoding open reading frame gene (ORF) in a retrovirus expression vector. The retrovirus expression vector is chosen to allow for the regulated expression of proteins of interest, and in a preferred embodiment allows fusion of the protein of interest to the GFP or modified GFP for visualization of expression. It is also possible to express both the Mus81 protein and GFP protein as separate proteins from the same expression vector.

Commercially available vectors suitable for expression of Mus81 protein include and are not limited to, for example, pRevTRE (Clontech) which are derived from the pLNCX (Clontech) retroviral expression vector (Gossen, M. & Bujard, H., 1992, "Tight control of gene expression in mammalian cells by tetracycline-responsive promoters" *PNAS* (*USA*) 89:5547-5551), or GFP fusion protein expressing retroviral expression vectors pLEGFP-N1 and pLEGFP-C1 (Clontech).

The retrovirus vector expressing human Mus81-GFP was used to infect A549 lung carcinoma cells containing an integrated copy of the tTA transactivator for regulated expression of the fusion protein. The cells were grown to allow expression of the fusion protein, and visualized by fluorescence microscopy three days after infection.

The microscopic evaluation indicated that human Mus81 was expressed as a fusion with the GFP protein in the A549 cells. Fluorescence was detected primarily in the nuclei of these cells. The nuclear localization of Hmus81 is in agreement with its role in DNA repair-associated functions.

EXAMPLE 4

Human Eme Identification and Cloning

Figure 3:
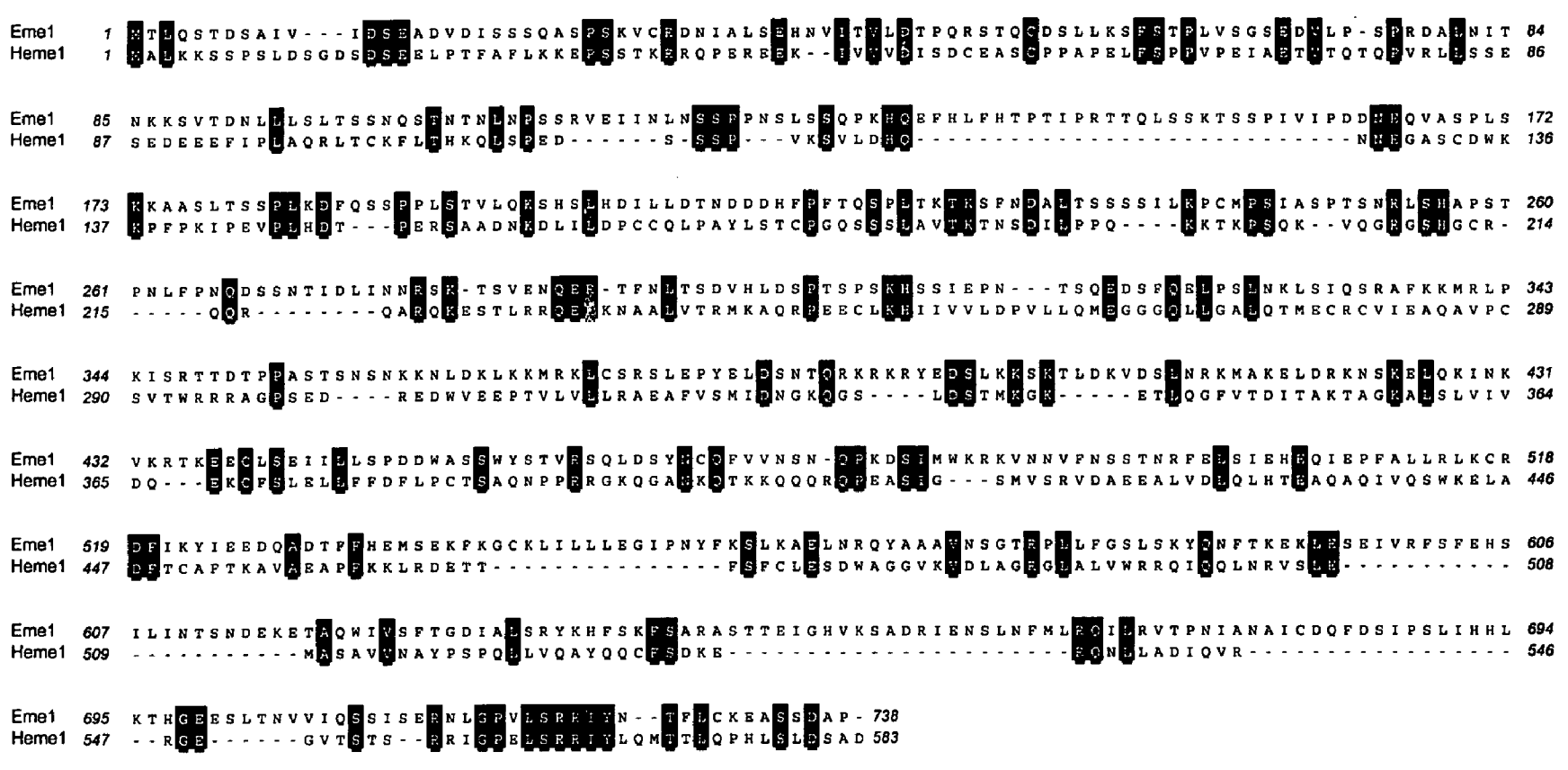
Figure 4:
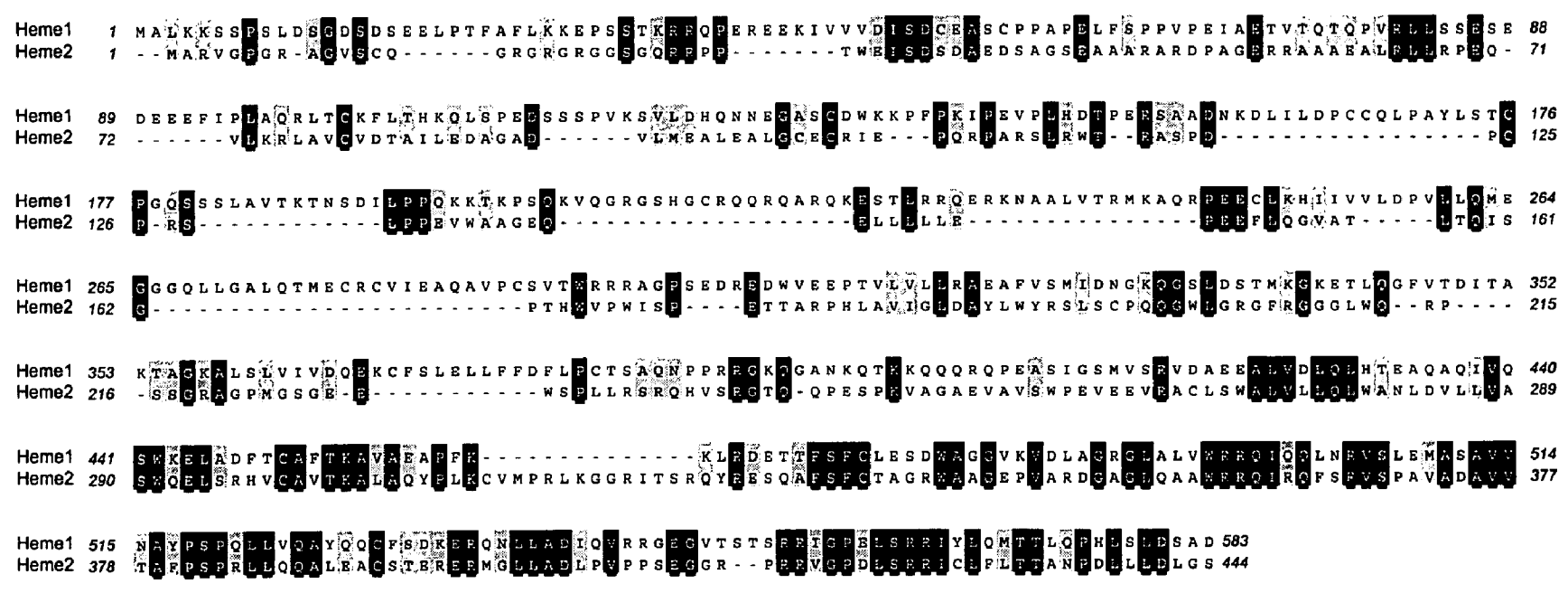

Homologs of *S. pombe* Eme1 were identified using database mining. Reiterative PSI-BLAST using *S. pombe* Eme1 as a starting sequence (SEQ ID NO: 23, FIG. 3) identified an uncharacterized ORF (AL356173) from *Neurospora crassa* having significant similarity to Eme1. Reiteration of the search using both *S. pombe* Eme1 and AL356173 identified two human sequences with significant similarity: SEQ ID NO: 9, Heme1A, and SEQ ID NO: 15, Heme2A (see FIGS. 3 and 4). A third iteration of this search also retrieved the sequence of Mms4. While Mms4 is a component of an endonuclease, it does not have significant similarity to Eme1 on a direct comparison.

Figure 5:
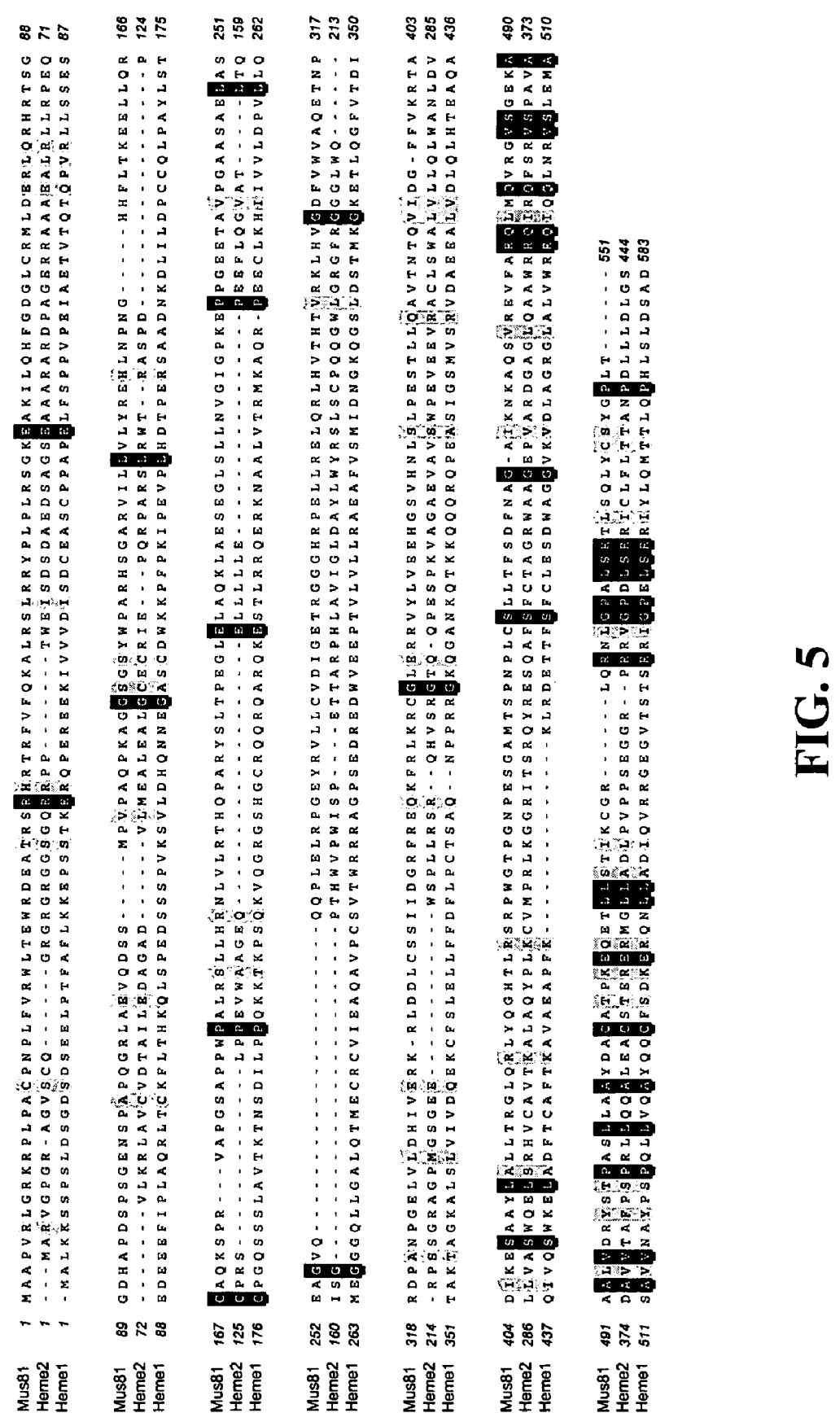

The alignment of *S. pombe* Mus81 to the *Neurospora crassa* sequence, and to the above-identified human sequences produced a position-specific score matrix that has significant similarity to Mms4. For convenience, the two human homologs have been designated Heme1 and Heme2. PSI-BLAST searching with Heme1 revealed a relationship not only with *S. pombe* Eme1, but also with Hmus81(FIG. 5). The similarity of Heme1 to Hmus81, although quite limited, may be of significance because a region of sequence similarity between XPF and ERRC1 has been reported. These regions of similarity are situated in portions of the proteins analogous to the regions through which XPF and ERRC1 interact in the ERRC1-XPF endonuclease. Thus, it is possible that the sequence relationship between Hmus81 and Heme1 is similar to the relationship of XPF and ERRC1 in the XPF-ERRC1 endonuclease. Although the sequence similarity between Eme1 and Heme1 is low, repeated BLAST searches failed to find a better candidate, and given that the Eme1 and Heme1 are more closely related than Eme1 and Mms4, there is no reason to suppose that the sequence similarity should be higher.

Three express sequence tags (ESTs) corresponding to Heme1 were obtained from the American Type Culture Collection (ATCC). PCR was utilized to generate a tagged version of the protein that could be expressed by transfection cells as described in detail below. Sequencing of the ESTs gave three slightly different versions of the protein (FIG. 6). The sequences suggest that the 3 ESTs likely represent alternatively or partially spliced versions of the same gene product. Some single nucleotide substitutions, likely polymorphic variants, were also detected. The polynucleotide of SEQ ID NO: 9 (pJ181) encodes a protein of 583 amino acids (Heme1A, SEQ ID NO: 10). The polynucleotide of SEQ ID NO: 11 (J179) encoding; Heme1B lacks 13 amino acids, corresponding to 372-384 of Heme1A (SEQ ID NO: 10), and lacks 29 amino acids corresponding to 303-331 of SEQ ID NO: 10 In addition, Heme1B lacks a glutamine residue at 138 (encoded by CAG) that is present in the other two variants. A single nucleotide difference (T for C) that results in a substitution of cysteine for arginine was detected in the nucleotide sequence (J180, SEQ ID NO: 13) encoding Heme1C (SEQ ID NO: 14). The sequences all map to a single locus at human chromosome 17q22.

Transfection of FLAG® (Sigma-Aldrich) tagged Heme1B and Heme1C into HeLa cells resulted in the expression of proteins of the expected molecular weights, as detected by anti-FLAG antibody. Human Mus81 was detected in FLAG immune-precipitates from cells that had been co-transfected with Hmus81 and Heme1-FLAG, but not from cells that were co-transfected with Hmus81 and empty vector. Preliminary investigations in which Heme1-FLAG was immune-precipitated from transfected HeLa cells showed that Heme1 has associated endonuclease activity that can resolve Holliday junction substrates into linear duplex DNA in vitro. The sequence similarity of Heme1 to S. pombe Eme1, together with the data showing association with 3HaMus81 (Chen, et al., 2001) strongly suggests that Heme1 is a functional equivalent of S. pombe Eme1.

Eme1 was FLAG tagged at the C' terminus using the following oligonucleotides forward CGGAATTCACCATG-GCTCTAAAGAAGTCATCACC (SEQ ID NO: 62) and reverse GCCCGCTCGAGTCACTTGTCATCGTCG TCCT-TGTAGTCAGCACTATCTAAAGAGAG (SEQ ID NO: 63), and was inserted into a pCDNA3 plasmid vector using EcoRI/XhoI. The same oligonucleotide primers were utilized for all three sequences (Heme1A, Heme1B and Heme1C). HeLa cells were transfected with the indicated plasmid vector using EFFECTENE® (Qiagen) or FUGENE® (Roche) transfection kits according to the manufacturers' recommended procedures.

Human Eme1 and human Mus81 were co-transected and co-expressed in the HeLa cells and demonstrated intrinsic endonuclease activity when co-expressed as described below.

The sequence of Heme2 (FIG. 7) derives, in part, from a conceptual translation of a region of chromosome 16q13.

EXAMPLE 5

Identification and Cloning of Murine Eme1 and Eme2

Murine Eme1 and Eme2 sequences were identified by performing BLAST searches of the EMBL and Incyte nucleotide and protein databases with the translation products of human Eme1 and Eme2 and identified murine ESTs encoding peptides that had significant homology to the targets. The so-identified amino acid sequences were used to identify murine nucleotide sequences corresponding to the 5' and 3' untranslated regions of the human mRNAs. Oligonucleotide primers corresponding to the mouse 5' and 3' untranslated regions were used to amplify DNA fragments from murine cDNA testis and brain libraries (Clonetech).

The following murine Eme1 and Eme2 PCR fragments were identified: Meme1TeA2 (SEQ ID NO: 44), Meme1TeA4 (SEQ ID NO: 46), Meme1TeA9 (SEQ ID NO: 48), Meme1TeB1 (SEQ ID NO: 50), Meme1TeB2 (SEQ ID NO: 52), Meme2Br2 (SEQ ID NO: 54), Meme2Br2 (SEQ ID NO: 56), Meme2Te5 (SEQ ID NO: 58) and Meme2Te6 (SEQ ID NO: 60), all of which are depicted in FIG. 11A-FIG. 11E. These fragments were then each cloned by PCR into a pCR4-pTOPO vector (Invitrogen) and the DNA of each vector was sequenced. The primers utilized in the PCR procedure were GGGGATAGATCTACTTCCGGG (SEQ ID NO: 62) for the 5' end and CATCATGAAAACAGGAGTCAGCC (SEQ ID NO: 63) for the 3' end.

EXAMPLE 6

Preparation of DNA Test Substrates

DNA test substrates X12, PX12 and Y12 were made by annealing two or more of the following PAGE purified oligonucleotides: X1 (GACGCTGCCGA ATTCTGGCT-TGCTAGGACATCTTTGCCCACGTTGACCCG, SEQ ID NO: 28), X2 (CGGGTCAACGTGGGCAAAGATGTC-CTAGCAATGTAATCGTCTATG ACGTC, SEQ ID NO: 29), X3 (GACGTCATAGACGATTACATTGCTAGGA CATGCTGTCTAGAGACTATCGC, SEQ ID NO: 30), and X4 (GCGATAGTC TCTAGACAGCATGTCCTAGCAAGC-CAGAATTCGGCAGCGTC, SEQ ID NO: 31). Radiolabeled DNA test substrates were made by annealing a $5'^{32}$P-labeled oligonucleotide with a 5-fold excess of cold oligonucleotides. Y12-1 consists of labeled oligonucleotide X1 and cold oligonucleotide X4. PX12-1 contains labeled oligonucleotide X1 and cold oligonucleotides 2 and 4. Four different X-structures, X12-1, X12-2, X12-3, and X12-4, were made by annealing $5'^{32}$P-labeled versions of oligonucleotide X1, X2, X3, or X4, respectively, with the other three cold oligonucleotides. X12 and PX12 contains a 12 base pair central core of homology in which the junction point is free to branch migrate. The junction is fixed in Y12. X0 was made by annealing oligonucleotides X01 (CAACGTCATAGACGATTACA TTGCTACATGGAGCTGTCTAGAGGATCCGA, SEQ ID NO: 32), X02 (GTCGGATCCTCTAGACAGCTCCATGAT-CACTGGCACTGGTAGAATTCGGC, SEQ ID NO: 33), X03 (TGCCGAATTCTACCAGTGCCAGTGATGGACAT CTTTGCCCACGTTGACCC, SEQ ID NO: 34), and X04 (TGGGTCAACGTG GGCAAAGATGTCCTAGCAATG-TAATCGTCTATGACGTT, SEQ ID NO: 35).

The annealing and gel purification of the substrates were carried out as previously described (Parsons et al., 1990). Annealing was achieved by incubating oligonucleotides for about 3 minutes at about 95° C., followed by subsequent 10 minute incubations at about 65° C., about 37° C., room temperature, and about 0° C. Labeled substrates were purified after separation by electrophoresis in a nondenaturing, 10% polyacrylamide gel, and stored in a a 50 mM NaCl buffer having a pH of about 7.5.

EXAMPLE 7

Endonuclease Assay

The ability of the endonucleases of the present invention to resolve Holliday junctions was determined by the procedure described in Boddy et al. 2001 incorporated herein by reference to the extent relevant. Unless otherwise indicated, reactions (15 µl) contained 1 nM labeled substrate, a total of about 6 µl of endonuclease and TEV-eluate buffer containing 15% glycerol (usually about 3 µl of a solution of endonuclease and about 3 µl of TEV-eluate buffer), 2.5 mM $MgCl_2$, 50 mM Tris buffer at pH of about 7.5, in 100 µg/ml BSA containing 1 mM 2-mercaptoethanol. In reactions containing ATP (2 mM), the chelation of $Mg^{2+}$ ions by ATP was taken into account to adjust the final concentration of free $Mg^{2+}$ ions at about 2.5 mM. Reactions were incubated at about 30° C. for about 45 minutes (unless otherwise indicated). Reaction products were analyzed by electrophoresis in 1x TBE (Tris-Borate EDTA) buffer in either a denaturing 12% polyacrylamide gel containing 7 M urea for nuclease assays, or in a nondenaturing 10% polyacrylamide gel for resolution assays. To map the sites of cleavage in the nuclease assays, Maxam-Gilbert piperidine and hydrazine sequencing reactions set up with each oligonucleotide were run in parallel (Maxam et al., 1980, *Methods Enymol.*, 65: 499-560). The endonuclease activity of the Mus81-Eme complexes of the invention were assessed utilizing substrates as described in Example 6.

EXAMPLE 8

Co-transfection of Human Mus81 and Human Eme1

HeLa cells were transiently transfected with 3HaMus81 (triple hemagglutinin (3Ha) tagged Hmus81) and FLAG tagged versions of Heme1A, Heme1B, and Heme1C. As shown in FIG. 13A, 3HaMus81 was detected in immune-precipitates of all three forms of Heme1. The amount of 3HaMus81 associated with FLAG-Heme1B was higher than FLAG-Heme1A or FLAG-Heme1C. Hmus81 and Heme1 immune complexes were assayed for associated endonuclease activity using this substrate (FIG. 13B). The activity of 3HaMus81 was greatly increased in cells that had been co-transfected with FLAG-Eme1B, but less affected by FLAG Heme1A or FLAG Heme1C. Likewise, when the different forms of Heme1 were immune-precipitated using the FLAG antibody, the B form had readily detectable activity. A longer exposure revealed a relatively weaker activity in FLAG-Heme1A and FLAG-Heme1C precipitates compared with the Heme1B version. More FLAG-Heme1B was precipitated with 3HaMus81 than with FLAG Heme 1A or 1C. Co-transfection of FLAG Heme1B with 3HaMus81 resulted in greater activation of 3HaMus8l than afforded by co-transfection with either Heme1A or Heme1C. The higher endonuclease activity in Heme1B containing immune-precipitates appeared to result mainly from increased association between 3HaMus81 and FLAG-Heme1B relative to Heme1A and Heme1C, but it is also possible that Heme1B stimulated Hmus81 activity more than Heme1A or Heme1C.

To determine which forms of Heme1 are naturally expressed in HeLa cells, oligonucleotide primers common for all three variants were used to amplify sequences from a HeLa cell cDNA library (data not shown). Only the B form of Heme1 was detected. Although this analysis does not exclude the possibility that the A or C form of Heme1 are expressed in other cell types, or at low levels in HeLa cells, transcripts corresponding to the B form of the protein were readily detectable.

As shown in FIG. 13C, FLAG-Heme1B associated both with wild-type Hmus81 and with a mutant version of Mus81 that lacks associated endonuclease activity. Endonuclease activity was detected in a FLAG-Heme1B immune-precipitate from cells that had been co-transfected with wild type 3HaMus81, but not in cells that had been transfected with FLAG-Heme1B alone (FIG. 13D). Thus, Heme1B associated endonuclease activity is dependent on co-expression of Hmus81. As previously reported by Mullen et al., *Genetics*, 2001; 157: 103-118, Ha-immune-precipitates from cells that had been transfected with 3HaMus81 had detectable endonuclease activity in the absence of transfected Eme1 (FIG. 13D). Eme1 is important for Mus81 activity and function in fission yeast. Likewise, Mms4 is important for Mus81 activity and function in budding yeast.

Figure 14:
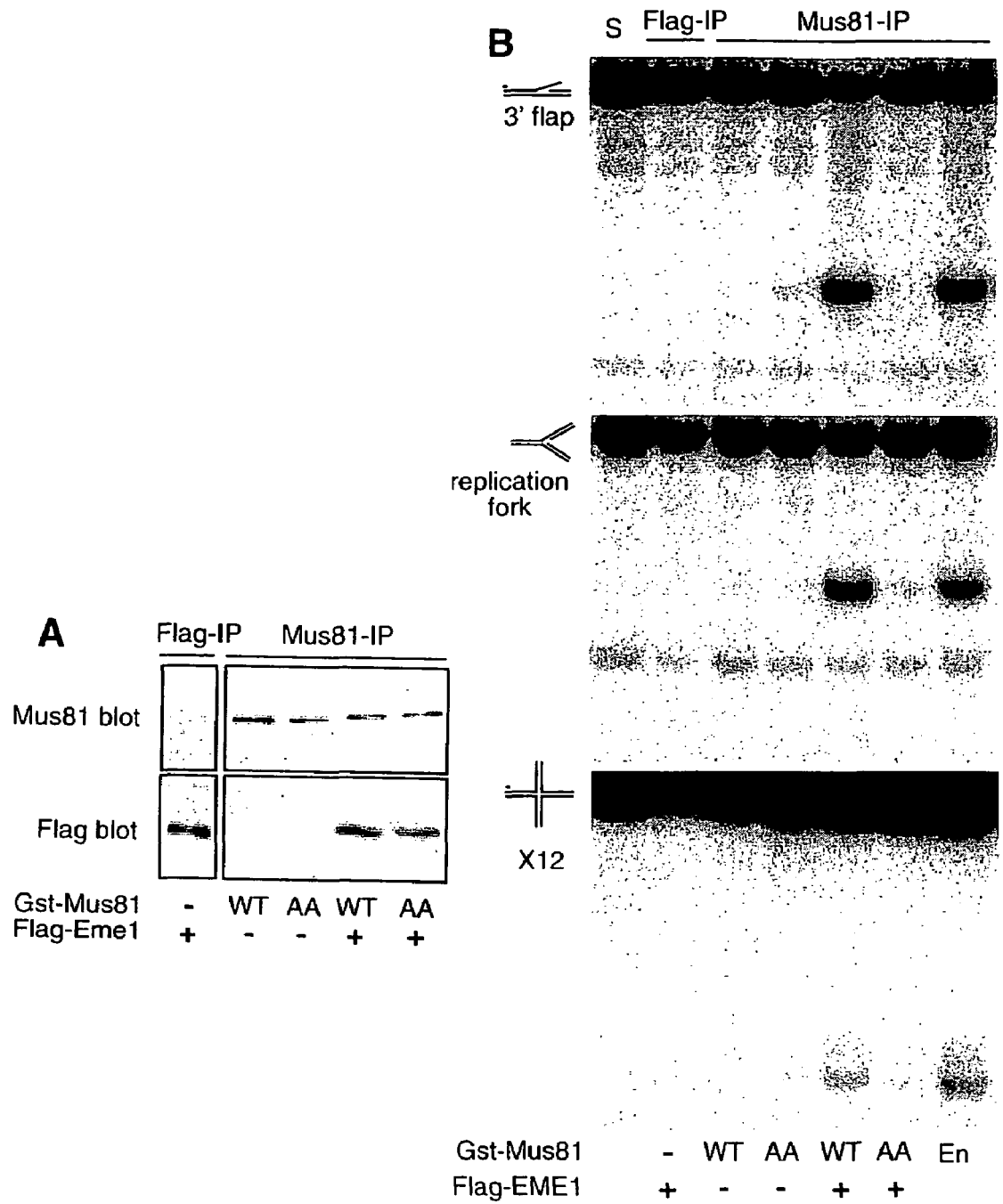
FIG. 14 depicts endonuclease activity of recombinant Mus81-Eme1.

To test whether human Eme proteins is required for the activity of human Mus81, insert cells were infected with baculo-viruses encoding Gst-Hmus81 (fusion protein of glutathione-S-trans with Hmus81), FLAG-Heme1B or both (FIG. 14A). Immune-precipitated Gst-Hmus81 and FLAG-Heme1B were assayed using a 3' flap, a replication fork, and a Holliday junction structure (X12). Gst-Hmus81 alone had no detectable activity on any of these substrates. Likewise, immune-precipitated FLAG-Heme1B had no detectable endonuclease activity (FIG. 14B). In contrast, when Gst-Hmus81 and FLAG-Heme1B were co-expressed, immune-precipitates of Hmus81-Eme1B complex readily cleaved a 3'structure. Thus, the endonuclease activity of Hmus81 depends on Heme protein, and vice-versa. Given that protein such as Heme1 is important for the activity of recombinant Hmus81, the activity detected in immune-precipitate of transfected 3HaMus81 (FIG. 13) likely reflects the ability of 3HaMus81 to associate with endogenous Eme protein.

As shown in FIG. 15A, FLAG-Mus81 was detected in an immune-precipitate of 3HaMus81. Control samples in which cells were transfected with one construct show that there is no cross reactivity between the immune-precipitating antibody. Likewise, when 3HaEme1 was co-transfected with FLAG-Eme1, 3HaEme1 was detected in immune-precipitates of FLAG-Eme1 (FIG. 15B). This analysis does not distinguish the number of Mus81, or Eme1, molecules that co-precipitate with each other; however, the analysis does demonstrate that at least two molecules of Mus81 and of Eme1, associate in vivo. The ability of Mus81-Eme1 to resolve the Holliday junctions into linear duplex DNA is likely dependent on the correct coordination of two active Hmus81-Eme1 heterodimers in a complex.

Cell Culture and Mitotic Recombination Assays.

HeLa cells (293 human embryonic kidney cells) and an SV40 transformed human fibroblast cell line (GM847L22) were grown in Dulbecco's Modified Eagle's Medium (D-MEM) supplemented with 10% enriched calf serum, about 100 µg/ml penicillin and streptomycin. For routine culture GM847L22 were maintained in presence of about 400 µg/mL G418 antibiotic. *Spodoptera frugiperda* Sf9 cells were grown in Excell-401 media (JRH Biosciences) with about 50 µg/ml penicillin and streptomycin. To assay mitotic recombination, about 5×10$^5$ cells were plated in G418-free medium for about 16 hours prior to transfection. A solution of about 2 mM thymidine was then added to the culture medium and cells were grown for about 16 hours. Cells were cultured in the normal growth medium for about 24 hours more. Cells were fixed with 2% formaldehyde in phosphate buffered saline (PBS) for about 10 minutes, washed with PBS twice, and assayed for β-galactosidase activity by incubation in PBS containing about 1 mg/mL X-Gal (5-bromo-4-chlora-3-indolyl-β-D-galactoside), about 4 mM potassium ferrocyanide, about 4 mM potassium ferricyanide, and about 2 mM MgCl$_2$ at 37° C. overnight. The number of blue cells was scored using a 20× objective on an inverted light microscope. The statistical significance of the resultant data was calculated using a Student's t-Test.

Expression of Recombinant Proteins and RNAi

Two variants of 3HaMus81 (wild type and endonuclease inactive) were cloned into pcDNA3 (Invitrogen) plasmid expression vectors using the EcoR1 and Xho1 sites. Human Eme1 was FLAG tagged at the C' terminus using GCCCGCTCGAGTCACTTGT-CATCGTCGTCCTTGTAGTCAGCACTATCTAAAGA (SEQ ID NO: 64) and inserted into a pCDNA3 phasmid expression vector using EcoR1 and Xhol. The Mus81 was FLAG tagged at the C' terminus using CTCGAGTCACT-TGTCATCGTCGTCCTTGTAGTCGGT-CAAGGGGCCGTAGC (SEQ ID NO: 65). 3HaEme1 was prepared by cloning Heme1B into pcDNA-3Ha using the NdeI and XhoI sites. Human HeLa cells were transfected using FUGENE® (Roche) or EFFECTENE® (Qiagen) transfection kits according to the manufacturers' instructions. For expression in Sf9 cells, Gst-Mus81 was cloned into pFastBac (BRL/Gibco) using EcoR1 and HindIII, and Eme1-FLAG was cloned using the EcoR1 and XhoI sites. The BAC-TO-BAC® system (BRL/Gibco) was used to generate recombinant viruses. All constructs were verified by sequencing. Two 19-nucleotide regions corresponding to residues 178-197 (pSuper-178) and 292-311 (pSuper-292) of SEQ ID NO:1, Hmus81 (1), were selected and cloned into pSUPER® RNAi vector (OligoEngine) and used as recommended by the manufacturer. PCR was carried out on a HeLa cell cDNA library (Clonetech) using sequences present in all three forms of human Eme1 (i.e., CGGAATTCACCATGGCTCTAAA-GAAGTCATCACC (SEQ ID NO: 66) and GCCCGCTC-GAGTCAGTCAGCACTATCTAAAGAGAG (SEQ ID NO: 67). The PCR products were cloned into pTopo (Invitrogen). Restriction enzyme analysis of 6 clones gave a pattern corresponding to Heme1B. Sequencing of 2 clones verified that the transcript corresponding to Heme1B is expressed in HeLa cells. A nuc-RusA-2Ha (wild type and inactive) was cloned into pCDNA3 for expression in human cells using pRep1-RusA and pRep1-RusA-D70N (Boddy, et al., 2001) as starting constructs.

Nuclease Assays and Western Analysis

Nuclease assays were carried out as described previously (see Chen et al., 2001). Antibody to the Ha-epitope was from Babco (Covance). Antibody to the FLAG-epitotpe (FLAG-M2) was from Sigma. Antibody to Mus81 was described in Chen et al., 2001. Cells lysates, immune-precipitates and immune-blots analysis was carried out as described in Chen et al., 2001.

Figure 16:
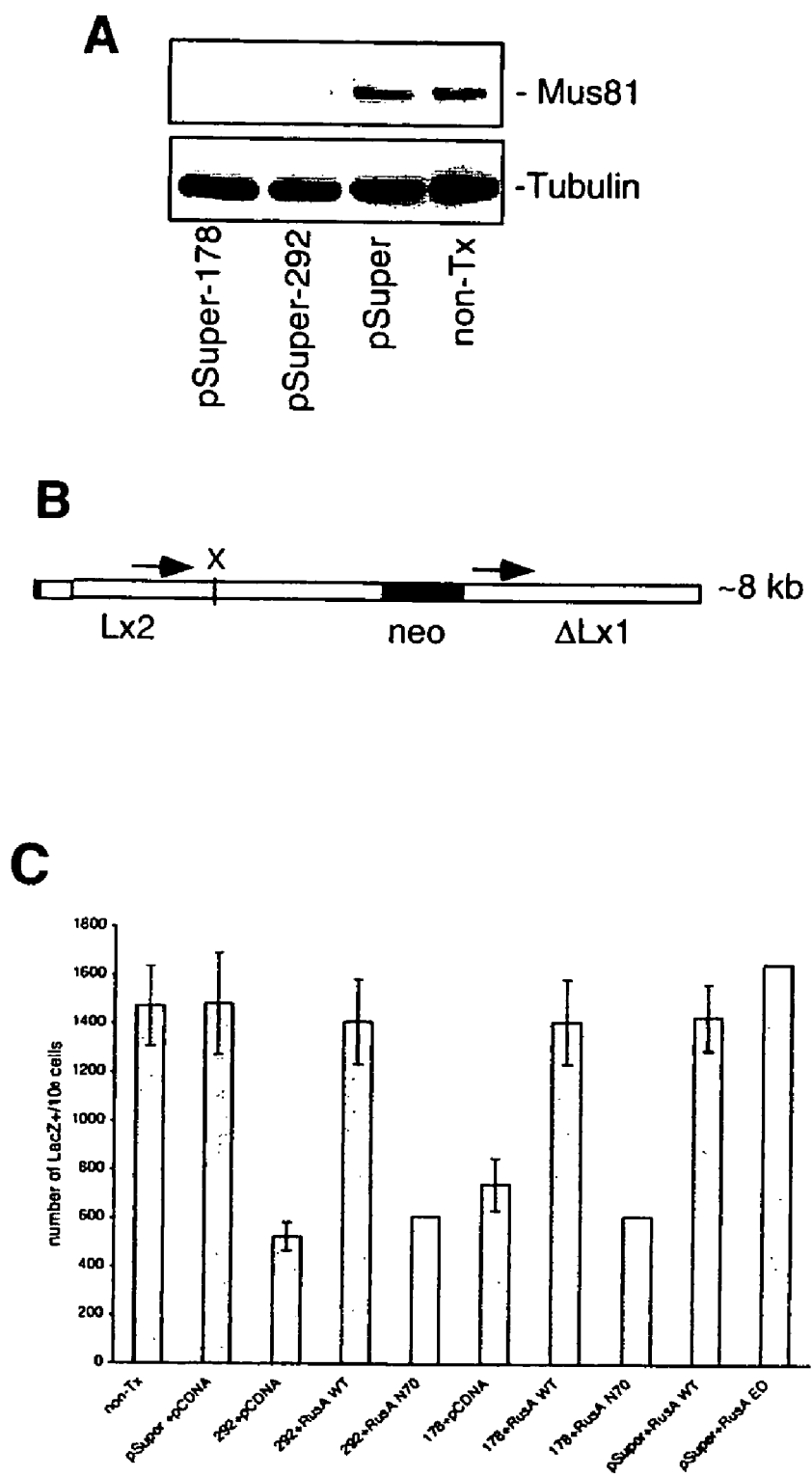
FIG. 16 depicts suppression of Mus81 expression by interference RNA (RNAi).

The role of Mus81 in human cells was investigated using interference RNA (RNAi) to suppress expression of Hmus81 as described in Brummelkamp et al., 2002, *Science*, 296: 550-553. As shown in FIG. 16A, Hmus81 protein levels were substantially reduced in cells that were transfected with pSuper vectors containing 19-nucleotide sequences that target two regions of Hmus81 messenger RNA (pSuper-178 and pSuper-292). No loss of Hmus81 was seen in cells transfected with control vector (pSuper). To determine whether Hmus81 is required for mitotic recombination we took advantage of an SV40 transformed human fibroblast line, GM847L22, which contains a single integrated copy of the mitotic recombination reporter plasmid pLrec. A schematic of the Lrec cassette is shown in FIG. 16B; it contains two direct repeats of genetically inactive β-galactosidase (LacZ) genes and can give rise to LacZ$^+$ cells by gene conversion by unequal sister chromatid exchange, or by intrachromosomal recombination. This system has previously been used to demonstrate that cells from ataxia telangiectasia patients have increased mitotic recombination rates, and that loss of the Werner syndrome protein (WRN) is associated with decreased productive mitotic recombination. A feature of this reporter gene is that β-galactosidase activity can be scored directly in single cells, thus it is compatible with transient down-regulation through use of RNAi. Following transfection with plasmids that suppress Hmus81 expression (pSuper-178, pSuper-292) or control plasmids, GM847L22 cells were grown in the presence of thymidine to increase the incidence of recombination. Following an additional 24 hours growth in normal medium, the cells were stained for β-galactosidase activity and the frequency of recombination was scored. Untransfected cultures generated about 1470 +/−180 recombinants per million cells (FIG. 16C). A similar number of LacZ$^+$ cells was seen following transfection of control pSuper and pCDNA vectors. The number of recombinants was reduced by about 4-fold (P=0.0003) and 2-fold (P=0.0006) in cells that had been transfected with the Hmus81-RNAi plasmids, pSuper-292 and pSuper-178, respectively. These data suggest that suppression of Hmus81 expression reduces mitotic recombination, but could also indicate that Hmus81-RNAi interfered with β-galactosidase expression. Control experiments in which cells were co-transfected with plasmids carrying a single intact copy of the β-galactosidase and with pSuper plasmid showed that a similar percentage (about 84±2%) of β-galactosidase positive cells was present in all cases. Therefore, we interpret these data to indicate that down-regulation of Hmus81 suppresses recombination between the two inactive LacZ alleles rather than suppressing expression of β-galactosidase activity per se.

RusA rescues the meiotic defect and hypersensitivity to agents that cause replication fork stalling of Mus81 mutants. We reasoned that if suppression of Hmus81 in human cells results in the accumulation of Holliday junctions, the reduction in recombination would be rescued by expression of active RusA. As shown in FIG. 16C, expression of wild type RusA did not significantly affect the incidence of recombination in cells that were transfected with empty vector (P=0.65), suggesting that at this level of expression, RusA does not drive increased recombination in human cells. In contrast, when active nuclear RusA (RusAWT) was co-transfected with plasmids encoding Hmus81-RNAi it increased the incidence of recombination to the levels seen in untransfected control cultures (FIG. 16C). An endonuclease-inactive version of RusA (RusAN70) did not significantly increase the number of recombinants in Hmus81-RNAi transfected cells. Immune-blotting showed that the wild type and mutant form of RusA were equally expressed. Ha-immune-precipitates confirmed that wild type, Hmus81 but not the mutant Hmus81 was active on the X12 substrate. The in vitro Holliday junction resolution activity of Hmus81-Eme1, in conjunction with the observation that Hmus81-dependent recombination was reused by expression of a bacterial Holliday junction resolvases, indicates that Hmus81-Eme1 also resolves Holliday junctions in vivo.

Evidence that Hmus81-Eme1 is active in vitro on 3' flaps and replication fork structures, as well as Holliday junctions, suggests a number of possible roles for Hmus81-Eme1 in recombination repair. Despite the ability of Hmus81-Eme1 to cleave replication fork-like structures in vitro, two lines of evidence suggest that Hmus81 does not act directly on replication forks in vivo. The camptothecin sensitivity of yeast strains that lack Mus81 activity strongly suggests that Mus81 activity is important following replication fork collapse, since camptothecin causes fork collapse. This observation is not consistent with the hypothesis that Mus81 activity is required to cleave stalled forks. Secondly, mutations in proteins that act early in recombination (Rad51, Rad52 and Rad54) suppress the synthetic lethality of Mus81-sgs1 strains as reported by Fabre et al., 2002, *Prac. Nat'l. Acad. Sci., USA*, 99: 16887-16892. If Hmus81-Eme1 acts directly on replication forks, its growth defects would not be rescued by disruption of these genes. The observation that Hmus81-Eme1 cleaves 3' flaps in vitro suggests a role in trimming flaps that might arise following extension of a 3' end during the process of synthesis-dependent strand annealing (SDSA), in which a strand of the sister chromatid is used as a template for extension of a free 3' end. SDSA is an attractive model for mitotic recombination because it can be accomplished without forming a Holliday junction and thus could account for mitotic recombination without cross-over. However, a failure to cleave a 3' flap that might be generated by SDSA is not expected to lead to Holliday junction accumulation, and thus, one would not expect RusA to rescue a defect in forms of SDSA that do not involve Holliday junction. The possibility that RusA acts non-specifically in human cells to cleave structures other than Holliday junction cannot be formally excluded. However, extensive analysis of RusA has shown that it is highly specific for Holliday junctions, and is unlikely to cleave other structures in vivo.

The invention, having been fully described in many of its aspects and claimed herein, can be made and executed without undue experimentation by one of skill in the art according to the teaching herein. While the compositions and methods of this invention have been described by way of example above, it will be apparent to those of skill in the art that many variations and modifications can be applied to the compositions and methods described herein without departing from the concept, spirit, and scope of the invention.

We claim:
1. An isolated protein comprising SEQ ID NO: 12.
2. An isolated endonuclease complex comprising SEQ ID NO: 2 and SEQ NO: 12.

* * * * *